US009801951B2

(12) United States Patent
Miao et al.

(10) Patent No.: US 9,801,951 B2
(45) Date of Patent: *Oct. 31, 2017

(54) DRUG-CONJUGATES, CONJUGATION METHODS, AND USES THEREOF

(71) Applicant: Concortis Biosystems, Corp., San Diego, CA (US)

(72) Inventors: Zhenwei Miao, San Diego, CA (US); Yufeng Hong, San Diego, CA (US); Tong Zhu, San Diego, CA (US)

(73) Assignee: Concortis Biosystems, Corp., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,318

(22) PCT Filed: May 14, 2013

(86) PCT No.: PCT/US2013/041028
§ 371 (c)(1),
(2) Date: Nov. 14, 2014

(87) PCT Pub. No.: WO2013/173393
PCT Pub. Date: Nov. 21, 2013

(65) Prior Publication Data
US 2015/0141646 A1  May 21, 2015

Related U.S. Application Data

(60) Provisional application No. 61/652,512, filed on May 29, 2012, provisional application No. 61/648,406, filed on May 17, 2012, provisional application No. 61/648,532, filed on May 17, 2012, provisional application No. 61/647,300, filed on May 15, 2012.

(51) Int. Cl.
| | | |
|---|---|---|
| A61K 38/07 | (2006.01) | |
| C07D 207/09 | (2006.01) | |
| A61K 47/48 | (2006.01) | |
| C07D 207/08 | (2006.01) | |
| C07D 277/593 | (2006.01) | |
| C07D 401/12 | (2006.01) | |
| C07D 403/12 | (2006.01) | |
| C07F 5/02 | (2006.01) | |
| C07K 5/06 | (2006.01) | |

(52) U.S. Cl.
CPC ........ *A61K 47/48584* (2013.01); *A61K 38/07* (2013.01); *A61K 47/48384* (2013.01); *A61K 47/48415* (2013.01); *A61K 47/48561* (2013.01); *A61K 47/48715* (2013.01); *C07D 207/08* (2013.01); *C07D 207/09* (2013.01); *C07D 277/593* (2013.01); *C07D 401/12* (2013.01); *C07D 403/12* (2013.01); *C07F 5/025* (2013.01); *C07K 5/06008* (2013.01)

(58) Field of Classification Search
CPC ........................... C07D 207/08; C07D 207/09
See application file for complete search history.

(56) References Cited

U.S. PATENT DOCUMENTS

| | | | |
|---|---|---|---|
| 5,780,588 A * | 7/1998 | Pettit | .................. C07K 5/0205 530/330 |
| 6,124,431 A | 9/2000 | Sakakibara et al. | |
| 6,569,834 B1 | 5/2003 | Pettit et al. | |
| 7,531,162 B2 | 5/2009 | Collins et al. | |
| 7,767,205 B2 | 8/2010 | Mao et al. | |
| 7,829,531 B2 | 11/2010 | Senter et al. | |
| 7,994,135 B2 | 8/2011 | Doronina et al. | |
| 8,088,387 B2 | 1/2012 | Steeves et al. | |
| 8,470,984 B2 | 6/2013 | Caruso et al. | |
| 2005/0238649 A1 | 10/2005 | Doronina et al. | |
| 2006/0128754 A1 | 6/2006 | Hoefle et al. | |
| 2007/0092940 A1 | 4/2007 | Eigenbrot et al. | |
| 2007/0134243 A1 | 6/2007 | Gazzard et al. | |
| 2011/0206658 A1 | 8/2011 | Crowley et al. | |
| 2011/0217321 A1 | 9/2011 | Torgov et al. | |
| 2011/0245295 A1 | 10/2011 | Chai et al. | |
| 2011/0263650 A1 | 10/2011 | Ellman et al. | |
| 2011/0268751 A1 | 11/2011 | Sievers et al. | |
| 2011/0301334 A1 | 12/2011 | Bhakta et al. | |
| 2012/0148610 A1 | 6/2012 | Doronina et al. | |
| 2013/0029900 A1 | 1/2013 | Widdison | |
| 2013/0101546 A1* | 4/2013 | Yurkovetskiy | ... A61K 47/48692 424/78.17 |
| 2013/0224228 A1 | 8/2013 | Jackson et al. | |
| 2014/0030282 A1 | 1/2014 | Polakis et al. | |
| 2015/0105539 A1 | 4/2015 | Miao et al. | |

(Continued)

FOREIGN PATENT DOCUMENTS

| | | | | |
|---|---|---|---|---|
| CA | 2813056 A1 | 4/2012 | | |
| DE | CA 2813056 A1 * | 4/2012 | ............. | A61K 38/08 |
| EP | 0624377 A2 | 11/1994 | | |

(Continued)

OTHER PUBLICATIONS

Pettit, Robin. Antimicrobial Agents and Chemotherapy (1998) 2961-2965.*

Cella, R., et al., "Steroselective Synthesis of the Dolastatin Units by Organotriflouroborates Additions to Alpha-Amino Aldehydes", Tetrahedron Letters, 49 (2008) 16-19.

Dosio et al. "Synthesis of Different Immunotoxins composed by Ribosome Inactivating Proteins Non-covalently Bound to Monoclonal Antibody" Il Farmaco, 1996, vol. 51, pp. 477-482.

Ducry, L et al., "Antibody-Drug Conjugates: Linking Cytotoxic Payloads to Monoclonal Antibodies" Bioconjugate Chemistry, 2010, vol. 21, No. 1, pp. 5-13.

(Continued)

*Primary Examiner* — Deepak Rao
*Assistant Examiner* — Laura Daniel
(74) *Attorney, Agent, or Firm* — McCarter & English, LLP; Danielle L. Herritt; Michael J. DeGrazia

(57) ABSTRACT

In certain aspects, compounds and uses thereof are provided. In certain aspects, compound-conjugates and uses thereof are provided.

18 Claims, 10 Drawing Sheets

(56) References Cited

U.S. PATENT DOCUMENTS

| | | |
|---|---|---|
| 2015/0105540 A1 | 4/2015 | Miao et al. |
| 2016/0067350 A1 | 3/2016 | Miao et al. |

FOREIGN PATENT DOCUMENTS

| | | | | |
|---|---|---|---|---|
| WO | 2005/081711 A2 | 9/2005 | | |
| WO | WO 2005081711 A2 * | 9/2005 | ....... | A61K 47/48415 |
| WO | 2007/109567 A1 | 9/2007 | | |
| WO | 2008/112873 A2 | 9/2008 | | |
| WO | 2009099719 A2 | 8/2009 | | |
| WO | 2010/009124 A2 | 1/2010 | | |
| WO | 2012/010287 A1 | 1/2012 | | |
| WO | 2012/166559 A1 | 12/2012 | | |
| WO | 2012/166560 A1 | 12/2012 | | |
| WO | 2013/085925 A1 | 6/2013 | | |
| WO | 2013/173391 A1 | 11/2013 | | |
| WO | 2013/173392 A1 | 11/2013 | | |
| WO | 2013/173393 A1 | 11/2013 | | |
| WO | 2013/185117 A1 | 12/2013 | | |
| WO | 2013/192360 A1 | 12/2013 | | |
| WO | 2015/057876 A1 | 4/2015 | | |
| WO | 2016/123412 A1 | 8/2016 | | |
| WO | 2016/127081 A1 | 8/2016 | | |

OTHER PUBLICATIONS

Geroni et al. "Nemorubicin: A doxorubicin-like structure with a novel mechanism of action different from anthracyclines" Proc. Amer. Assoc. Cancer Res., 2006, vol. 47, abstract No. 3845.

Kingston, David "Tubulin Interactive Natural Products as Anticancer Agents" J Nat Prod. Mar. 2009; 72(3): 507-515.

Pettit, et al., "Specific Activities of Dolastatin 10 and Peptide Derivatives Against Crypococcus neoformans" Antimicrobial Agents and Chemotherapy, Nov. 1998, p. 2961-2965.

PubChemCompound datasheet (online compound summary) CID 56841603; Create Date: Mar. 21, 2012; http://pubchem.ncbi.nlm.nih.gov/summary/summary.cgi?cid=56841603.

Copending U.S. Appl. No. 14/401,114, filed Nov. 13, 2014.
Copending U.S. Appl. No. 14/401,115, filed Oct. 13, 2014.
Copending U.S. Appl. No. 14/515,352, filed Nov. 15, 2014.
Copending U.S. Appl. No. 15/009,775, filed Jan. 28, 2016.
Copending U.S. Appl. No. 15/017,174, filed Feb. 5, 2016.

Younes, A. et al., "Brentuximab Vedotin (SGN-35) for Relapsed CD30-Positive Lymphomas" The New England Journal of Medicine, 363; 19, 2010, 1812-1821.

Smith et al. "Protein Modification, Bioconjugation, and Disulfide Bridging Using Bromomaieimides," J.AM. Chem. Soc. 132(6): 1960-1965 (2010).

Pettit, G. et al. "Antineoplastic Agents. 592. Highly Effective Cancer Cell Growth Inhibitory Structural Modifications of Dolastatin 10" Jouranl of Natural Products, 2011, 74, 962-968.

Tannock et al., The Basic Science of Oncology, Ch. 19—Experimental Chemotherapy, p. 338 and p. 352-359, New York, 1992.

Antibody Structure, http://www.biology.arizona.edu/immunology/tutorials/antibody/structure.html, accessed Sep. 8, 2016.

Axup et al., "Synthesis of site-specific antibody-drug conjugates using unnatural amino acids", Proceedings of the National Academy of Science, vol. 109, No. 40, Oct. 2, 2012, pp. 16101-16106.

Leamon et al., "Preclinical Antitumor Activity of a Novel Folate-Targeted Dual Drug Conjugate" Molecular Pharmaceutics, vol. 4, No. 5, Oct. 1, 2007, pp. 659-667.

* cited by examiner

DRUG-CONJUGATES, CONJUGATION METHODS, AND USES THEREOF

BACKGROUND

Cytotoxic agents can provide therapeutic benefits in the treatment of various conditions, including various cancers. Accordingly, it is desirable to provide cytotoxic agents with therapeutically useful properties, for example, as chemotherapies in cancer treatments.

Clinical uses of cytotoxic agents as chemotherapies usually develop drug resistances, and thus, drop their therapeutic efficacies. Accordingly, it is desirable to provide cytotoxic agents with improved drug resistance profiles. One possibility is to design cytotoxic compounds with efflux pump resistances. Another possibility is to design cytotoxic compounds potentially act on more than one targets.

Tubulins are a class of targets for anti-mitotic agents as chemotherapies alone or in combination with other chemotherapies or as active agent-conjugates. Examples of Tubulin-Binding Agents include, but are not limited to, the following compounds:

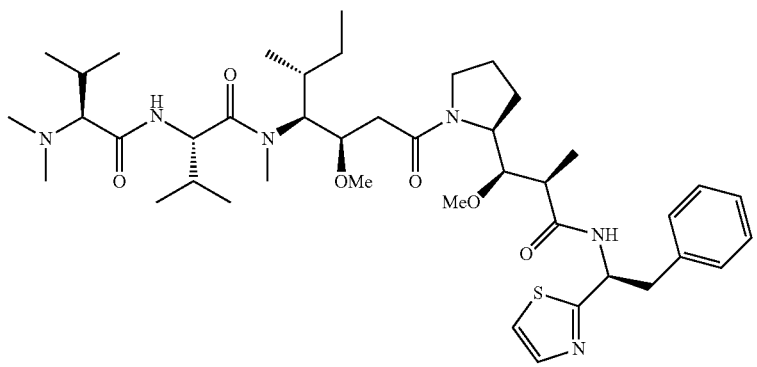

Dolostatin 10

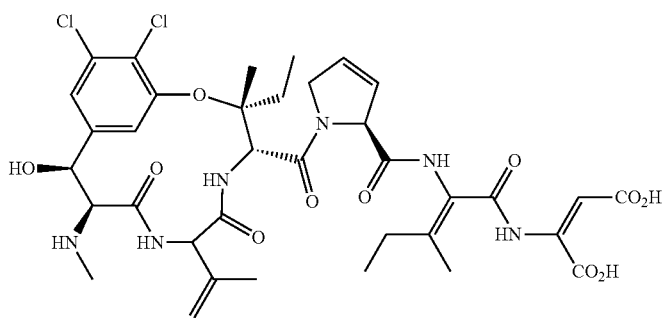

Phomopsin A

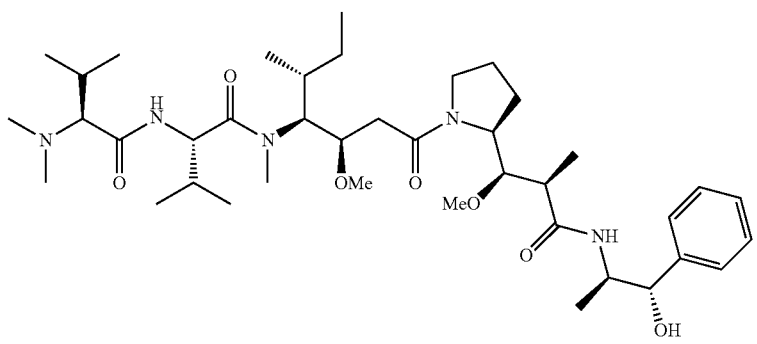

Auristatin E

-continued
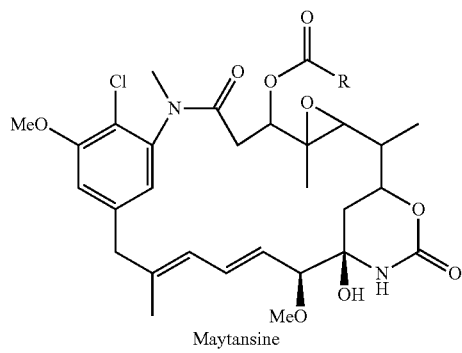
Maytansine
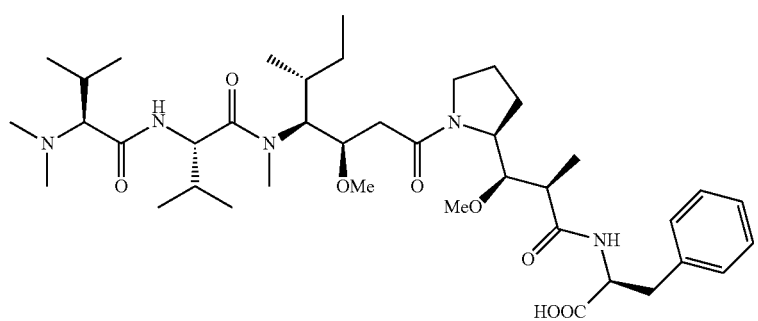
Auristatin F
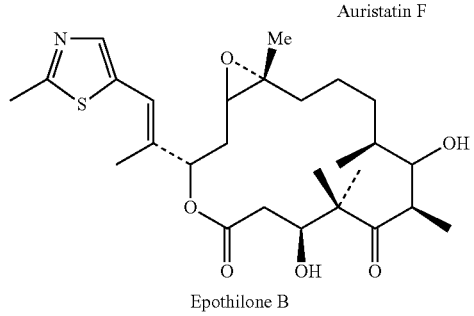
Epothilone B
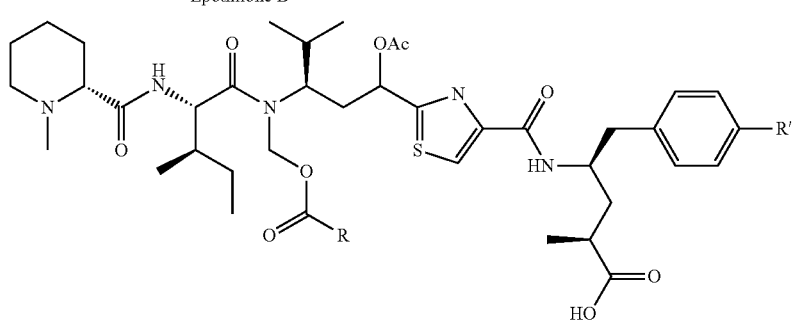
Tubulysins
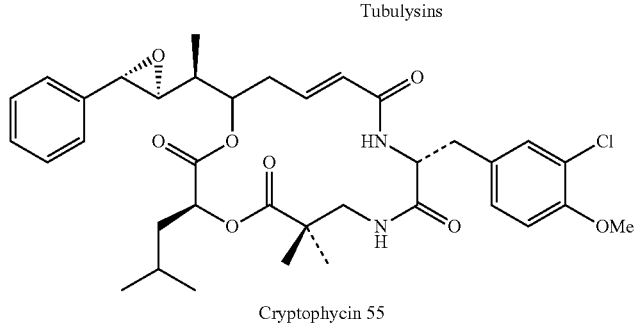
Cryptophycin 55
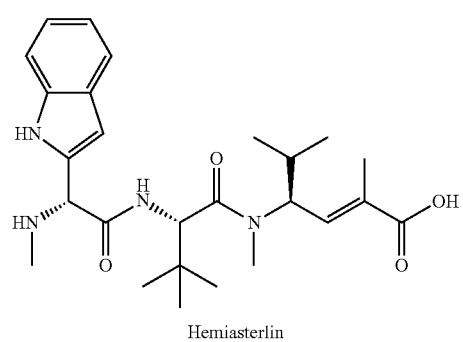
Hemiasterlin

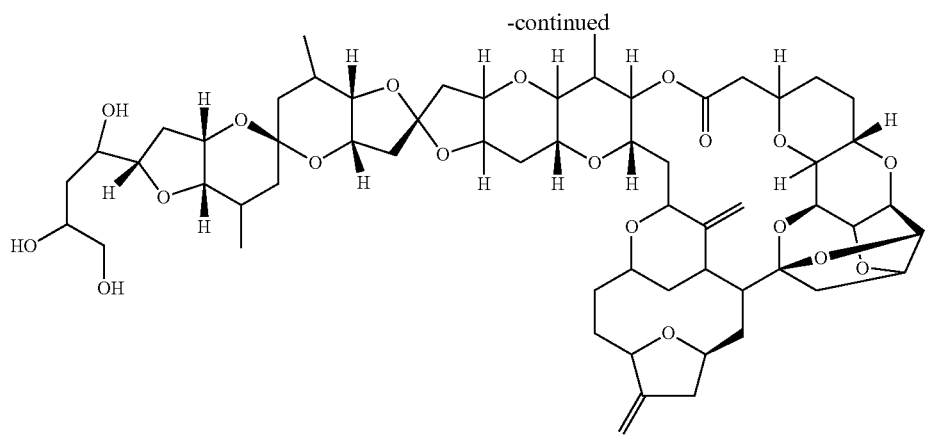
Hailichondrin B
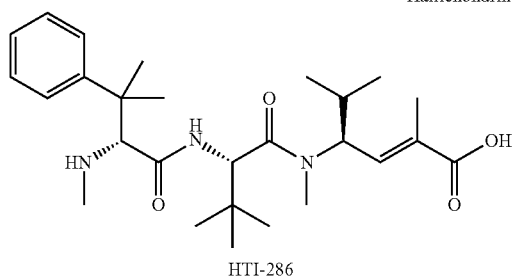
HTI-286
Many enzymes, for example, proteasome, MMAP, FAP and uPA, are considered as cancer therapy targets due to their involvements in cancer proliferations and metastases. Examples of Proteasome inhibitors include, but are not limited to, the following compounds:
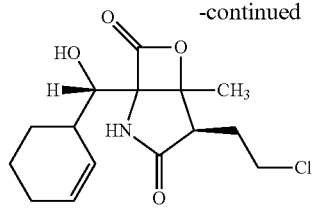
Salinosporamide A
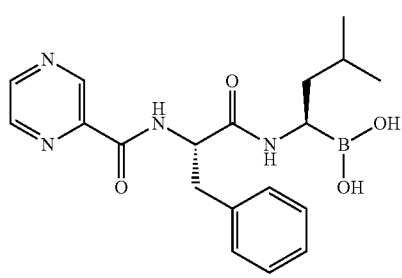
Bortezomib
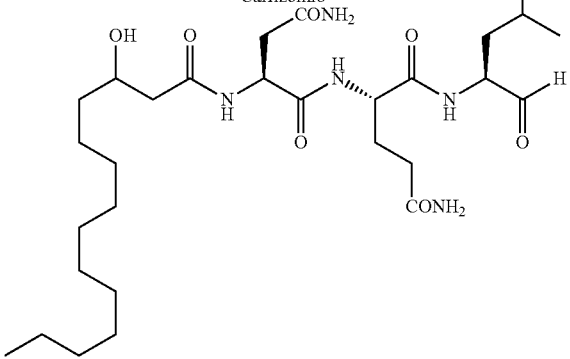
Carfizomib
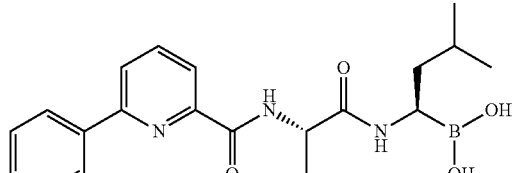
CEP-18770
Fellutamide B Example of FAP Inhibitors, not Limited to:

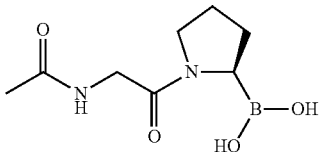

Examples of uPA Inhibitors, not Limited to:

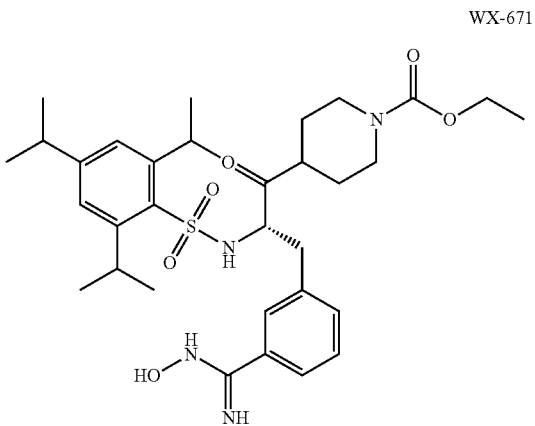

WX-671

Examples of MMP Inhibitors Disclosed in, not Limited to:

Compounds disclosed in Bioorganic & Medicinal Chemistry 15 (2007) 2223-2268.

Compounds disclosed in Cancer Metastasis Rev (2006) 25: 115-136.

SUMMARY

Some embodiments provide compounds, methods of preparing compounds, and uses thereof.

Some embodiments provide compound-conjugates, methods of preparing compound-conjugates, and uses thereof.

Some embodiments provide a compound having the structure of Formula I:

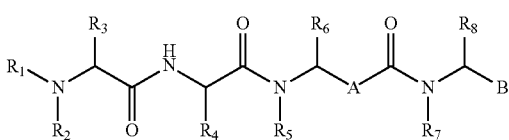

I

Some embodiments provide a compound having the structure of Formula Ia:

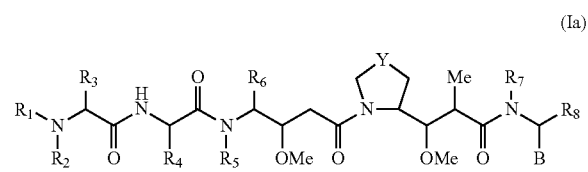

(Ia)

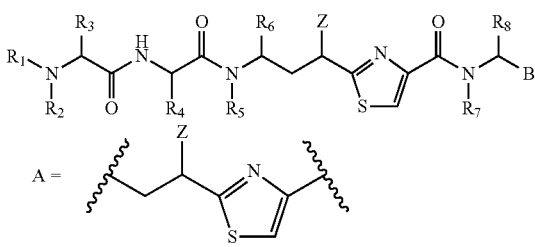

or a pharmaceutically acceptable salt thereof,
wherein
B is a moiety might have contribution to enzyme inhibition or efflux pump resistance;

$R_1$-$R_8$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring;

Y is $CH_2$, S, S=O, C=O, CHF, CHCN, $CHN_3$CH—OH, CH—$ONH_2$, or CHOR, where R is $C_1$-$C_8$ alkyl or substituted $C_1$-$C_8$ alkyl.

In some embodiments, B may be CN, CHO, $CH_2OH$, $CH_2F$, $CH_2CN$, $CH_2N_3$, COOH, CO—N(R)OR, CO—N(R)CO—R, CO—CO—NHR, CO—N(R)—$SO_2R$, $(CH_2)_p$COOH, $(CH_2)_p$—CH(OH)—COOH, CO—$(CH_2)_p$—COOH, CH=CH—COOH, CO—CH=CH—COOH, CH=CH—CONHOH, CH=CH—CONH—SO2R, CO—CH=CH—CONHOH, $B(OH)_2$, $(CH_2)_p$—$B(OH)_2$, $PO(OH)_2$, or $(CH_2)_p$—$PO(OH)_2$, —R—COOH, —R—CO—N(R)OR, —R—CO—NHR, —R—CO—N(R)—$SO_2R$, where each occurrence of R is independently selected from H (hydrogen), $C_1$-$C_8$ alkyl, $C_3$-$C_8$ cycloalkyl, substituted $C_1$-$C_8$ alkyl, substituted $C_3$-$C_8$ cycloalkyl, aryl, substituted aryl, heteroaryl, substituted heteroaryl, and $NR^ER^F$, and p is 0, 1, 2, 3, 4, 5, 6, 7, 8, 9, or 10.

In some embodiments, the compound having the structure of Formula I has the structure of Formula Ib:

(Ib)

or a pharmaceutically acceptable salt thereof,
B is a moiety might have contribution to enzyme inhibition or efflux pump resistance;

$R_1$-$R_8$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring;

Z is —F, —SR, —N$_3$, —NRR, —ONHR, —OAc, or —OR, where each R is independently H, C$_1$-C$_8$ alkyl or substituted C$_1$-C$_8$ alkyl.

In some embodiments, B may be CN, CHO, CH$_2$OH, CH$_2$F, CH$_2$CN, CH$_2$N$_3$, COOH, CO—NHOH, CO—CO—NHR, CO—NH—SO$_2$R, (CH$_2$)$_n$COOH, (CH$_2$)$_n$—CH(OH)—COOH, CO—(CH$_2$)$_n$—COOH, CH=CH—COOH, CO—CH=CH—COOH, CH=CH—CONHOH, CO—CH=CH—CONHOH, B(OH)$_2$, (CH$_2$)$_n$—B(OH)$_2$, PO(OH)$_2$, or (CH$_2$)$_n$—PO(OH)$_2$, where R=C$_1$-C$_8$ alkyl or substituted C$_1$-C$_8$ alkyl, and n is 0, 1, 2, 3, 4, 5, 6, 7, 8, 9, or 10.

Some embodiments provide a compound having the structure of Formula IIa:

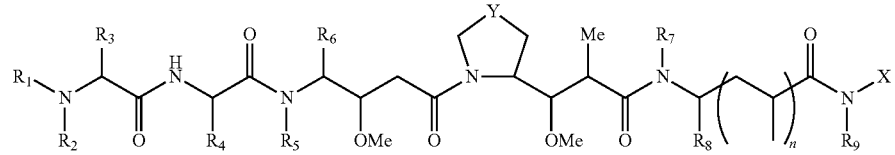

or a pharmaceutically acceptable salt thereof,
wherein X is OR$^{10}$, selected from, but not limited to, a group consisting of at least one hetero atom:

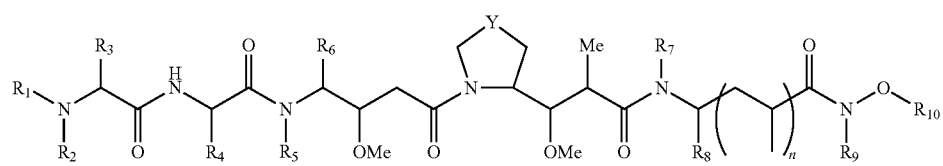

(IIa-1)

wherein, X is SO$_2$R$^{10}$, selected from, but not limited to, a group consisting of at least one hetero atom:

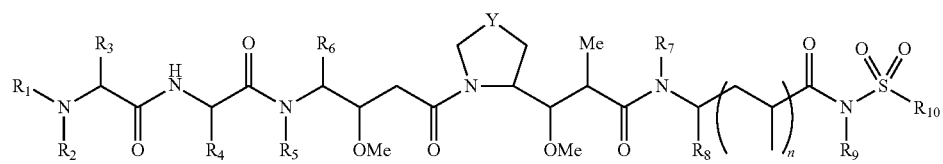

(IIa-2)

R$_1$-R$_{10}$ are each independently selected from the group consisting of H (hydrogen), C$_1$-C$_8$ alkyl, and substituted or cyclic C$_1$-C$_8$ alkyl, or optionally R$_1$ and R$_3$ together with the atoms to which they are attached are a cyclic 5- to 7-membered ring, or optionally and respectively R$_7$, R$_8$ and R$_9$ together with the atoms to which they are attached are a cyclic 5- to 7-membered ring;

X is a group consisting of at least one heteroatom;
Y is CH$_2$, S, S=O, C=O, CHF, CHCN, CHN$_3$CH—OH, CH—ONH$_2$, or CHOR, where R is C$_1$-C$_8$ alkyl or substituted C$_1$-C$_8$ alkyl.

In some embodiments, the dual active compound having the structure of Formula I has the structure of Formula IIb:

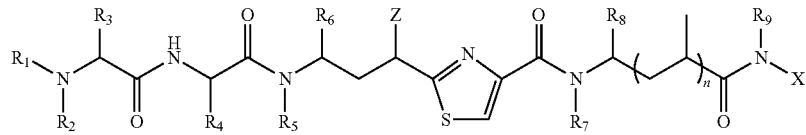

or a pharmaceutically acceptable salt thereof, wherein, n is 0 or 1; X is $OR^{10}$, selected from, but not limited to, a group consisting of at least one hetero atom:

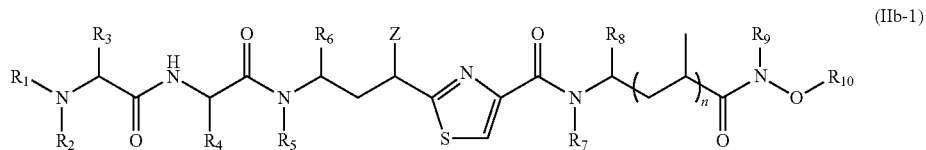
(IIb-1)

wherein, n is 0 or 1; X is $SO_2R^{10}$, selected from, but not limited to, a group consisting of at least one hetero atom:

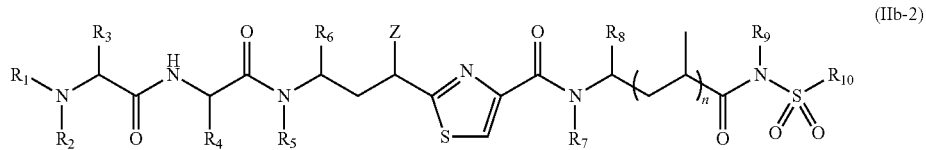
(IIb-2)

$R_1$-$R_{10}$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally and respectively $R_7$, $R_8$ and $R_9$ together with the atoms to which they are attached are a cyclic 5- to 7-membered ring;

X is a group of at least one heteroatom;

Z is —F, —SR, —$N_3$, —NRR, —ONHR, —OAc, or —OR, where each R is independently H, $C_1$-$C_8$ alkyl or substituted $C_1$-$C_8$ alkyl.

Also provided herein are the compounds described above conjugated to a targeting moiety with a linker. Also provided herein are the compounds described above with a linker.

Some embodiments provide a compound having the structure of Formula IV:

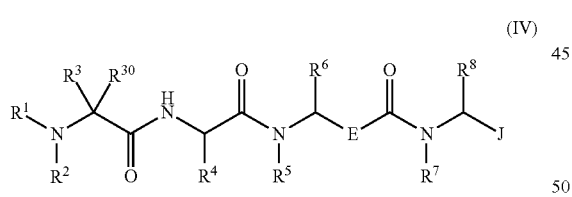
(IV)

or a pharmaceutically acceptable salt thereof, wherein:

$R^1$-$R^8$ are each independently selected from the group consisting of H (hydrogen), optionally substituted $C_1$-$C_8$ alkyl, optionally substituted $C_1$-$C_8$ alkoxy, optionally substituted $C_3$-$C_8$ cycloalkyl, optionally substituted aryl, and optionally substituted heteroaryl, or optionally $R^1$ and $R^2$ together with the nitrogen to which they are attached are an optionally substituted cyclic 5- to 7-membered ring, or optionally $R^1$ and $R^3$ together with the atoms to which they are attached are an optionally substituted cyclic 5- to 7-membered ring, or optionally $R^7$ and $R^8$ together with the atoms to which they are attached are an optionally substituted cyclic 5- to 7-membered ring, or optionally $R^1$ is $R^{1A}$ or $R^{1B}$;

$R^{1A}$ comprises a targeting moiety;
$R^{1B}$ is -$L^1(CH_2)_nR^C$, -$L^1O(CH_2)_nR^C$ or —$(CH_2)_nR^C$;

$R^C$ is $C_1$-$C_8$ alkyl, $C_3$-$C_8$ cycloalkyl, aryl, heteroaryl, and heterocyclyl, each optionally substituted with one or more $R^D$, or optionally $R^C$ comprises a targeting moiety;

each $R^D$ is independently selected from the group consisting of —OH, —$N_3$, halo, cyano, nitro, —$(CH_2)_n$$NR^ER^F$, —$(CH_2)_nC(=O)NR^ER^F$, —$O(CH_2)NR^ER^F$, —$O(CH_2)_nC(=O)NR^ER^F$, —$O(CH_2)_mOC(=O)NR^ER^F$, —$NR^GC(=O)R^H$, —$NR^GS(O)_zR^H$, —$O(CH_2)_mO(CH_2)_mR^J$, —$O(CH_2)_nC(=O)R^J$, —$O(CH_2)_nR^J$, optionally substituted $C_1$-$C_8$ alkyl, optionally substituted $C_3$-$C_8$ cycloalkyl, optionally substituted aryl, optionally substituted heteroaryl, optionally substituted heterocyclyl, and optionally substituted —O—($C_1$-$C_8$ alkyl);

each $NR^ER^F$ is independently selected, wherein $R^E$ and $R^F$ are each independently selected from hydrogen, -[($L^1)_s(C(R^{2A})_2)_r(NR^{2A})_s(C(R^{2A})_2)_r]$-$[L^1(C(R^{2A})_2)_r(NR^{2A})_s(C(R^{2A})_2)_r]_s$-$(L^1)_s$-$R^J$, -$[(L^1)_s(C(R^{2A})_2)_r(NR^{2A})_s(C(R^{2A})_2)_r]$-$(L^1)_s[(C(R^{2A})_2)_rO(C(R^{2A})_2)_r(L^2)_s]_s$-$(L^1)_s$-$R^J$, optionally substituted $C_{1-8}$ alkyl, optionally substituted $C_{3-8}$ cycloalkyl, optionally substituted aryl, optionally substituted heteroaryl, and optionally substituted heterocyclyl;

each $R^G$ is independently hydrogen, optionally substituted $C_1$-$C_8$ alkyl, optionally substituted $C_3$-$C_8$ cycloalkyl, optionally substituted aryl, optionally substituted heteroaryl, or optionally substituted heterocyclyl;

each $R^H$ is independently hydrogen, optionally substituted $C_1$-$C_8$ alkyl, optionally substituted $C_3$-$C_8$ cycloalkyl, optionally substituted aryl, optionally substituted heteroaryl, optionally substituted heterocyclyl, or —$NR^ER^F$;

each $R^J$ is independently selected from the group consisting of hydrogen, optionally substituted $C_1$-$C_8$ alkyl, optionally substituted —O—($C_1$-$C_8$ alkyl), optionally substituted $C_3$-$C_8$ cycloalkyl, optionally substituted aryl, optionally substituted heteroaryl, optionally substituted heterocyclyl, —$(CH_2)_nOR^{2B}$, —$O(CH_2)_nOR^{2B}$, —$(CH_2)_nNR^{2B}R^{2B}$, —$C(R^{2A})_2NR^{2B}R^{2B}$, —$(CH_2)_nC(=O)OR^{2B}$, and —$C(=O)NHR^{2B}$;

each $R^{2A}$ is independently selected, wherein $R^{2A}$ is selected from the group consisting of hydrogen, halo, —OH, optionally substituted $C_1$-$C_8$ alkyl, optionally substituted —O—($C_1$-$C_8$ alkyl), optionally substituted $C_3$-$C_8$ cycloalkyl, optionally substituted aryl, optionally substituted heteroaryl, optionally substituted heterocyclyl, —$(CH_2)_nOR^{2B}$, —$(CH_2)_nNR^{2C}R^{2C}$, —$C(=O)OR^{2B}$, —$C(=O)NR^{2C}R^{2C}$, or optionally two geminal $R^{2A}$ and the carbon to which they are attached are together an optionally substituted three- to six-membered carbocyclic ring;

each $R^{2B}$ is independently selected from the group consisting of hydrogen, —OH, —$(CH_2)_nC(=O)OH$, —$C(=O)(C(R^{2D})_2)_nL^3R^{2E}$, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl;

each $NR^{2C}R^{2C}$ is independently selected, wherein each $R^{2C}$ is independently selected from the group consisting of hydrogen, —OH, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl, or optionally both $R^{2C}$ together with the nitrogen to which they are attached are an optionally substituted heterocyclyl;

each $R^{2D}$ is independently selected from the group consisting of hydrogen, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl;

each $R^{2E}$ is independently selected from the group consisting of optionally substituted $C_1$-$C_8$ alkyl, optionally substituted $C_3$-$C_8$ cycloalkyl, optionally substituted aryl, optionally substituted heteroaryl, and optionally substituted heterocyclyl, and —$(CH_2)_nC(=O)OR^{2F}$;

each $R^{2F}$ is independently selected from the group consisting hydrogen, optionally substituted $C_1$-$C_8$ alkyl, optionally substituted $C_3$-$C_8$ cycloalkyl, optionally substituted aryl, optionally substituted heteroaryl, and optionally substituted heterocyclyl;

each $L^1$ is independently selected from the group consisting of —C(=O)—, —S(=O)—, —C(=S)—, —S(=O)$_2$—, —C(=O)O—, —C(=O)$NR^{2A}$—, —S(=O)$NR^{2A}$—, —S(=O)$_2NR^{2A}$—, —C(=O) $NR^{2A}C(=O)$—, and —$C(CF_3)_2NR^{2A}$—;

each $L^2$ is independently selected from the group consisting of optionally substituted aryl, optionally substituted heteroaryl, and optionally substituted heterocyclyl;

each $L^3$ is independently selected from the group consisting of —C(=O)—, —S(=O)—, —C(=S)—, —S(=O)$_2$—, —C(=O)O—, —C(=O)$NR^{2A}$—, —S(=O)$NR^{2A}$—, —S(=O)$_2NR^{2A}$—, —C(=O) $NR^{2A}C(=O)$—, and —$C(CF_3)_2NR^{2A}$—;

each m independently is 1 or 2;
each n independently is 0, 1, 2, 3, 4, 5, or 6;
each r independently is 0, 1, 2, 3, 4, 5, or 6;
each s independently is 0 or 1; and
each z independently is 1 or 2

$R^7$ is selected from the group consisting of H (hydrogen), optionally substituted $C_1$-$C_8$ alkyl, optionally substituted $C_3$-$C_8$ cycloalkyl, optionally substituted aryl, and optionally substituted heterocyclyl;

$R^8$ is selected from the group consisting of H (hydrogen), —$(CH_2)_nR^C$, optionally substituted $C_1$-$C_8$ alkyl, optionally substituted $C_3$-$C_8$ cycloalkyl, optionally substituted aryl, and optionally substituted heteroaryl;

E is selected from the group consisting of:

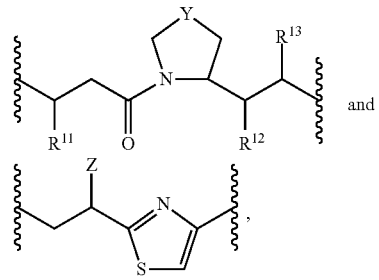

where Y is $CH_2$, S, S=O, C=O, CHF, CHCN, $CHN_3$CH—OH, CH—$ONH_2$, or $CHOR^{14}$, where $R^{14}$ is optionally substituted $C_1$-$C_8$ alkyl, and Z is —F, —$SR^{14}$, —$N_3$, —$NR^{14}R^{14}$, —$ONHR^{14}$, —OAc, or —$OR^{14}$, where each $R^{14}$ is independently H (hydrogen), $C_1$-$C_8$ alkyl substituted $C_1$-$C_8$ alkyl, or $NR^ER^F$;

$R^{11}$-$R^{13}$ are each independently selected from the group consisting of H (hydrogen), optionally substituted $C_1$-$C_8$ alkyl, optionally substituted $C_1$-$C_8$ alkoxy, optionally substituted $C_3$-$C_8$ cycloalkyl, optionally substituted aryl, and optionally substituted heteroaryl; and J is selected from: CN, CHO, $CH_2OH$, $CH_2F$, $CH_2CN$, $CH_2N_3$, COOH, CO—$N(R^{15})OR^{15}$, CO—$N(R^{15})$ CO—$R^{15}$, CO—CO—$NHR^{15}$, CO—$N(R^{15})$—$SO_2R^{15}$, $(CH_2)_pCOOH$, $(CH_2)_p$—CH(OH)—COOH, CO—$(CH_2)_p$—COOH, CH=CH—COOH, CO—CH=CH—COOH, CH=CH—CONHOH, CH=CH—CONH—SO2R, CO—CH=CH—CONHOH, $B(OH)_2$, $(CH_2)_p$—$B(OH)_2$, $PO(OH)_2$, or $(CH_2)_p$—$PO(OH)_2$, —$R^{15}$—COOH, —CO—$N(R^{15})OR^{15}$, —CO—$N(R^{15})OR^{15}$, —$R^{15}$—CO—$N(R^{15})OR^{15}$, —$R^{15}$—CO—$NHR^{15}$, —$R^{15}$—CO—$N(R^{15})$—$SO_2R^{15}$, where each occurrence of $R^{15}$ is independently selected from H (hydrogen), $C_1$-$C_8$ alkyl, $C_3$-$C_8$ cycloalkyl, substituted $C_1$-$C_8$ alkyl, substituted $C_3$-$C_8$ cycloalkyl, aryl, substituted aryl, heteroaryl, substituted heteroaryl and $NR^ER^F$, and p is 0, 1, 2, 3, 4, 5, 6, 7, 8, 9, or 10.

BRIEF DESCRIPTION OF THE DRAWINGS

FIG. 1 shows a comparison of compound 13 tested for internal concentrations in SKBR3, HCC1954, MCF7, and MDA-MB-468 cell lines.

FIG. 2 shows a comparison of compound 53 tested for internal concentrations in SKBR3, HCC1954, MCF7, and MDA-MB-468 cell lines.

FIG. 3 shows a comparison of compound 56 tested for internal concentrations in SKBR3, HCC1954, MCF7, and MDA-MB-468 cell lines.

FIG. 4 shows a comparison of compound 57 tested for internal concentrations in SKBR3, HCC1954, MCF7, and MDA-MB-468 cell lines.

FIG. 5 shows a comparison of compound 58 tested for internal concentration in SKBR3 cell line.

FIG. 6 shows a comparison of compound 84 tested for internal concentration in SKBR3 cell line.

FIG. 7 shows a comparison of compound 88 tested for internal concentration in SKBR3 cell line.

FIG. 8 shows a comparison of compound 92 tested for internal concentration in SKBR3 cell line.

FIG. 9 shows a comparison of compound 93 tested for internal concentration in SKBR3 cell line.

FIG. 10 shows a comparison of compound 98 tested for internal concentration in SKBR3 cell line.

DETAILED DESCRIPTION

Figure 1:
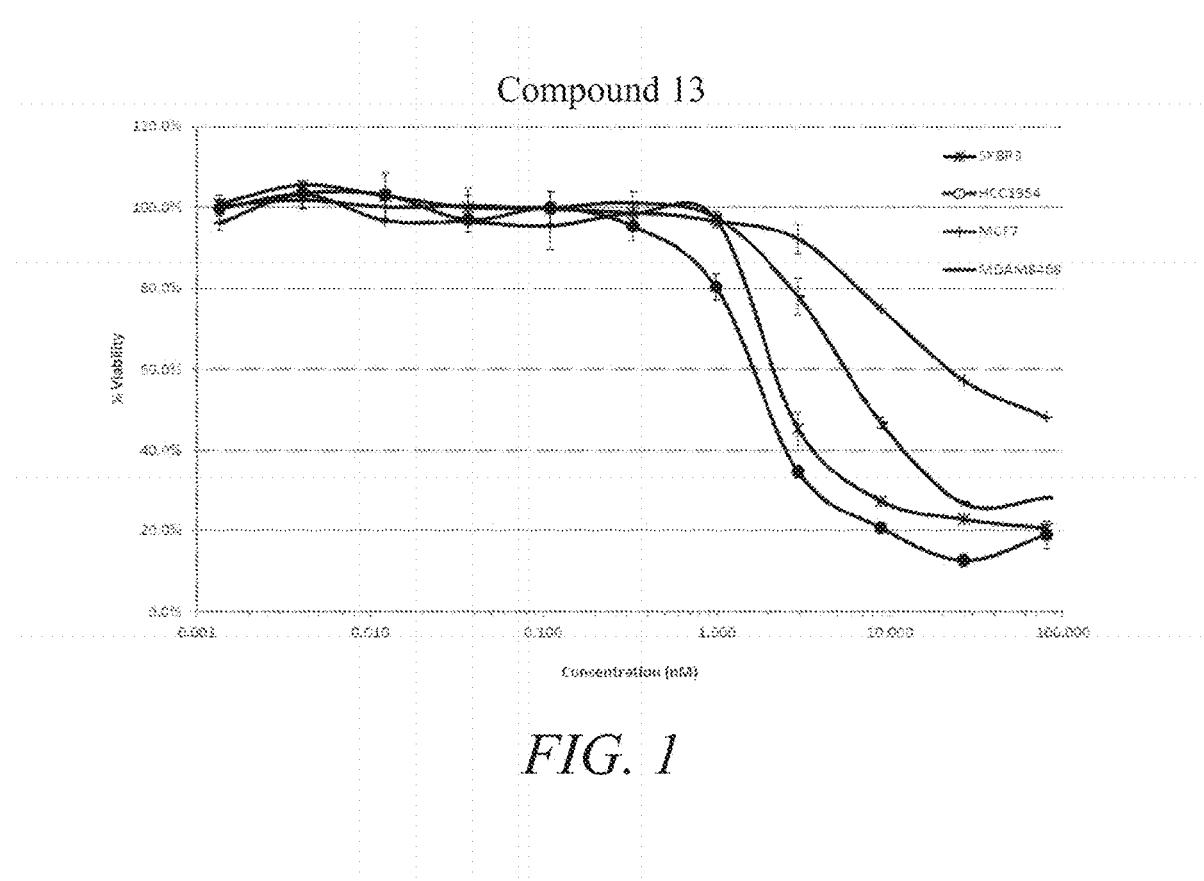
FIGS. 1-10 shows the cytotoxic effects of compounds or antibody drug conjugates (ADCs) on various cell types. The antibody used in the antibody drug conjugates is Trastuzumab.

Some embodiments provide a compound.

In some embodiments, the compound includes a linker.

In some embodiments, the compound includes a cytotoxic agent.

In some embodiments, the compound includes a functional group that has tubulin-binding properties or tubulin inhibitory properties.

In some embodiments, the compound includes a functional group that has protease inhibitory or efflux pump resistant properties. For example, the functional group may have proteasome inhibitory properties.

Definitions

As used herein, common organic abbreviations are defined as follows:
Ac Acetyl
aq. Aqueous
BOC or Boc tert-Butoxycarbonyl
BrOP bromo tris(dimethylamino)phosphonium hexafluorophosphate
Bu n-Butyl
° C. Temperature in degrees Centigrade
DCM methylene chloride
DEPC Diethylcyanophosphonate
DIC diisopropylcarbodiimide
DIEA Diisopropylethylamine
DMF N,N'-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOAt 1-Hydroxy-7-azabenzotriazole
HOBT N-Hydroxybenzotriazole
HOSu N-Hydroxysuccinimide
HPLC High-performance liquid chromatography
LC/MS Liquid chromatography-mass spectrometry
Me Methyl
MeOH Methanol
MeCN Acetonitrile
mL Milliliter(s)
MS mass spectrometry
RP-HPLC reverse phase HPLC
rt room temperature
t-Bu tert-Butyl
TEA Triethylamine
Tert, t tertiary
TFA Trifluoracetic acid
THF Tetrahydrofuran
THP Tetrahydropyranyl
TLC Thin-layer chromatography
μL Microliter(s)

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-prop en-1-yl, 2-methyl-prop en-1-yl, 1-ethyl-ethen-1-yl, 2-methyl-prop en-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidonyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "urea" group refers to a "—N(R$_A$)C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

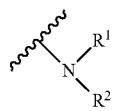

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

where ring E is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

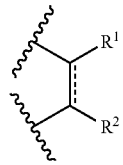

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

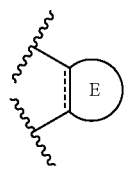

where E is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

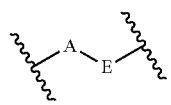

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

Compounds

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element present in a compound either specifically or generically described herein may include any isotope of said element. For example, in a compound specifically or generically described herein a hydrogen atom may be explicitly disclosed or understood to be present in the compound and each such hydrogen atom is any isotope of hydrogen, including but not limited to hydrogen-1 (protium) and hydrogen-2 (deuterium). Thus, reference herein to a compound encompasses all potential isotopic forms unless the context clearly dictates otherwise.

Utilities and Applications

Some embodiments provide a method of treating a patient in need thereof comprising administering a compound as disclosed and described herein to said patient. In some embodiments, the patient may have cancer, an infection, or an immune system disease. In some embodiments, the compound may have anti-tumor, antibiotic, or anti-inflammatory activity.

Structures

Some embodiments provide a compound having the structure

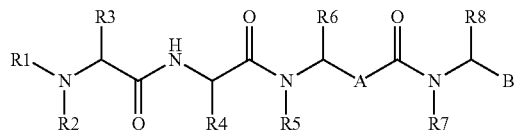

or a pharmaceutically acceptable salt thereof, wherein: A is a tubulin binding moiety; B is a group might have protease inhibitory or efflux pump resistant properties; and $R_1$-$R_8$ are each independently selected from the group consisting of H (hydrogen), $C_1$-$C_8$ alkyl, substituted or cyclic $C_1$-$C_8$ alkyl, aryl, and substituted aryl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring. In some embodiments, the compound may be used alone as API (active pharmaceutical ingredient) or in a prodrug form. In some embodiments, the compound may be included in a conjugate including a linker and another component. In some embodiments, the compound may be included in a conjugate including a linker and a targeting moiety, such as antibody, Fab, peptide, protein ligand, and the like. In some embodiments, the compound may be included in a conjugate including a linker and a carrier molecule, such as HSA, lipid, polymers, nanoparticles, and the like. In some embodiments, the compound may be included in a conjugate including a linker and a small molecule drug/ligand, such as folic acid.

As used herein, the term "tubulin binding moiety" refers to a structural component of a compound that inhibits tubulin polymerization under a certain set of conditions. In some embodiments, the compound may inhibit tubulin polymerization under in vivo or in vitro conditions. For example, the compound may inhibit tubulin polymerization in PBS. Examples of compounds that inhibit tubulin polymerization are described in Peltier, et al., "The Total Synthesis of Tubulysin D," *J. Am. Chem. Soc.*, 2006, 128 (50): 16018-16019, and U.S. Publication No.: 2005/0239713 the disclosures of which are incorporated herein by reference in their entirety.

As used herein, the term "functional moiety" refers to a structural component of a compound that interacts with a biological moiety or fragment of the biological moiety under a certain set of conditions. In some embodiments, the functional moiety may interact with a biological moiety or fragment of the biological moiety under in vivo or in vitro conditions. For example, the functional moiety may interact with a biological moiety or fragment of the biological moiety in PBS. In some embodiments, the functional moiety may afford a desirable effect in a compound comparison to a compound that does not include the functional moiety. In some embodiments, the functional moiety may contribute to enzyme inhibition or efflux pump resistance in a compound.

In some embodiments, the cytotoxic compound having the structure of Formula Ia:

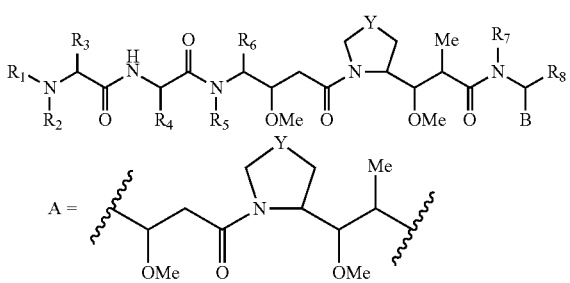

or a pharmaceutically acceptable salt thereof,
wherein,

B is a moiety might have contribution to enzyme inhibition or efflux pump resistance;

$R_1$-$R_8$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring;

Y is $CH_2$, S, S=O, C=O, CHF, CHCN, $CHN_3$CH—OH, CH—$ONH_2$, or CHOR, where R is $C_1$-$C_8$ alkyl or substituted $C_1$-$C_8$ alkyl.

In some embodiments, B may be CN, CHO, $CH_2OH$, $CH_2F$, $CH_2CN$, $CH_2N_3$, COOH, CO—NHOH, CO—CO—NHR, CO—NH—$SO_2R$, $(CH_2)_n$COOH, $(CH_2)_n$—CH(OH)—COOH, CO—$(CH_2)_n$—COOH, CH=CH—COOH, CO—CH=CH—COOH, CH=CH—CONHOH, CO—CH=CH—CONHOH, $B(OH)_2$, $(CH_2)_n$—$B(OH)_2$, $PO(OH)_2$, or $(CH_2)_n$—$PO(OH)_2$, where R is $C_1$-$C_8$ alkyl or substituted $C_1$-$C_8$ alkyl, and n is 0, 1, 2, 3, 4, 5, 6, 7, 8, 9, or 10.

In some embodiments, the dual active compound having the structure of Formula I has the structure of Formula Ib:

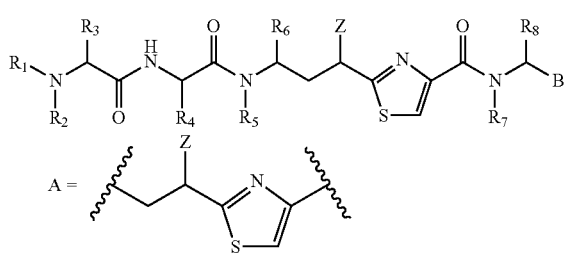

or a pharmaceutically acceptable salt thereof,

B is a moiety might have contribution to enzyme inhibition or efflux pump resistance;

$R_1$-$R_8$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring;

Z is —F, —SR, —$N_3$, —NRR, —ONHR, —OAc, or —OR, where each R is independently H, $C_1$-$C_8$ alkyl or substituted $C_1$-$C_8$ alkyl In some embodiments, B may be CN, CHO, $CH_2OH$, $CH_2F$, $CH_2CN$, $CH_2N_3$, COOH, CO—NHOH, CO—CO—NHR, CO—NH—$SO_2R$, $(CH_2)_n$COOH, $(CH_2)_n$—CH(OH)—COOH, CO—$(CH_2)_n$—COOH, CH=CH—COOH, CO—CH=CH—COOH, CH=CH—CONHOH, CO—CH=CH—CONHOH, $B(OH)_2$, $(CH_2)_n$—$B(OH)_2$, $PO(OH)_2$, or $(CH_2)_n$—$PO(OH)_2$, where R=$C_1$-$C_8$ alkyl or substituted $C_1$-$C_8$ alkyl, and n is 0, 1, 2, 3, 4, 5, 6, 7, 8, 9, or 10.

Some embodiments provide a compound having the structure of Formula IIa:

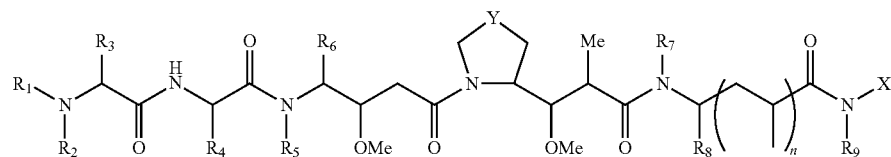

or a pharmaceutically acceptable salt thereof,
wherein X is $OR^{10}$, selected from, but not limited to, a group consisting of at least one hetero atom:

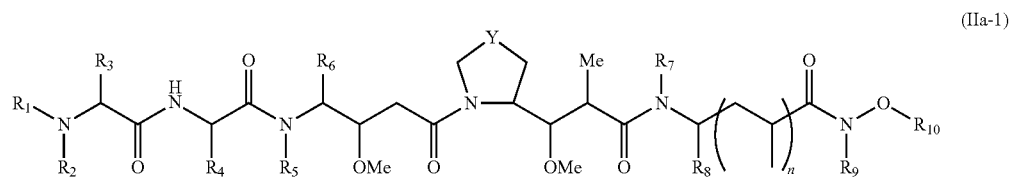

(IIa-1)

wherein, X is $SO_2R^{10}$, selected from, but not limited to, a group consisting of at least one hetero atom:

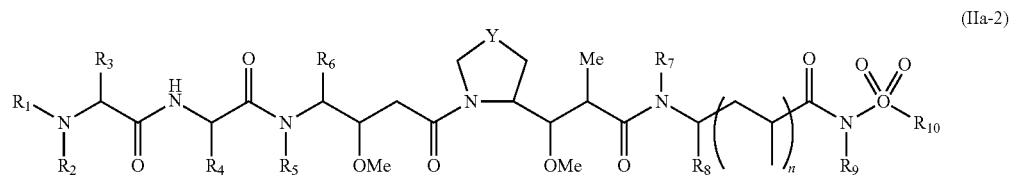

(IIa-2)

$R_1$-$R_{10}$ are each independently selected from the group consisting of H (hydrogen), $C_1$-$C_8$ alkyl, and substituted or cyclic $C_1$-$C_8$ alkyl, or optionally $R_1$ and $R_3$ together with the atoms to which they are attached are a cyclic 5- to 7-membered ring, or optionally and respectively $R_7$, $R_8$ and $R_9$ together with the atoms to which they are attached are a cyclic 5- to 7-membered ring;

X is a group consisting of at least one heteroatom;

Y is $CH_2$, S, S=O, C=O, CHF, CHCN, $CHN_3$CH—OH, CH—$ONH_2$, or CHOR, where R is $C_1$-$C_8$ alkyl or substituted $C_1$-$C_8$ alkyl.

In some embodiments, the dual active compound having the structure of Formula I has the structure of Formula IIb:

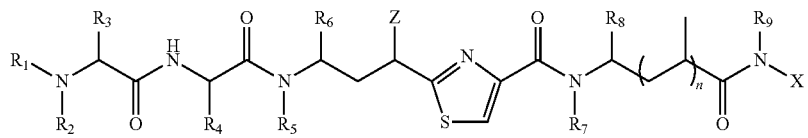

or a pharmaceutically acceptable salt thereof, wherein, n is 0 or 1; X is $OR^{10}$, selected from, but not limited to, a group consisting of at least one hetero atom:

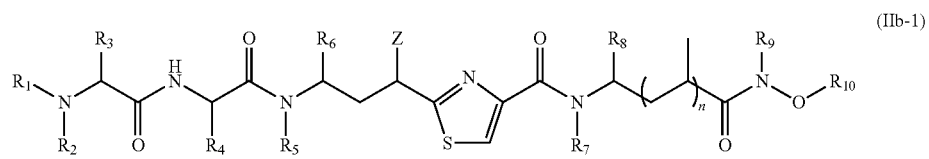

(IIb-1)

wherein, n is 0 or 1; X is $SO_2R^{10}$, selected from, but not limited to, a group consisting of at least one hetero atom:

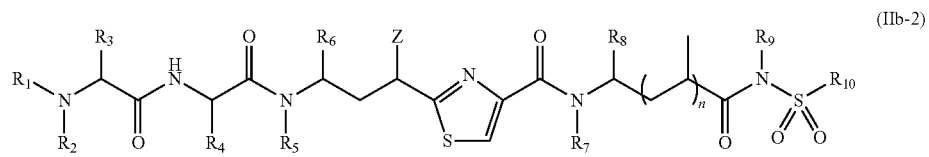

(IIb-2)

$R_1$-$R_{10}$ are each independently selected from the group consisting of H (hydrogen), $C_1$-$C_8$ alkyl, and substituted or cyclic $C_1$-$C_8$ alkyl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally and respectively $R_7$, $R_8$ and $R_9$ together with the atoms to which they are attached are a cyclic 5- to 7-membered ring;

X is a group of at least one heteroatom;

Z is —F, —SR, —$N_3$, —NRR, —ONHR, —OAc, or —OR, where each R is independently H, $C_1$-$C_8$ alkyl or substituted $C_1$-$C_8$ alkyl Examples of compounds having the structure of Formula Ia include but not limited to the following:

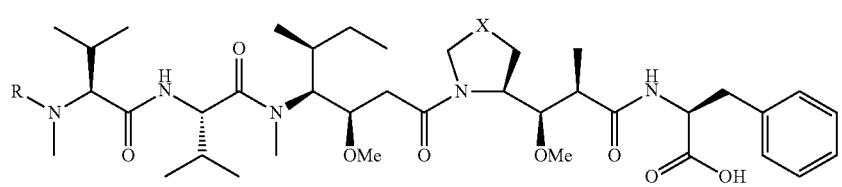

1a-k

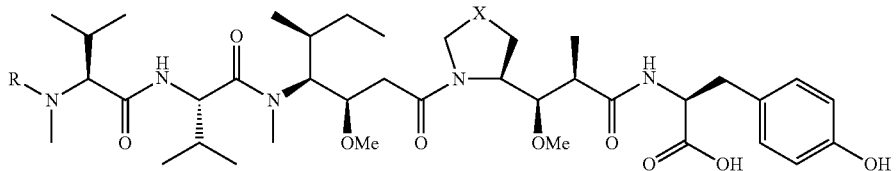
2a-k
Examples of compounds having the structure of Formula Ia include the following:
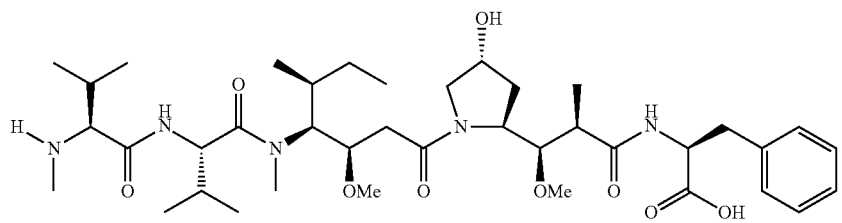
1a
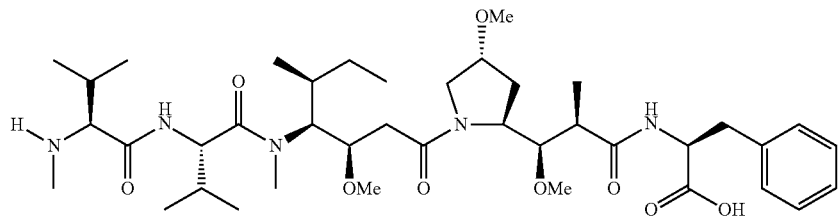
1b
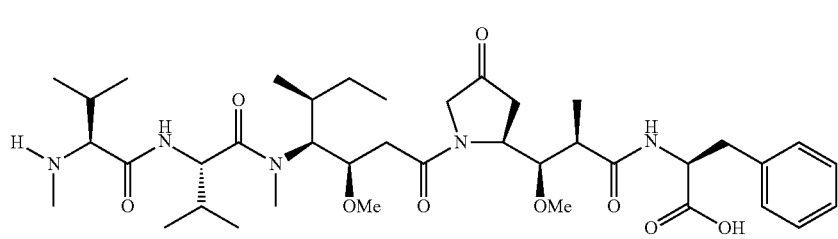
1c
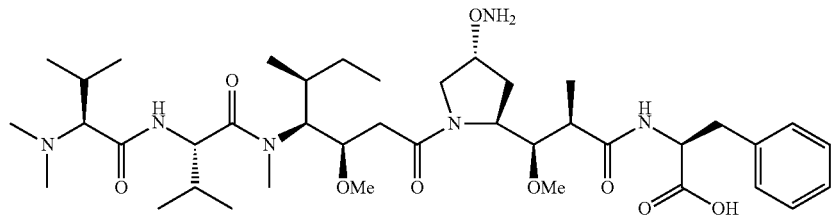
1d
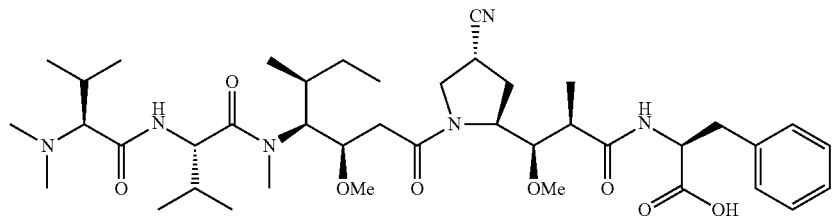
1e

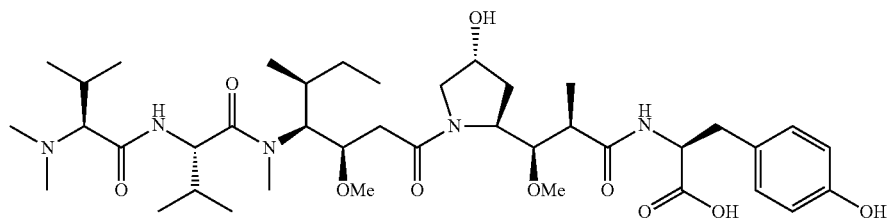
2a
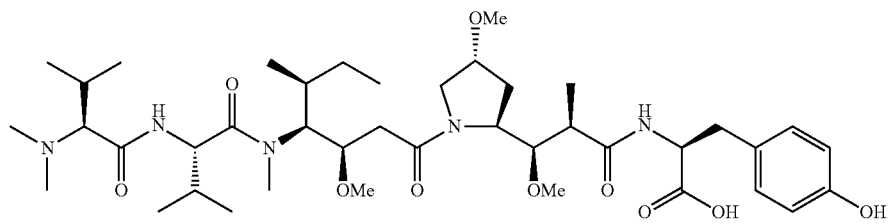
2b
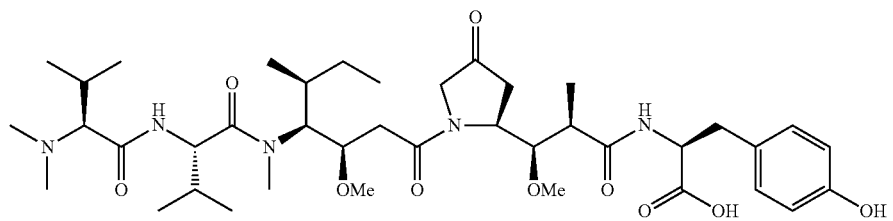
2c
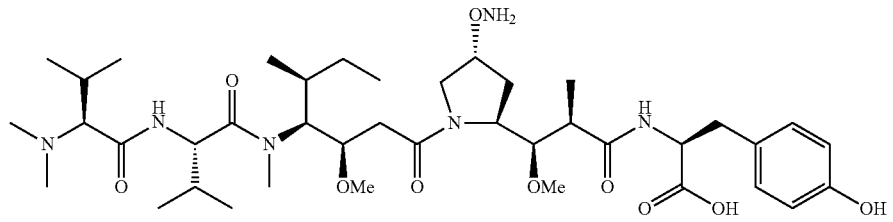
2d
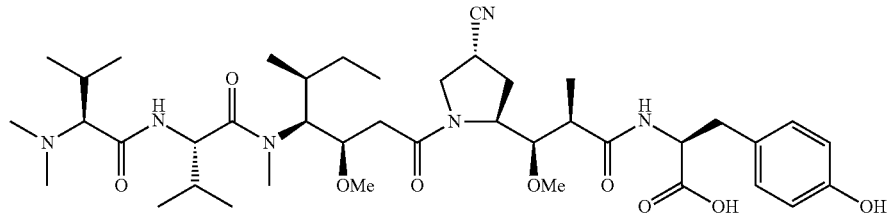
2e
Examples of general compounds having the structure of Formula Ia include the following:
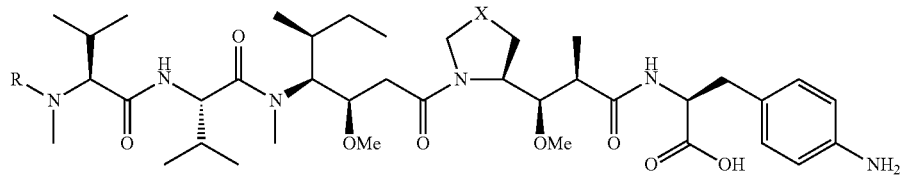
3a-k

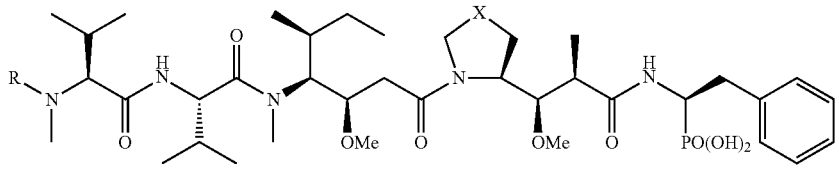
4a-k
Examples of compounds having the structure of Formula Ia include the following:
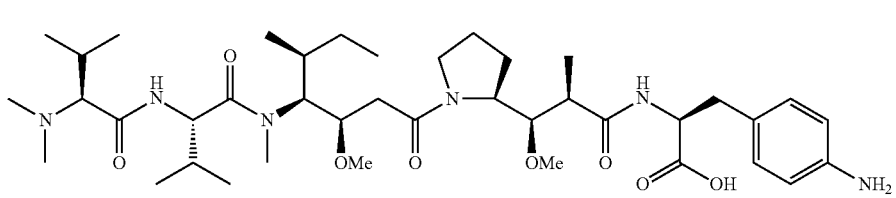
3a
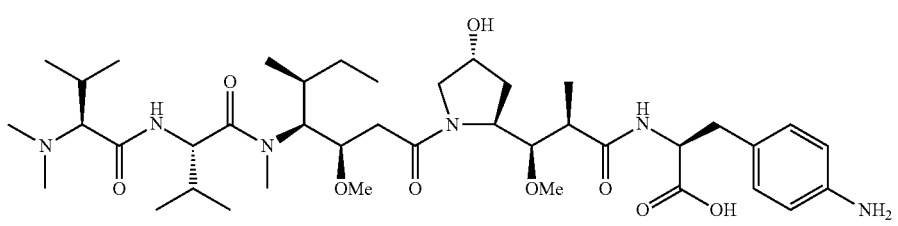
3b
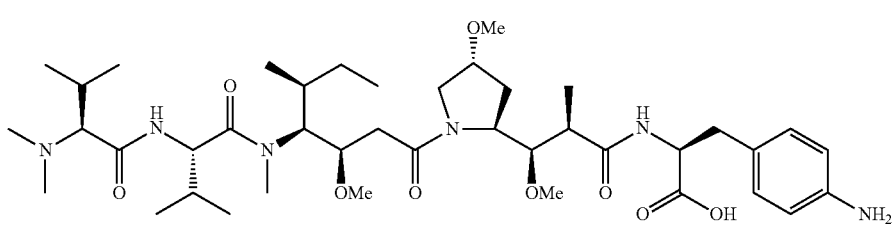
3c
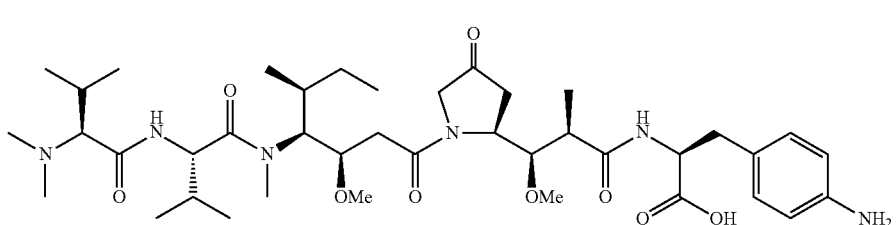
3d
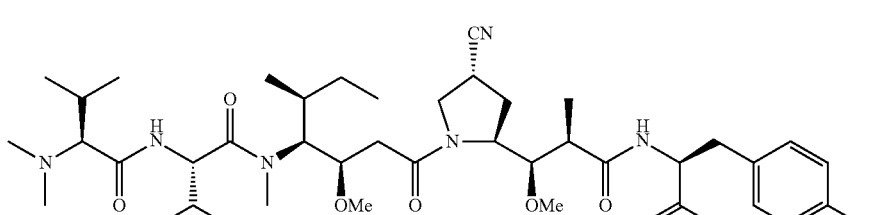
3e
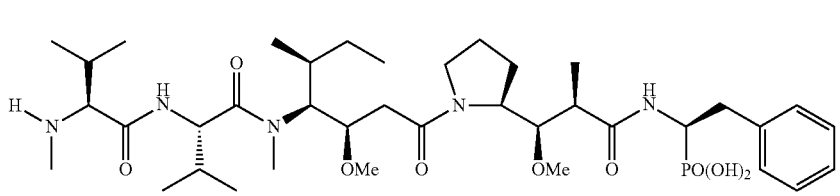
4a

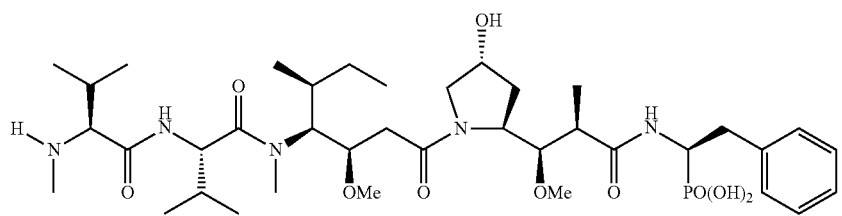
4b
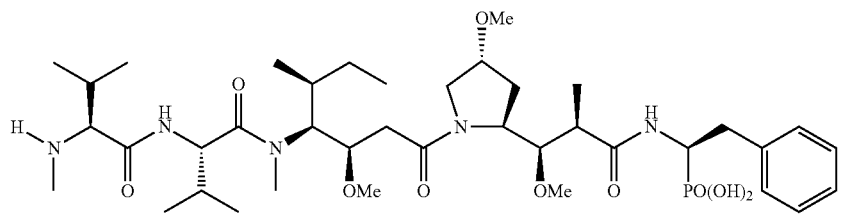
4c
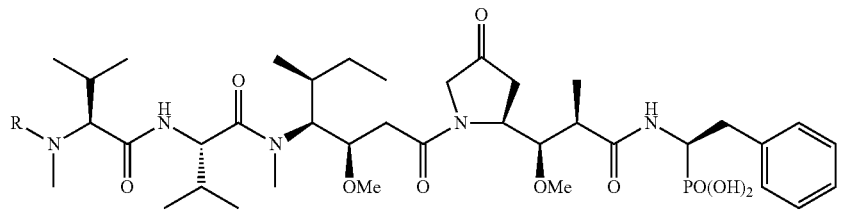
4d
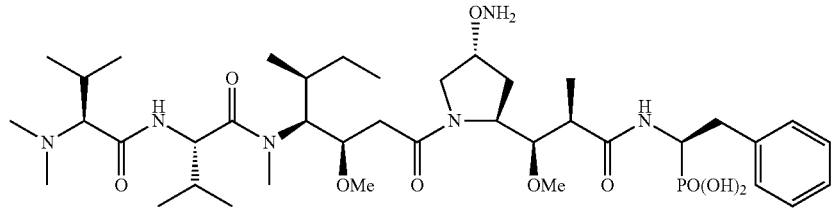
4e
Examples of general compounds having the structure of Formula Ia include the following:
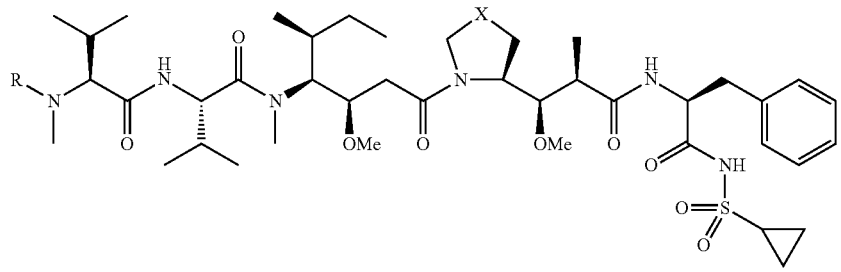
5a-k
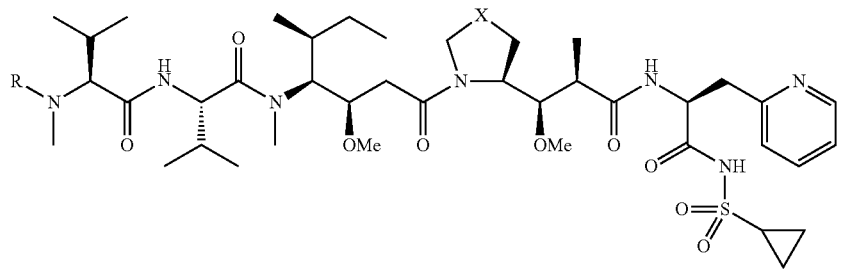
6a-k Examples of compounds having the structure of Formula Ia include the following:
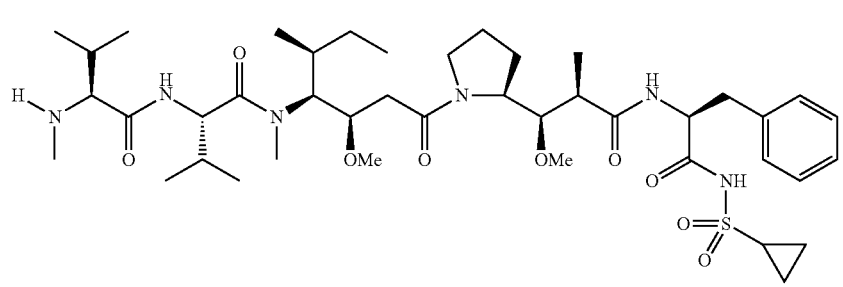
5a
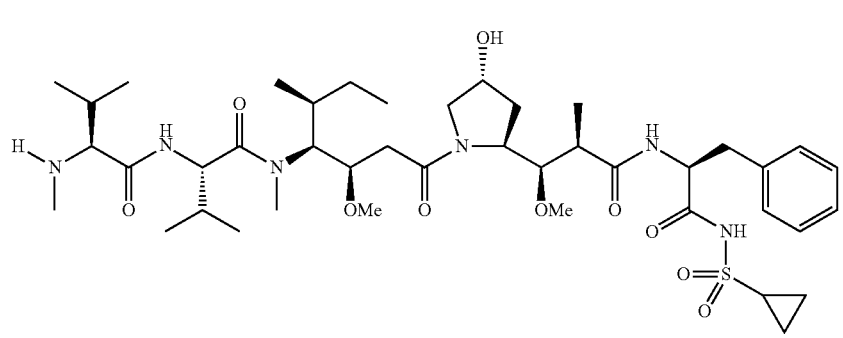
5b
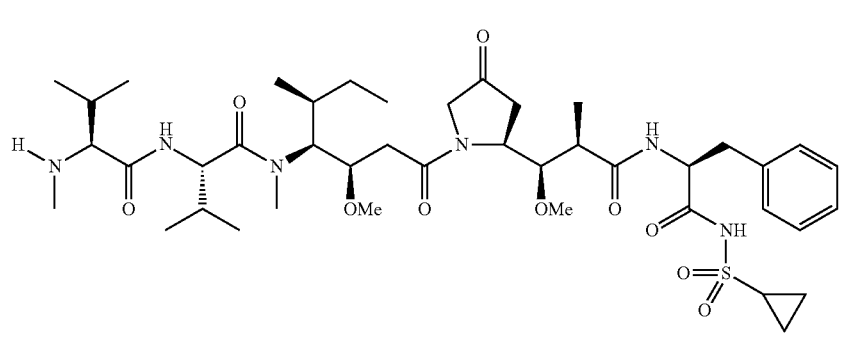
5c
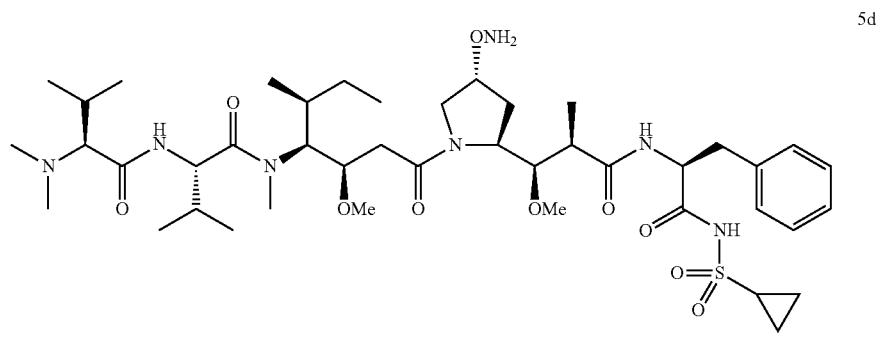
5d
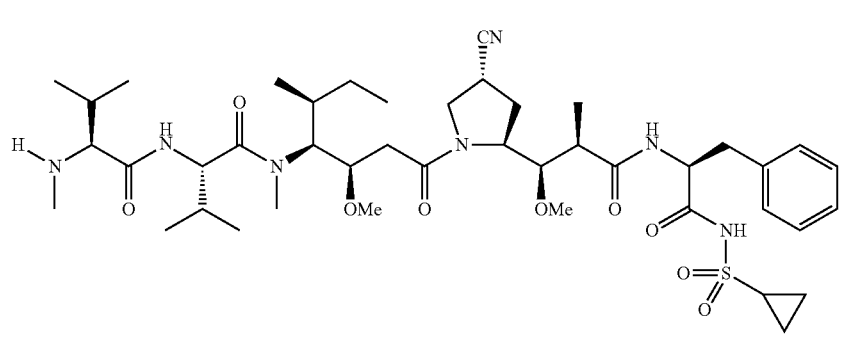
5e

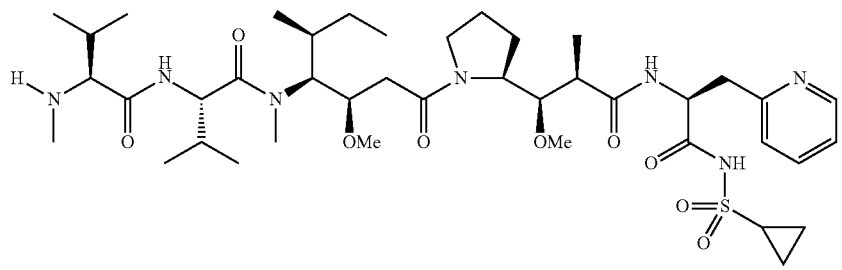
6a
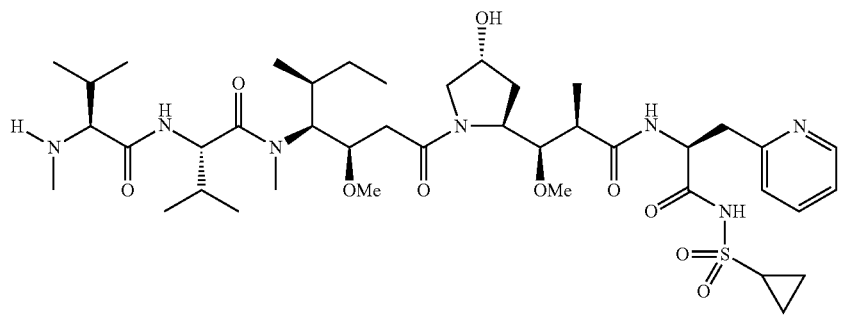
6b
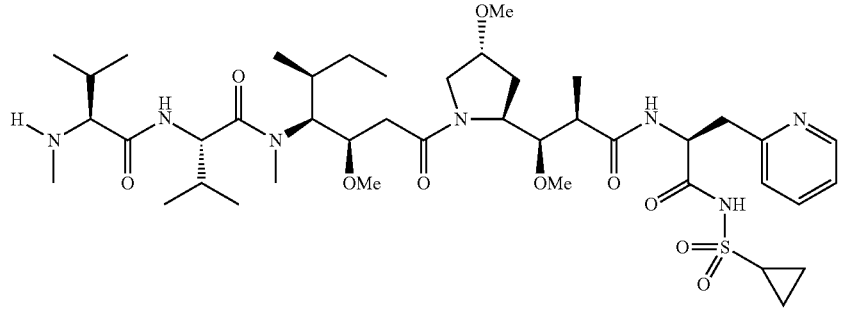
6c
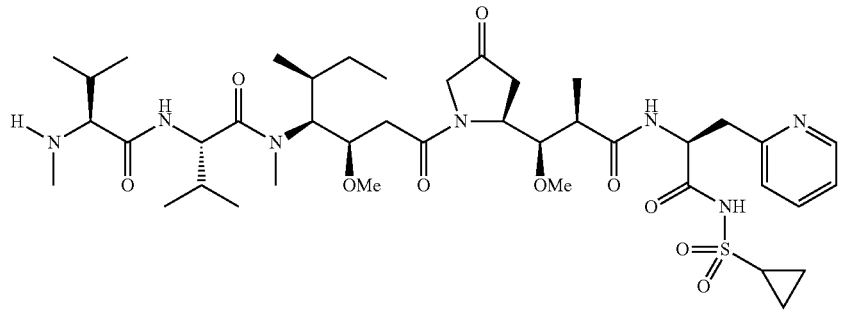
6d
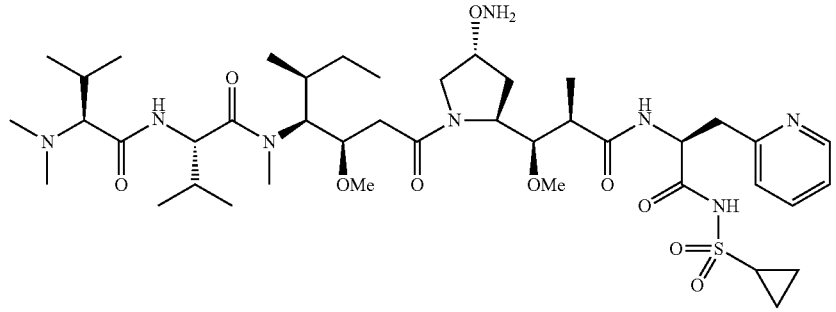
6e

Examples of general compounds having the structure of Formula Ia include the following:
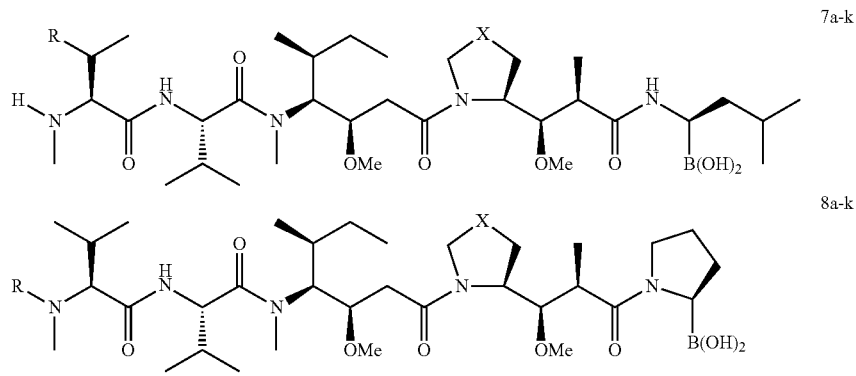
7a-k
8a-k
Examples of compounds having the structure of Formula Ia include the following:
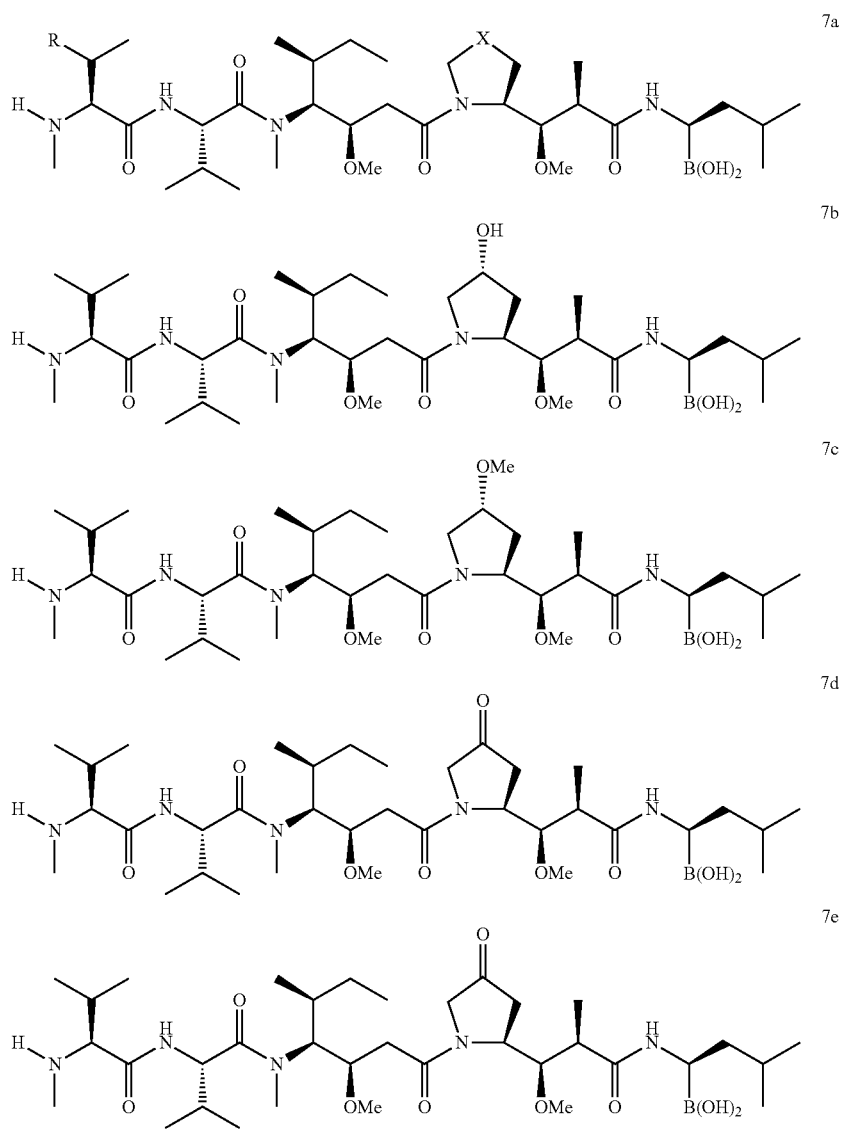
7a
7b
7c
7d
7e

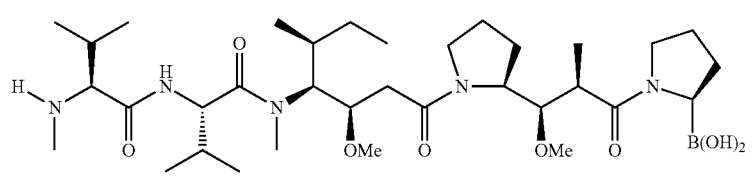
8a
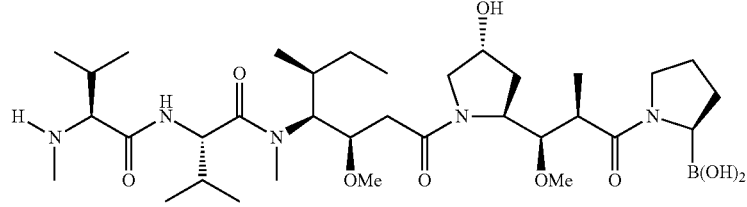
8b
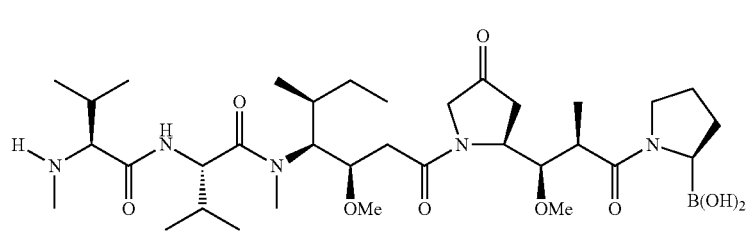
8c
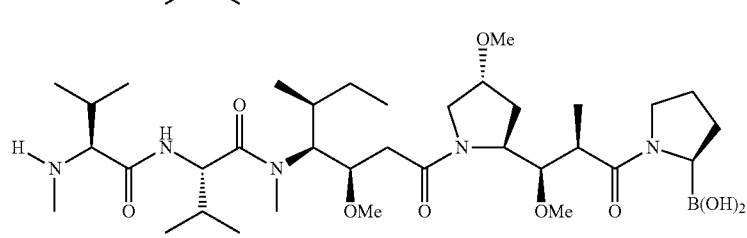
8d
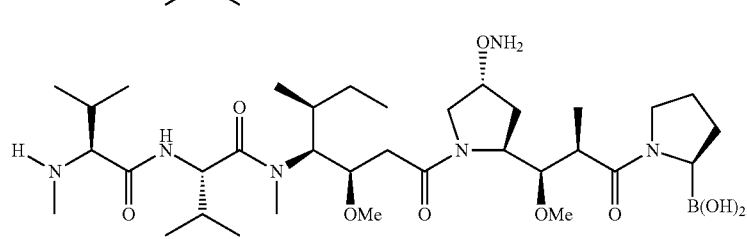
8e
Examples of general compounds having the structure of Formula Ia include the following:
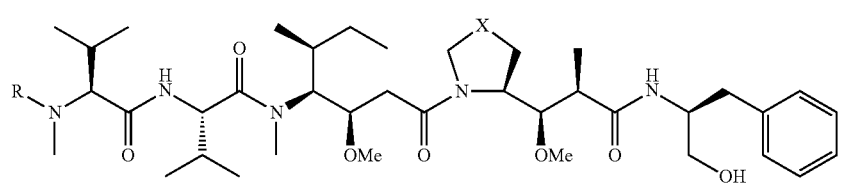
9a-e
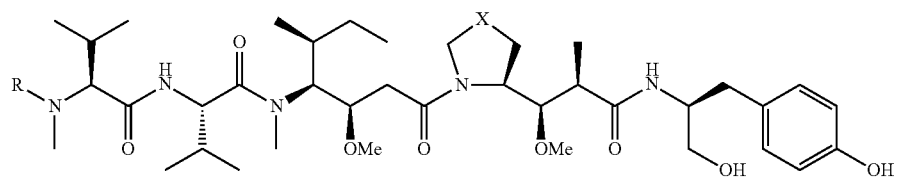
15a-e Examples of compounds having the structure of Formula Ia include the following:
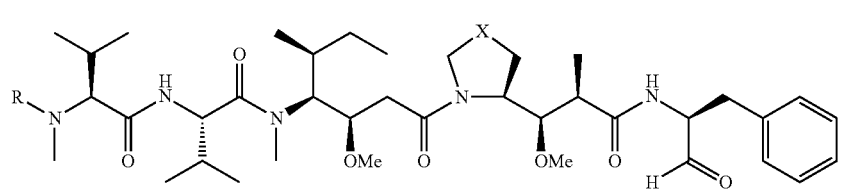
10-e
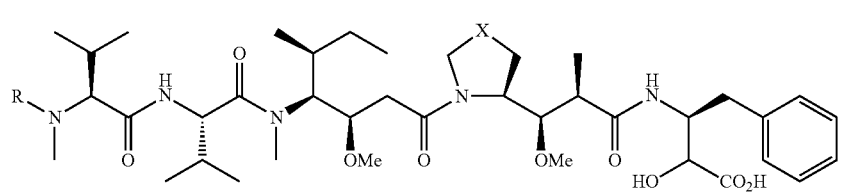
11a-e
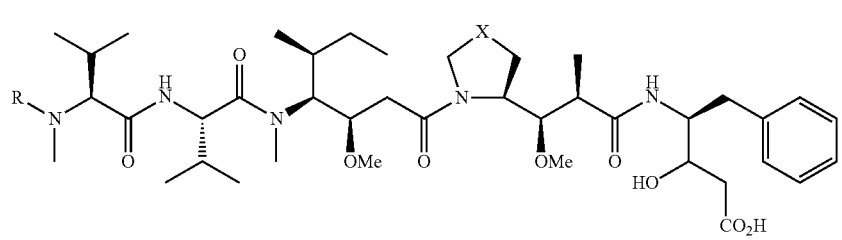
12a-e
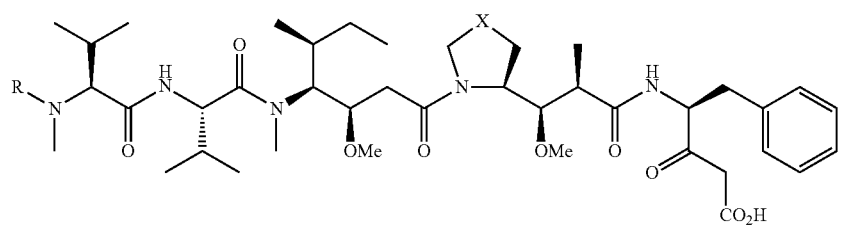
13a-e
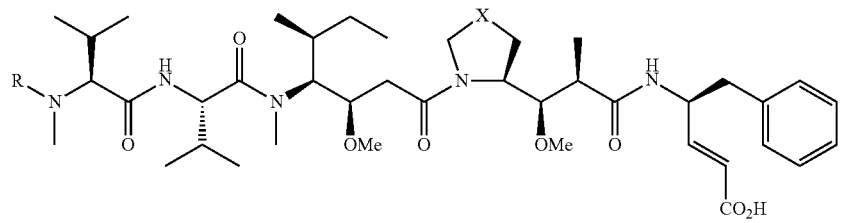
14a-e
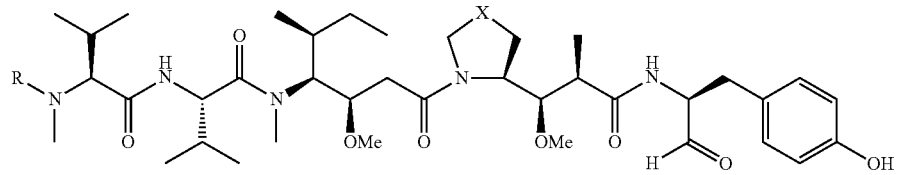
16-e
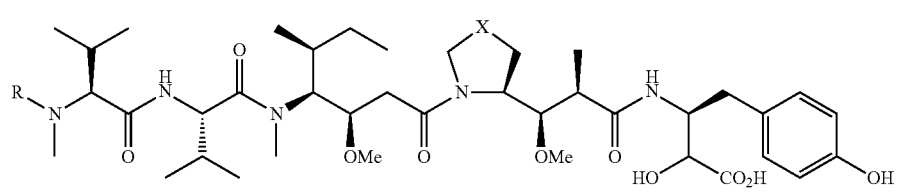
17a-e -continued
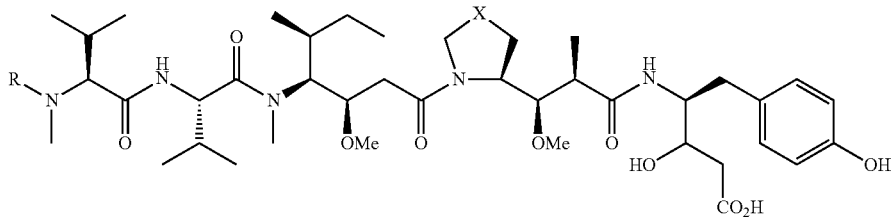
18a-e
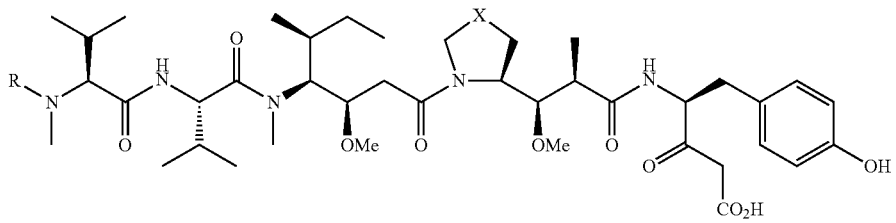
19a-e
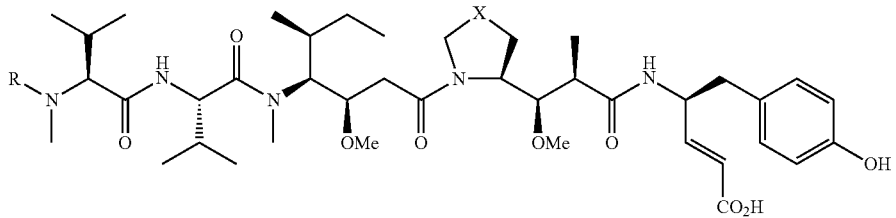
20a-e
30
Examples of general compounds having the structure of Formula Ia include the following:
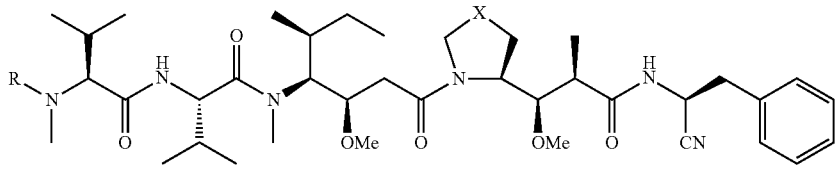
21a-e
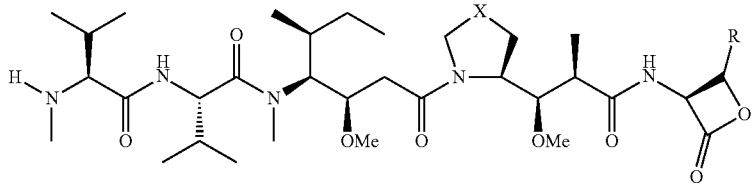
27a-e
Examples of compounds having the structure of Formula Ia include the following:
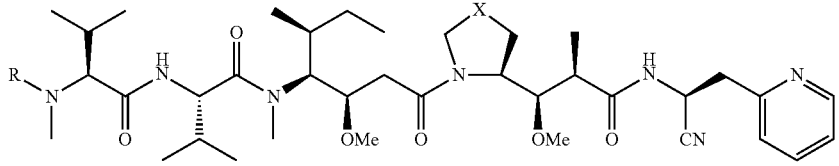
22a-e 23a-e
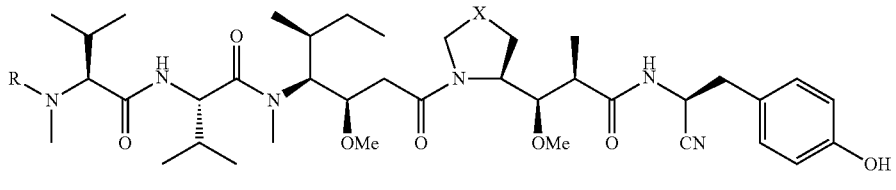
24a-k
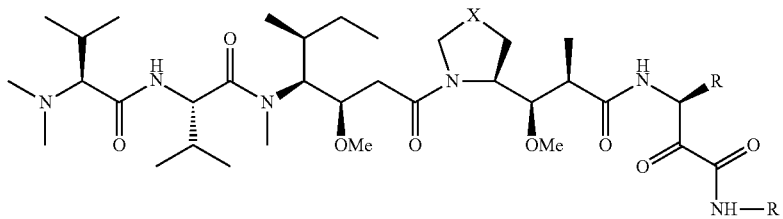
25a-k
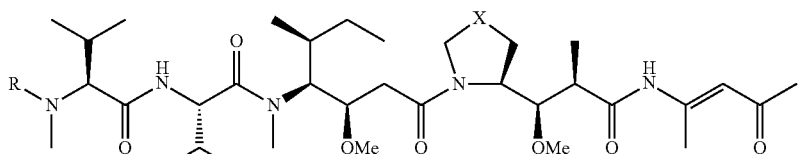
26a-e
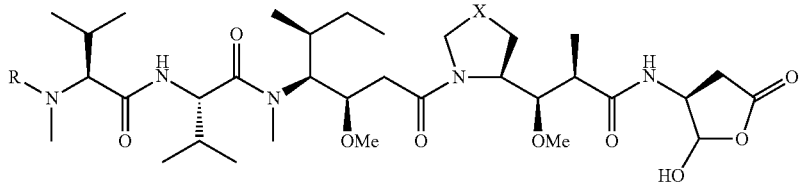
28a-k
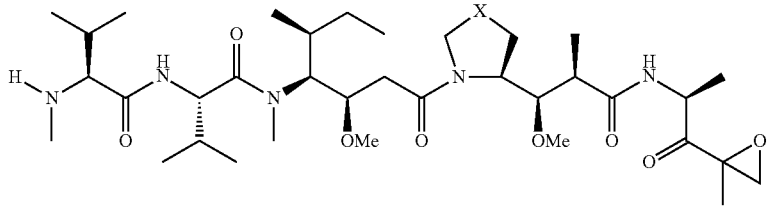
29a-q
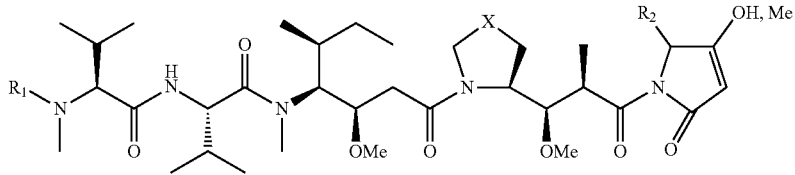
30a-k
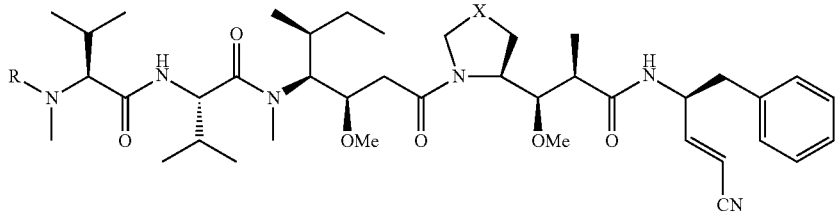
31a-k
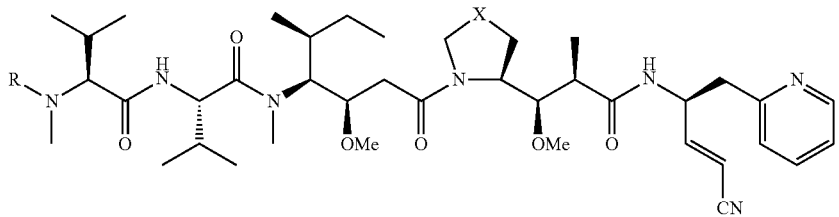

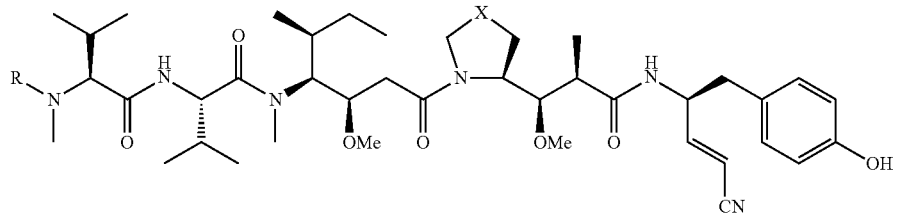
32a-k
Examples of general compounds having the structure of Formula Ia include the following:
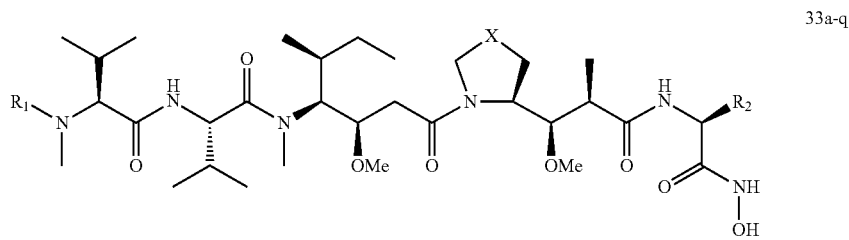
33a-q
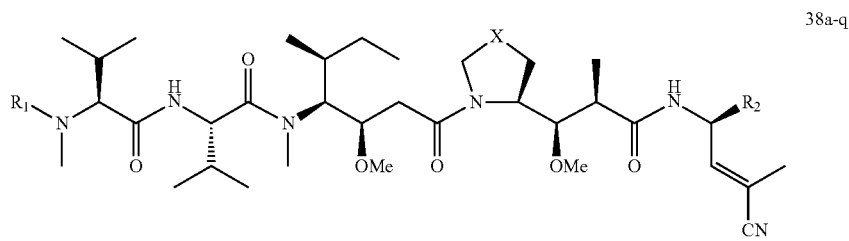
38a-q
40
Examples of compounds having the structure of Formula Ia include the following:
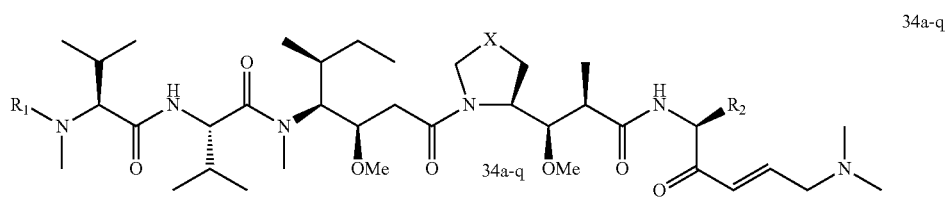
34a-q
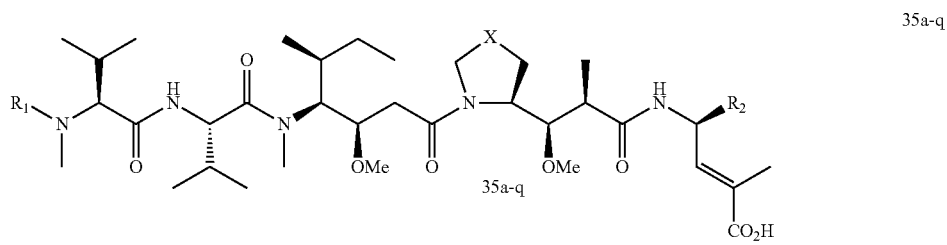
35a-q

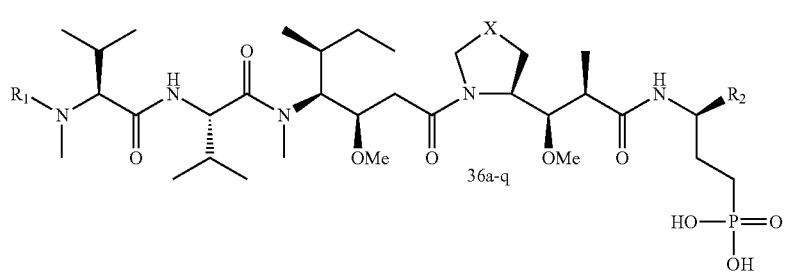
36a-q
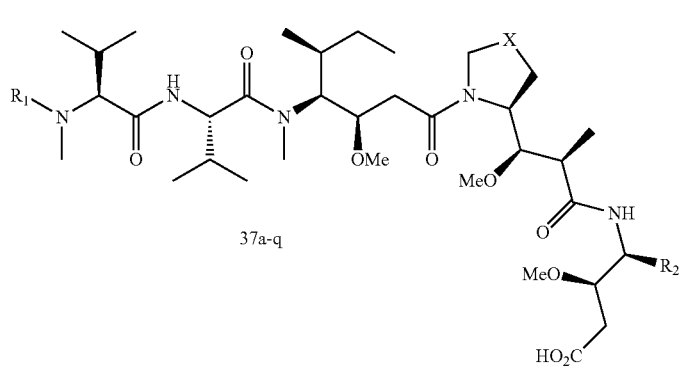
37a-q
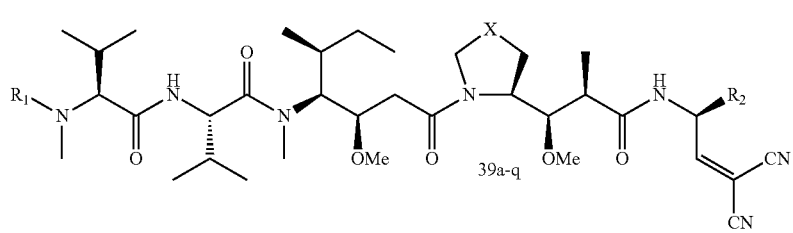
39a-q
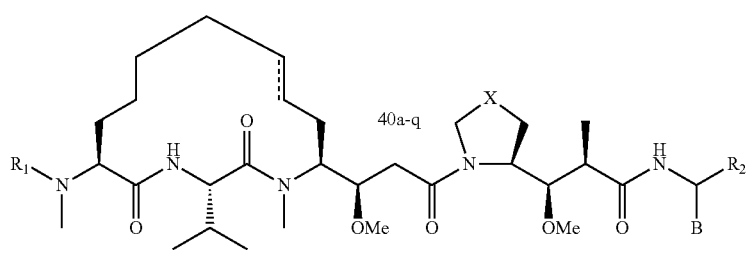
40a-q
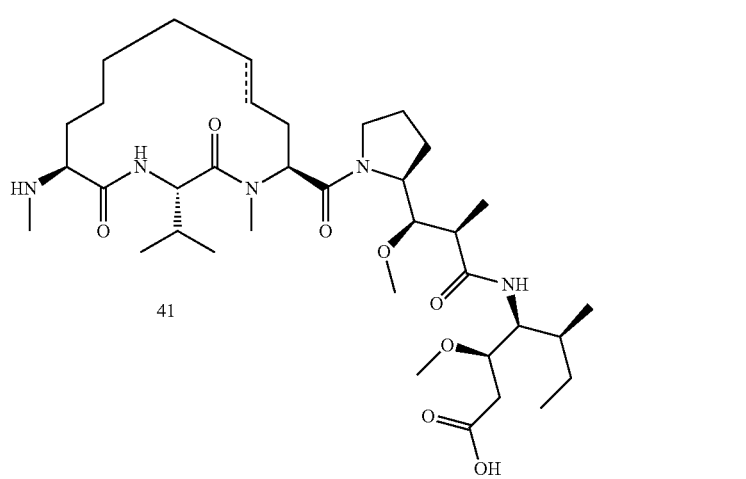
41

42
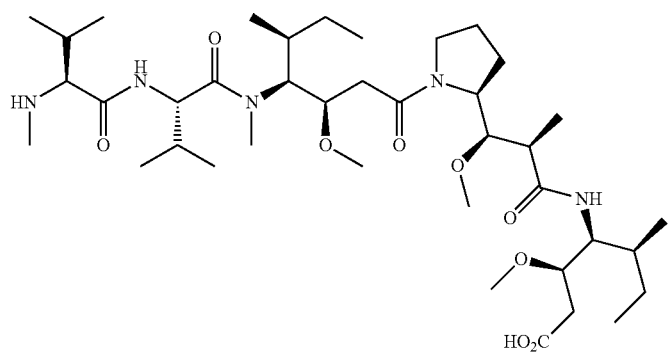
Examples of compounds having the structure of Formula Ib include the following:
43
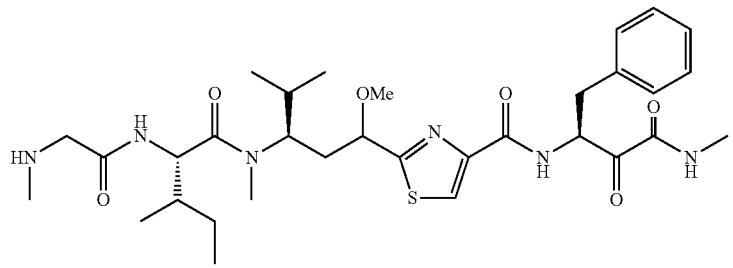
44
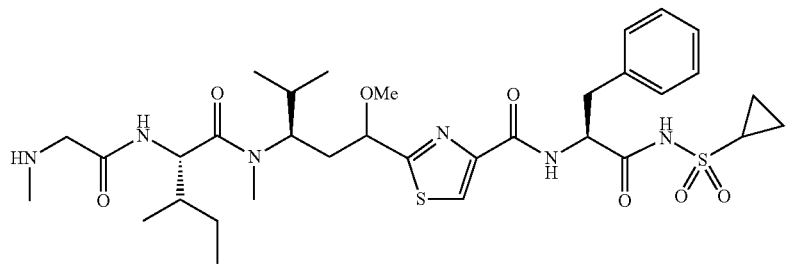
45
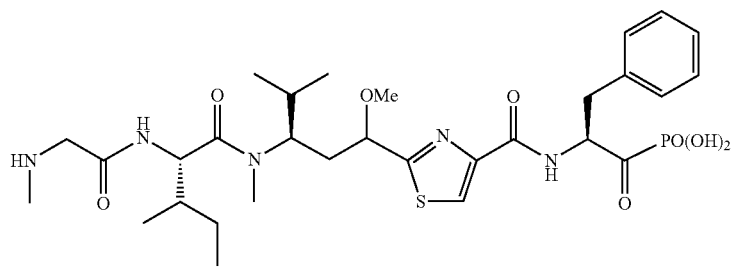
46
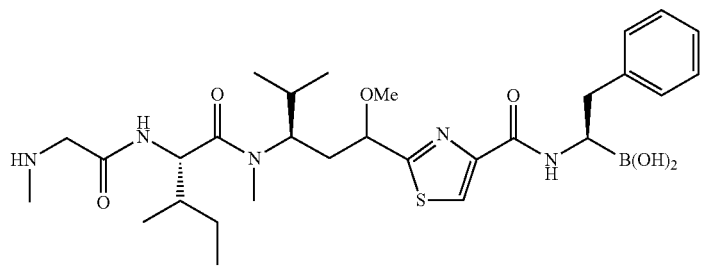

-continued
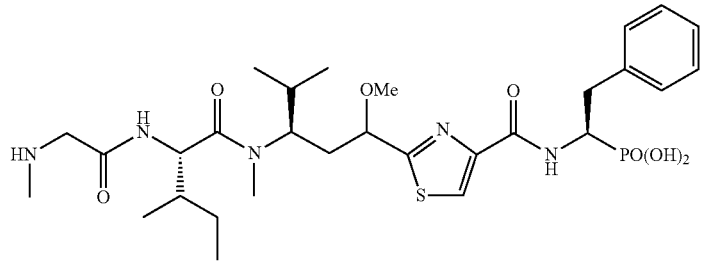
47
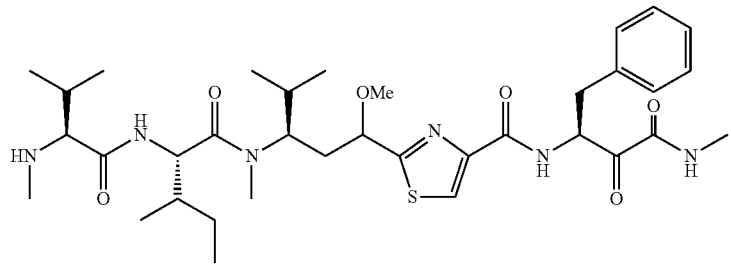
48
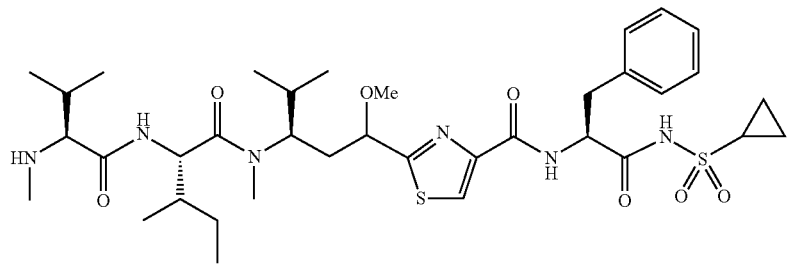
49
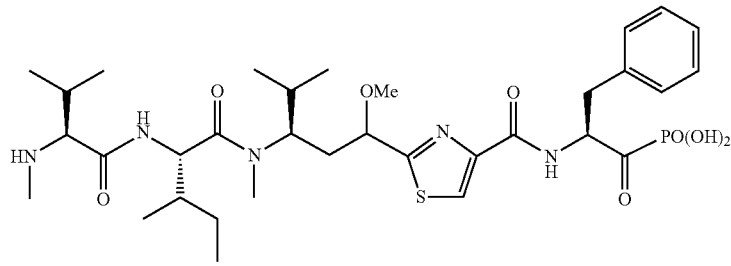
50
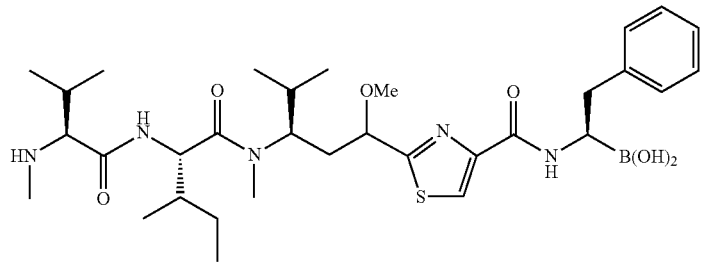
51

52
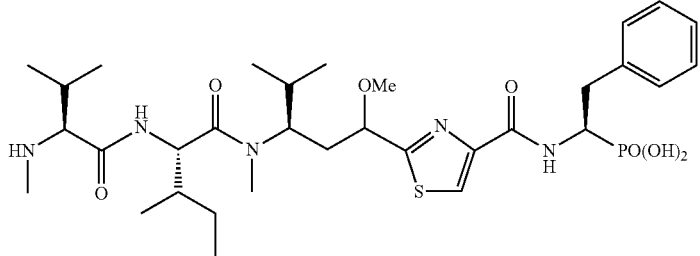
Examples of compounds having the structure of Formula Ib include the following:
53
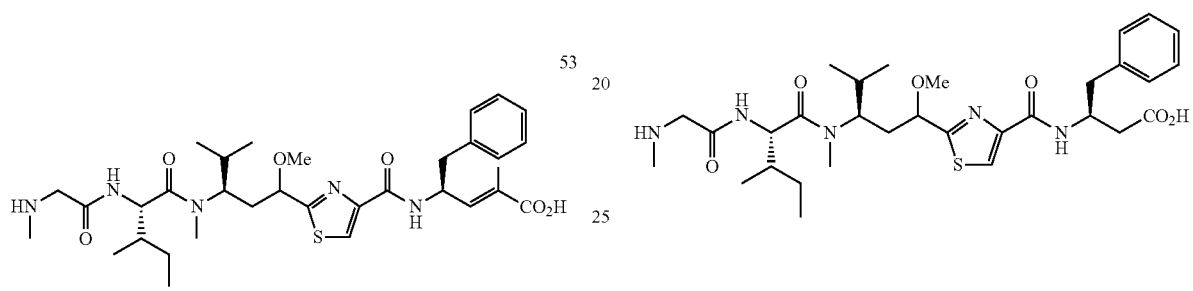
54
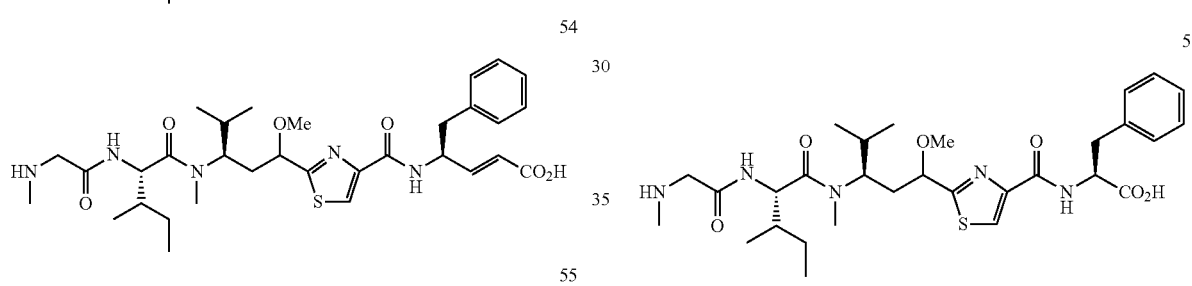
55
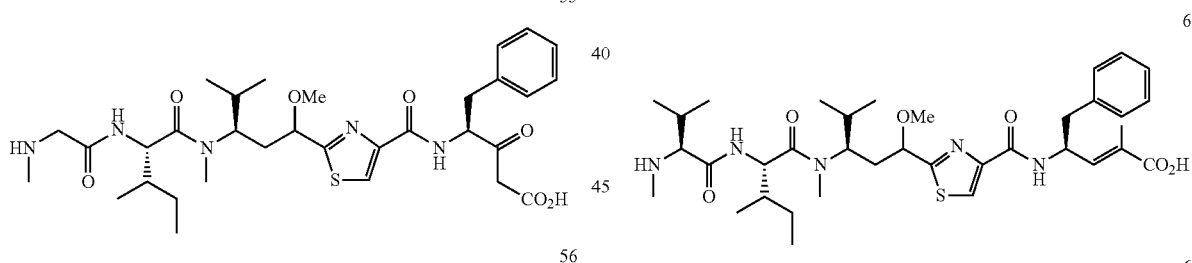
56
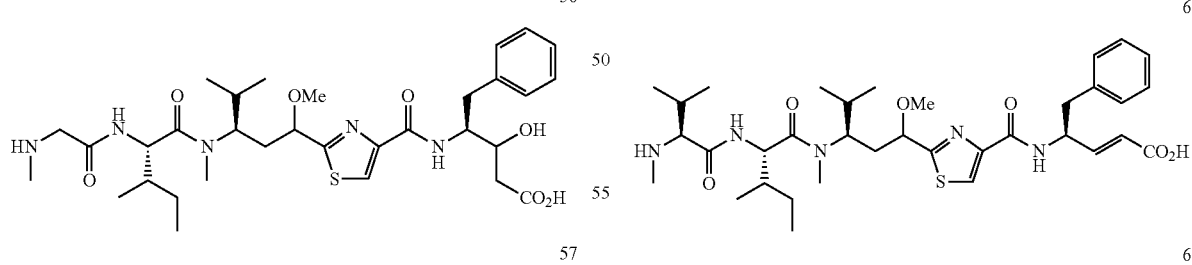
57
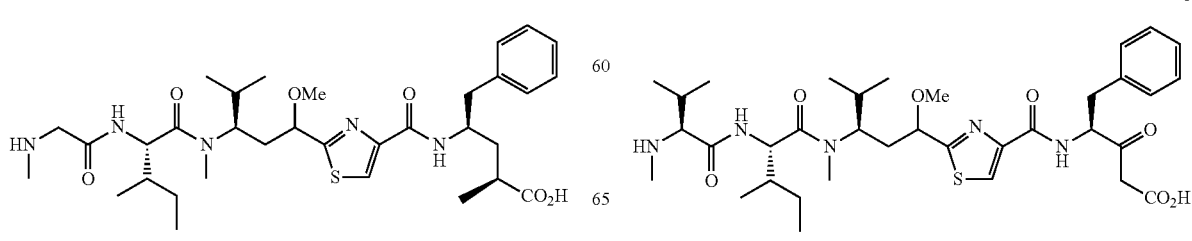
58
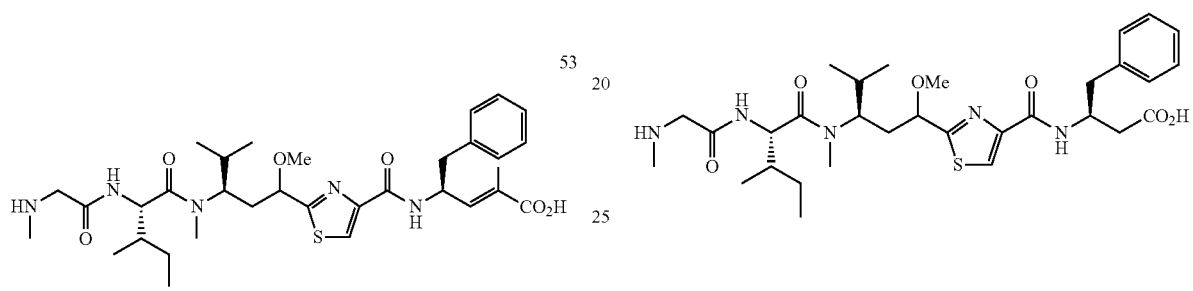
59
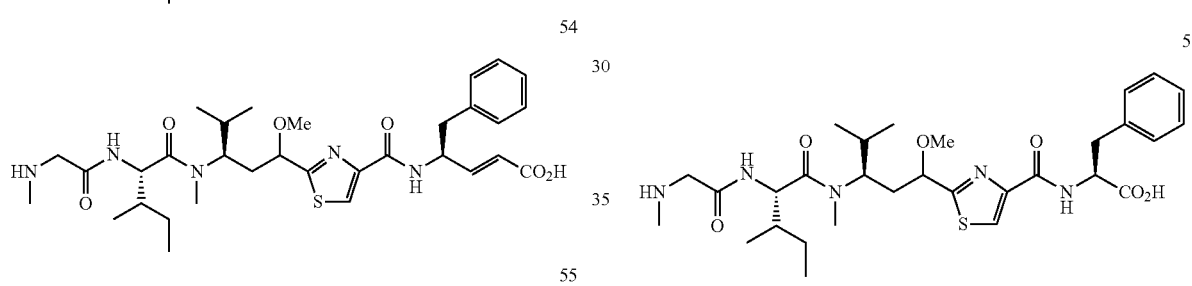
60
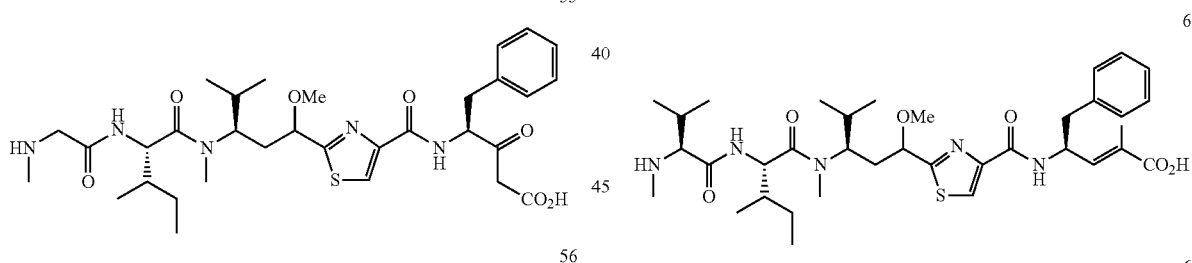
61
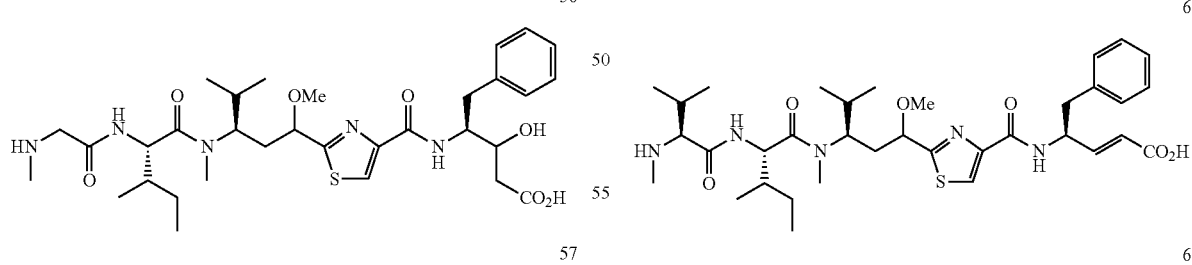
62
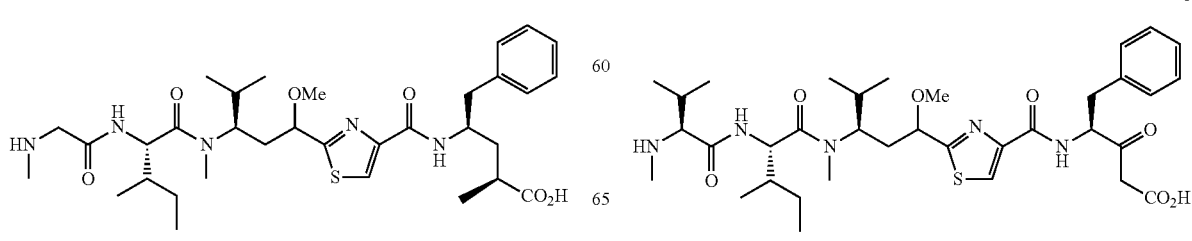

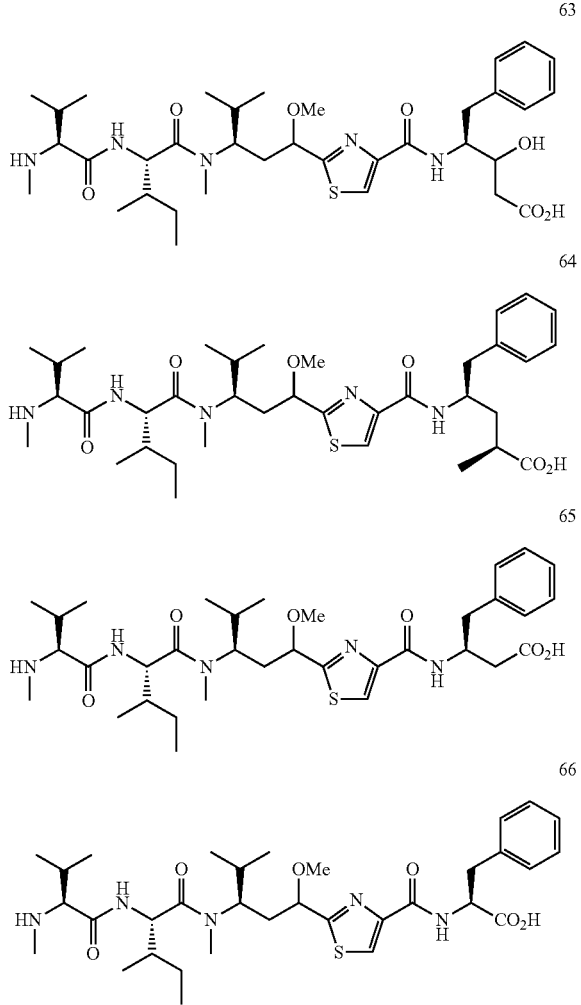

or multifunctional linker may include a group including a N (nitrogen) atom. In some embodiments, the spacer or multifunctional linker may include a cyclic group including a N (nitrogen) atom.

In some embodiments, the spacer connects to the mAB by a sulfide bond. In some embodiments, the multifunctional linker connects to the mAB by a sulfide bond. In some embodiments, the spacer or multifunctional linker may be optionally connected to an auxiliary moiety. In some embodiments, the auxiliary moiety may be a second targeting moiety such as mAB and peptide. In some embodiments, the auxiliary moiety may be a hydrophilic polymer such as polyethylene glycol (PEG), and the like. In some embodiments, the spacer or multifunctional linker may include a 2- to 5-atom bridge. In some embodiments, the spacer or multifunctional linker may include a 4C bridge.

Conjugation Methods, Spacers and Linkers Involved

Some embodiments provide a method of conjugating of a targeting moiety through a spacer or a multifunctional linker.

In some embodiments, the spacer or multifunctional linker may include a 2- to 5-atom bridge. In some embodiments, the method includes a single-step or sequential conjugation approach. In some embodiments, the compound includes a spacer or a multifunctional linker. In some embodiments, the spacer or multifunctional linker may include a noncleavable or cleavable unit such as peptides.

In some embodiments, the spacer or multifunctional linker may include a group including a N (nitrogen) atom. In some embodiments, the method includes a single-step or sequential conjugation approach. In some embodiments, the spacer or multifunctional linker may include a noncleavable or cleavable unit such as a peptide.

Some embodiments provide a compound-conjugate having the structure of Formula IIa:

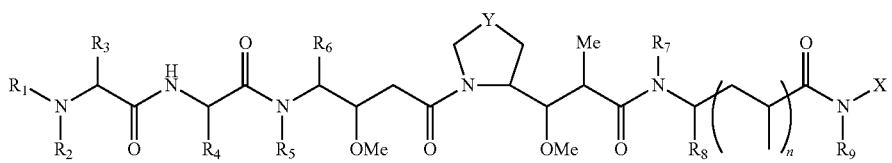

(IIa)

In some embodiments, the compound is conjugated to a targeting moiety.

In some embodiments, the targeting moiety includes a monoclonal antibody (mAB). In some embodiments, the compound includes a spacer or a multifunctional linker.

In some embodiments, the spacer connects to the mAB by a group including a N (nitrogen) atom. In some embodiments, the multifunctional linker connects to the mAB by a group including a N (nitrogen) atom. In some embodiments, the spacer or multifunctional linker may be optionally connected to an auxiliary moiety. In some embodiments, the auxiliary moiety may be a second targeting moiety such as mAB and peptide. In some embodiments, the auxiliary moiety may be a hydrophilic polymer such as polyethylene glycol (PEG), and the like. In some embodiments, the spacer or a pharmaceutically acceptable salt thereof, wherein:

$R^1$-$R^9$ are each independently selected from the group consisting of H (hydrogen), optionally substituted $C_1$-$C_8$ alkyl, optionally substituted $C_3$-$C_8$ cycloalkyl, optionally substituted aryl, and optionally substituted heteroaryl, or optionally $R^1$ and $R^2$ together with the nitrogen to which they are attached are an optionally substituted cyclic 5- to 7-membered ring, or optionally $R^1$ and $R^3$ together with the atoms to which they are attached are an optionally substituted cyclic 5- to 7-membered ring, or optionally $R^7$, $R^8$ and $R^9$ together with the atoms to which they are attached are an optionally substituted cyclic 5- to 7-membered ring, or optionally $R^1$ is $R^{1A}$ or $R^{1B}$;

$R^{1A}$ comprises a targeting moiety;

$R^{1B}$ is -L$^1$(CH$_2$)$_n$R$^C$, -L$^1$O(CH$_2$)$_n$R$^C$ or —(CH$_2$)$_n$R$^C$, $R^C$ is C$_1$-C$_8$ alkyl, C$_3$-C$_8$ cycloalkyl, aryl, heteroaryl, and heterocyclyl, each optionally substituted with one or more R$^D$, or optionally R$^C$ comprises a targeting moiety;

each R$^D$ is independently selected from the group consisting of —OH, —N$_3$, halo, cyano, nitro, —(CH$_2$)$_n$NR$^E$R$^F$, —(CH$_2$)$_n$C(=O)NR$^E$R$^F$, —O(CH$_2$)$_n$NR$^E$R$^F$, —O(CH$_2$)$_n$C(=O)NR$^E$R$^F$, —O(CH$_2$)$_m$OC(=O)NR$^E$R$^F$, —NR$^G$C(=O)R$^H$, —NR$^G$S(O)$_z$R$^H$, —O(CH$_2$)$_m$O(CH$_2$)$_m$R$^J$, —O(CH$_2$)$_n$C(=O)R$^J$, —O(CH$_2$)$_n$R$^J$, optionally substituted C$_1$-C$_8$ alkyl, optionally substituted C$_3$-C$_8$ cycloalkyl, optionally substituted aryl, optionally substituted heteroaryl, optionally substituted heterocyclyl, and optionally substituted —O—(C$_1$-C$_8$ alkyl);

each NR$^E$R$^F$ is independently selected, wherein R$^E$ and R$^F$ are each independently selected from hydrogen, -[(L$^1$)$_s$(C(R$^{2A}$)$_2$)$_r$(NR$^{2A}$)$_s$(C(R$^{2A}$)$_2$)$_r$]-[L$^1$(C(R$^{2A}$)$_2$)$_r$(NR$^{2A}$)$_s$(C(R$^{2A}$)$_2$)$_r$]$_s$-(L$^1$)$_s$-R$^J$, -[(L$^1$)$_s$(C(R$^{2A}$)$_2$)$_r$(NR$^{2A}$)$_s$(C(R$^{2A}$)$_2$)$_r$]-(L$^1$)$_s$[(C(R$^{2A}$)$_2$)$_r$O(C(R$^{2A}$)$_2$)$_r$(L$^2$)$_s$]$_s$-(L$^1$)$_s$-R$^J$, optionally substituted C$_{1-8}$ alkyl, optionally substituted C$_{3-8}$ cycloalkyl, optionally substituted aryl, optionally substituted heteroaryl, and optionally substituted heterocyclyl;

each R$^G$ is independently hydrogen, optionally substituted C$_1$-C$_8$ alkyl, optionally substituted C$_3$-C$_8$ cycloalkyl, optionally substituted aryl, optionally substituted heteroaryl, or optionally substituted heterocyclyl;

each R$^H$ is independently hydrogen, optionally substituted C$_1$-C$_8$ alkyl, optionally substituted C$_3$-C$_8$ cycloalkyl, optionally substituted aryl, optionally substituted heteroaryl, optionally substituted heterocyclyl, or —NR$^E$R$^F$;

each R$^J$ is independently selected from the group consisting of hydrogen, optionally substituted C$_1$-C$_8$ alkyl, optionally substituted —O—(C$_1$-C$_8$ alkyl), optionally substituted C$_3$-C$_8$ cycloalkyl, optionally substituted aryl, optionally substituted heteroaryl, optionally substituted heterocyclyl, —(CH$_2$)$_n$OR$^{2B}$, —O(CH$_2$)$_n$OR$^{2B}$, —(CH$_2$)$_n$NR$^{2B}$R$^{2B}$, —C(R$^{2A}$)$_2$NR$^{2B}$R$^{2B}$, —(CH$_2$)$_n$C(=O)OR$^{2B}$, and —C(=O)NHR$^{2B}$;

each R$^{2A}$ is independently selected, wherein R$^{2A}$ is selected from the group consisting of hydrogen, halo, —OH, optionally substituted C$_1$-C$_8$ alkyl, optionally substituted —O—(C$_1$-C$_8$ alkyl), optionally substituted C$_3$-C$_8$ cycloalkyl, optionally substituted aryl, optionally substituted heteroaryl, optionally substituted heterocyclyl, —(CH$_2$)$_n$OR$^{2B}$, —(CH$_2$)$_n$NR$^{2C}$R$^{2C}$, —C(=O)OR$^{2B}$, —C(=O)NR$^{2C}$R$^{2C}$, or optionally two geminal R$^{2A}$ and the carbon to which they are attached are together an optionally substituted three- to six-membered carbocyclic ring;

each R$^{2B}$ is independently selected from the group consisting of hydrogen, —OH, —(CH$_2$)$_n$C(=O)OH, —C(=O)(C(R$^{2D}$)$_2$)$_n$L$^3$R$^{2E}$, optionally substituted C$_1$-C$_8$ alkyl, optionally substituted C$_3$-C$_8$ cycloalkyl, optionally substituted —O—(C$_1$-C$_8$ alkyl), optionally substituted aryl, optionally substituted heteroaryl, and optionally substituted heterocyclyl;

each NR$^{2C}$R$^{2C}$ is independently selected, wherein each R$^{2C}$ is independently selected from the group consisting of hydrogen, —OH, optionally substituted C$_1$-C$_8$ alkyl, optionally substituted C$_3$-C$_8$ cycloalkyl, optionally substituted —O—(C$_1$-C$_8$ alkyl), optionally substituted aryl, optionally substituted heteroaryl, and optionally substituted heterocyclyl, or optionally both R$^{2C}$ together with the nitrogen to which they are attached are an optionally substituted heterocyclyl;

each R$^{2D}$ is independently selected from the group consisting of hydrogen, optionally substituted C$_1$-C$_8$ alkyl, optionally substituted C$_3$-C$_8$ cycloalkyl, optionally substituted —O—(C$_1$-C$_8$ alkyl), optionally substituted aryl, optionally substituted heteroaryl, and optionally substituted heterocyclyl;

each R$^{2E}$ is independently selected from the group consisting of optionally substituted C$_1$-C$_8$ alkyl, optionally substituted C$_3$-C$_8$ cycloalkyl, optionally substituted aryl, optionally substituted heteroaryl, and optionally substituted heterocyclyl, and —(CH$_2$)$_n$C(=O)OR$^{2F}$;

each R$^{2F}$ is independently selected from the group consisting hydrogen, optionally substituted C$_1$-C$_8$ alkyl, optionally substituted C$_3$-C$_8$ cycloalkyl, optionally substituted aryl, optionally substituted heteroaryl, and optionally substituted heterocyclyl;

each L$^1$ is independently selected from the group consisting of —C(=O)—, —S(=O)—, —C(=S)—, —S(=O)$_2$—, —C(=O)O—, —C(=O)NR$^{2A}$—, —S(=O)NR$^{2A}$—, —S(=O)$_2$NR$^{2A}$—, —C(=O)NR$^{2A}$C(=O)—, and —C(CF$_3$)$_2$NR$^{2A}$—;

each L$^2$ is independently selected from the group consisting of optionally substituted aryl, optionally substituted heteroaryl, and optionally substituted heterocyclyl;

each L$^3$ is independently selected from the group consisting of —C(=O)—, —S(=O)—, —C(=S)—, —S(=O)$_2$—, —C(=O)O—, —C(=O)NR$^{2A}$—, —S(=O)NR$^{2A}$—, —S(=O)$_2$NR$^{2A}$—, —C(=O)NR$^{2A}$C(=O)—, and —C(CF$_3$)$_2$NR$^{2A}$—;

each m independently is 1 or 2;

each n independently is 0, 1, 2, 3, 4, 5, or 6;

each r independently is 0, 1, 2, 3, 4, 5, or 6;

each s independently is 0 or 1; and each z independently is 1 or 2

$R^7$ is selected from the group consisting of H (hydrogen), optionally substituted C$_1$-C$_8$ alkyl, optionally substituted C$_3$-C$_8$ cycloalkyl, optionally substituted aryl, and optionally substituted heterocyclyl;

$R^8$ is selected from the group consisting of H (hydrogen), —(CH$_2$)$_n$R$^C$, optionally substituted C$_1$-C$_8$ alkyl, optionally substituted C$_3$-C$_8$ cycloalkyl, optionally substituted aryl, and optionally substituted heterocyclyl;

X is a group consisting of at least one heteroatom, or selected from groups consisting of —OR$^{10}$, —SO2-R$^{10}$, where R$^{10}$ is R$^C$.

In some embodiments, the active compound having the structure of Formula I has the structure of Formula IIb:

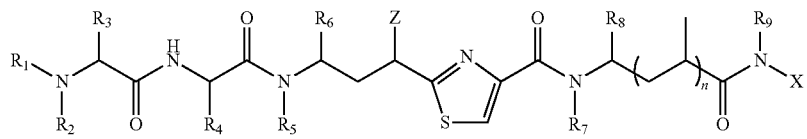

or a pharmaceutically acceptable salt thereof, wherein:

$R^9$ is selected from the group consisting of H (hydrogen), optionally substituted $C_1$-$C_8$ alkyl, optionally substituted $C_3$-$C_8$ cycloalkyl, substituted $C_1$-$C_8$ alkyl, substituted $C_3$-$C_8$ cycloalkyl, optionally substituted aryl, optionally substituted heteroaryl, or optionally $R^7$, $R^8$ and $R^9$ together with the atoms to which they are attached are an optionally substituted cyclic 5- to 7-membered ring, X is selected from groups consisting of —$OR^{10}$, —$SO_2$-$R^{10}$, where $R^{10}$ is $R^C$; and n is 0 or 1.

In some embodiments, at least one of $R^1$, $R^{10}$ and X comprises a targeting moiety. In some embodiments, at least one of $R^1$, $R^{10}$ and X further comprises a linker. In some embodiments, at least one of $R^1$, $R^{10}$ and X comprises —$(CH_2)_n$— where n is 1, 2, 3, 4, 5, 6, 7, 8, 9, or 10. In some embodiments, at least one of $R^1$, $R^{10}$ and X comprises —$(CH_2CH_2O)_n$— where n is 1, 2, 3, 4, 5, 6, 7, 8, 9, or 10. In some embodiments, at least one of $R^1$, $R^{10}$ and X comprises Val-Cit-PAB, Val-Ala-PAB, Phe-Lys-PAB, D-Val-Leu-Lys, Gly-Gly-Arg, or Ala-Ala-Asn-PAB. In some embodiments, at least one of $R^1$, $R^{10}$ and X comprises a peptide, oligosaccharide, —$(CH_2)_n$—, —$(CH_2CH_2O)_n$—, Val-Cit-PAB, Val-Ala-PAB, Phe-Lys-PAB, D-Val-Leu-Lys, Gly-Gly-Arg, Ala-Ala-Asn-PAB, or combinations thereof. In some embodiments, the targeting moiety is a monoclonal antibody (mAB). In some embodiments, the targeting moiety is an antibody fragment, surrogate, or variant. In some embodiments, the targeting moiety is a protein ligand. In some embodiments, the targeting moiety is a protein scaffold. In some embodiments, the targeting moiety is a peptide. In some embodiments, the targeting moiety is a small molecule ligand. In some embodiments, the linker includes a 4-carbon bridge and at least two sulfur atoms. In some embodiments, the linker includes a fragment selected from the group consisting of:

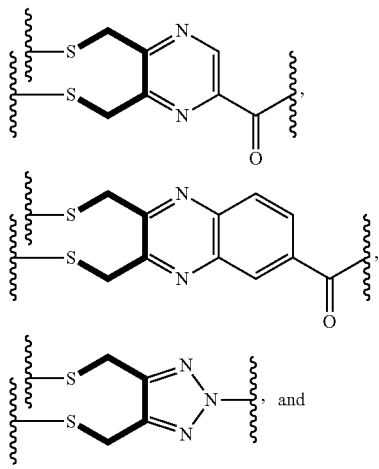

-continued

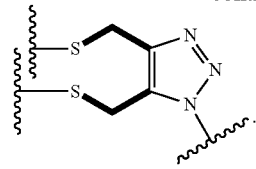

In some embodiments, at least one of $R^1$, $R^{10}$ and X comprises:

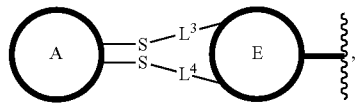

wherein: the A-component is the targeting moiety; the E-component is an optionally substituted heteroaryl or an optionally substituted heterocyclyl; $L^3$ is an optionally substituted $C_1$-$C_6$ alkyl, or $L^3$ is null, when $L^3$ is null the sulfur is directly connected to the E-component; and $L^4$ is an optionally substituted $C_1$-$C_6$ alkyl, or $L^4$ is null, when $L^4$ is null the sulfur is directly connected to the E-component. In some embodiments, the E-component includes a fragment selected from the group consisting of:

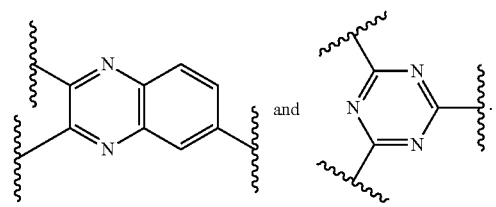 [SMILES: *c1ccc2nc(*)c(*)nc2c1 ; *c1nc(*)nc(*)n1]

In some embodiments, $L^3$ is —$(CH_2)$—; and $L^4$ is —$(CH_2)$—. In some embodiments, $L^3$ is null; and $L^4$ is null. In some embodiments,

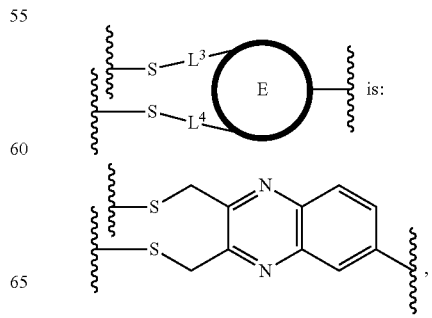

-continued

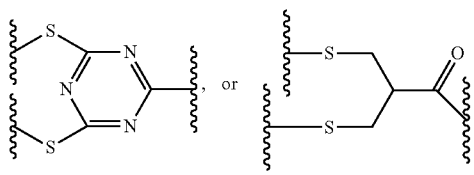

In some embodiments, at least one of $R^1$, $R^{10}$ and X comprises:

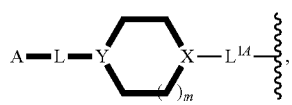

wherein: A is the targeting moiety; X is N (nitrogen) or CH; Y is N (nitrogen), or CH; m is 0, 1, or 2; L is a linker, or null; and $L^{14}$ is a linker, or null. In some embodiments, L is null. In some embodiments, L includes —C(=O)—, —NH—C(=O)—, —C(=O)—O—, —NH—C(=O)—NH— or —NH—C(=O)—O—. In some embodiments, L is —C(=O)—, —NH—C(=O)—, —C(=O)—O—, —NH—C(=O)—NH or —NH—C(=O)—O—. In some embodiments, L is —C(=O)—. In some embodiments,

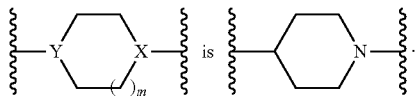

In some embodiments, at least one of $R^1$, $R^{10}$ and X comprises, consists of, or consists essentially of:

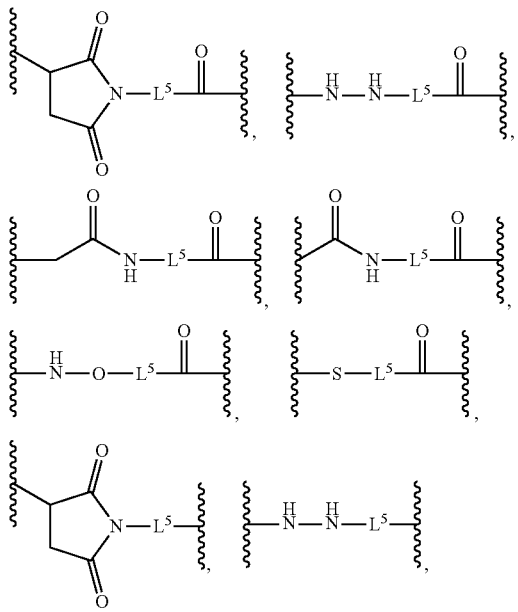

-continued

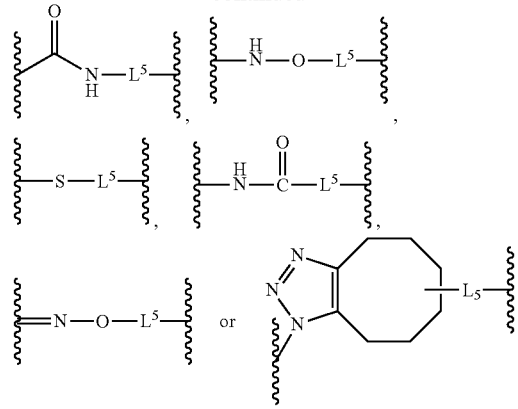

wherein $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

In some embodiments, at least one of $R^1$, $R^{10}$ and X comprises, consists of, or consist essentially of:

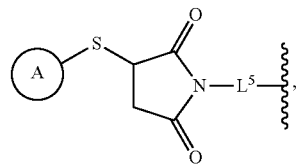

wherein A is the targeting moiety, $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

In some embodiments, at least one of $R^1$, $R^{10}$ and X comprises, consists of, or consist essentially of:

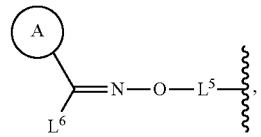

wherein A is the targeting moiety, $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl. $L^6$ may be H, optionally substituted $C_1$-$C_8$ alkyl, optionally substituted $C_3$-$C_8$ cycloalkyl, optionally substituted aryl, optionally substituted heteroaryl, optionally substituted heterocyclyl, or combination thereof.

In some embodiments, at least one of $R^1$, $R^{10}$ and X comprises, consists of, or consist essentially of:

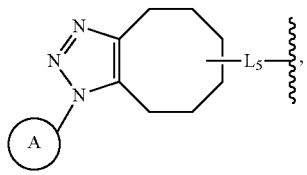

wherein A is the targeting moiety, $L^5$ may be optionally substituted $C_1$-$C_8$ alkyl, optionally substituted $C_3$-$C_8$ cycloalkyl, optionally substituted C3-C8 cycloalkyl annulated to cyclooctyl ring, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

Some embodiments provide a compound-conjugate having the structure of Formula V:

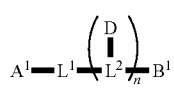

(V)

or a pharmaceutically acceptable salt thereof, wherein: $A^1$ may be a targeting moiety; $B^1$ is an auxiliary moiety that optionally includes a second targeting moiety, or $B^1$ is null; $L^1$ includes a group including a N (nitrogen) atom or a group including a 2- to 5-carbon bridge and at least one sulfur atom; each D is independently selected, where each D includes a compound; each $L^2$ is independently a linker, wherein at least one $L^2$ links to $L^1$; and n is 1, 2, 3, 4, 5, 6, 7, 8, 9, or 10. In some embodiments, $A^1$ may be a monoclonal antibody (mAB). In some embodiments, $A^1$ may be an antibody fragment, surrogate, or variant. In some embodiments, $A^1$ may be a protein ligand. In some embodiments, $A^1$ may be a protein scaffold. In some embodiments, $A^1$ may be a peptide. In some embodiments, $A^1$ may be RNA or DNA. In some embodiments, $A^1$ may be a RNA or DNA fragment. In some embodiments, $A^1$ may be a small molecule ligand. In some embodiments, $B^1$ may be a hydrophilic polymer. In some embodiments, the hydrophilic polymer may polyethylene glycol (PEG), and the like. In some embodiments, $B^1$ may be a biodegradable polymer. In some embodiments, the biodegradable polymer may be unstructured proteins polyamino acids, polypeptides polysaccharides and combinations thereof. In some embodiments, $B^1$ may be a monoclonal antibody (mAB). In some embodiments, $B^1$ may be an antibody fragment, surrogate, or variant. In some embodiments, $B^1$ may be a protein ligand. In some embodiments, $B^1$ may be a protein scaffold. In some embodiments, $B^1$ may be a peptide. In some embodiments, $B^1$ may be RNA or DNA. In some embodiments, $B^1$ may be a RNA or DNA fragment. In some embodiments, $B^1$ may be a small molecule ligand. In some embodiments, D may includes a biologically active compound. In some embodiments, D may includes a core from tubulin-binder or tubulin-binder derivative. In some embodiments, D include a core from epothilone A, epothilone B, paclitaxel, or derivatives thereof. In some embodiments, D includes

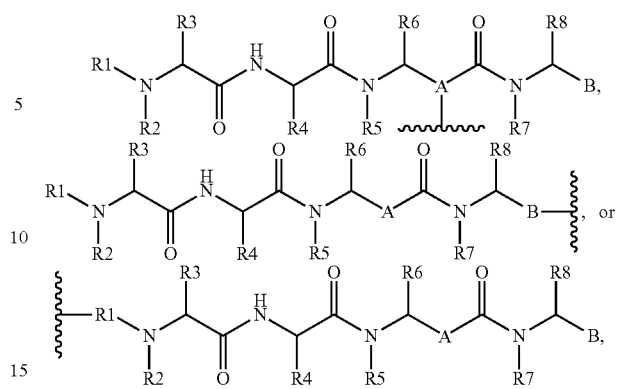

wherein: A is a tubulin binding moiety; B is a protease inhibition moiety; and $R_1$-$R_8$ are each independently selected from the group consisting of H (hydrogen), $C_1$-$C_8$ alkyl, substituted or cyclic $C_1$-$C_8$ alkyl, aryl, and substituted aryl, or optionally $R_1$ and $R_2$ together with the nitrogen to which they are attached are a cyclic 5- to 7-membered ring, or optionally $R_1$ and $R_3$ together with the atoms to which they are attached are a cyclic 5- to 7-membered ring, or optionally $R_7$ and $R_8$ together with the atoms to which they are attached are a cyclic 5- to 7-membered ring. In some embodiments, A may be

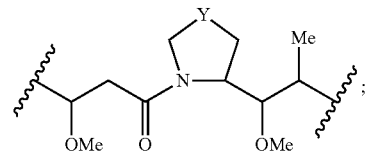

and Y may be $CH_2$, S, S=O, C=O, CHF, CHCN, $CHN_3CH$—OH, CH—$ONH_2$, or CHOR, where R is $C_1$-$C_8$ alkyl or substituted $C_1$-$C_8$ alkyl. In some embodiments, A may be

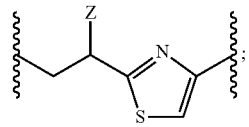

Z may be N (nitrogen), CH, C—OH, C—OR, CSH, CSR, where R is $C_1$-$C_8$ alkyl or substituted $C_1$-$C_8$ alkyl; X may be F, OH, $N_3$, OMe, or OR, where R is $C_1$-$C_8$ alkyl or substituted $C_1$-$C_8$ alkyl; and Y may be $CH_2$, S, S=O, C=O, CHF, CHCN, $CHN_3CH$—OH, CH—$ONH_2$, or CHOR, where R is $C_1$-$C_8$ alkyl or substituted $C_1$-$C_8$ alkyl. In some embodiments, $L^2$ may include a spacer or a multifunctional linker. In some embodiments, $L^2$ may include a spacer and a multifunctional linker. In some embodiments, $L^2$ may include a multifunctional linker. In some embodiments, each $L^2$ may be a linker, wherein the linker may be cleavable or non-cleavable under biological conditions. In some embodiments, the linker may be cleavable by an enzyme. In some embodiments, $L^2$ may include Linker. In some embodiments, $L^1$ includes a cyclic group including at least one N (nitrogen) atom. In some embodiments, $L^1$ includes a cyclic group including at least two N (nitrogen) atoms. In some embodiments, $L^1$ includes a cyclic group including at least one N (nitrogen) atom and a spacer. In some embodiments, $L^1$ includes a cyclic group including at least two N (nitrogen) atoms and a spacer. In some embodiments, the spacer connects to the mAB by an amide bond. In some embodiments, the spacer connects to the mAB through an amine bond. In some embodiments, $L^1$ includes a 2- to 5-carbon bridge and at least one sulfur atom. In some embodiments, $L^1$ includes a 2- to 5-carbon bridge and at least two sulfur atoms. In some embodiments, $L^1$ includes a 2- to 5-carbon bridge and a spacer. In some embodiments, $L^1$ includes a 2- to 5-carbon bridge, at least two sulfur atoms and a spacer. In some embodiments, $L^1$ may include one or more sulfurs. In some embodiments, the $L^1$ may include two or more sulfurs. In some embodiments, the $L^1$ may include exactly two sulfurs. In some embodiments, may include a 4-carbon bridge and/or a spacer. In some embodiments, $L^1$ include a 4-carbon bridge or a spacer. In some embodiments, $L^1$ may include a 4-carbon bridge and a spacer. In some embodiments, $L^1$ includes a 4-carbon bridge and at least two sulfur atoms. In some embodiments, the spacer connects to the mAB by a sulfide bond. In some embodiments, the spacer connects to the mAB through a thioether. In some embodiments, $A^1$ comprises at least one modified n-butyl L-α-amino acid. In some embodiments, at least one modified L-Lysine residue is from an L-Lysine residue of a peptide before conjugation. In some embodiments, at least one nitrogen of $L^1$ is from an at least one modified n-butyl L-α-amino acid of a peptide before conjugation. In some embodiments, $A^1$ and $L^1$ together comprise at least one modified L-Lysine residue. In some embodiments, the terminal nitrogen of the side chain of an L-Lysine residue of a peptide before conjugation is the at least one N (nitrogen) atom of $L^1$. In some embodiments, $A^1$ comprises the $-(CH_2)_4-$ of the side chain of an L-Lysine residue of a peptide before conjugation that provides the at least one N (nitrogen) atom of $L^1$. In some embodiments, $A^1$ comprises a modified n-butyl α-amino acid residue. In some embodiments, Linker may be a peptide. In some embodiments, Linker may include an oligosaccharide. For example, Linker may include chitosan. In some embodiments, $L^2$ may include Linker and $-(CH_2)_n-$ where n is 1, 2, 3, 4, 5, 6, 7, 8, 9, or 10. In some embodiments, $L^2$ may include Linker and $-(CH_2CH_2O)_n-$ where n is 1, 2, 3, 4, 5, 6, 7, 8, 9, or 10. In some embodiments, Linker may include $-(CH_2)_n-$ where n is 1, 2, 3, 4, 5, 6, 7, 8, 9, or 10. In some embodiments, Linker may include $-(CH_2CH_2O)_n-$ where n is 1, 2, 3, 4, 5, 6, 7, 8, 9, or 10. In some embodiments, Linker may include Val-Cit-PAB, Val-Ala-PAB, Phe-Lys-PAB, D-Val-Leu-Lay, Gly-Gly-Arg, Ala-Ala-Asn-PAB, or the like. In some embodiments, Linker may include any combination of peptide, oligosaccharide, $-(CH_2)_n-$, $-(CH_2CH_2O)_n-$, Val-Cit-PAB, Val-Ala-PAB, Phe-Lys-PAB, D-Val-Leu-Lay, Gly-Gly-Arg, Ala-Ala-Asn-PAB, and the like. In some embodiments, the spacer may include a peptide. In some embodiments, the spacer may include an oligosaccharide. For example, the spacer may include chitosan. In some embodiments, the spacer may include $-(CH_2)_n-$ where n is 1, 2, 3, 4, 5, 6, 7, 8, 9, or 10. In some embodiments, $L^1$ may include a component including a 4-carbon bridge and $-(CH_2)_n-$ where n is 1, 2, 3, 4, 5, 6, 7, 8, 9, or 10. In some embodiments, the spacer may include $-(CH_2CH_2O)_n-$ where n is 1, 2, 3, 4, 5, 6, 7, 8, 9, or 10. In some embodiments, $L^1$ may include a component including a 4-carbon bridge and $-(CH_2CH_2O)_n-$ where n is 1, 2, 3, 4, 5, 6, 7, 8, 9, or 10. In some embodiments, the spacer may include Val-Cit-PAB, Val-Ala-PAB, Phe-Lys-PAB, Ala-Ala-Asn-PAB, or the like. In some embodiments, the spacer may be any combination of peptide, oligosaccharide, $-(CH_2)_n-$, $-(CH_2CH_2O)_n-$, Val-Cit-PAB, Val-Ala-PAB, Phe-Lys-PAB, Ala-Ala-Asn-PAB, and the like. In some embodiments, $L^1$ may include,

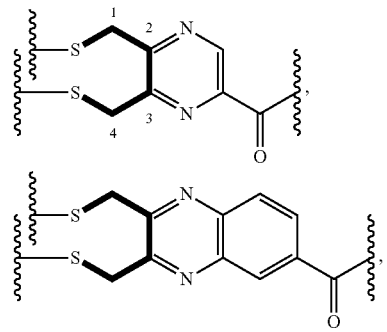

but is not limited to,

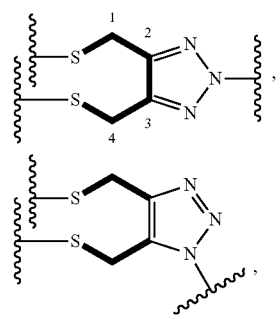

and the like. In some embodiments, $L^1$ may include, but is not limited to,

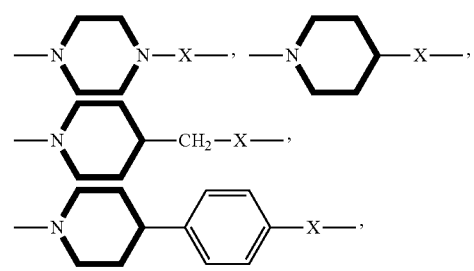

and the like.

In some embodiments, the compound-conjugates may include one or more components selected from the group consisting of an amino acid, an amino acid residue, an amino acid analog, and a modified amino acid.

As used herein, the term "peptide" refers to a structure including one or more components each individually selected from the group consisting of an amino acid, an amino acid residue, an amino acid analog, and a modified amino acid. The components are typically joined to each other through an amide bond.

As used herein, the term "amino acid" includes naturally occurring amino acids, a molecule having a nitrogen available for forming an amide bond and a carboxylic acid, a molecule of the general formula $-NH_2-CHR-COOH$ or the residue within a peptide bearing the parent amino acid, where "R" is one of a number of different side chains. "R" can be a substituent found in naturally occurring amino acids. "R" can also be a substituent referring to one that is not of the naturally occurring amino acids.

As used herein, the term "amino acid residue" refers to the portion of the amino acid which remains after losing a water molecule when it is joined to another amino acid.

As used herein, the term "amino acid analog" refers to a structural derivative of an amino acid parent compound that often differs from it by a single element.

As used herein, the term "modified amino acid" refers to an amino acid bearing an "R" substituent that does not correspond to one of the twenty genetically coded amino acids.

As used herein, the abbreviations for the genetically encoded L-enantiomeric amino acids are conventional and are as follows: The D-amino acids are designated by lower case, e.g. D-proline=p, etc.

TABLE 1

| Amino Acids | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Certain amino acid residues in the compound-conjugate can be replaced with other amino acid residues without significantly deleteriously affecting, and in many cases even enhancing, the activity of the peptides. Thus, also contemplated by the preferred embodiments are altered or mutated forms of the active agent-conjugate wherein at least one defined amino acid residue in the structure is substituted with another amino acid residue or derivative and/or analog thereof. It will be recognized that in preferred embodiments, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into nonpolar and aromatic amino acids. The definitions of the various categories of amino acids are as follows:

The term "hydrophilic amino acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R).

The term "hydrophobic amino acid" refers to an amino acid exhibiting a hydrophobicity of greater than zero according to the normalized consensus hydrophobicity scale of Eisenberg, 1984, J. Mol. Biol. 179:1.25-142. Genetically encoded hydrophobic amino acids include Pro (P), Ile (I), Phe (F), Val (V), Leu (L), Trp (W), Met (M), Ala (A), Gly (G) and Tyr (Y).

The term "acidic amino acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

The term "basic amino acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

The term "polar amino acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

The term "nonpolar amino acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Leu (L), Val (V), Ile (I), Met (M), Gly (G) and Ala (A).

The term "aromatic amino acid" refers to a hydrophobic amino acid with a side chain having at least one aromatic or heteroaromatic ring. In some embodiments, the aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

The term "aliphatic amino acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the preferred embodiments Cys (C) is categorized as a polar hydrophilic amino acid, notwithstanding the general classifications defined above.

As used herein, the term "targeting moiety" refers to a structure that binds or associates with a biological moiety or fragment thereof.

In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

In some embodiments, the targeting moiety may be an antibody fragment described in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045, the disclosure of which is incorporated herein by reference in its entirety. In some embodiments, the targeting moiety may be an antibody fragment described in Trail, P A, "Antibody Drug Conjugates as Cancer Therapeutics," *Antibodies* 2013, 2, 113-129, the disclosure of which is incorporated herein by reference in its entirety.

In some embodiments, the targeting moiety may be HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544. In some embodiments, the targeting moiety may comprise, consist of, or consist essentially of the antibody portion of HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the targeting moiety may be Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of the antibody portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the targeting moiety may comprise, consist of, or consist essentially of Brentuximab, Inotuzumab, Gemtuzumab, Milatuzumab, Trastuzumab, Glembatumomab, Lorvotuzumab, or Labestuzumab.

As used herein, the term "linker" refers to a moiety that connects two or more components to each other.

In some embodiments, the linker may be a linker disclosed in Janthur et al., "Drug Conjugates Such as Antibody Drug Conjugates (ADCs), Immunotoxins and Immunoliposomes Challenge Daily Clinical Practice," *Int. J. Mol. Sci.* 2012, 13, 16020-16045. In some embodiments, the linker may be a linker disclosed in Trail, P A, "Antibody Drug Conjugates as Cancer Therapeutics," *Antibodies* 2013, 2, 113-129. In some embodiments, the linker may be a linker disclosed in U.S. Pat. No. 7,829,531.

In some embodiments, the linker may comprise, consist of, or consist essentially of the linker portion of HuM195-Ac-225, HuM195-Bi-213, Anyara (naptumomab estafenatox; ABR-217620), AS1409, Zevalin (ibritumomab tiuxetan), BIIB015, BT-062, Neuradiab, CDX-1307, CR011-vcMMAE, Trastuzumab-DM1 (R3502), Bexxar (tositumomab), IMGN242, IMGN388, IMGN901, $^{131}$I-labetuzumab, IMMU-102 ($^{90}$Y-epratuzumab), IMMU-107 ($^{90}$Y-clivatuzumab tetraxetan), MDX-1203, CAT-8015, EMD 273063 (hu14.18-IL2), Tucotuzumab celmoleukin (EMD 273066; huKS-IL2), $^{188}$Re-PTI-6D2, Cotara, L19-IL2, Teleukin (F16-IL2), Tenarad (F16-$^{131}$I), L19-$^{131}$I, L19-TNF, PSMA-ADC, DI-Leu16-IL2, SAR3419, SGN-35, or CMC544.

In some embodiments, the linker may comprise, consist of, or consist essentially of the linker portion of Brentuximab vedotin, Trastuzumab emtansine, Inotuzumab ozogamicin, Lorvotuzumab mertansine, Glembatumumab vedotin, SAR3419, Moxetumomab pasudotox, Moxetumomab pasudotox, AGS-16M8F, AGS-16M8F, BIIB-015, BT-062, IMGN-388, or IMGN-388.

In some embodiments, the linker may comprise, consist of, or consist essentially of Valine-citrulline residue, hydrazine, 4-mercaptobutanoyl, 4-(N-succinimidomethyl)cyclohexanecarbonyl (SMCC), Maleimidocaproyl, Phenylalaninelysine, 6-(3-(thio)propanamido)hexanoyl, 3-mercaptopropanoyl, 4-mercaptopentanoyl, or lysine residue.

In some embodiments, the linker may comprise, consist of, or consist essentially of:

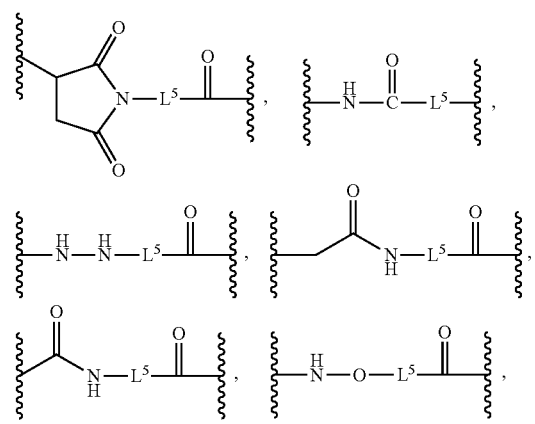

-continued

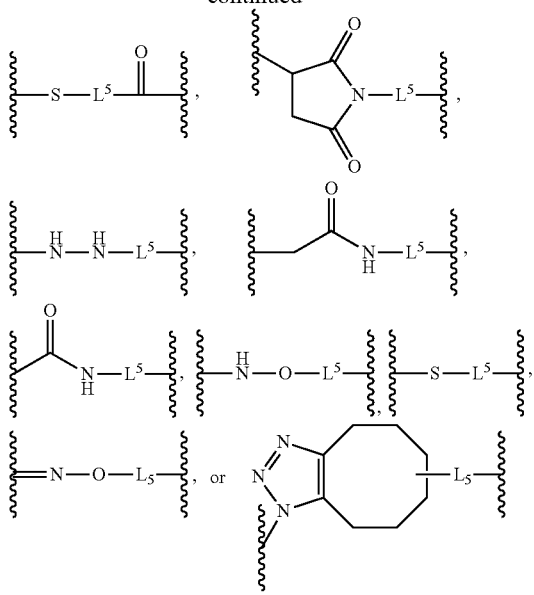

wherein $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

In some embodiments, the linker may comprise, consist of, or consist essentially of:

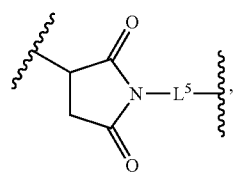

wherein A is the targeting moiety, $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

In some embodiments, the linker may comprise, consist of, or consist essentially of:

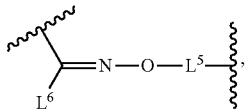

wherein A is the targeting moiety, $L^5$ may be optionally substituted $C_1$-$C_8$ alkyl, optionally substituted $C_3$-$C_8$ cycloalkyl, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl. $L^6$ may be H, optionally substituted $C_1$-$C_8$ alkyl, optionally substituted $C_3$-$C_8$ cycloalkyl, optionally substituted aryl, optionally substituted heteroaryl, optionally substituted heterocyclyl, or combination thereof.

In some embodiments, the linker may comprise, consist of, or consist essentially of:

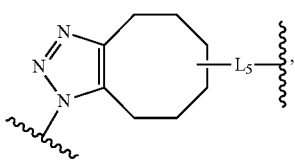

wherein A is the targeting moiety, $L^5$ may be optionally substituted $C_1$-$C_8$ alkyl, optionally substituted $C_3$-$C_8$ cycloalkyl, optionally substituted C3-C8 cycloalkyl annulated to cyclooctyl ring, optionally substituted $C_1$-$C_8$ alkoxy, optionally substituted aryl, optionally substituted heteroaryl, optionally substituted heterocyclyl, or combination thereof. In some embodiments, $L^5$ is an optionally substituted $C_1$-$C_8$ alkyl. In some embodiments, $L^5$ is $C_1$-$C_8$ alkyl.

In some embodiments, the linker may comprise, consist of, or consist essentially of:

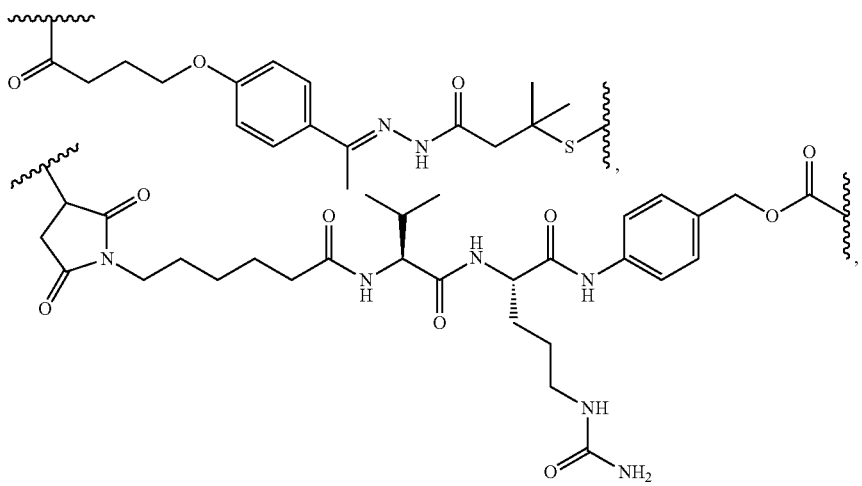

-continued
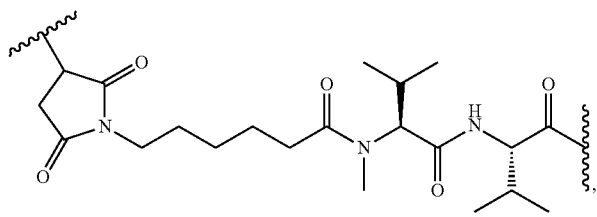 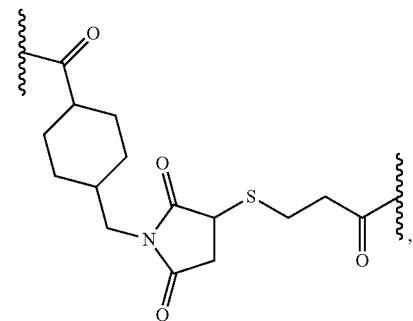
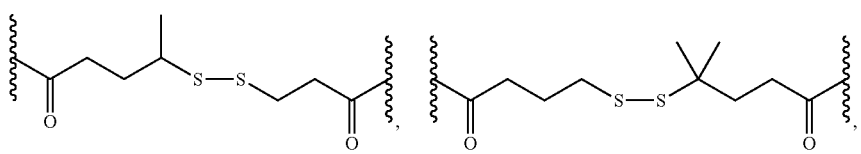
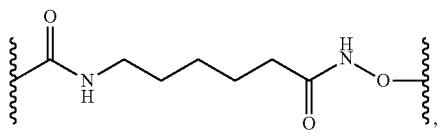
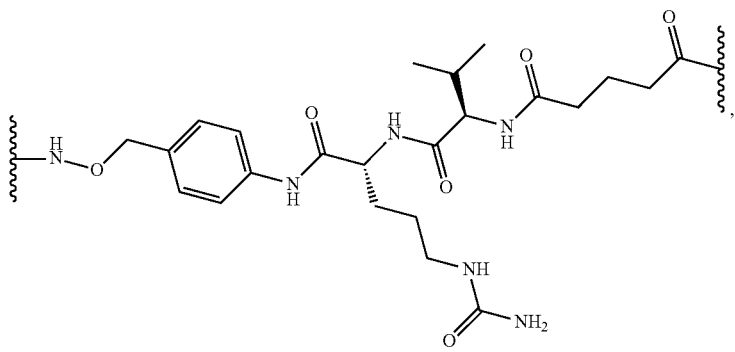
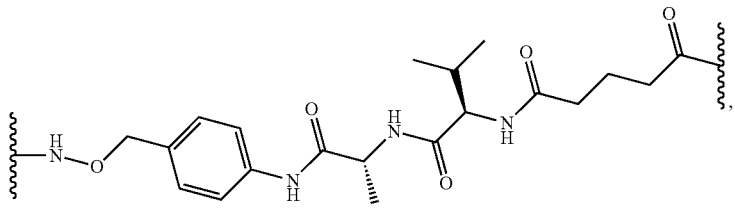
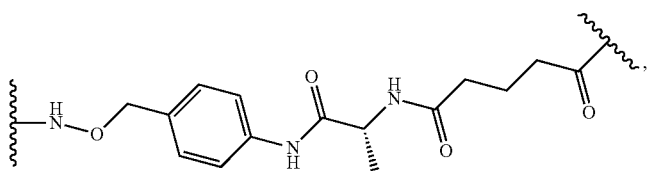
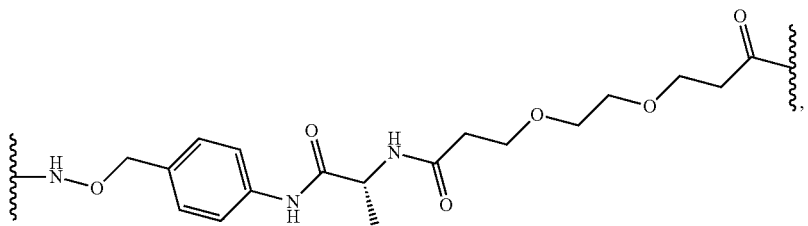

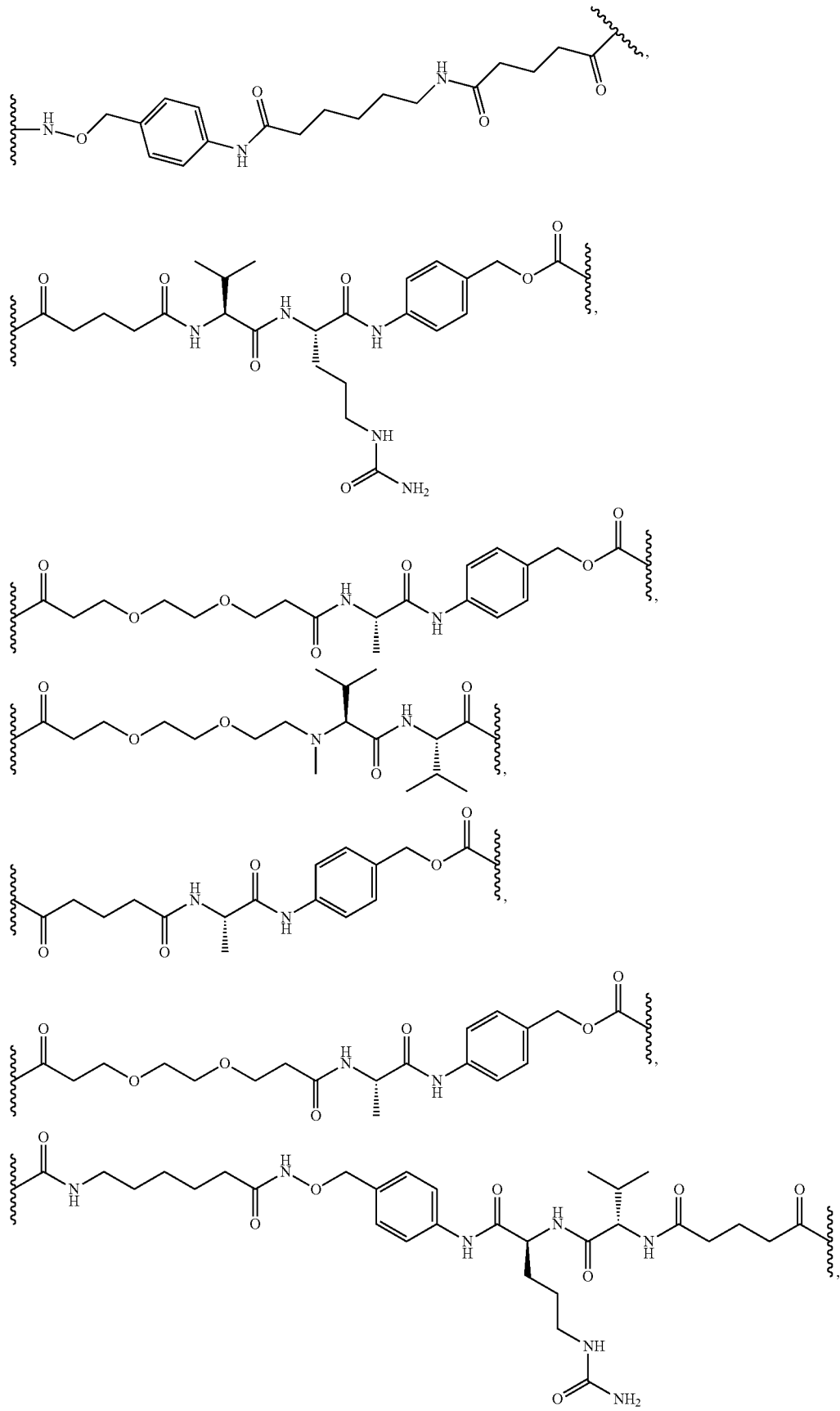

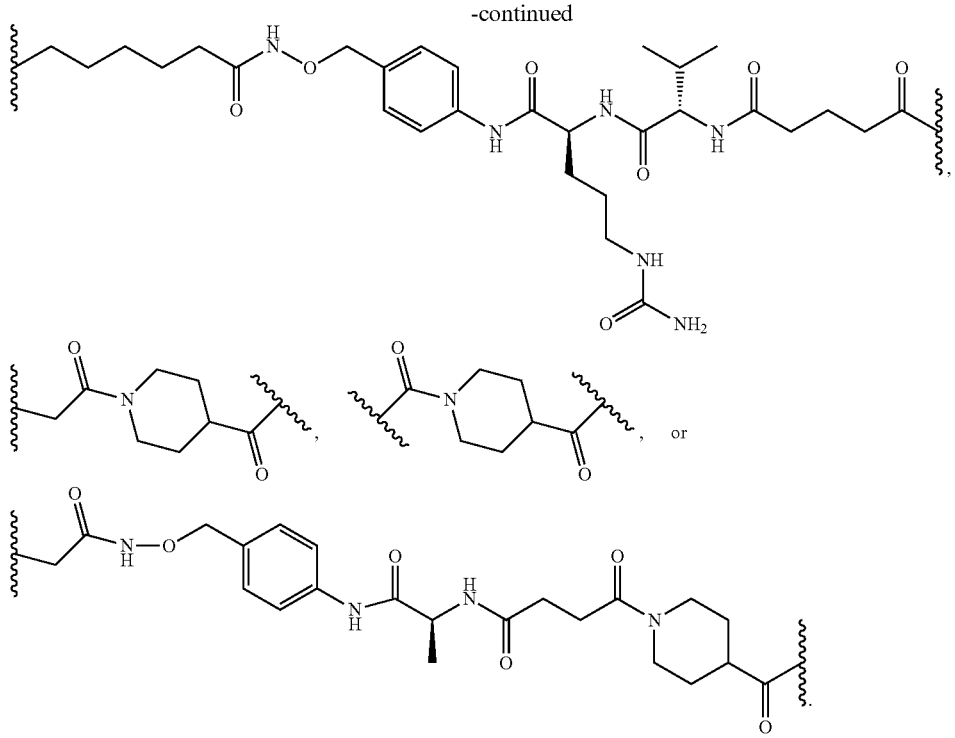

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

While the above-defined categories have been exemplified in terms of the genetically encoded amino acids, the amino acid substitutions need not be, and in certain embodiments preferably are not, restricted to the genetically encoded amino acids. In some embodiments, the active agent-conjugate may contain genetically non-encoded amino acids. Thus, in addition to the naturally occurring genetically encoded amino acids, amino acid residues in the active agent-conjugate may be substituted with naturally occurring non-encoded amino acids and synthetic amino acids.

Certain commonly encountered amino acids which provide useful substitutions for the active agent-conjugates include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-phenylphenylalanine, 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

Other amino acid residues not specifically mentioned herein can be readily categorized based on their observed physical and chemical properties in light of the definitions provided herein.

The classifications of the genetically encoded and common non-encoded amino acids according to the categories defined above are summarized in Table 2, below. It is to be understood that Table 2 is for illustrative purposes only and does not purport to be an exhaustive list of amino acid residues and derivatives that can be used to substitute the active agent-conjugate described herein.

TABLE 2

CLASSIFICATIONS OF COMMONLY ENCOUNTERED AMINO ACIDS

| Classification | Genetically Encoded | Non-Genetically Encoded |
|---|---|---|
| Hydrophobic | | |
| Aromatic | F, Y, W | Phg, Nal, Thi, Tic, Phe (4-Cl), Phe (2-F), Phe (3-F), Phe (4-F), hPhe |
| Nonpolar | L, V, I, M, G, A, P | t-BuA, t-BuG, MeIle, Nle, MeVal, Cha, McGly, Aib |

TABLE 2-continued

CLASSIFICATIONS OF COMMONLY ENCOUNTERED AMINO ACIDS

| Classification | Genetically Encoded | Non-Genetically Encoded |
|---|---|---|
| Aliphatic | A, V, L, I | b-Ala, Dpr, Aib, Ahx, MeGly, t-BuA, t-BuG, MeIle, Cha, Nle, MeVal |
| Hydrophilic | | |
| Acidic | D, E | |
| Basic | H, K, R | Dpr, Orn, hArg, Phe(p-NH$_2$), Dbu, Dab |
| Polar | C, Q, N, S, T | Cit, AcLys, MSO, bAla, hSer |
| Helix-Breaking | P, G | D-Pro and other D-amino acids (in L-peptides) |

Other amino acid residues not specifically mentioned herein can be readily categorized based on their observed physical and chemical properties in light of the definitions provided herein.

While in most instances, the amino acids of the compound-conjugate will be substituted with L-enantiomeric amino acids, the substitutions are not limited to L-enantiomeric amino acids. In some embodiments, the peptides may advantageously be composed of at least one D-enantiomeric amino acid. Peptides containing such D-amino acids are thought to be more stable to degradation in the oral cavity, gut or serum than are peptides composed exclusively of L-amino acids.

Examples of compound-conjugates include, but are not limited to, the following general compounds:

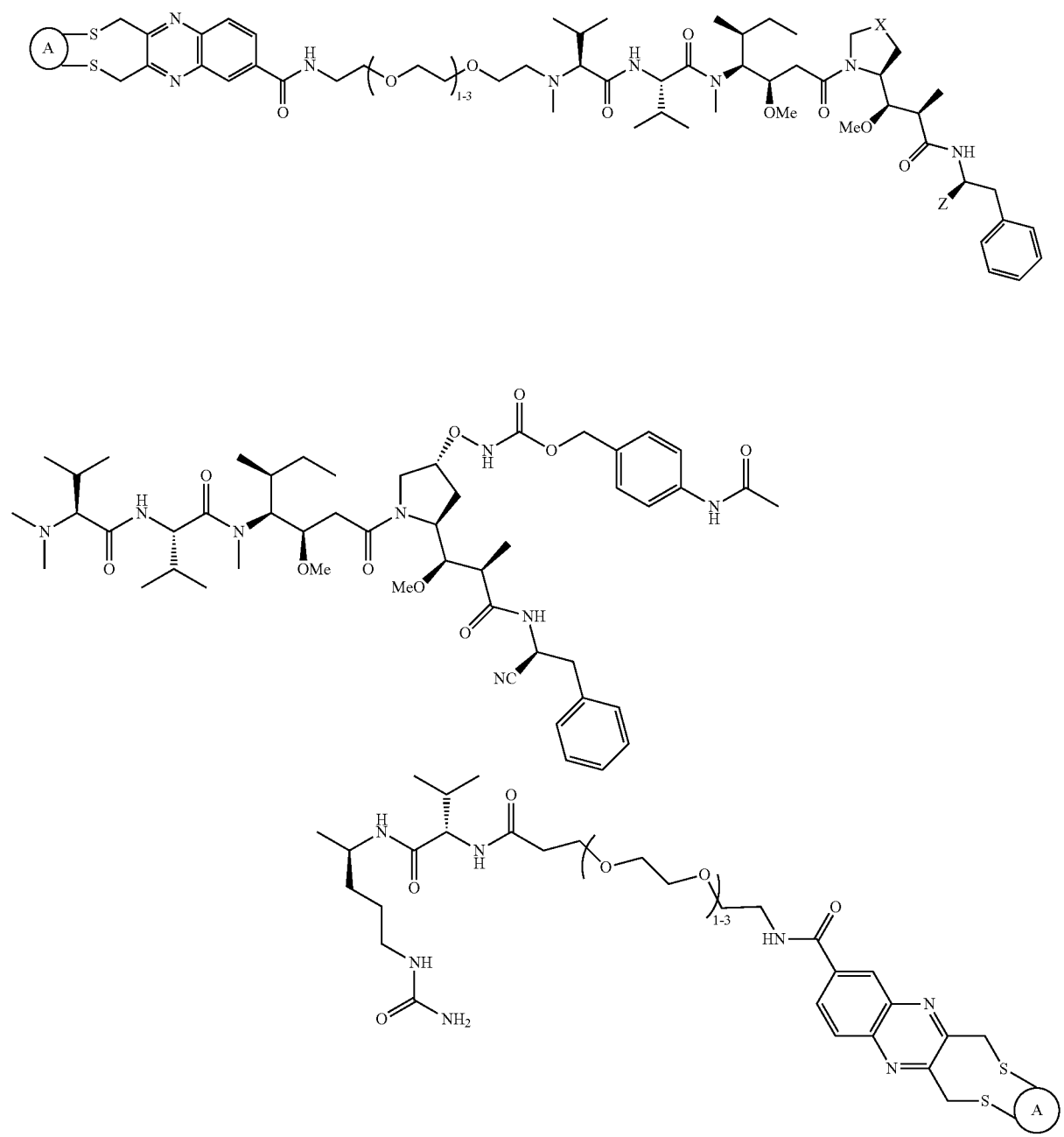

R may be H (hydrogen), $C_1$-$C_8$ alkyl, substituted or cyclic $C_1$-$C_8$ alkyl
X may be S (sulfur), $CH_2$, CH—OH, CH—OR, CH—$ONH_2$, or C=O.
Examples of compounds include, but are not limited to, the following general compounds:
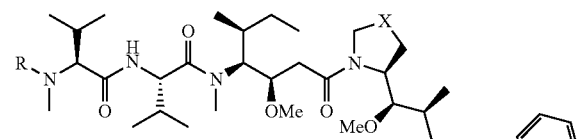
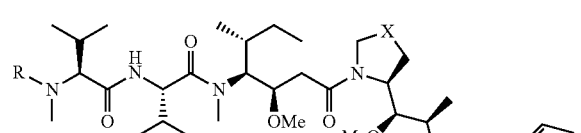
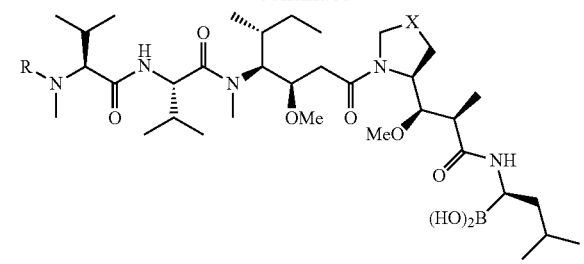
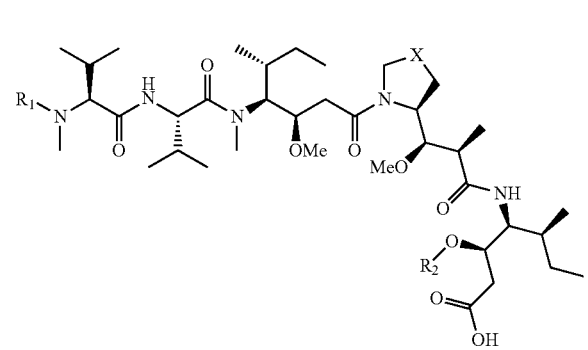
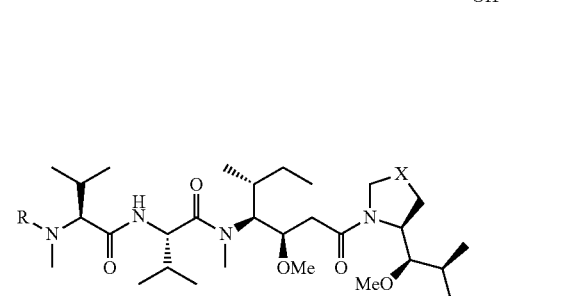
and
Examples of compound-conjugates include, but are not limited to, the following general compounds:

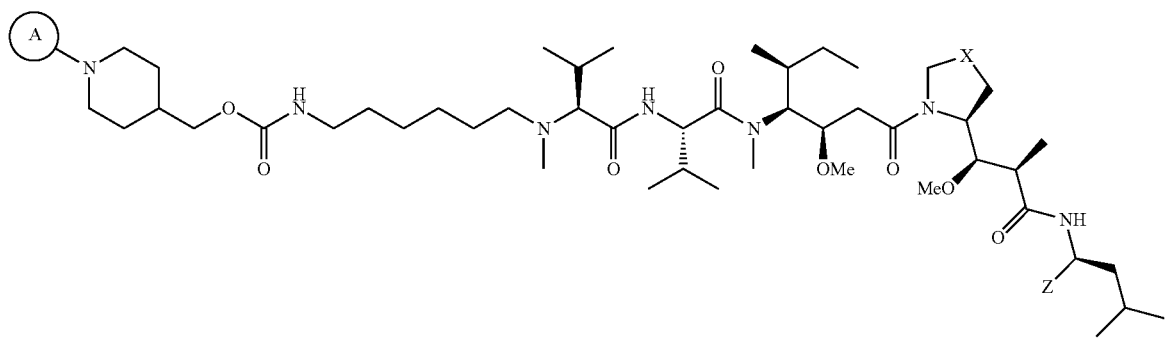
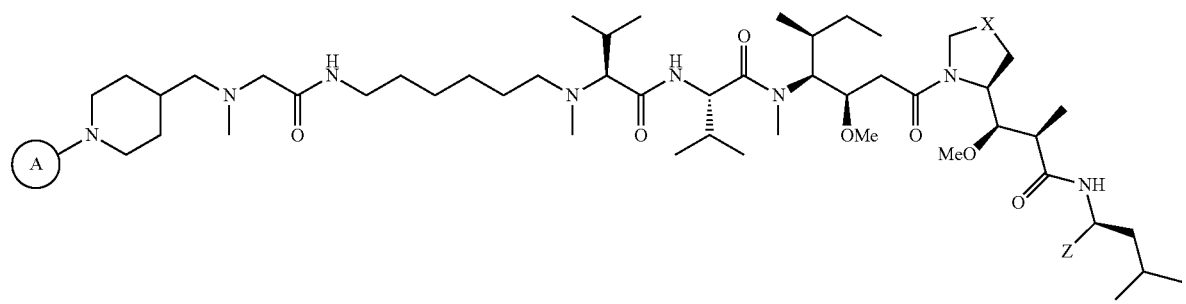
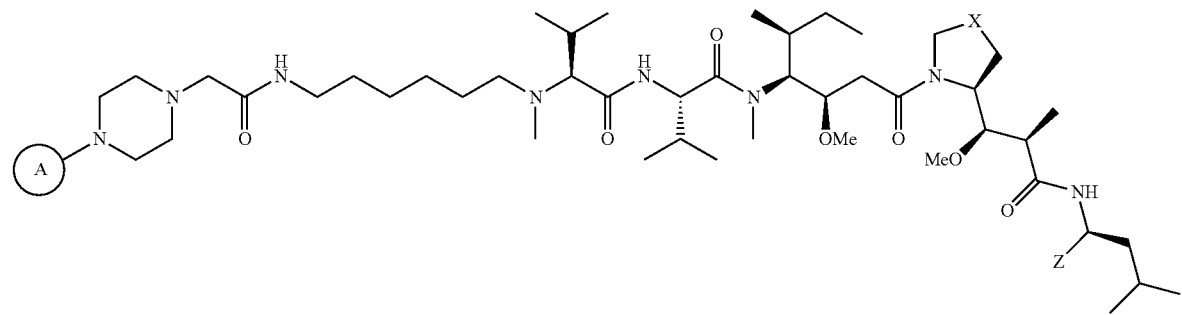
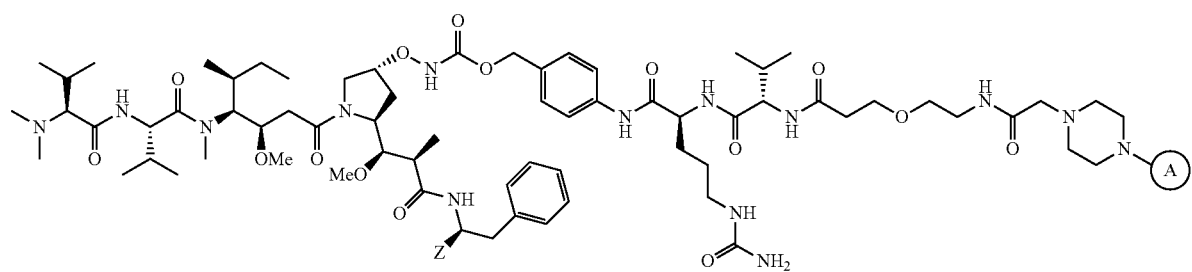

R may be H (hydrogen), $C_1$-$C_8$ alkyl, substituted or cyclic $C_1$-$C_8$ alkyl, and the like X may be S (sulfur), $CH_2$, CH—OH, CH—OR, CH—$ONH_2$, C=O, and the like.

Examples of compounds include, but are not limited to, the following compound and general compounds:

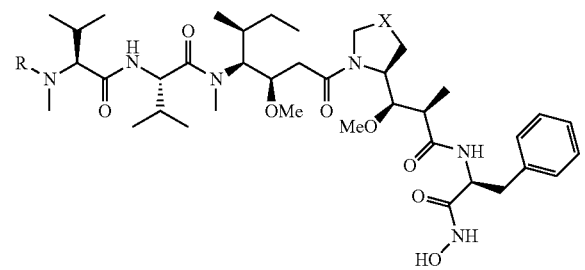

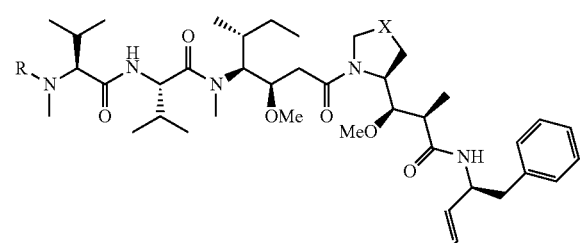

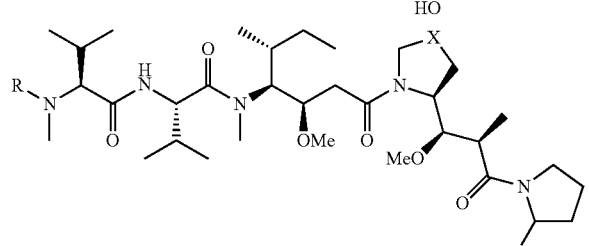

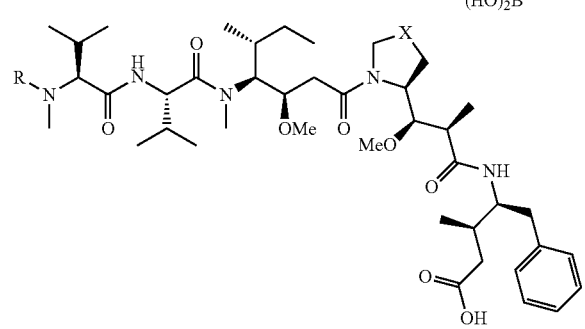

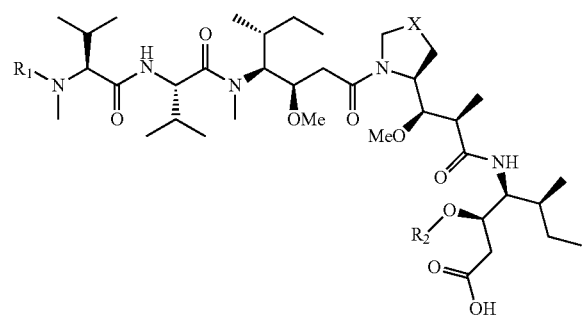

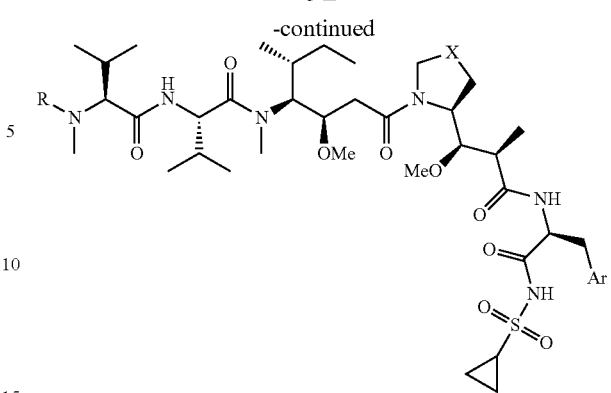

-continued

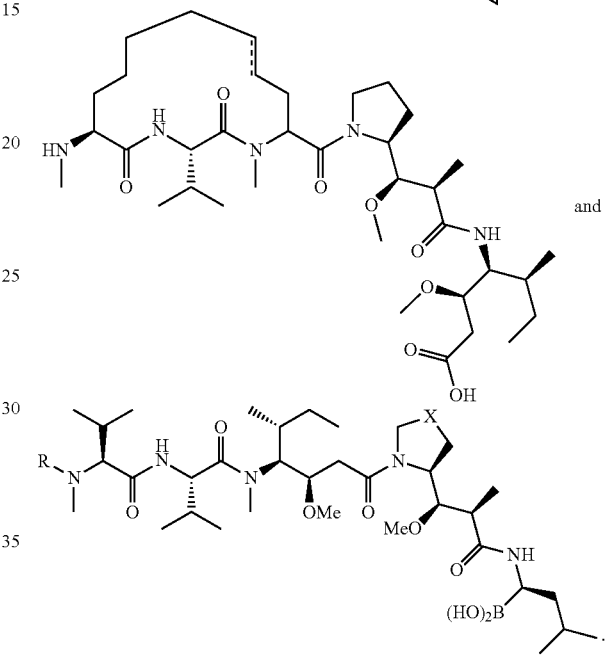

and

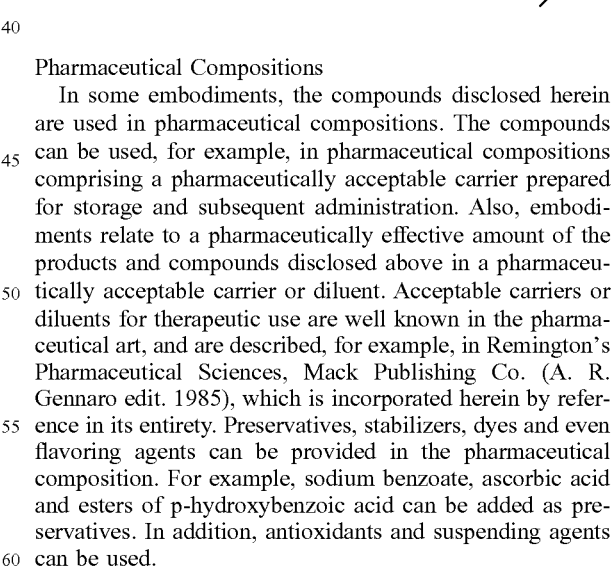

Pharmaceutical Compositions

In some embodiments, the compounds disclosed herein are used in pharmaceutical compositions. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The compositions can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

To formulate the compounds of Formulae I and II as an anti-cancer agent, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

When used as an anti-cancer compound, for example, the compounds of Formulae I and II or compositions including compounds of Formulae I and II can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer agent can be mixed with additional substances to enhance their effectiveness.

Methods of Administration

In an alternative embodiment, the disclosed compounds and the disclosed pharmaceutical compositions are administered by a particular method as an anti-cancer, or anti-inflammatory. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed compounds and pharmaceutical compositions including modes of administration through intraocular, intranasal, and intraauricular pathways.

The pharmaceutically effective amount of the compositions that include the described compounds required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. In a typical embodiment, a compound represented by Formulae I and II can be administered to a patient in need of an anti-cancer agent, until the need is effectively reduced or preferably removed.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages can be between about 10 mg/kg and 100 mg/kg body weight, preferably between about 100 mg/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

As will be understood by one of skill in the art, "need" is not an absolute term and merely implies that the patient can benefit from the treatment of the anti-cancer agent in use. By "patient" what is meant is an organism that can benefit by the use of an anti-cancer agent.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

In one embodiment, a described compound, preferably a compound having any one of Formulas I and II, including those as described herein, is considered an effective anti-cancer agent if the compound can influence 10% of the cancer cells, for example. In a more preferred embodiment, the compound is effective if it can influence 10 to 50% of the cancer cells. In an even more preferred embodiment, the compound is effective if it can influence 50-80% of the cancer cells. In an even more preferred embodiment, the compound is effective if it can influence 80-95% of the cancer cells. In an even more preferred embodiment, the compound is effective if it can influence 95-99% of the cancer cells. "Influence" is defined by the mechanism of action for each compound.

EXAMPLES

General Synthetic Procedures

General Procedure A—HATU Mediated Amide Bond Formation

To an acid (1.1 eq with respect to amine) in anhydrous DMF was added HATU (1 eq with respect to acid) and DIEA (2 eq with respect to acid) and the mixture was stirred at room temperature for 1 minute. The mixture was then added to a solution of amine in DMF and the reaction mixture was stirred at room temperature till the completion of the reaction (monitored by LC/MS). The solvent was removed under reduced pressure and the residue was optionally purified by reverse phase HPLC to give final pure product.

General Procedure B—DIC/HOAt Mediated Amide Bond Formation

To a stirred solution of carboxylic acid (1.1 eq), amine and HOAt (1.1 eq) in anhydrous DMF was added DIC (1.1 eq) and the reaction mixture was stirred at room temperature. Upon completion (monitored by LC/MS), the solvent was removed under reduced pressure and the residue was optionally purified by reverse phase HPLC to give final pure product.

General Procedure C—Removal of Acid Sensitive Protecting Groups (Boc, THP, t-Bu) Using HCl/Dioxane The acid sensitive protecting groups containing compound was dissolved in 4N HCl/dioxane and the mixture was stirred at room temperature for 2 h. The solution was then concentrated under reduced pressure and the residue was washed twice with cold ether. Purification was carried out on reverse phase HPLC if necessary.

General Procedure D—Removal of Fmoc Group

The Fmoc containing compound was dissolved in 2-5% piperidine in DMF. The mixture was stirred at room temperature for 1 h. The solvents were removed under reduced pressure. Purification was carried out on reverse phase HPLC if necessary.

General Procedure E—Reductive Alkylation

An amine was dissolved in DMF and aldehyde (5 eq) was added, followed by addition of sodium cyanoborohydride (5 eq). HOAc was added to adjust the pH of the reaction mixture to 4-5. The mixture was stirred at room temperature till completion (1-4 h, monitored by HPLC). Purification was carried out on reverse phase HPLC if necessary.

General Procedure F—Saponification—Removal of Me/et from Esters

To a stirred solution of an ester in MeOH was added 1M aq. solution of LiOH till pH of the mixture was about 13-14 and the reaction mixture was stirred at room temperature till completion (~16 h, monitored by HPLC). Citric acid (~10% aq,) was added to neutralize the reaction and the solvents were removed under reduced pressure. The crude product was optionally purified by RP-HPLC or used directly in the next step.

General Procedure G—Activation of a Hydroxyl/Phenol Group with Bis(p-Nitrophenyl)Carbonate To a stirred solution of an alcohol/phenol in THF/DMF (2/1) was added bis(p-nitrophenyl) carbonate (3-5 eq), followed by DIEA (2-4 eq) and the reaction mixture was stirred at room temperature until most of the starting material was consumed. The progress of the reaction was monitored by LC/MS. The crude product was optionally purified by flash column chromatography or by precipitation and washing.

General Procedure H—Reaction of an Amine with a Cyclic Anhydride (Glutaric Anhydride or Succinic Anhydride)

An amine containing compound was dissolved in DMF. Glutaric anhydride (3 eq) was added, followed by addition of DIEA (4 eq). The reaction mixture was stirred at room temperature until most of the starting material was consumed. The progress of the reaction was monitored by LC/MS. The crude product was purified by RP-HPLC to yield the pure carboxylic acid.

General Procedure I—Formation of Carbamate with p-Nitrophenyl Carbonate (e.g. FmocVC-PAB-PNP)

An amine containing compound was dissolved in DMF and alkyl/aryl p-nitrophenyl carbonate (1.5 eq) was added, followed by addition of DIEA (2 eq) and HOBt (cat., 5%). The reaction mixture was stirred at room temperature until most of the amine was consumed. The progress of the reaction was monitored by LC/MS. The crude product was optionally purified by RP-HPLC to yield the pure carbamate.

General Procedure J—Formation of an Activated Ester (e.g. NHS) from an Acid

An acid was dissolved in DCM and DMF was added to aid dissolution if necessary. N-hydroxysuccinimide (1.5 eq) was added, followed by EDC.HCl (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic layer was dried and concentrated to dryness. The crude product was optionally purified by RP-HPLC or silica gel column chromatography.

General Scheme for Active Agent Conjugates Formation
Conjugation Method A. Conjugation on Lys Residues Via an Activated Carboxylic Acid

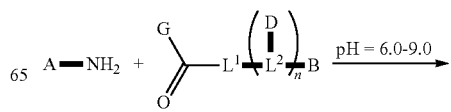

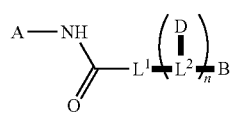

Conjugation Method B. Conjugation on Lys Residues Via Reductive Alkylation with an Dialdehyde

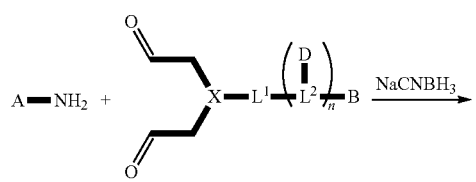

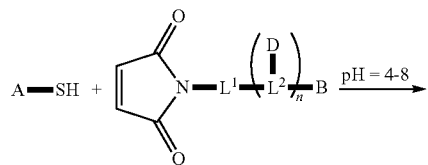

Conjugation Method C. Conjugation on Individual Cys Side Chain Employing Maleimide Chemistry

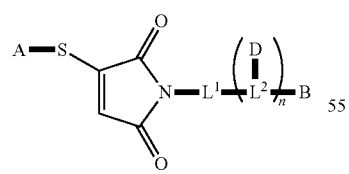

Conjugation Method D. Conjugation on Two Cys Side Chains by Forming a Cyclic Structure

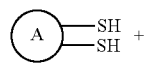

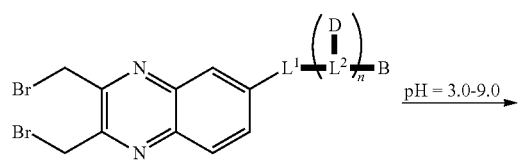

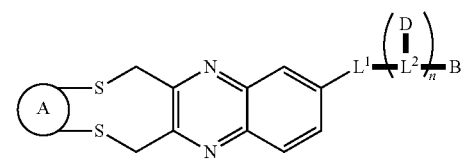

Conjugation Method E. Conjugation on Carbonyl (Ketone/Aldehyde) Bearing Biologics by Formation of an Oxime Moiety

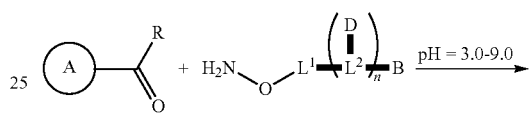

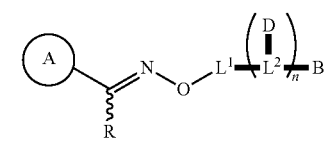

Conjugation Method F. Conjugation on Azide Bearing Biologics Using Copper-Free Click Chemistry:

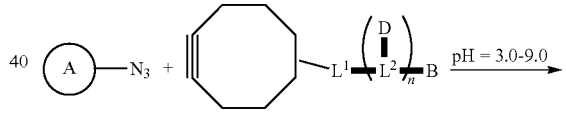

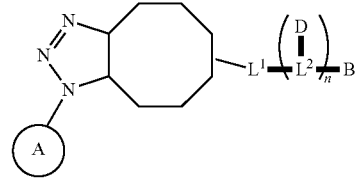

Experimental Description

Step 1. Drug-Linker Construct Synthesis ($-L^2-D$)

Methods of Drug-Linker Construct Synthesis, but not Limited to:

Method 1-1: Linker and Drug Connected Via a Carbamate Bond. The Following General Procedures were Employed:

General Procedure G and I for Activation and Carbamate Formation General Procedure C, D, and F for Removal of Protective Groups for Further Derivatization.

101 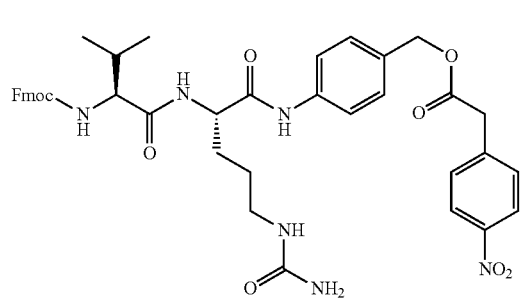 102 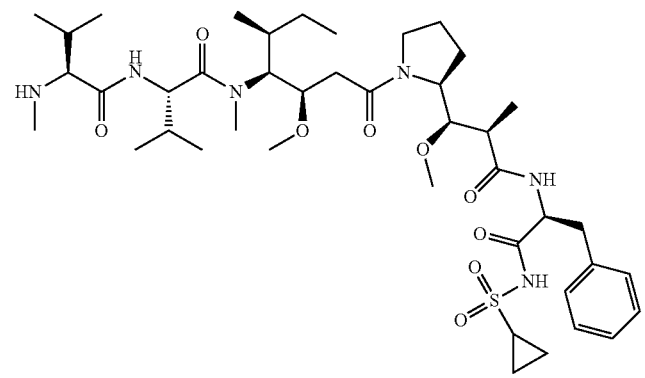
HOBt, DIEA
Piperidine, DMF
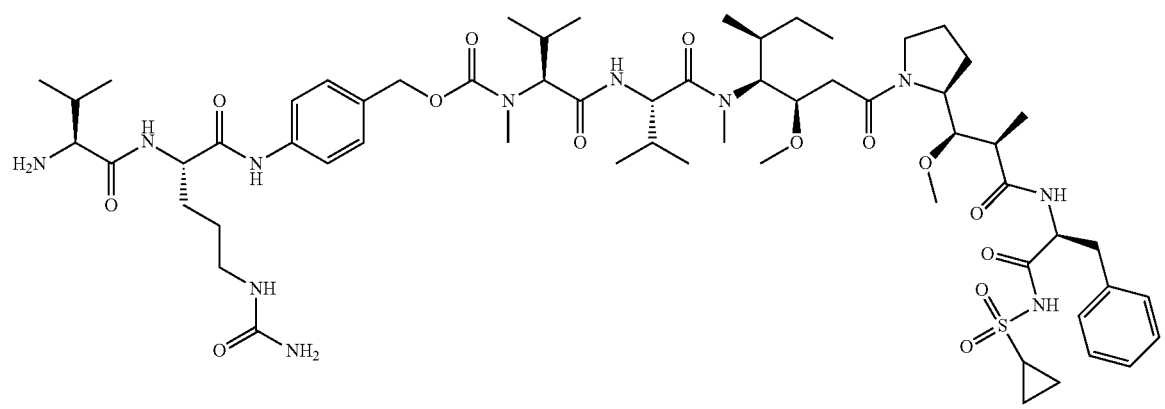
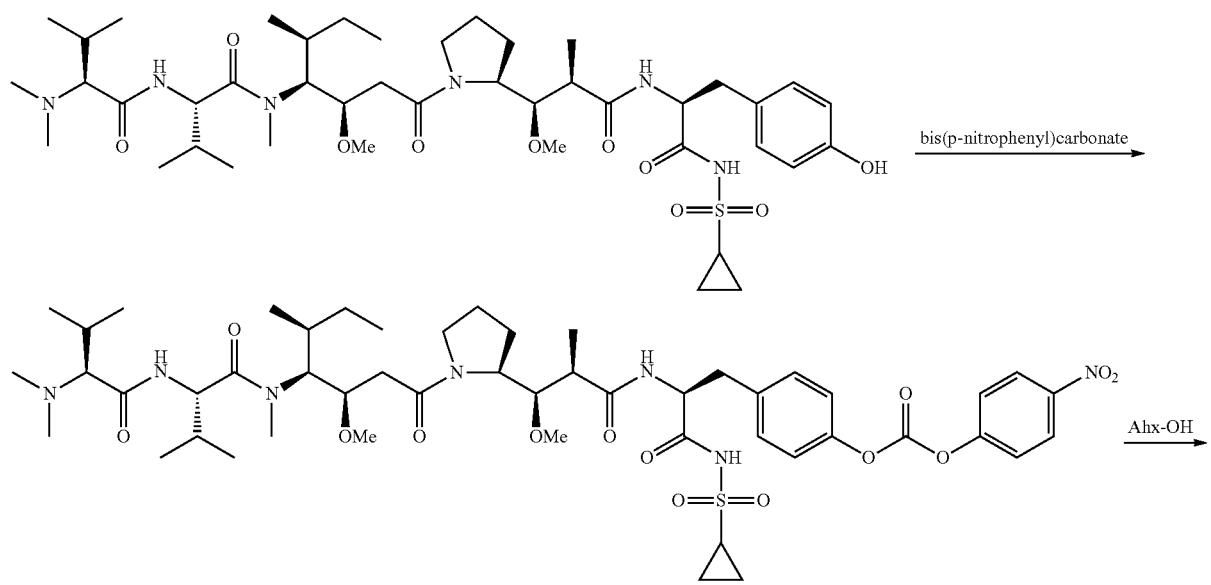
bis(p-nitrophenyl)carbonate
Ahx-OH

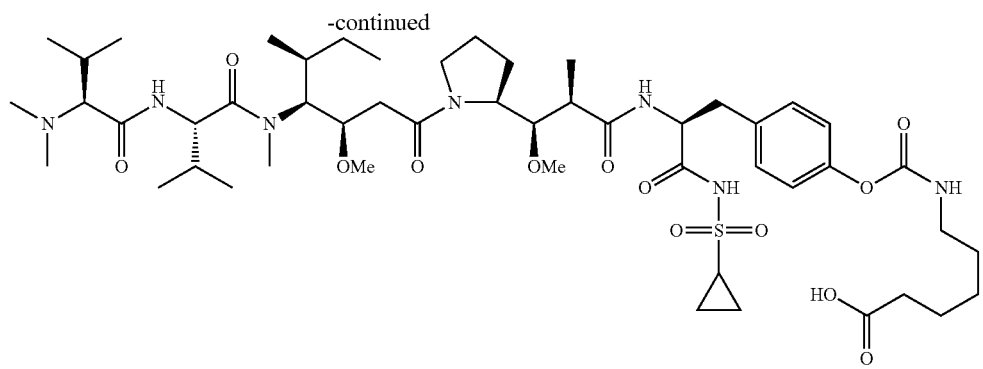
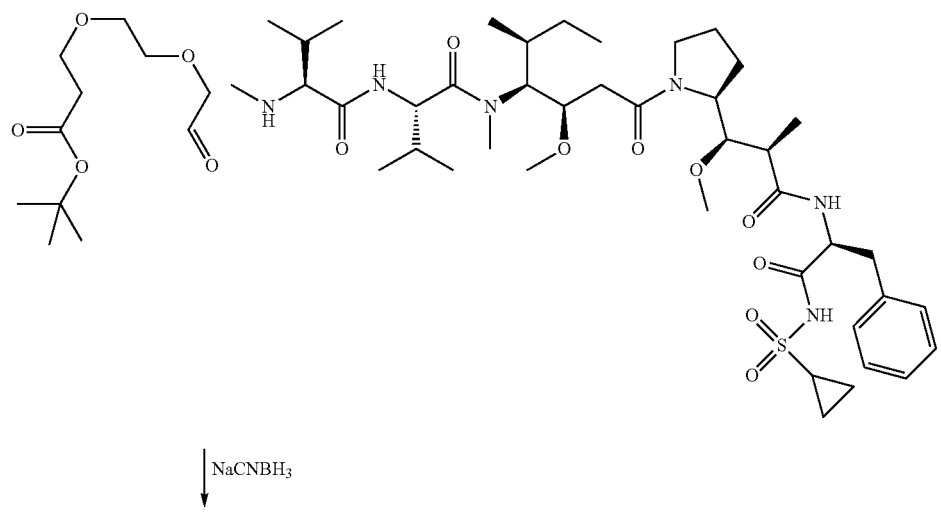
Method 1-2: Linker and Drug Connected Via Reductive Alkylation (General Procedure E)
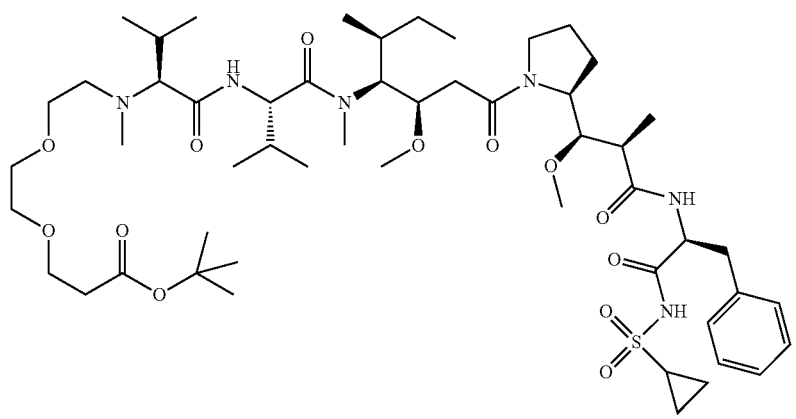

Method 1-3. Active Molecule Containing a Carboxylic Acid Moiety Connected to an Alkoxyamino Linker Via Formation of Hydoxamate (General Procedure A or B), Followed by Removal of Protective Groups.

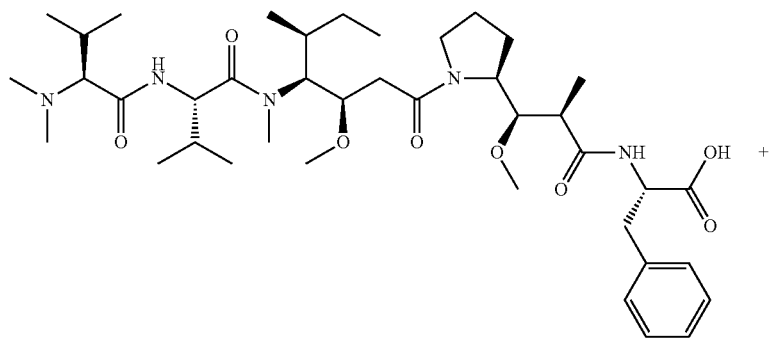

+

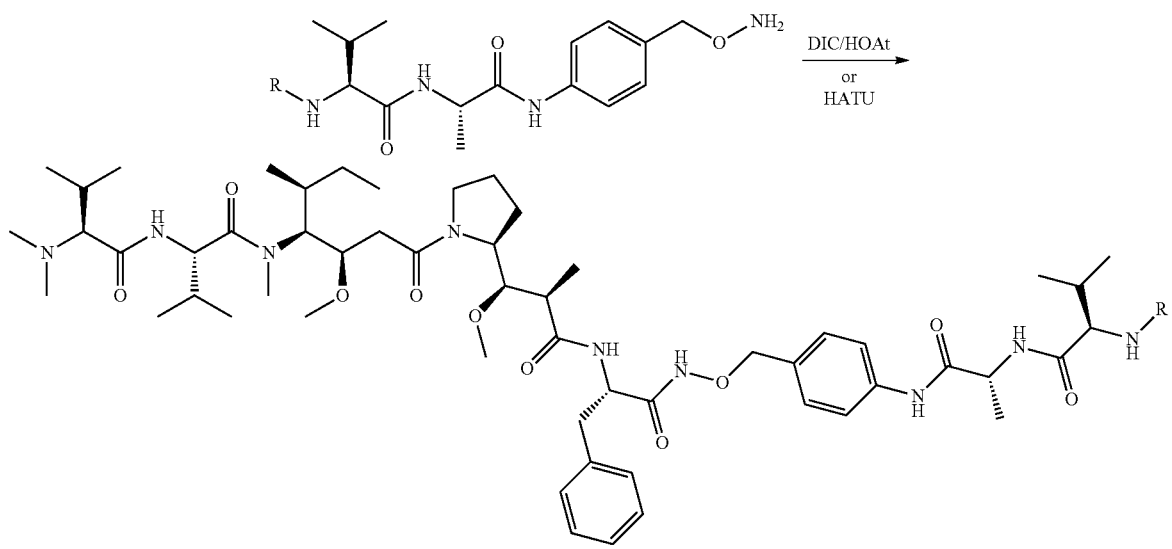

For active molecules that are hydoxamic acids, the above method still can be employed since the construct will release hydroxamic acid under enzymatic cleavage conditions. The reaction needs to start from its corresponding carboxylic acid.

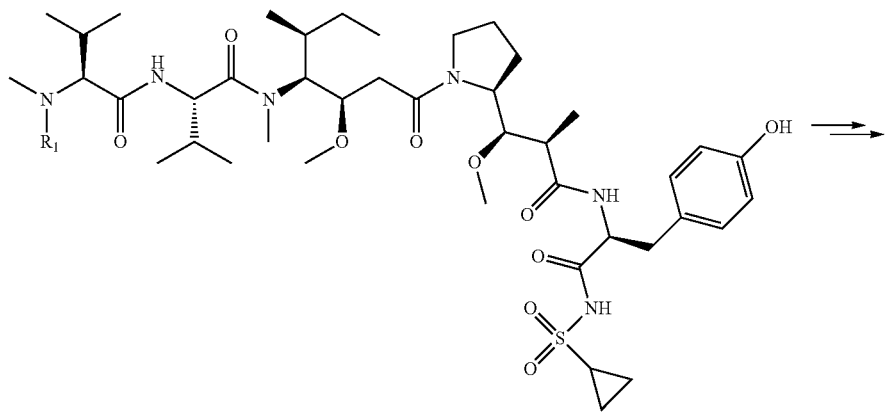

-continued
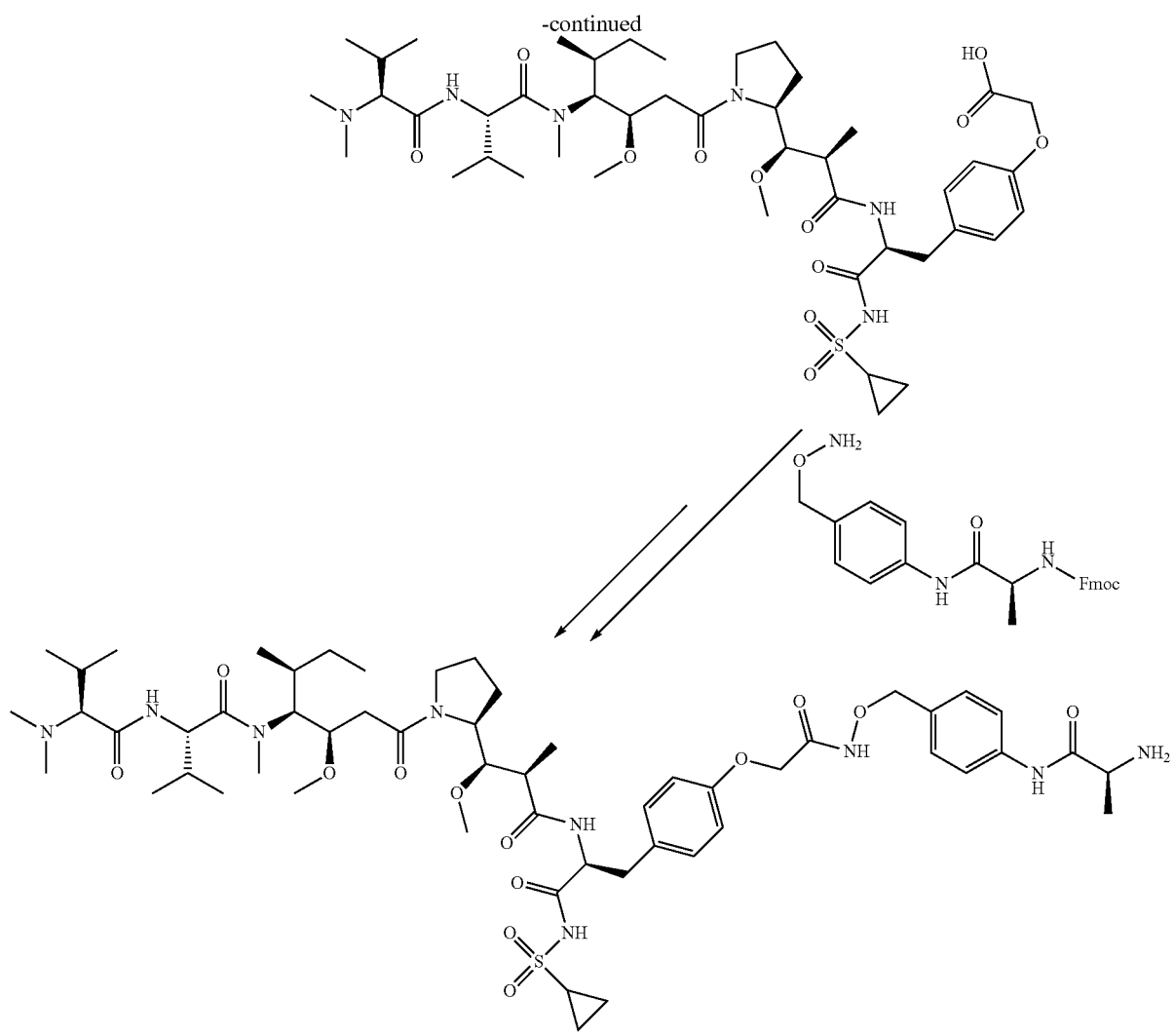
Step 2. Introducing Functional Groups to L1-(L2-D)
Methods to Introduce Functional Groups that Suitable for Conjugation Reaction, but No Limited to:
Method 2-1. Compounds Bearing Free Amino Group to React with an Cyclic Anhydride to Introduce Carboxylic Acid (General Procedure H).
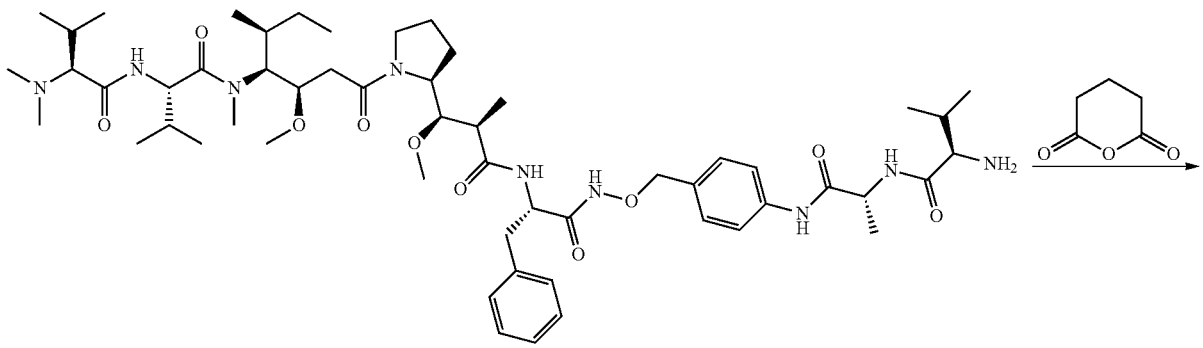

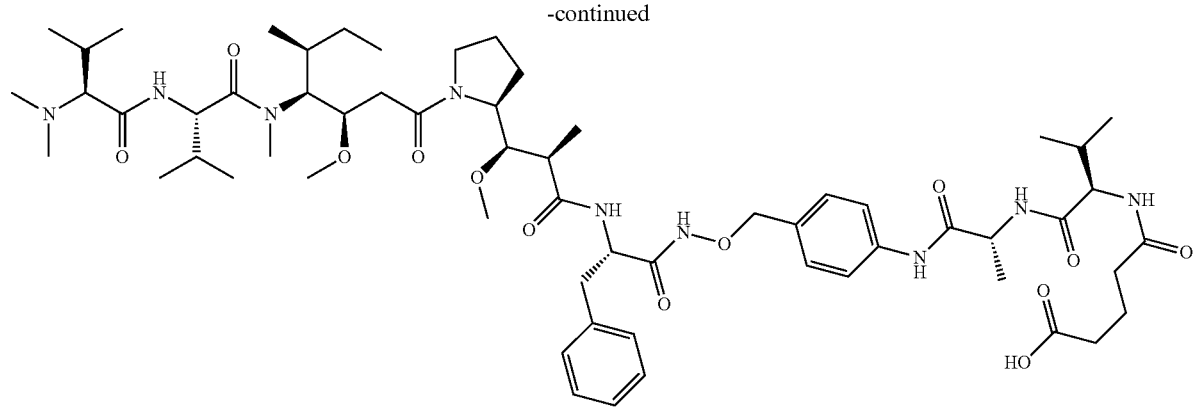
Method 2-2. Compounds Bearing Free Amino Group to React with a Di-Acid to Introduce Carboxylic Acid (General Procedure B).
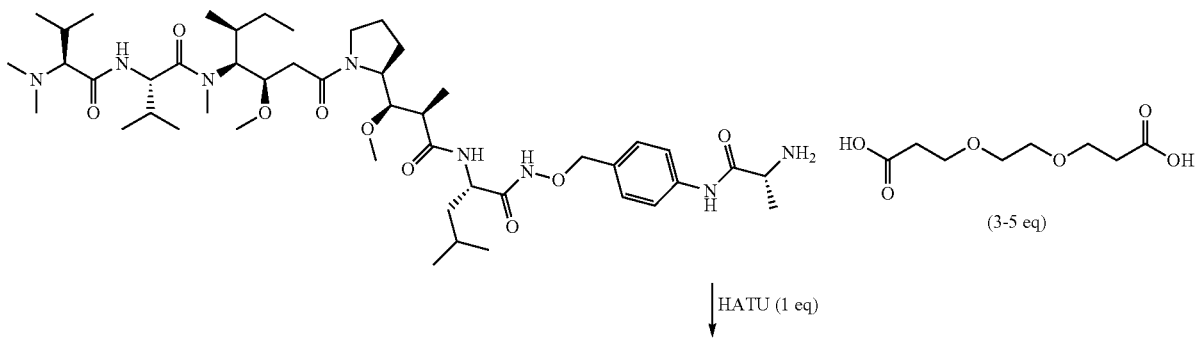
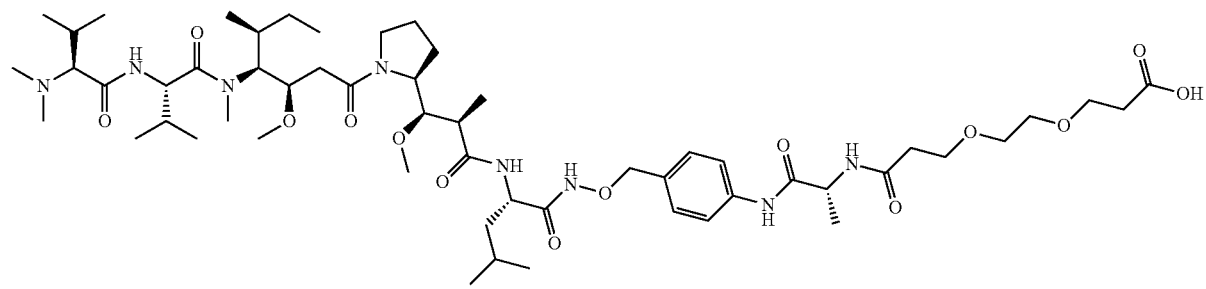

Method 2-3. Removal of Carboxylic Acid Protective Group to Reveal the Free Carboxylic Acid (General Procedure C, F)

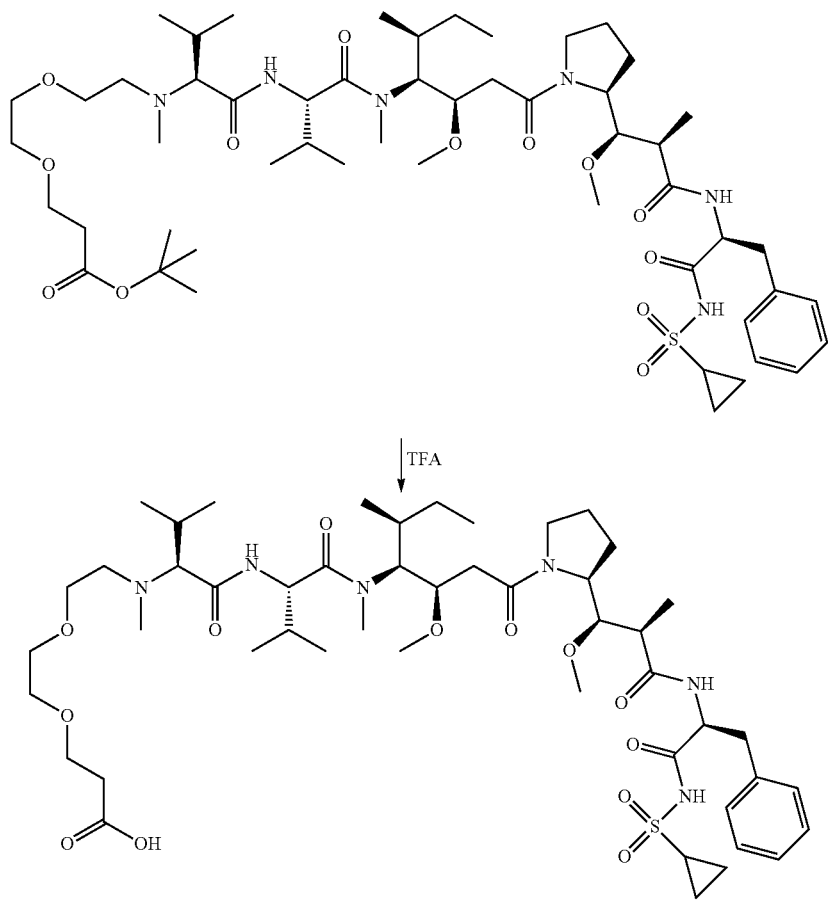 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)CCOCCOCCC(=O)OC(C)(C)C)C(C)C ; CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)CCOCCOCCC(=O)O)C(C)C]

Method 2-4. Reductive Alkylation of a Primary Amine with a Dialdehyde Bearing a Carboxylic Acid Moiety (General Procedure E)

The amine (NH$_2$-Ahx-Maytansinol) (20 mg) was dissolved in acetonitrile (2 mL) and 1 mL of NaOAc buffer (100 mM, pH=4.0) was added. The dialdehyde (0.5 M solution in water, 0.2 mL) was added, followed by NaCNBH$_3$ (10 mg). The reaction mixture was stirred at room temperature for 30 mins and purified directly by RP-HPLC to give the desired acid (16 mg) as a white solid after lyophilization. MS found: 790.5 (M+H)$^+$.

The dialdehyde carboxylic acid was synthesized according to the following scheme:

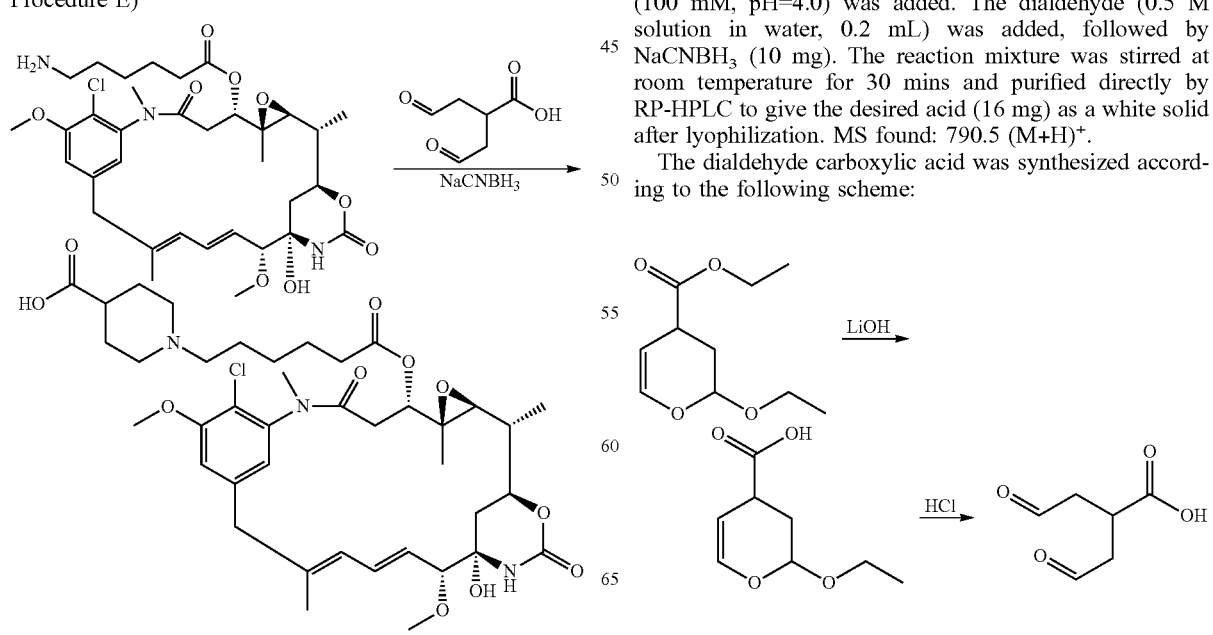

The ester, 2H-Pyran-4-carboxylic acid, 2-ethoxyl-3,4-dihydro-ethyl ester was synthesized according to a literature procedure (*Chem Communications*, (1) 25-26, 1998) was saponified using General procedure F, followed by treatment with 1N aq. HCl at room temperature for 1 h. The aq. solution of dialdehyde was used directly without further purification.

Method 2-5. Introduction of o-Phenylenediamine Moiety

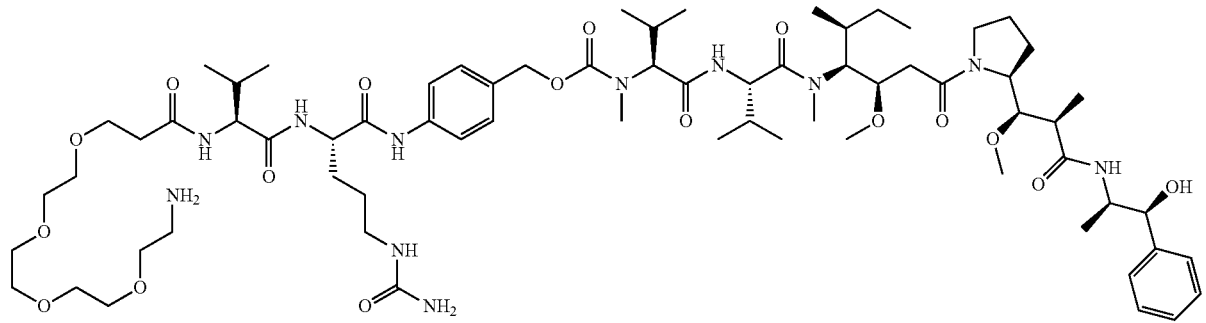

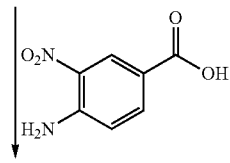

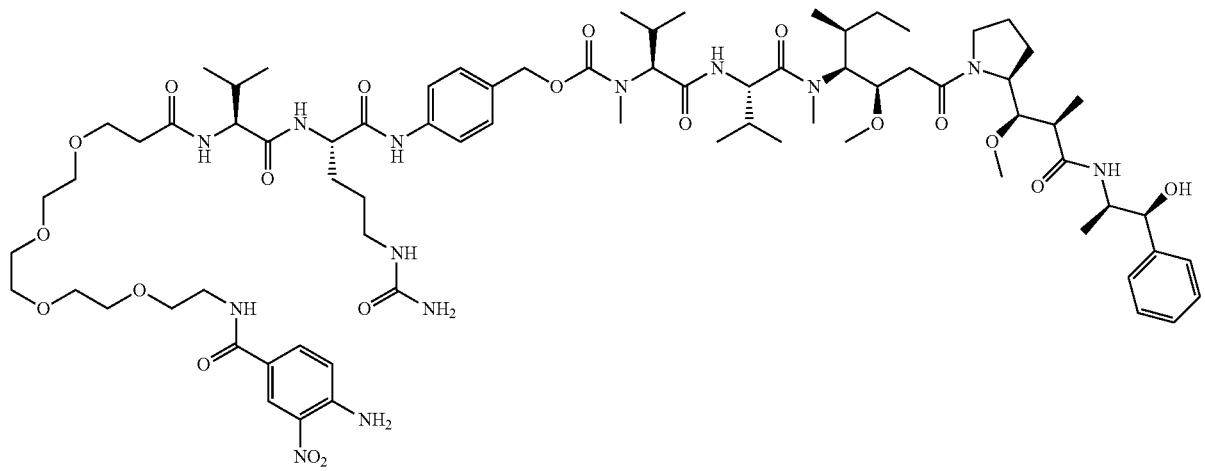

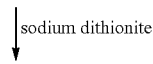

-continued

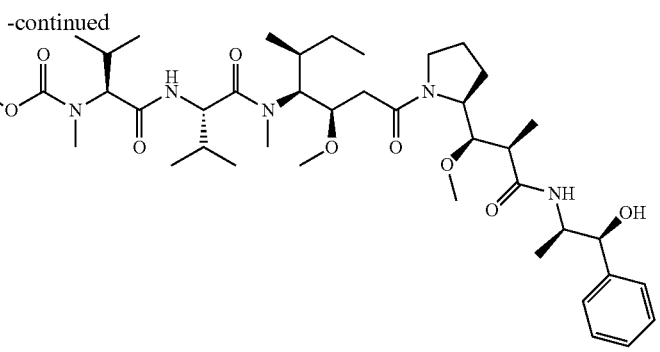
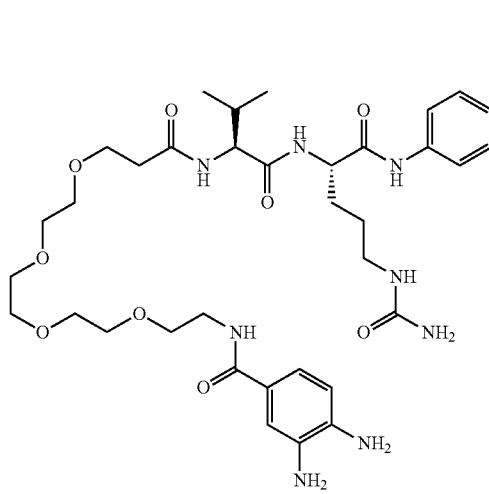

The 3-nitro-4-amino benzoic acid was incorporated using standard amidation reaction (General procedure B). The nitro group was reduced using sodium dithionite (3 eq) in acetonitrile/water to give the desired o-phenylene diamine. MS found: 1504.8 (M+H)$^+$.

Step 3. Introducing the Final Functional Groups Prior to Conjugation

Methods of Introduction of Final Reactive Group Prior to Conjugation Reaction, but not Limited to Method 3-1. Activation of a Carboxylic Acid to its Corresponding Activated Form

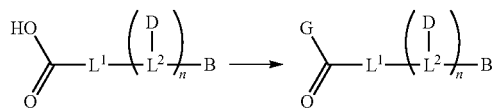

G is a leaving group selected from —F, —Cl, —Br, —I, —N$_3$, —OR (R=alkyl, aryl, heteroaryl, substituted aryl, substituted heteroaryl), SR (R=alkyl, aryl heteroaryl, substituted aryl, substituted heteroaryl), —ON(R$^1$)R$^2$, (R$^1$, R$^2$ are each independently selected from —(C=O)—R, R=H, alkyl, aryl, heteroaryl, substituted aryl, substituted heteroaryl or R$^1$ and R$^2$ are connected to form a cyclic structure, or R$^1$=R$^2$=(=C—R), RC(=O)O—, and RSO$_2$—O— (R=alkyl, aryl, heteroaryl, substituted aryl, substituted heteroaryl).

The carboxylic acid can be activated using a variety of methods to afford an activated form. For example, the carboxylic acid can be activated using the following methods: A) *Tetrahedron* 61 (2005) 10827-10852; B) Beckwith, A. L. J. In The Chemistry of Amides; Zabicky, J., Ed.; Synthesis of Amides; Interscience: London, 1970; pp 105-109; C) Handbook of Reagents for Organic Synthesis: Activating Agents and Protecting Groups; Pearson, A. J., Roush, W. R., Eds.; Wiley: New York, 1999; pp 370-373; D) Lloyd-Williams, P., Albericio, F., and Giralt, E. (1997). Chemical approaches to the synthesis of peptide and proteins (Series ed. C. W. Rees). CRC Press, New York; E) Peptide chemistry: A practical textbook: By M Bodansky. Springer-Verlag, Heidelberg. 1988; and F) The practice of peptide synthesis, 2nd ed., by M. Bodansky and A. Bodansky, Springer-Verlag, New York, each of which is incorporated herein by reference in its entirety.

Method 3-2. Introducing a Maleimido Moiety a. Via Amidation (General Procedure A, or B, or from an Activated Ester Bearing a Maleimido Moiety)

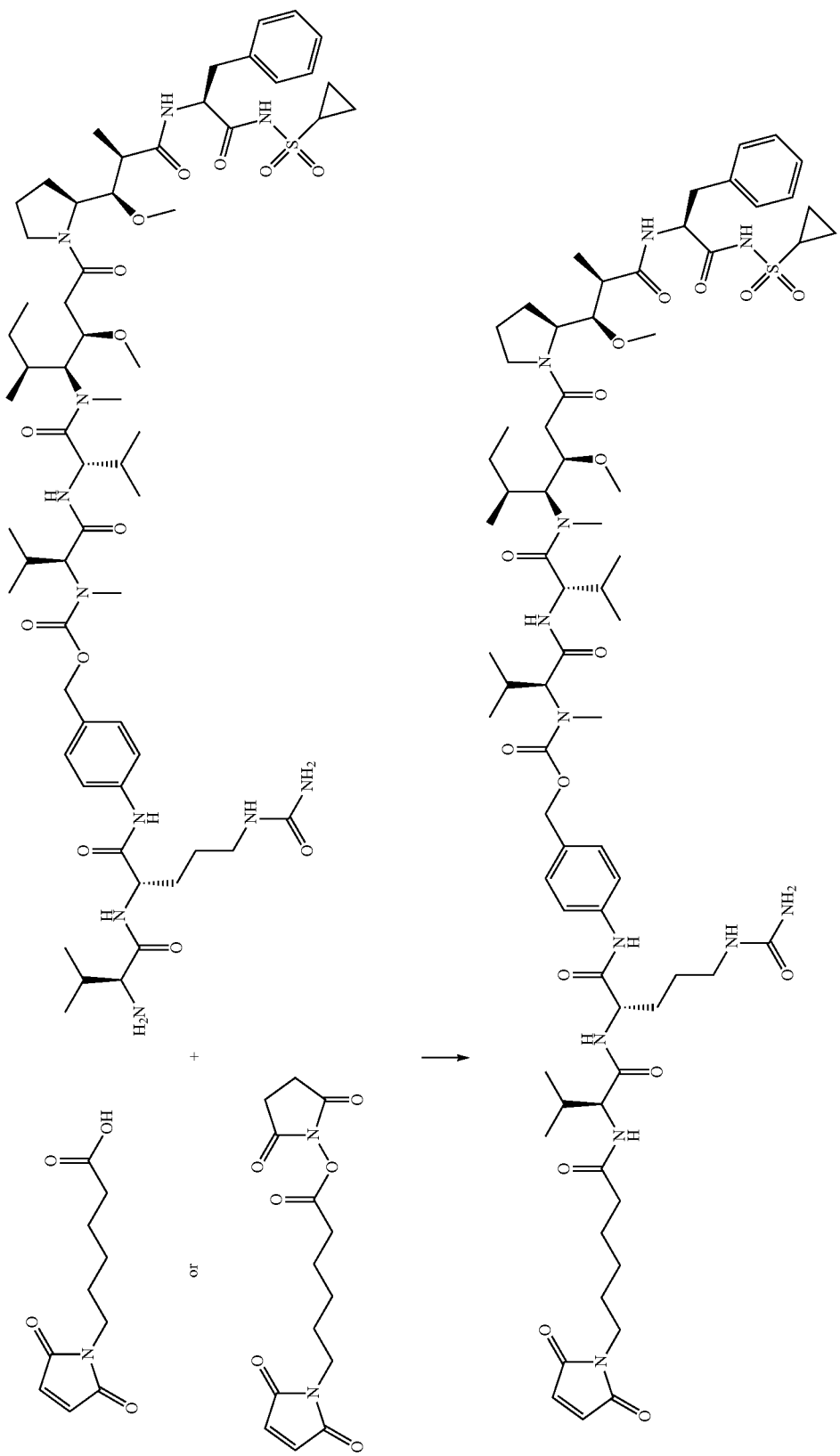

b. Converting an Existing Amino Group to Maleimide Directly Using N-Methoxy-Carbonylmaleimide
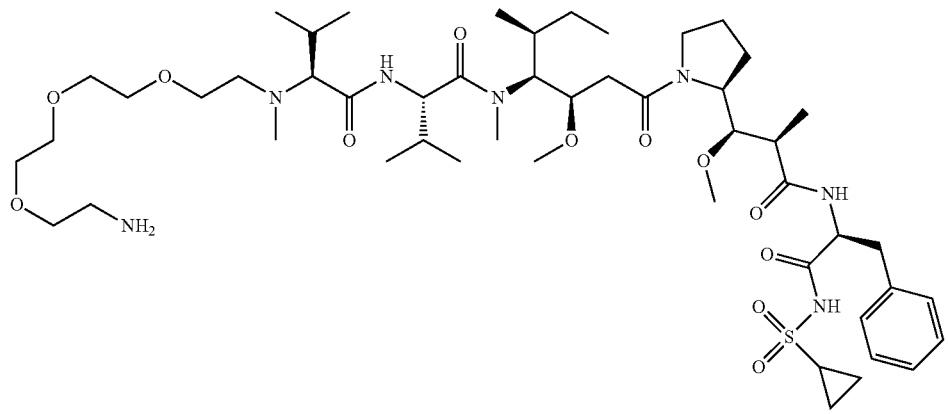
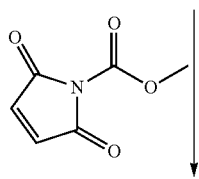
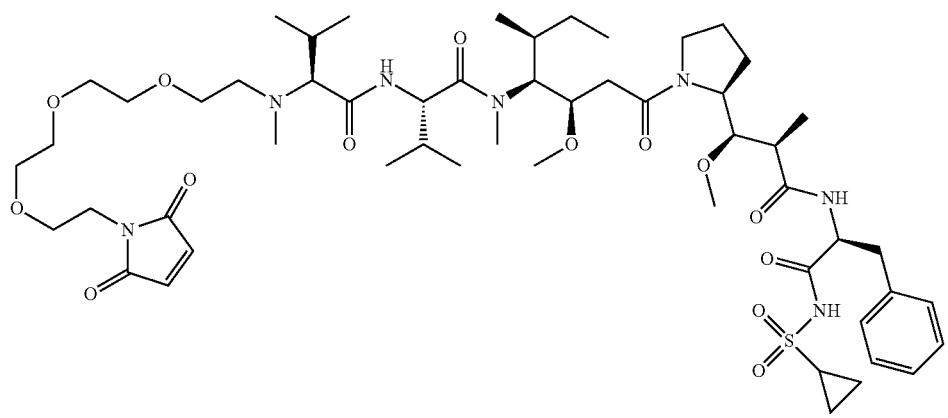

The amine (0.1 mmol) was dissolved in acetonitrile/water (6/4, v/v, 3 mL). The mixture was cooled in an ice-water bath and treated with sat. aq. NaHCO$_3$ (0.5 mL), followed by N-methoxycarbonylmaleimide (0.12 mmol). The mixture was stirred at room temperature for 1 h. The pH was adjusted to 6-7 with citric acid and the solution was concentrated. The residue was purified by RP-HPLC to yield the desired maleimide as a white powder after lyophilization (58%). MS found: 1091.2 (M+H)$^+$.

Method 3-3. Formation of Dibromomethyl Quinoxaline

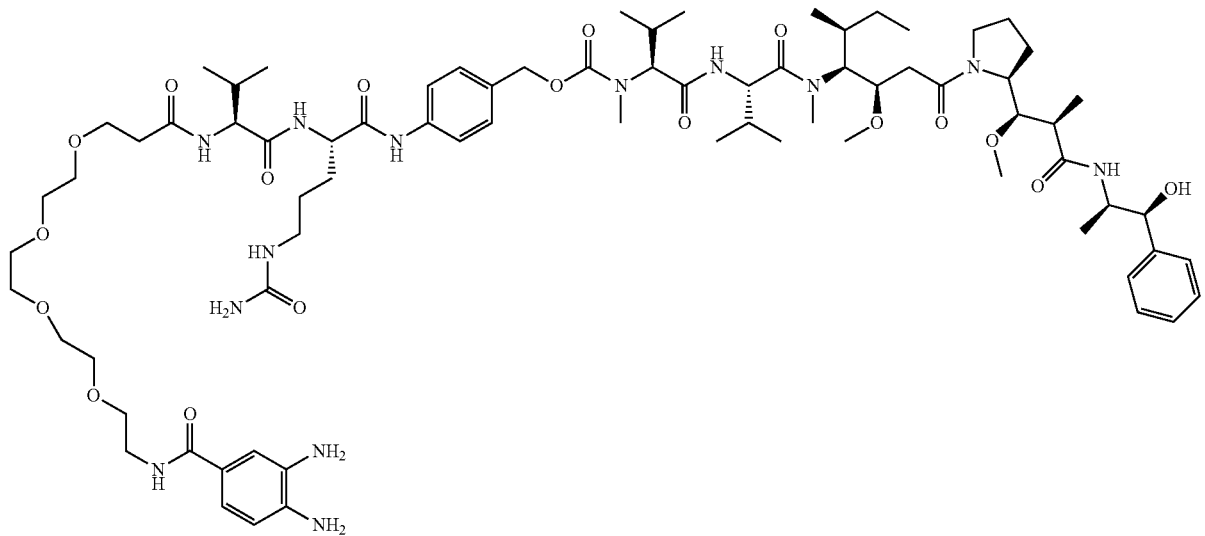

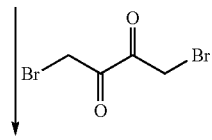

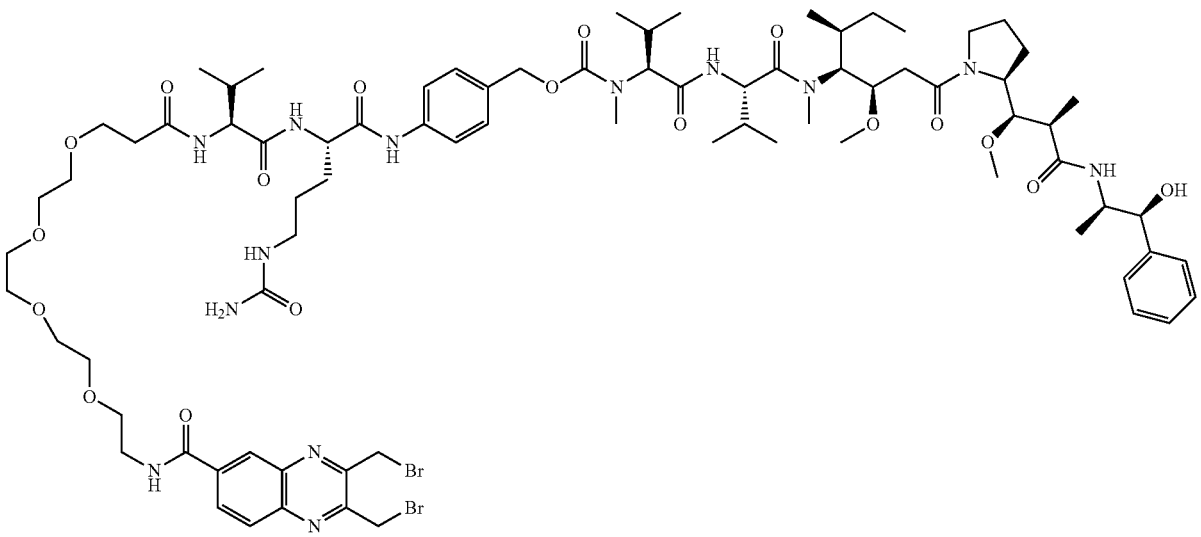

The o-phenylenediamino compound (12 mg) was dissolved in acetonitrile/water. Dibromomethyl diketone (10 mg) was added. The mixture was stirred at room temperature for 10 min and purified directly by RP-HPLC to give the desired quinoxaline as a white powder (12 mg) after lyophilization. MS found 1713.0 (M+H)$^+$.
Method 3-4. Incorporation of Hydroxylamine Moiety
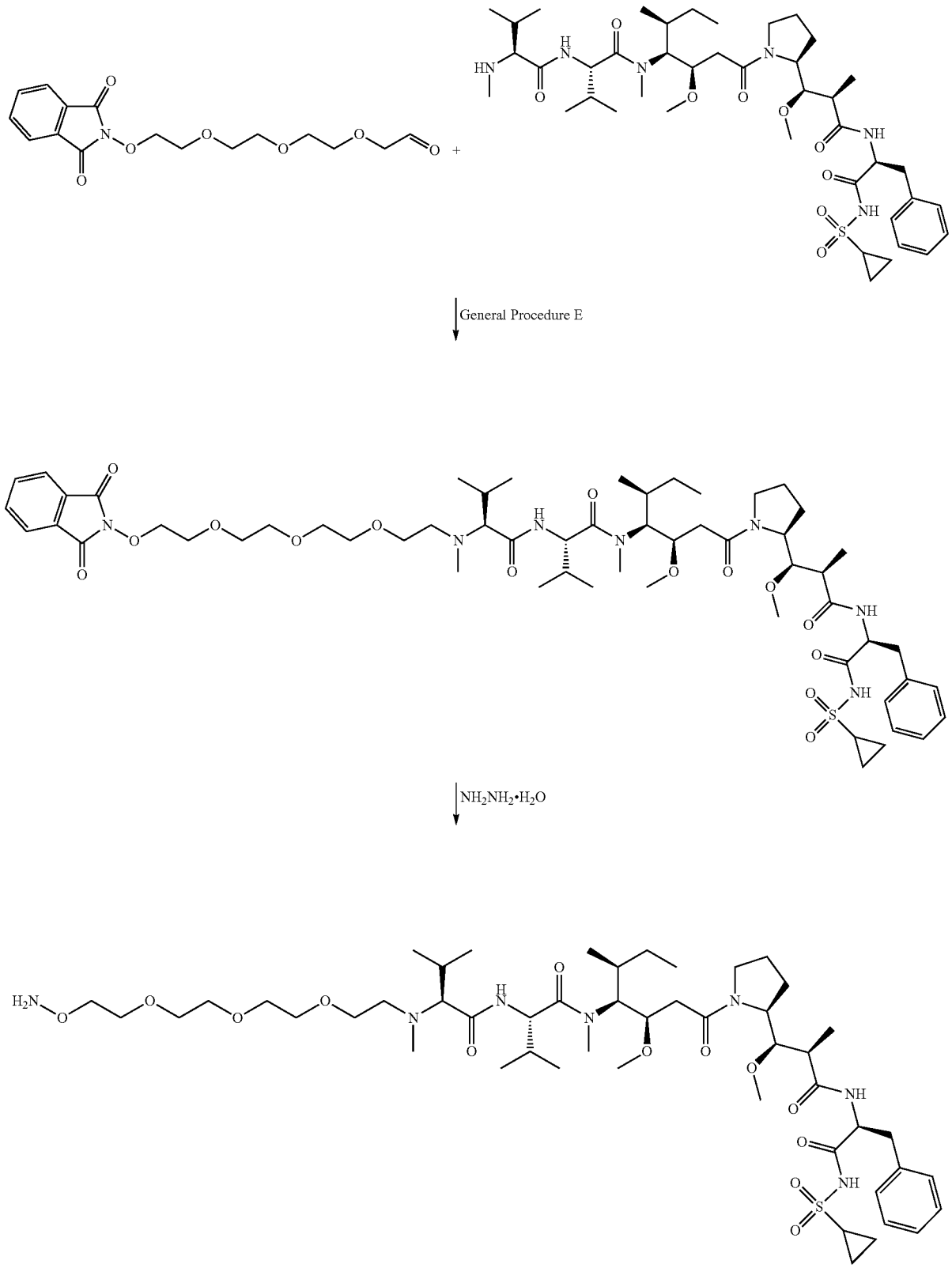

Method 3-5. Introduction of Cyclooctyne Moiety
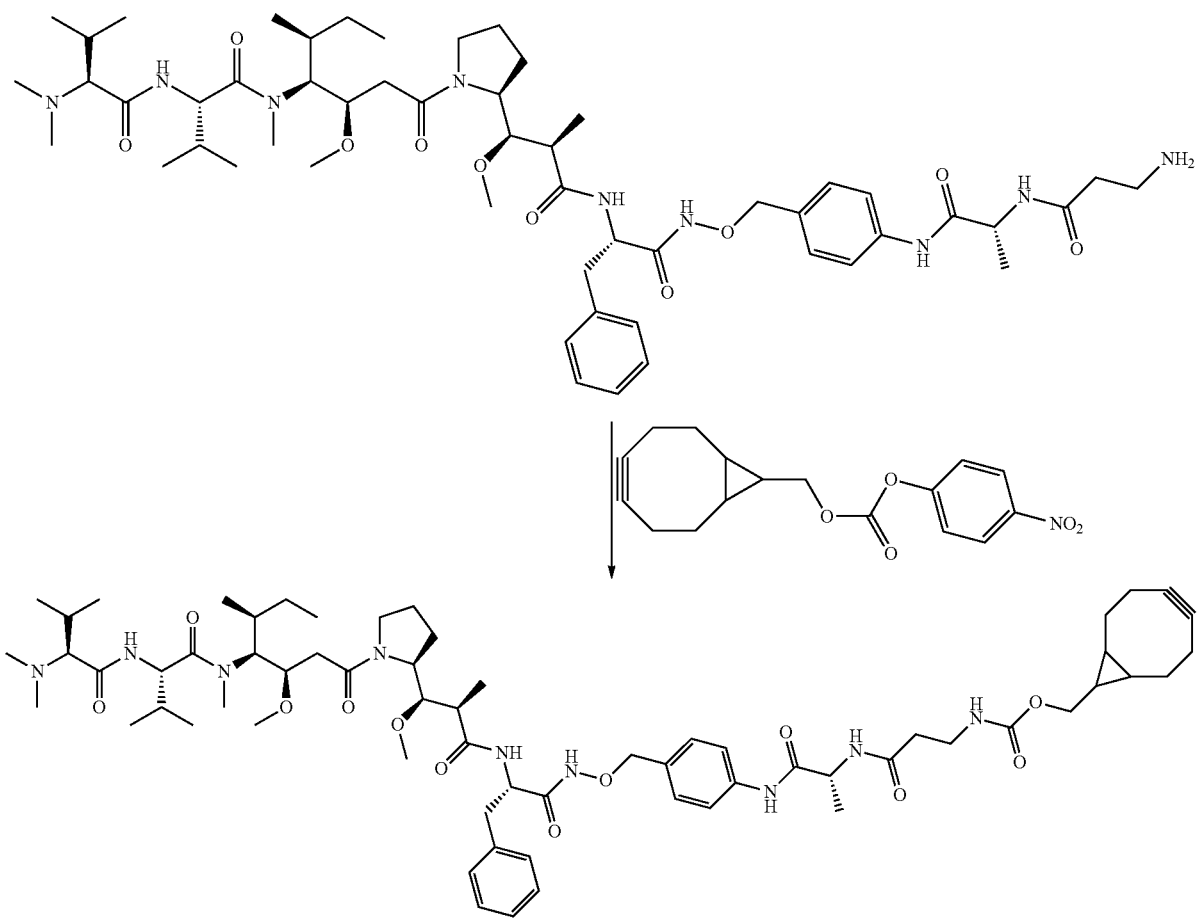
Example I
Synthesis of Compound 10
Scheme I.
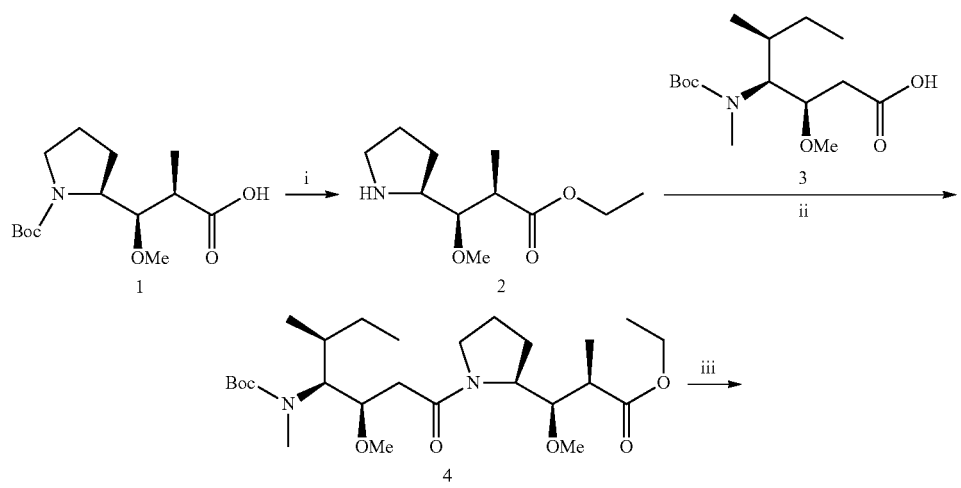

-continued

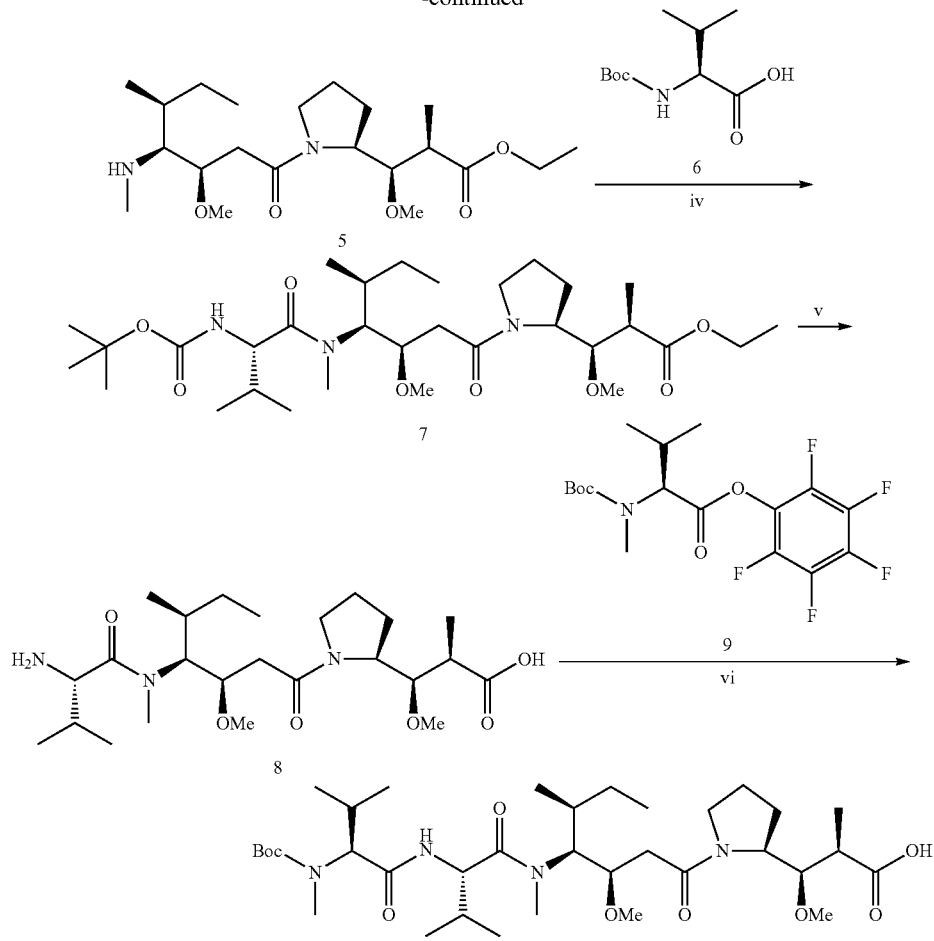

Reagents and conditions:
i. SOCl₂, EtOH;
ii. DEPC, TFA, DCM;
iii. TFA, DCM;
iv. BrOP, DCM, DIEA;
v. TFA, DCM;
vi. DIEA, DCM, HOBt.

To a solution of compound 1 (23.4 g, 81.53 mmol) in dry EtOH (200 mL) was added SOCl₂ (100 mL) at 0° C. The mixture was stirred for overnight and the solvent was removed by evaporation in vacuo. The residue was immediately used for the next step without further purification. To a solution of compound 2 (81.53 mmol), compound 3 (50 g, 163.1 mmol) in dry DMF (150 mL) was added DEPC (15.9 g, 97.8 mmol), TEA (41 g, 0.408 mol) at 0° C. The mixture was stirred for 2 h at 0° C. Then the mixture was stirred overnight at room temperature. Solvent was removed by evaporation in vacuo. The residue was diluted with ethyl acetate-toluene (2:1, 900 ml) and washed with 1M KHSO₄, water, sat. NaHCO₃, and brine. The organic layer was dried and concentrated to give a residue, which was purified by column (hexanes:ethyl acetate:DCM=5:1:1) to give 38 g of compound 4.

To a solution of Boc-Val-OH (30.6 g, 0.142 mol), compound 5 (from 25 g of compound 4) in DCM (400 mL) was added BrOP (28 g, 70.87 mmol), DIEA (30 g, 0.236 mol) at 0° C. The mixture was shielded from light and stirred for 0.5 h at 0° C. Then the mixture was stirred for 48 h at room temperature. The solvent was removed by evaporation in vacuo. The residue was diluted with ethyl acetate-toluene (3:1, 900 mL) and washed with 1M KHSO₄, water, sat. NaHCO₃, and brine. The organic layer was dried and concentrated to give a residue, which was purified by silica gel column (hexanes:ethyl acetate:DCM=3:1:1) to give 22 g of compound 7.

To a solution of compound 7 (40 g, 66.7 mmol) in THF (600 mL) was added a mixture of LiOH (14 g, 0.33 mol) in water (300 mL) below 10° C. The mixture was stirred for 5 days at 25° C. THF was removed by evaporation. The aqueous layer was washed with Et₂O (200 mL×3). The aqueous layer was acidified to pH 2 with 1N HCl at 0° C., the mixture was extracted with ethyl acetate and the organic layer was washed with water and brine. The organic layer was dried and concentrated to give a residue, which was purified by Prep-HPLC to give 14 g of compound 8.

To a solution of compound 8 (3 g) in DCM (100 mL) was added compound 9 (3 g, prepared according to General procedure J from Boc-N-Me-Val-OH using EDC and pentafluorophenol). DIEA (2.6 mL) was added, followed by HOBt (cat. 100 mg) and the reaction mixture was stirred at room temperature for 16 h. The solvents were removed under reduced pressure and the residue was purified on a silica gel column to give compound 10 as a white powder (3.1 g). MS m/z Calcd for $C_{35}H_{64}N_4O_9$ 684.5, Found 707.6 ([M+Na]⁺).

Example II

Preparation of Cytotoxic Compounds—Sulfonamide Derivatives

| ID | Cytotoxic compound (D) | -L1-(L2-D) Synthetic method | Conj. Method | MS found [M + H]$^+$ |
|---|---|---|---|---|
| 13 | | 1-1, 1-2, 2-1, 2-2, 2-3, 2-4, 2-5, 3-1, 3-2, 3-3, 3-4 | A, B, C, D, E, F | 835.6 |
| 14 | | 1-1, 1-2, 2-1, 2-2, 2-3, 2-4, 2-5, 3-1, 3-2, 3-3, 3-4 | A, B, C, D, E, F | 809.6 |
| 16 | | 1-1, 1-2, 2-1, 2-2, 2-3, 2-4, 2-5, 3-1, 3-2, 3-3, 3-4 | A, B, C, D, E, F | 801.7 |

| ID | Cytotoxic compound (D) | -L1-(L2-D) Synthetic method | Conj. Method | MS found [M + H]+ |
|---|---|---|---|---|
| 18 | | 1-1, 1-2, 2-1, 2-2, 2-3, 2-4, 2-5, 3-1, 3-2, 3-3, 3-4 | A, B, C, D, E, F | 836.6 |
| 30 | | 1-1, 1-2, 2-1, 2-2, 2-3, 2-4, 2-5, 3-1, 3-2, 3-3, 3-4 | A, B, C, D, E, F | 827.5 |
| 31 | | 1-1, 1-2, 2-1, 2-2, 2-3, 2-4, 2-5, 3-1, 3-2, 3-3, 3-4 | A, B, C, D, E, F | 807.8 |

-continued

| ID | Cytotoxic compound (D) | -L1-(L2-D) Synthetic method | Conj. Method | MS found [M + H]+ |
|---|---|---|---|---|
| 32 | | 1-1, 1-2, 2-1, 2-2, 2-3, 2-4, 2-5, 3-1, 3-2, 3-3, 3-4 | A, B, C, D, E, F | 793.4 |
| 35 | | 1-1, 1-2, 1-3, 2-1, 2-2, 2-3, 2-4, 2-5, 3-1, 3-2, 3-3, 3-4 | A, B, C, D, E, F | 839.6 |
| 37 | | 1-1, 1-2, 1-3, 2-1, 2-2, 2-3, 2-4, 2-5, 3-1, 3-2, 3-3, 3-4 | A, B, C, D, E, F | 865.7 |

-continued

| ID | Cytotoxic compound (D) | -L1-(L2-D) Synthetic method | Conj. Method | MS found [M + H]+ |
|---|---|---|---|---|
| 121 | | 1-1, 1-2, 2-1, 2-2, 2-3, 2-4, 2-5, 3-1, 3-2, 3-3, 3-4 | A, B, C, D, E, F | 838.3 |
| 122 | | 1-1, 1-2, 2-1, 2-2, 2-3, 2-4, 2-5, 3-1, 3-2, 3-3, 3-4 | A, B, C, D, E, F | 864.5 |
| 44 | | 1-3, 2-1, 2-2, 2-3, 2-4, 3-1, 3-2, 3-4 | A, B, C, D, E, F | 1011.8 |

-continued

| ID | Cytotoxic compound (D) | -L1-(L2-D) Synthetic method | Conj. Method | MS found [M + H]+ |
|---|---|---|---|---|
| 45 | | 1-3, 2-1, 2-2, 2-3, 2-4, 3-1, 3-2, 3-4 | A, B, C, D, E, F | 1037.5 |
| 123 | | 1-1, 1-2, 2-1, 2-2, 2-3, 2-4, 2-5, 3-1, 3-2, 3-3, 3-4 | A, B, C, D, E, F | 823.2 |
| 124 | | 1-1, 1-2, 2-1, 2-2, 2-3, 2-4, 2-5, 3-1, 3-2, 3-3, 3-4 | A, B, C, D, E, F | 837.5 |

| ID | Cytotoxic compound (D) | -L1-(L2-D) Synthetic method | Conj. Method | MS found [M + H]⁺ |
|---|---|---|---|---|
| 125 | | 1-1, 1-2, 2-1, 2-2, 2-3, 2-4, 2-5, 3-1, 3-2, 3-3, 3-4 | A, B, C, D, E, F | 835.7 |
| 126 | | 1-1, 1-2, 2-1, 2-2, 2-3, 2-4, 2-5, 3-1, 3-2, 3-3, 3-4 | A, B, C, D, E, F | 871.7 |
| 127 | | 1-1, 1-2, 2-1, 2-2, 2-3, 2-4, 2-5, 3-1, 3-2, 3-3, 3-4 | A, B, C, D, E, F | 851.3 |

| ID | Cytotoxic compound (D) | -L1-(L2-D) Synthetic method | Conj. Method | MS found [M + H]+ |
|---|---|---|---|---|
| 128 | | 1-1, 1-2, 2-1, 2-2, 2-3, 2-4, 2-5, 3-1, 3-2, 3-3, 3-4 | A, B, C, D, E, F | 817.5 |
| 129 | | 1-1, 1-2, 2-1, 2-2, 2-3, 2-4, 2-5, 3-1, 3-2, 3-3, 3-4 | A, B, C, D, E, F | 817.1 |

-continued

| ID | Cytotoxic compound (D) | -L1-(L2-D) Synthetic method | Conj. Method | MS found [M + H]+ |
|---|---|---|---|---|
| 130 | | 1-1, 1-2, 2-1, 2-2, 2-3, 2-4, 2-5, 3-1, 3-2, 3-3, 3-4 | A, B, C, D, E, F | 818.4 |

Example IIa

Synthesis of Compound 13, 14, 16, 18

Scheme IIa.

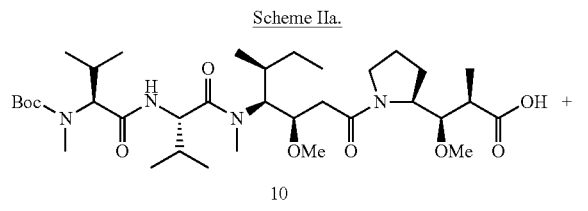

10

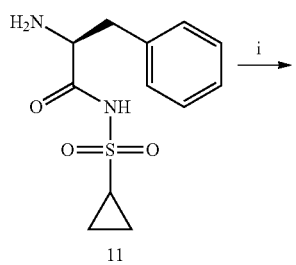

11

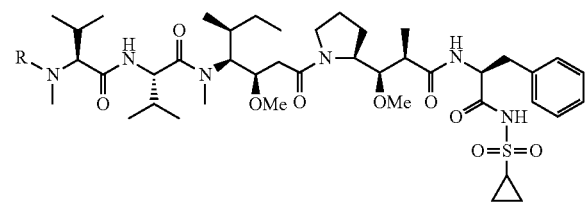

12 R = Boc
13 R = H

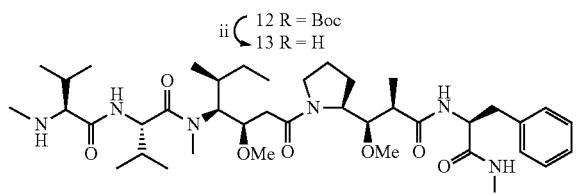

14

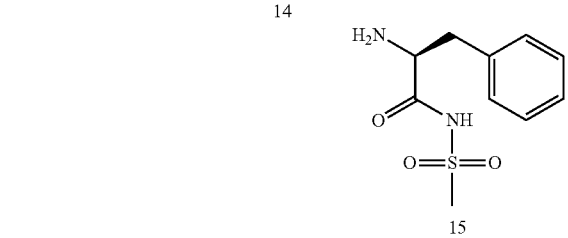

15

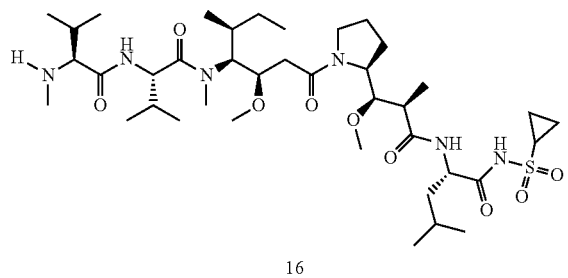

16

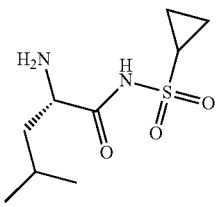

17

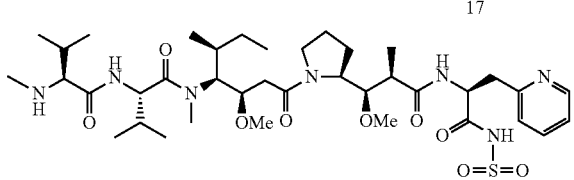

18

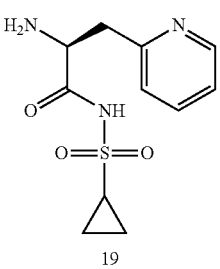

19

Reactions and conditions:
i. DIC/HOAt, DMF, rt, 16 h;
ii. HCl/Dioxane

The amino acid sulfonamide derivatives 11, 15, 17, 19 were synthesized according to previously reported procedure (ARKIVOC 2004 (xii) 14-22) using Boc protected amino acid and cyclopropyl/methyl sulfonamide, followed by removal of Boc

General Procedure C

Example IIa-1

Synthesis of Compound 13

Compound 13 was synthesized using the general procedures described above as following: DIC/HOAt mediated amide bond formation (General procedure B) between Boc-N-Me-Val-Val-Dil-Dap-OH (compound 1) and amine 11, followed by removal of Boc (General procedure C). The final compound was purified by reverse phase HPLC to give compound 13 as a white powder after lyophilization. MS m/z Calcd for $C_{42}H_{70}N_6O_9S$ 834.5, Found 835.6 ([M+H]$^+$).

Example IIa-2

Synthesis of Compound 14

Compound 14 was synthesized using the general procedures described above as following: DIC/HOAt mediated amide bond formation (General procedure B) between Boc-N-Me-Val-Val-Dil-Dap-OH (compound 10) and amine 15, followed by removal of Boc (General procedure C). The final compound was purified by reverse phase HPLC to give compound 14 as a white powder after lyophilization. MS m/z Calcd for $C_{40}H_{68}N_6O_9S$ 808.5, Found 809.6 ([M+H]$^+$).

Example IIa-3

Synthesis of Compound 16

Compound 16 was synthesized using the general procedures described above as following: DIC/HOAt mediated amide bond formation (General procedure B) between Boc-N-Me-Val-Val-Dil-Dap-OH (compound 10) and amine 17, followed by removal of Boc (General procedure C). The final compound was purified by reverse phase HPLC to give compound 16 as a white powder after lyophilization. MS m/z Calcd for $C_{39}H_{72}N_6O_9S$ 800.5, Found 801.7 ([M+H]$^+$).

Example IIa-4

Synthesis of Compound 18

Compound 18 was synthesized using the general procedures described above as following: DIC/HOAt mediated amide bond formation (General procedure B) between Boc-N-Me-Val-Val-Dil-Dap-OH (compound 10) and amine 19, followed by removal of Boc (General procedure C). The final compound was purified by reverse phase HPLC to give compound 18 as a white powder after lyophilization. MS m/z Calcd for $C_{41}H_{69}N_7O_9S$ 835.5, Found 836.6 ([M+H]$^+$).

Example IIb

Synthesis of Compound 27

Scheme IIb.

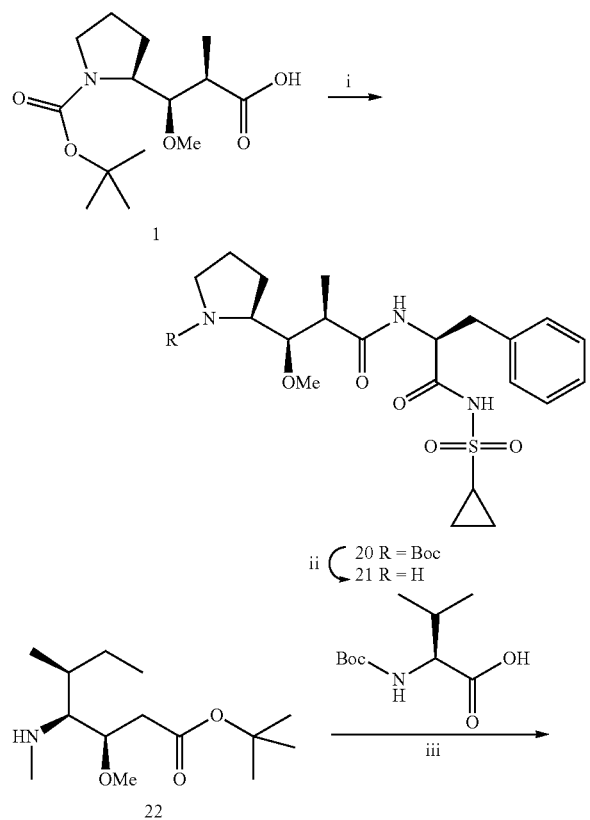

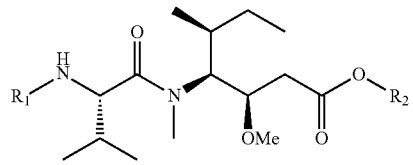

iv ⎰ 23 R1 = Boc, R2 = t-Bu
   ⎱ 24 R1, R2 = H v ⎱ 25 R1 = Boc, R2 = H

25 + 21 →(vi)

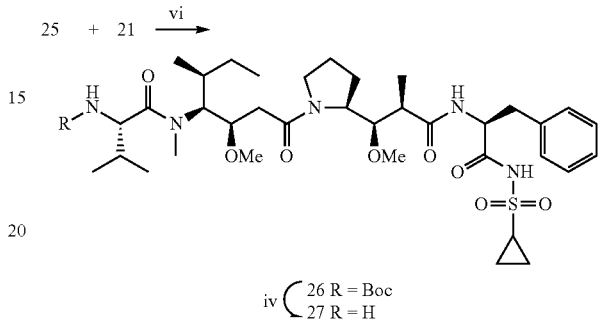

iv ⎰ 26 R = Boc
   ⎱ 27 R = H

Reagents and conditions:
i. compound 11, EDC, HOBt, DMF;
ii. HCl, iPrOH;
iii. PyBrOP, DIEA, DCM;
iv. TFA, DCM;
v. Boc$_2$O, NaHCO$_3$, dioxane, water;
vi. HATU, DIEA, DMF.

To a stirred solution of compound 1 (2.9 g, 10 mmol) and compound 11 (HCl salt, 3 g) in anhydrous DMF (100 mL) was added HOBt (1.54 g) and EDC.HCl (2 g). DIEA (20 mmol) was added and the mixture was stirred at room temperature for 16 h. The solvents were removed under reduced pressure and the residue was dissolved in ethyl acetate (500 mL) and washed successively with Citric acid (10%, aq., 200 mL), NaHCO3 (sat. aq., 200 mL) and brine. The organic layer wad dried and evaporated to dryness to give compound 20 as a syrup which was treated with 6N HCl in iPr—OH (100 mL) for 1 h to give compound 21 after concentration. Compound 21 was used directly without further purification.

To a solution of Boc-Val-OH (2.5 g), compound 22 in DCM (150 mL) was added PyBrOP (11 mmol), DIEA (22) at 0° C. The mixture was shielded from light and stirred for 0.5 h at 0° C. Then the mixture was stirred for 24 h at room temperature. The solvent was removed by evaporation in vacuo. The residue was diluted with ethyl acetate (300 mL) and washed with 1M KHSO$_4$, water, sat. NaHCO$_3$, and brine. The organic layer was dried and concentrated to give a residue, which was purified by silica gel column (hexanes: ethyl acetate) to give 3.2 g of compound 23.

The compound 23 (3 g) was dissolved in DCM (100 mL) and TFA (30 mL) was added. The mixture was stirred at room temperature for 2 h and concentrated under reduced pressure. The residue was dissolved in dixoane (200 mL). Sat. aq. NaHCO$_3$ (80 mL) was added, followed by Boc anhydride (2.2 g). The mixture was stirred at room temperature for 4 h and neutralized to pH 3-4 using 1N HCl. Solvents were removed and the residue was dissolved in ethyl acetate, which was washed with water and brine. The organic layer was concentrated and the residue was purified on a silica gel column to give compound 25 as a syrup.

Compound 27 was synthesized using the general procedures described above as following: HATU mediated amide bond formation (General procedure A) between compound 21 and amine 25, followed by removal of Boc (General procedure C). The final compound was purified by reverse phase HPLC to give compound 27 as a white powder after lyophilization. MS m/z Calcd. for $C_{36}H_{59}N_5O_8S$ 721.4, Found 722.5 ([M+H]+).

Example IIc

Synthesis of Compounds 30, 31, and 31

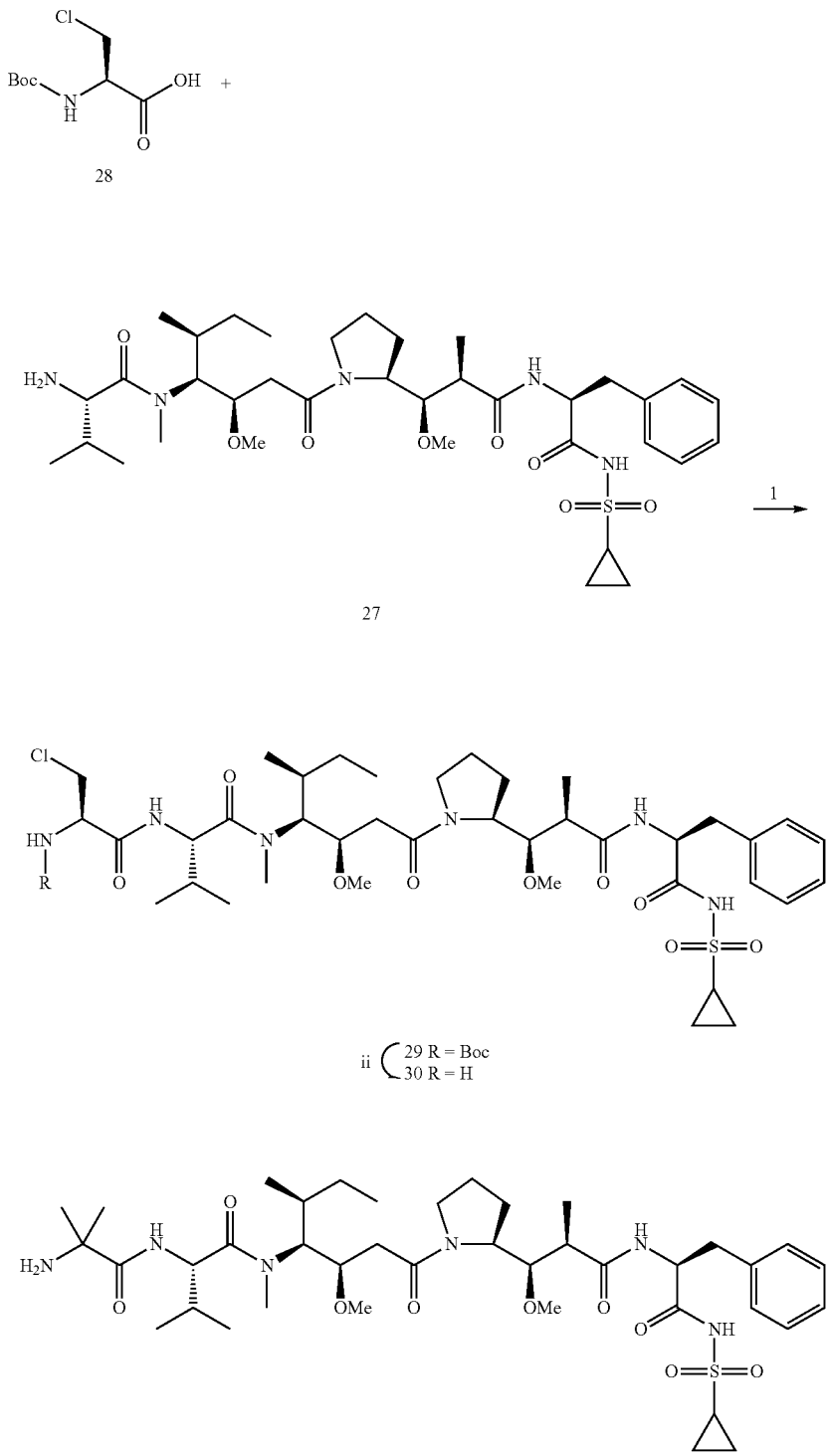

-continued

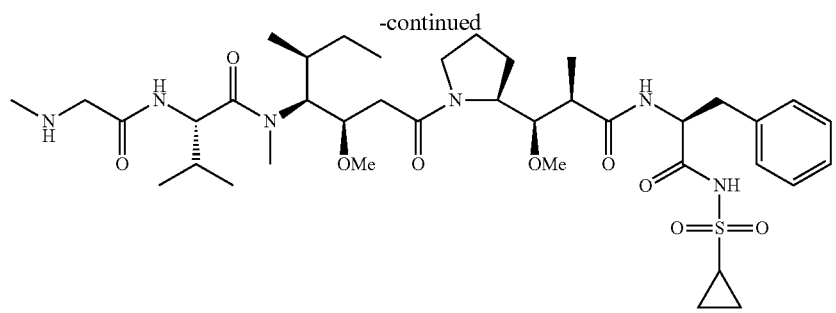

32

Reactions and conditions:
i. HATU, DIEA, DMF;
ii. HCl/dioxane, MeOH

Example IIc-1

Synthesis of Compound 30

Compound 30 was synthesized using the general procedures described above as following: HATU mediated amide bond formation (General procedure A) between β-Cl-N-Boc-Ala-OH (compound 28) and amine 27, followed by removal of Boc (General procedure C). The final compound was purified by reverse phase HPLC to give compound 30 as a white powder after lyophilization. MS m/z Calcd for $C_{39}H_{63}ClN_6O_9S$ 826.4, Found 827.5 ([M+H]$^+$).

Example IIc-2

Synthesis of Compound 31

Compound 31 was synthesized using the general procedures described above as following: HATU mediated amide bond formation (General procedure A) between N-Boc-Aib-OH and amine 27 followed by removal of Boc (General procedure C). The final compound was purified by reverse phase HPLC to give compound 31 as a white powder after lyophilization. MS m/z Calcd. for $C_{40}H_{66}N_6O_9S$ 806.5, Found 807.8 ([M+H]$^+$).

Example IIc-3

Synthesis of Compound 32

Compound 32 was synthesized using the general procedures described above as following: HATU mediated amide bond formation (General procedure A) between N-Boc-Sar-OH and amine 27, followed by removal of Boc (General procedure C). The final compound was purified by reverse phase HPLC to give compound 32 as a white powder after lyophilization. MS m/z Calcd. for $C_{39}H_{64}N_6O_9S$ 792.5, Found 793.4 ([M+H]$^+$).

Example IId

Synthesis of Compounds 35 and 37

Scheme IId.

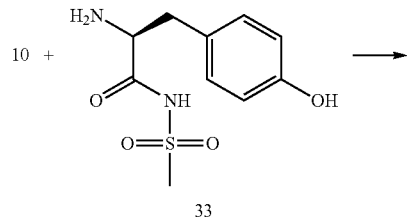

10 +

33

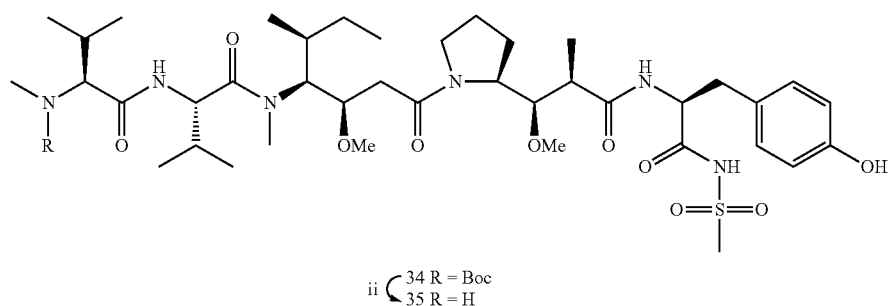

ii ⎰ 34 R = Boc
  ⎱ 35 R = H

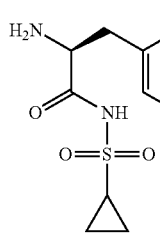

36

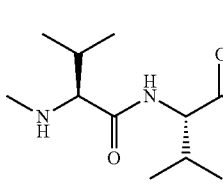

-continued

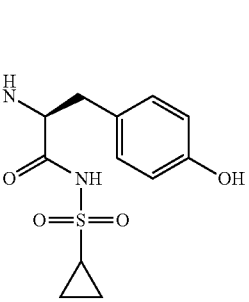

37

Reagents and conditions:
i. DIC/HOAt, DMF, rt, 16 h;
ii. HCl/Dioxane

The amino acid sulfonamide derivatives 33 and 36 were synthesized according to previously reported procedure (WO 2007146695) using Boc protected amino acid and cyclopropyl/methyl sulfonamide, followed by removal of Boc (General procedure C)

Example IId-1

Synthesis of Compound 35

Compound 35 was synthesized using the general procedures described above as following: DIC/HOAt mediated amide bond formation (General procedure B) between Boc-N-Me-Val-Val-Dil-Dap-OH (compound 10) and amine 33, followed by removal of Boc (General procedure C). The final compound was purified by reverse phase HPLC to give compound 35 as a white powder after lyophilization. MS m/z Calcd for $C_{41}H_{70}N_6O_{10}S$ 838.5, Found 839.6 ([M+H]$^+$).

Example IId-2

Synthesis of Compound 37

Compound 37 was synthesized using the general procedures described above as following: DIC/HOAt mediated amide bond formation (General procedure B) between Boc-N-Me-Val-Val-Dil-Dap-OH (compound 10) and amine 36, followed by removal of Boc (General procedure C). The final compound was purified by reverse phase HPLC to give compound 37 as a white powder after lyophilization. MS m/z Calcd for $C_{43}H_{72}N_6O_{10}S$ 864.5, Found 865.7 ([M+H]$^+$).

Example IIe

Synthesis of Compounds 44 and 45

Scheme IIe.

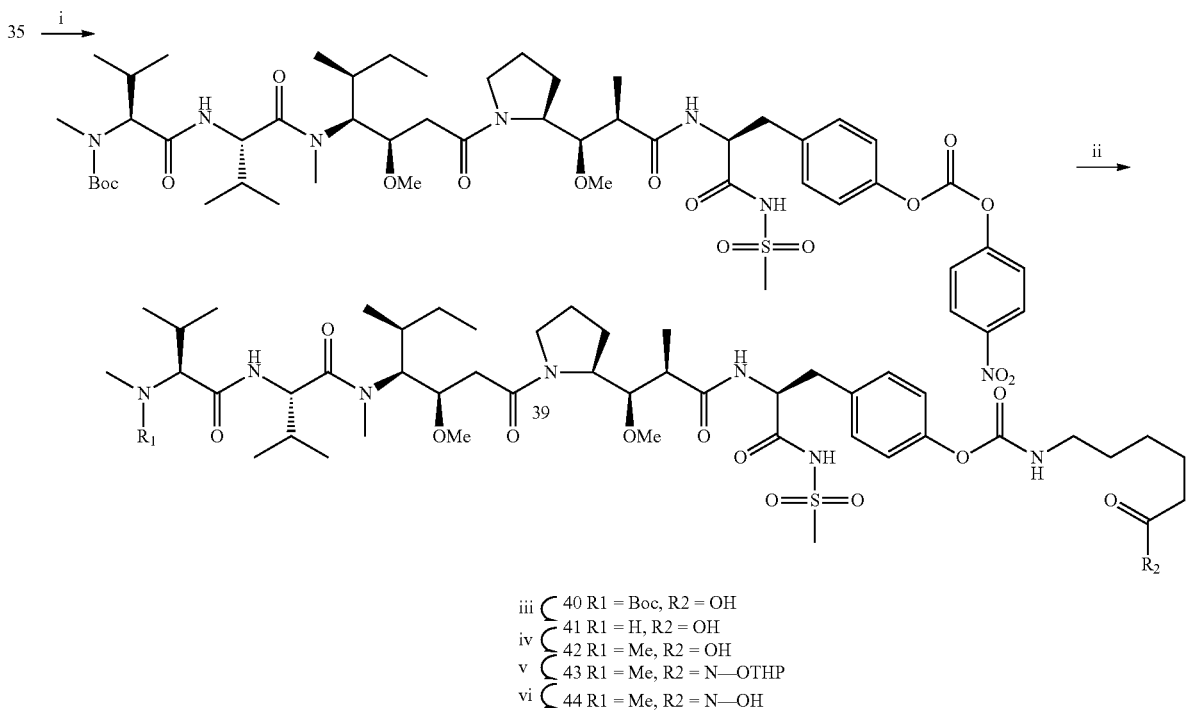

iii ⎰ 40 R1 = Boc, R2 = OH
iv ⎱ 41 R1 = H, R2 = OH
   ⎰ 42 R1 = Me, R2 = OH
v  ⎱ 43 R1 = Me, R2 = N—OTHP
vi ⎰ 44 R1 = Me, R2 = N—OH -continued

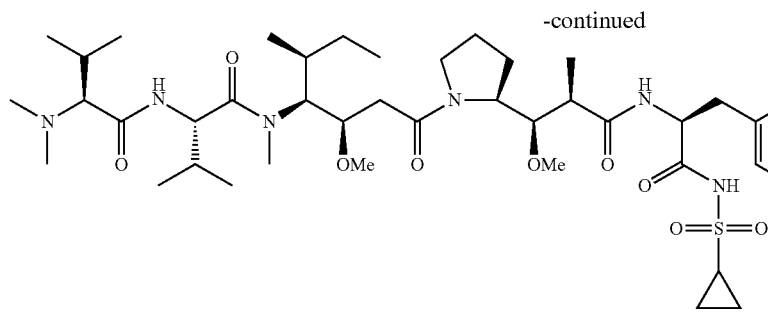

45

Reagents and conditions:
i. bis(nitrophenyl) carbonate, DIEA, THF/DMF, r.t.;
ii. 6-aminohexanoic acid, NaHCO₃ (aq.);
iii. HCl/Dixoane (4N);
iv. HCHO, NaCNBH₃, DMF, HOAc;
v. DIC, HOAt, NH₂—O-THP;
vi. HCl/H₂O (4N), DMF.

Example IIe-1

Synthesis of Compound 44

The phenol 35 (1 mmol) was treated with 3 eq of bis(p-nitrophenyl)carbonate to form the activated carbonate 39 (general procedure G). The crude product was used directly without further purification. 6-Aminohexanoic acid (5 eq) was dissolved in sat. aq. NaHCO₃ (5 mL) and the solution was added. The reaction mixture was stirred at room temperature for 16 h. Citric acid (aq. 10%) was added to acidify the reaction (pH=4-5) and then diluted with EtOAc (150 mL). Organic layer was dried (over Na₂SO₄) and concentrated to give the crude product 40 which underwent the following procedures: removal of Boc (General procedure C), reductive alkylation using HCHO (General procedure E), DIC/HOAt mediated amide bond formation (General procedure B) between compound 42 and THP—O—NH₂, followed by removal of THP (General procedure C, using 4N aq. HCl). The final compound was purified by reverse phase HPLC to give compound 44 as a white powder after lyophilization. MS m/z Calcd for $C_{48}H_{82}N_8O_{13}S$ 1010.6, Found 1011.8 ([M+H]⁺).

Example IIe-2

Synthesis of Compound 45

The compound 45 was synthesized according to the same procedures as described for the synthesis of compound 44. The final compound was purified by reverse phase HPLC to give compound 45 as a white powder after lyophilization. MS m/z Calcd for $C_{50}H_{84}N_8O_{13}S$ 1036.6, Found 1037.5 ([M+H]⁺).

Example III

Synthesis of Cytotoxic Compounds

| ID | Cytotoxic compound (D) | -L¹-(L²-D) Synthetic method | Conjugation Method | MS found [M + H]⁺ |
|---|---|---|---|---|
| 49 | 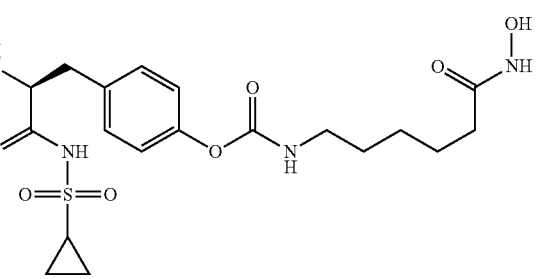 | 1-3, 2-1, 2-2, 2-3, 2-4, 3-1, 3-2, 3-4 | A, B, C, D, E, F | 712.5 |

-continued

| ID | Cytotoxic compound (D) | -L¹-(L²-D) Synthetic method | Conjugation Method | MS found [M + H]⁺ |
|---|---|---|---|---|
| 50 | | 1-3, 2-1, 2-2, 2-3, 2-4, 3-1, 3-2, 3-4 | A, B, C, D, E, F | 738.5 |
| 52 | | 1-3, 2-1, 2-2, 2-3, 2-4, 3-1, 3-2, 3-4 | A, B, C, D, E, F | 784.7 |
| 53 | | 1-3, 2-1, 2-2, 2-3, 2-4, 3-1, 3-2, 3-4 | A, B, C, D, E, F | 788.7 |
| 54 | | 1-3, 2-1, 2-2, 2-3, 2-4, 3-1, 3-2, 3-4 | A, B, C, D, E, F | 772.5 |

| ID | Cytotoxic compound (D) | -L¹-(L²-D) Synthetic method | Conjugation Method | MS found [M + H]⁺ |
|---|---|---|---|---|
| 137 | | 1-3, 2-1, 2-2, 2-3, 2-4, 3-1, 3-2, 3-4 | A, B, C, D, E, F | 682.4 |
| 138 | | 1-3, 2-1, 2-2, 2-3, 2-4, 3-1, 3-2, 3-4 | A, B, C, D, E, F | 698.6 |
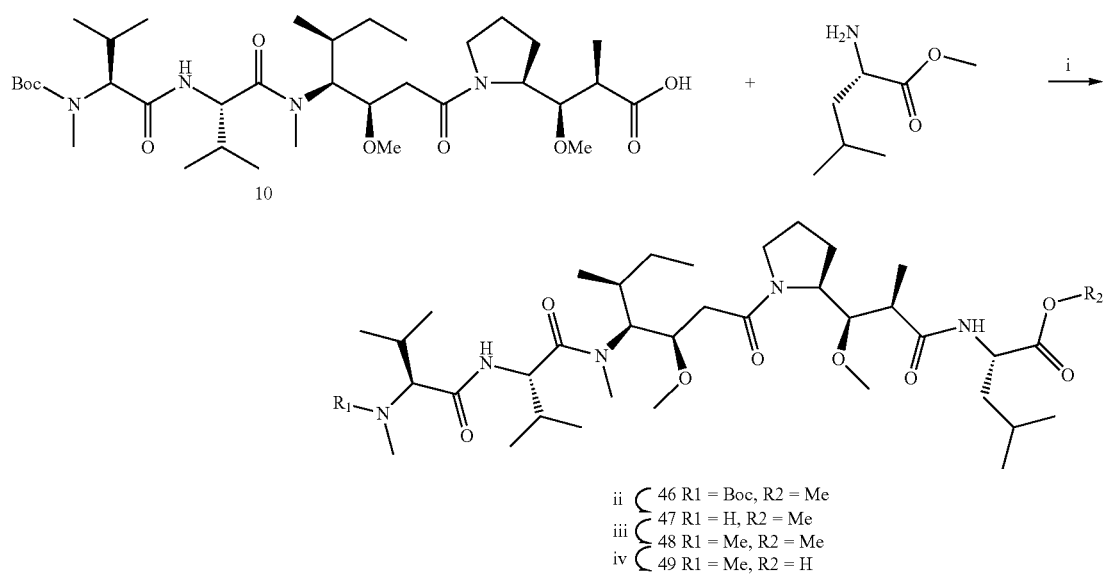
Scheme III.
ii  46 R1 = Boc, R2 = Me
iii 47 R1 = H, R2 = Me
iii 48 R1 = Me, R2 = Me
iv  49 R1 = Me, R2 = H

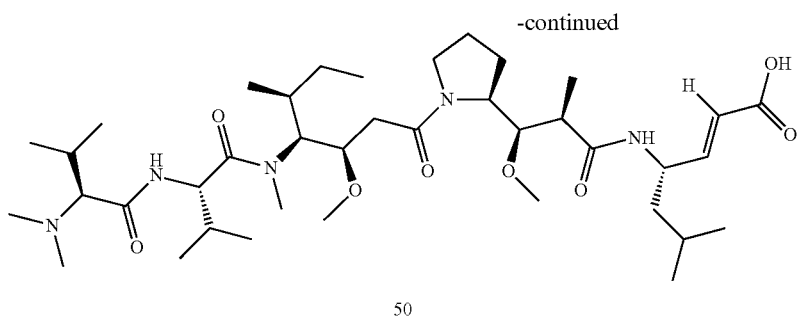

50

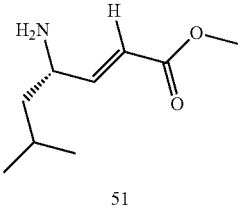

51

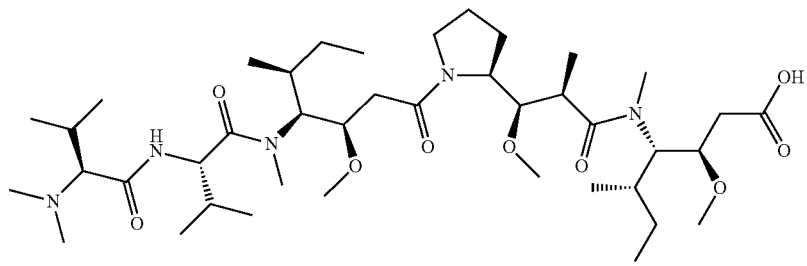

52

Reagents and conditions:
i. HATU, DIEA, DMF;
ii. HCl/dioxane;
iii. HCHO, NaCNBH₃, DMF, HOAc;
iv. LiOH, MeOH/H₂O

Example III-1

Synthesis of Compound 49

Compound 49 was synthesized using the general procedures described above as following: HATU mediated amide bond formation (General procedure A) between Boc-N-Me-Val-Val-Dil-Dap-OH (compound 10) and NH₂-Leu-OMe, followed by removal of Boc (General procedure C), reductive alkylation with HCHO (General procedure E) and saponification to remove methyl group from ester (General procedure F). The final compound was purified by reverse phase HPLC to give compound 49 as a white powder after lyophilization. MS m/z Calcd for $C_{37}H_{69}N_5O_8$ 711.5, Found 712.5 ([M+H]⁺).

Example III-2

Synthesis of Compound 50

Compound 50 was synthesized using the general procedures described above as following: HATU mediated amide bond formation (General procedure A) between Boc-N-Me-Val-Val-Dil-Dap-OH (compound 10) and amine 51, followed by removal of Boc (General procedure C), reductive alkylation with HCHO (General procedure E) and saponification to remove methyl group from ester (General procedure F). The final compound was purified by reverse phase HPLC to give compound 51 as a white powder after lyophilization. MS m/z Calcd for $C_{39}H_{71}N_5O_8$ 737.5, Found 738.5 ([M+H]⁺).

Compound 51 was synthesized according to literature procedures (J. Org. Chem., 2001, 66, 7355-7364)

Example III-3

Synthesis of Compound 52

Compound 52 was synthesized using the general procedures described above as following: HATU mediated amide bond formation (General procedure A) between Boc-N-Me-Val-Val-Dil-Dap-OH (compound 1) and amine 22, followed by removal of Boc and t-Bu (General procedure C), reductive alkylation with HCHO (General procedure E). The final compound was purified by reverse phase HPLC to give compound 52 as a white powder after lyophilization. MS m/z Calcd for $C_{41}H_{66}N_5O_8$ 783.6, Found 784.7 ([M+H]⁺).

Example III-4

Other Compounds Synthesized Using the Same Procedures as Described for the Synthesis of Compound 49

For compound 53: MS m/z Calcd for $C_{43}H_{73}N_5O_8$ 787.6, Found 788.7 ([M+H]⁺).

For compound 54: MS m/z Calcd for $C_{42}H_{69}N_5O_8$ 771.5 Found 772.5 ([M+H]⁺).

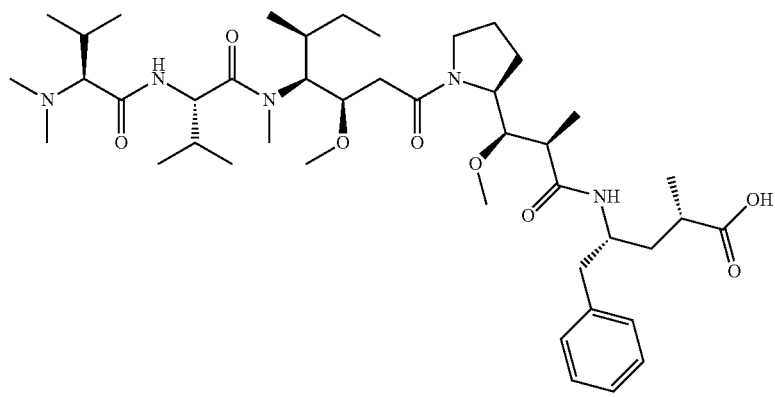 [SMILES: CC[C@H](C)[C@@H]([C@@H](CC(=O)N1CCC[C@H]1[C@H](OC)[C@@H](C)C(=O)N[C@@H](Cc1ccccc1)C[C@H](C)C(=O)O)OC)N(C)C(=O)[C@@H](NC(=O)[C@H](C(C)C)N(C)C)C(C)C]
53
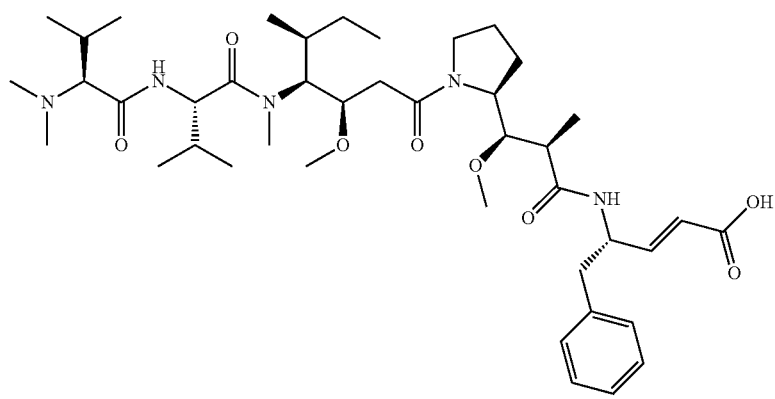 [SMILES: CC[C@H](C)[C@@H]([C@@H](CC(=O)N1CCC[C@H]1[C@H](OC)[C@@H](C)C(=O)N[C@H](/C=C/C(=O)O)Cc1ccccc1)OC)N(C)C(=O)[C@@H](NC(=O)[C@H](C(C)C)N(C)C)C(C)C]
54
Example III-5
Scheme III-5.
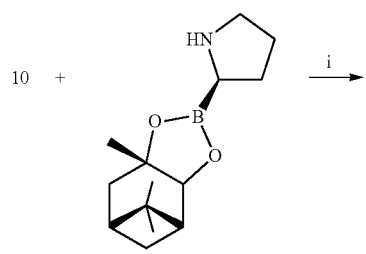
134

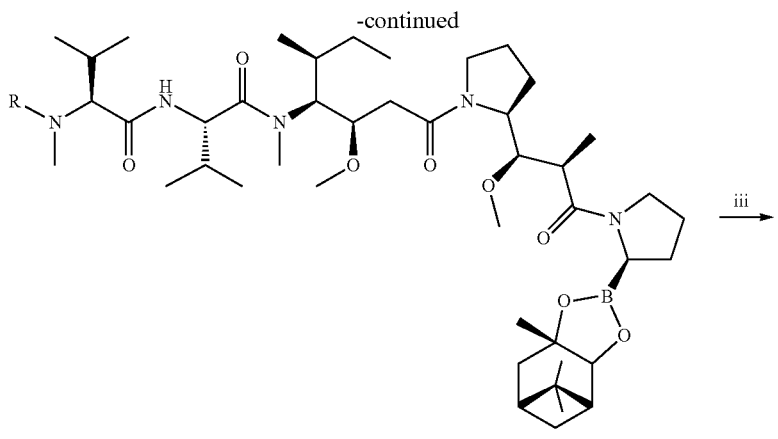

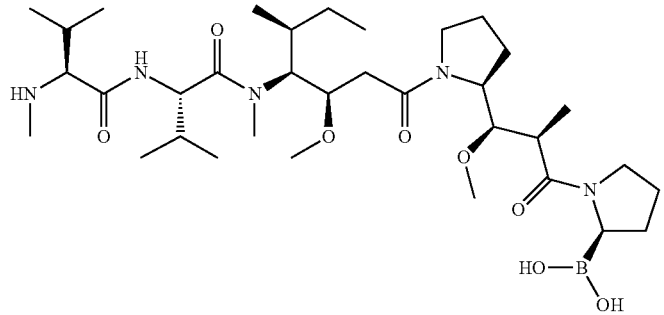 [SMILES: CC[C@H](C)[C@@H]([C@@H](CC(=O)N1CCC[C@H]1[C@H](OC)[C@@H](C)C(=O)N1CCC[C@H]1B(O)O)OC)N(C)C(=O)[C@@H](NC(=O)[C@@H](NC)C(C)C)C(C)C]

137

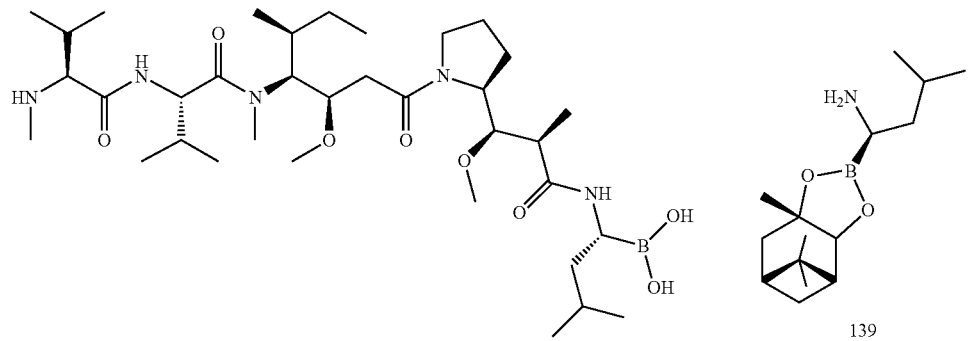

138

Reagents and conditions:
i. HATU, DIEA, DMF, rt, 1 h;
ii. HCl/Dioxane, MeOH;
iii. phenylboronic acid, hexanes, water, rt, 18 h.

Scheme III-5. Reagents and conditions: i. HATU, DIEA DMF, rt, 1 h; ii. HCl/Dioxane, MeOH; iii. phenylboronic acid, hexanes, water, rt, 18 h.

Example III-5a

Synthesis of Compound 137

The intermediate 136 was synthesized using the general procedures described above as following (0.1 mmol scale): HATU mediated amide bond formation (General procedure A) between Boc-N-Me-Val-Val-Dil-Dap-OH (compound 1) and amine 134, followed by removal of Boc (General procedure C). The HCl salt 11 was dissolved in water (5 mL) and hexane (5 mL) was added. Phenylboronic acid (10 eq) was added and the suspension was stirred vigorously at room temperature for 1 h. Hexane layer was removed and fresh hexane (5 mL) was added. The mixture was agitated for another 2 h and the aqueous layer was collect and concentrated. The final compound was purified by reverse phase HPLC to give compound 12 as a white powder after lyophilization. MS m/z Calcd for $C_{34}H_{64}BN_5O_8$ 681.5, Found 682.4 ([M+H]$^+$).

Example III-5b

Synthesis of Compound 138

The compound 138 was synthesized employing the same sequence as described for the preparation of compound 137.(compound 139 as a starting material). It was obtained as a white powder after RP-HPLC purification and lyophilization. MS m/z Calcd for $C_{35}H_{68}BN_5O_8$ 697.5, Found 698.6 ([M+H]$^+$).

Example IV
Preparation of Cytotoxic Compounds Hydroxamic Acid Derivatives
| ID | Cytotoxic compound (D) | -L¹(L²-D) Synthetic method | Conjugation Method | MS found [M + H]⁺ |
|---|---|---|---|---|
| 56 | 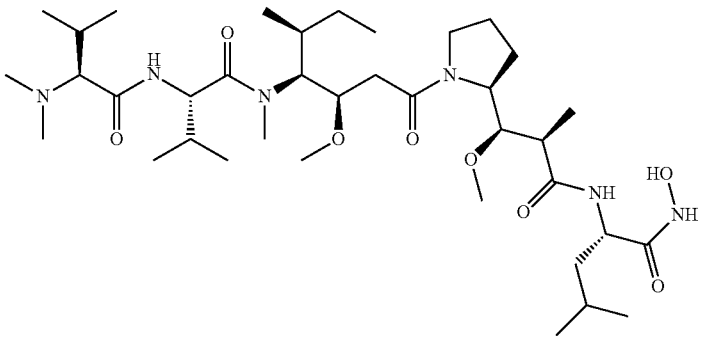 [SMILES: CC[C@H](C)[C@@H]([C@@H](CC(=O)N1CCC[C@H]1[C@H](OC)[C@@H](C)C(=O)N[C@@H](CC(C)C)C(=O)NO)OC)N(C)C(=O)[C@@H](NC(=O)[C@H](C(C)C)N(C)C)C(C)C] | 1-3, 2-1, 2-2, 2-3, 2-4, 3-1, 3-2, 3-4 | A, B, C, D, E, F | 727.6 |
| 57 | 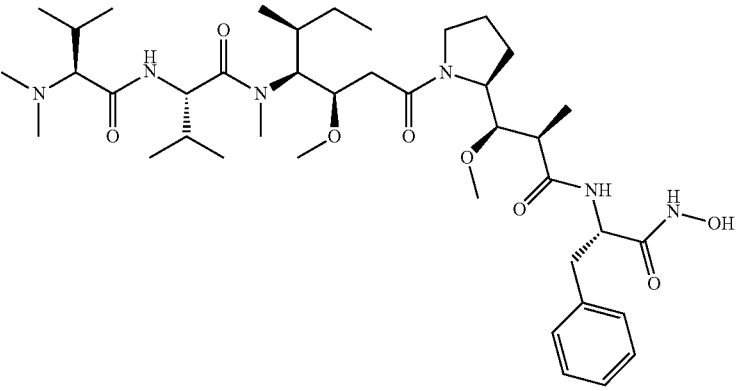 [SMILES: CC[C@H](C)[C@@H]([C@@H](CC(=O)N1CCC[C@H]1[C@H](OC)[C@@H](C)C(=O)N[C@@H](Cc1ccccc1)C(=O)NO)OC)N(C)C(=O)[C@@H](NC(=O)[C@H](C(C)C)N(C)C)C(C)C] | 1-3, 2-1, 2-2, 2-3, 2-4, 3-1, 3-2, 3-4 | A, B, C, D, E, F | 761.6 |
| 59 | 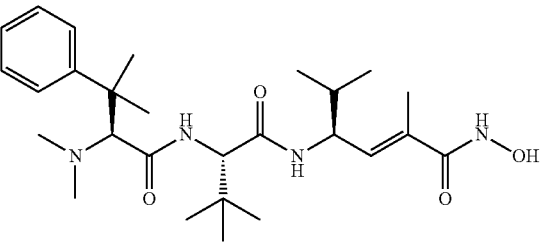 [SMILES: C/C(=C\[C@@H](NC(=O)[C@@H](NC(=O)[C@@H](N(C)C)C(C)(C)c1ccccc1)C(C)(C)C)C(C)C)C(=O)NO] | 1-3, 2-1, 2-2, 2-3, 2-4, 3-1, 3-2, 3-4 | A, B, C, D, E, F | 489.5 |
| 58 | 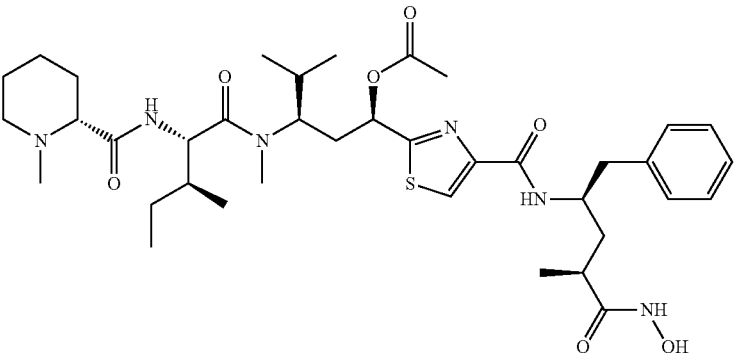 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccccc2)C[C@H](C)C(=O)NO)cs1)C(C)C] | 1-3, 2-1, 2-2, 2-3, 2-4, 3-1, 3-2, 3-4 | A, B, C, D, E, F | 743.5 |

-continued

| ID | Cytotoxic compound (D) | -L¹-(L²-D) Synthetic method | Conjugation Method | MS found [M + H]⁺ |
|---|---|---|---|---|
| 60 | | 1-3, 2-1, 2-2, 2-3, 2-4, 3-1, 3-2, 3-4 | A, B, C, D, E, F | 753.5 |
| 61 | | 1-3, 2-1, 2-2, 2-3, 2-4, 3-1, 3-2, 3-4 | A, B, C, D, E, F | 799.5 |
| 73 | | 1-3, 2-1, 2-2, 2-3, 2-4, 3-1, 3-2, 3-4 | A, B, C, D, E, F | 719.3 |
| 74 | | 1-3, 2-1, 2-2, 2-3, 2-4, 3-1, 3-2, 3-4 | A, B, C, D, E, F | 759.4 |
| 75 | | 1-3, 2-1, 2-2, 2-3, 2-4, 3-1, 3-2, 3-4 | A, B, C, D, E, F | 725.2 |

-continued
| ID | Cytotoxic compound (D) | -L¹(L²-D) Synthetic method | Conjugation Method | MS found [M + H]⁺ |
|---|---|---|---|---|
| 76 | | 1-3, 2-1, 2-2, 2-3, 2-4, 3-1, 3-2, 3-4 | A, B, C, D, E, F | 685.7 |
Scheme IV.
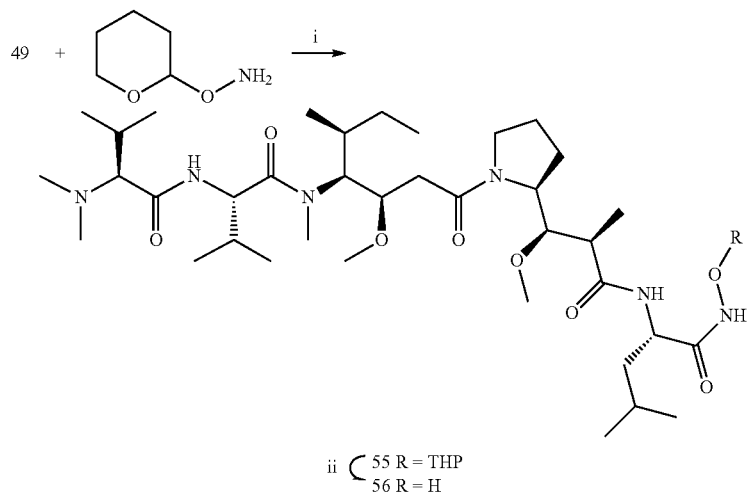
ii ⎰ 55 R = THP
  ⎱ 56 R = H
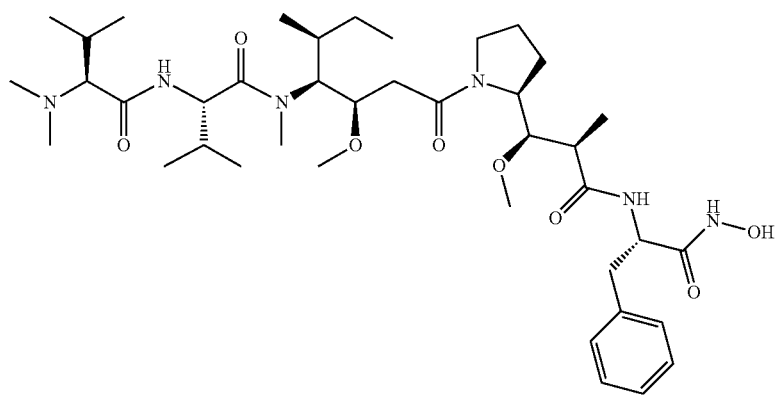
57

-continued

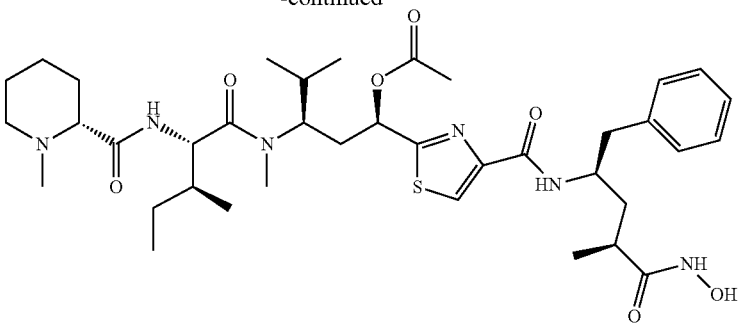

58

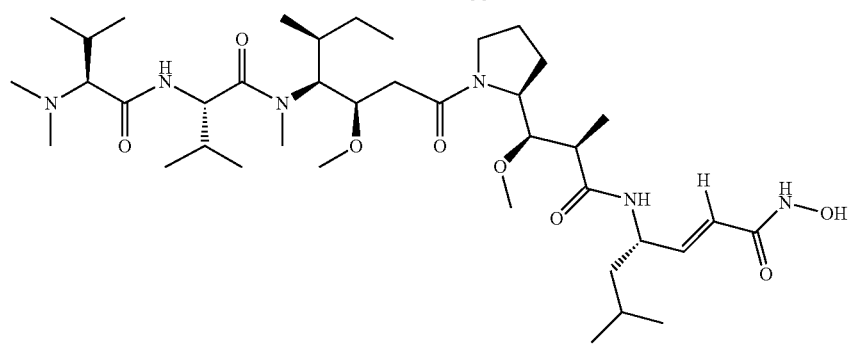 [SMILES: CC[C@H](C)[C@@H]([C@@H](CC(=O)N1CCC[C@H]1[C@H](OC)[C@@H](C)C(=O)N[C@H](/C=C/C(=O)NO)CC(C)C)OC)N(C)C(=O)[C@@H](NC(=O)[C@H](C(C)C)N(C)C)C(C)C]

60

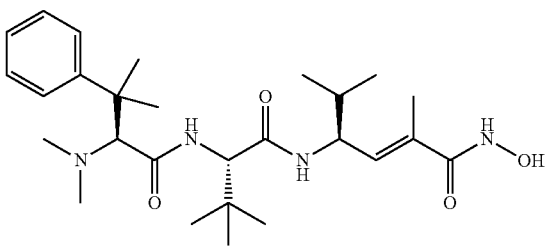

59

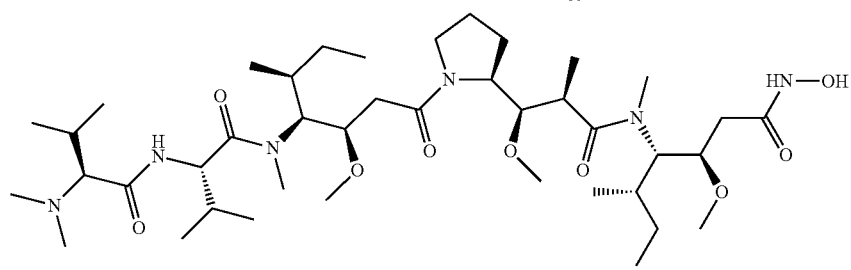

61

Reagents and conditions:
i. DIC/HOAt, DMF;
ii. HCl/water, DMF

Example IV-1

Synthesis of Compound 56

Compound 56 was synthesized using the general procedures described above as following: DIC/HOAt mediated amide bond formation (General procedure B) between Me$_2$-Val-Val-Dil-Dap-LeuOH (compound 49) and THP—O—NH$_2$, followed by removal of THP (General procedure C, using 4N aq. HCl). The final compound was purified by reverse phase HPLC to give compound 56 as a white powder after lyophilization. MS m/z Calcd for $C_{37}H_{70}N_6O_8$ 726.5, Found 727.6 ([M+H]$^+$).

Example IV-2

Synthesis of Compound 57

Dimethyl Auristatin F was synthesized from compound 10 and NH$_2$-Phe-OMe using the synthetic procedures described above for the synthesis of compound 49.

Compound 57 was synthesized using the general procedures described above as following: DIC/HOAt mediated amide bond formation (General procedure B) between dimethyl auristatin F and THP—O—NH$_2$, followed by removal of THP (General procedure C, using 4N aq. HCl). The final compound was purified by reverse phase HPLC to give compound 57 as a white powder after lyophilization. MS m/z Calcd for C$_{40}$H$_{68}$N$_6$O$_8$ 760.5, Found 761.6 ([M+H]$^+$).

Example IV-3

Synthesis of Compound 58

Compound 58 was synthesized using the general procedures described above as following: DIC/HOAt mediated amide bond formation (General procedure B) between Tubulysin (*J. Am. Chem. Soc.*, 2006, 128 (50), pp 16018-16019) and THP—O—NH$_2$, followed by removal of THP (General procedure C, using 4N aq. HCl). The final compound was purified by reverse phase HPLC to give compound 45 as a white powder after lyophilization. MS m/z Calcd for C$_{38}$H$_{58}$N$_6$O$_7$S 742.4, Found 743.5 ([M+H]$^+$).

Example IV-4

Synthesis of Compound 59

Compound 59 was synthesized using the general procedures described above as following: DIC/HOAt mediated amide bond formation (General procedure B) between HTI-286 (*Bioorg Med Chem Lett.* 2004, 14(16):4329-32) and THP—O—NH$_2$, followed by removal of THP (General procedure C, using 4N aq. HCl). The final compound was purified by reverse phase HPLC to give compound 59 as a white powder after lyophilization. MS m/z Calcd for C$_{27}$H$_{44}$N$_4$O$_4$ 488.3, Found 489.5 ([M+H]$^+$).

Example IV-5

Synthesis of Compound 60

Compound 60 was synthesized using the general procedures described above as following: DIC/HOAt mediated amide bond formation (General procedure B) between compound 50 and THP—O—NH$_2$, followed by removal of THP (General procedure C, using 4N aq. HCl). The final compound was purified by reverse phase HPLC to give compound 47 as a white powder after lyophilization. MS m/z Calcd for C$_{39}$H$_{72}$N$_6$O$_8$ 752.5, Found 753.5 ([M+H]$^+$).

Example IV-6

Synthesis of Compound 61

Compound 61 was synthesized using the general procedures described above as following: DIC/HOAt mediated amide bond formation (General procedure B) between compound 52 and THP—O—NH$_2$, followed by removal of THP (General procedure C, using 4N aq. HCl). The final compound was purified by reverse phase HPLC to give compound 61 as a white powder after lyophilization. MS m/z Calcd for C$_{41}$H$_{78}$N$_6$O$_9$ 798.5, Found 799.5 ([M+H]$^+$).

Example V

Synthesis of Alkoxyamine Linkers 65, 66, 67, and 68

| ID | Structure |
|---|---|
| 65 | ![structure] |
| 66 | ![structure] |
| 67 | ![structure] |
| 68 | ![structure] |

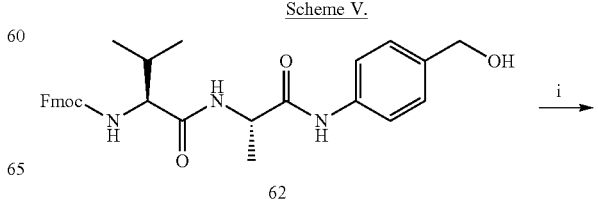

Scheme V.

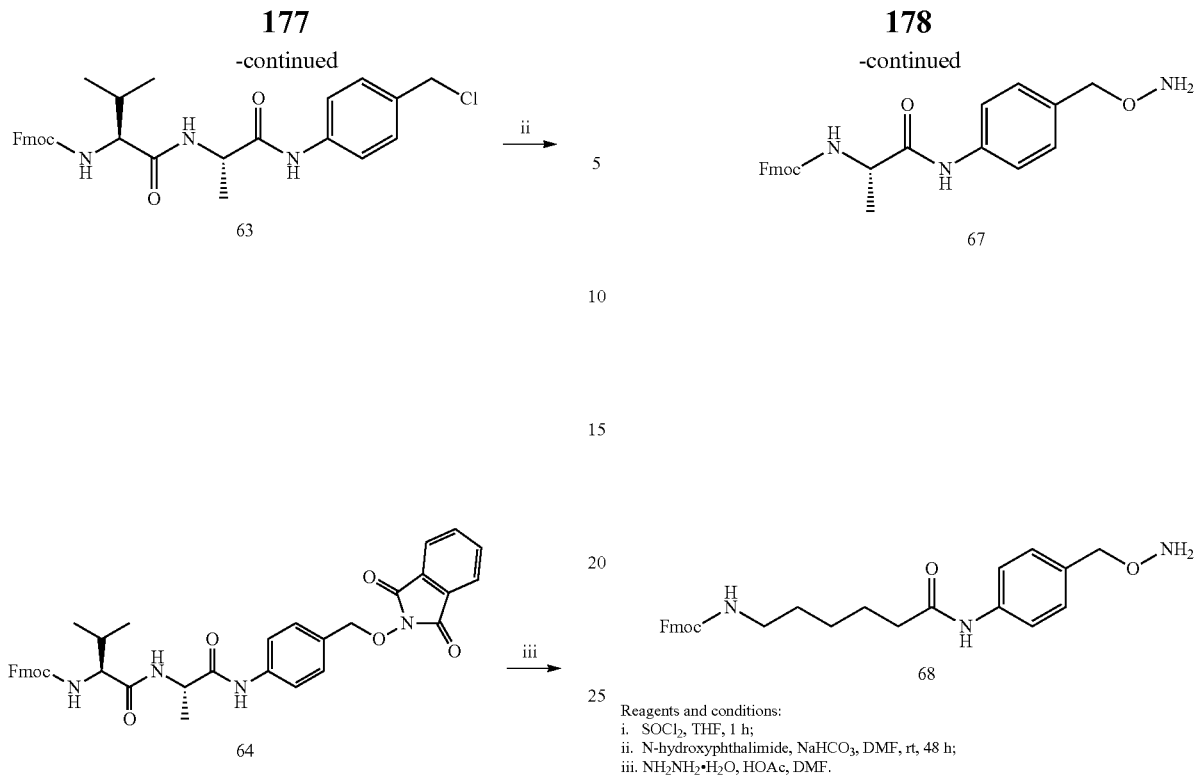

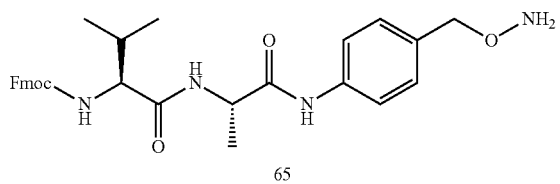

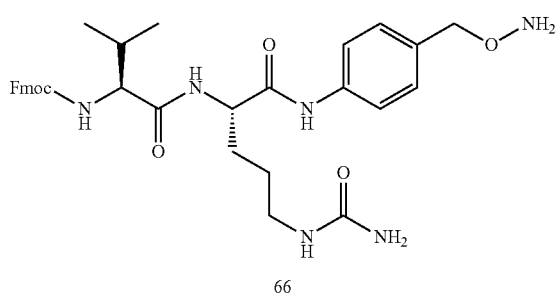

Reagents and conditions:
i. SOCl₂, THF, 1 h;
ii. N-hydroxyphthalimide, NaHCO₃, DMF, rt, 48 h;
iii. NH₂NH₂•H₂O, HOAc, DMF.

Example V-1

Synthesis of Compound 65

To a stirred solution of Fmoc-VA-PAB (62) (*Bioconjugate Chem.*, 2002, 13, 855-859) (9 g, 15 mmol) in THF (200 mL) was added thionyl chloride (18 mmol) dropwise. After the addition was complete, the reaction mixture was stirred at room temperature for 1 h. TLC analysis (ethyl acetate/hexane, 1/1, v/v) showed the completion of the reaction. The solvents were removed under reduced pressure and the residue was washed with hexanes (100 mL) to give compound 63 as a slightly yellowish solid (8.8 g).

Compound 63 (6.2 g, 10 mmol) was dissolved in anhydrous DMF (100 mL). N-Hydroxy-phthalimide (3.2 g, 20 mmol) was added, followed by solid NaHCO₃ (3.4 g, 40 mmol). The reaction mixture was stirred at room temperature for 48 h. TLC analysis showed that most of compound 61 was consumed. The reaction was then diluted with ethyl acetate (500 mL) and washed successively with sat. aq. NaHCO₃ (3×200 mL) and brine (200 mL). The organic layer was dried and concentrated to give compound 64 as a tan solid, which was used directly without further purification.

The crude compound 64 from previous step was dissolved in DMF (100 mL). HOAc (6 mL) was added, followed by hydrazine hydrate (5 mL). The reaction was stirred at room temperature for 1 h. LC/MS showed the completion of the reaction. The reaction mixture was then poured into a beaker containing 1 L of water under stirring. The precipitated solid was collected via filtration and washed twice with water to give compound 65 as a white solid (purity >85%, can be used directly). Pure compound 63 was obtained after RP-HPLC purification. MS m/z Calcd for $C_{30}H_{34}N_4O_5$ 530.3, Found 531.4 ($[M+H]^+$).

Example V-2

Synthesis of Compound 66

Compound 66 was synthesized starting from compound Fmoc-VC-PAB (*Bioconjugate Chem.*, 2002, 13, 855-859) using the procedures described above for the synthesis of compound 63. MS m/z Calcd for $C_{33}H_{40}N_6O_6$ 616.3, Found 617.5 ($[M+H]^+$).

Example V-3

Synthesis of Compound 67

Compound 64 was synthesized starting from compound Fmoc-A-PAB (synthesized according to the procedure reported: *Bioconjugate Chem.*, 2002, 13, 855-859) using the procedures described above for the synthesis of compound 63. MS m/z Calcd for $C_{25}H_{25}N_3O_4$ 431.2, Found 432.6 ($[M+H]^+$).

Example V-4

Synthesis of Compound 68

Compound 68 was synthesized starting from compound Fmoc-Ahx-PAB using the procedures described above for the synthesis of compound 68. MS m/z Calcd for $C_{28}H_{31}N_3O_4$ 473.2, Found 474.3 ($[M+H]^+$).

Example VIII

Synthesis of -$L^1$-($L^2$-D)-

| ID | Structure of -L¹-(L²-D) | Conj. Method | MS found [M + H]⁺ |
|---|---|---|---|
| 83 | 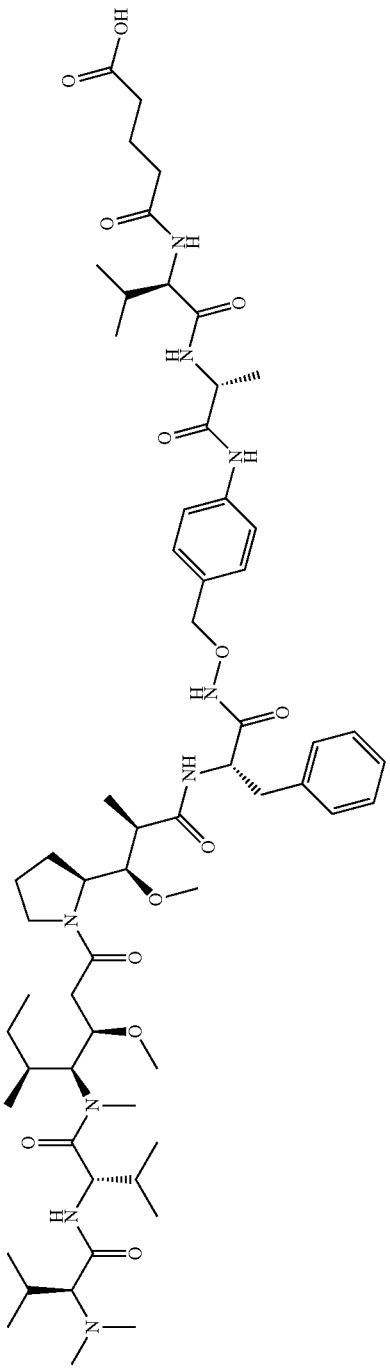 | A | 1150.9 |
| 84 | 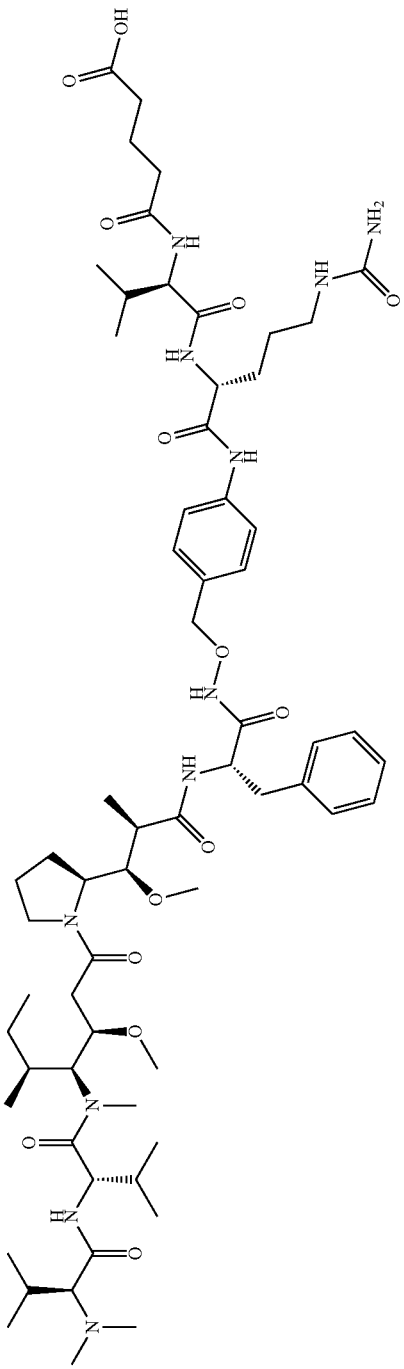 | A | 1237.1 |

| ID | Structure of -L¹-(L²-D) | Conj. Method | MS found [M + H]⁺ |
|---|---|---|---|
| 85 | 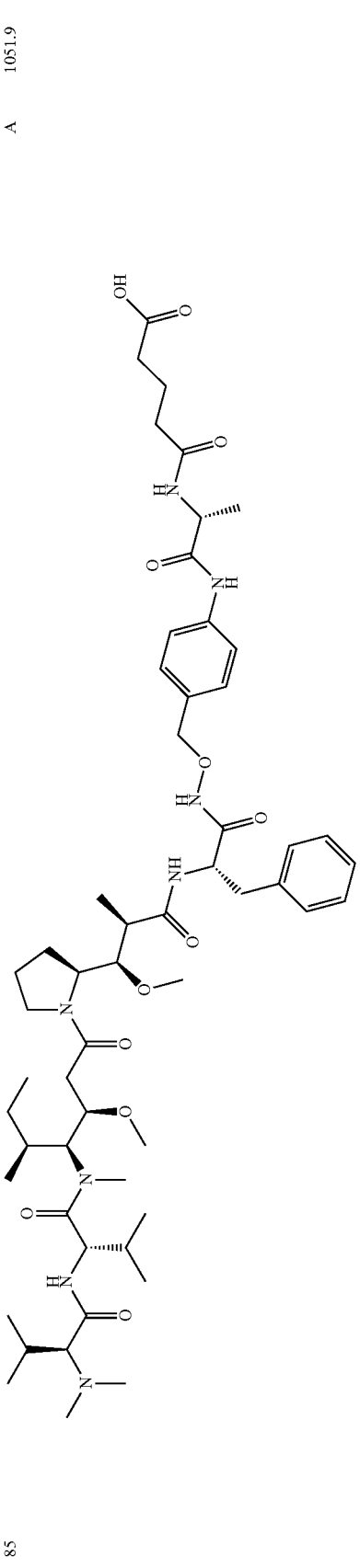 | A | 1051.9 |
| 86 | 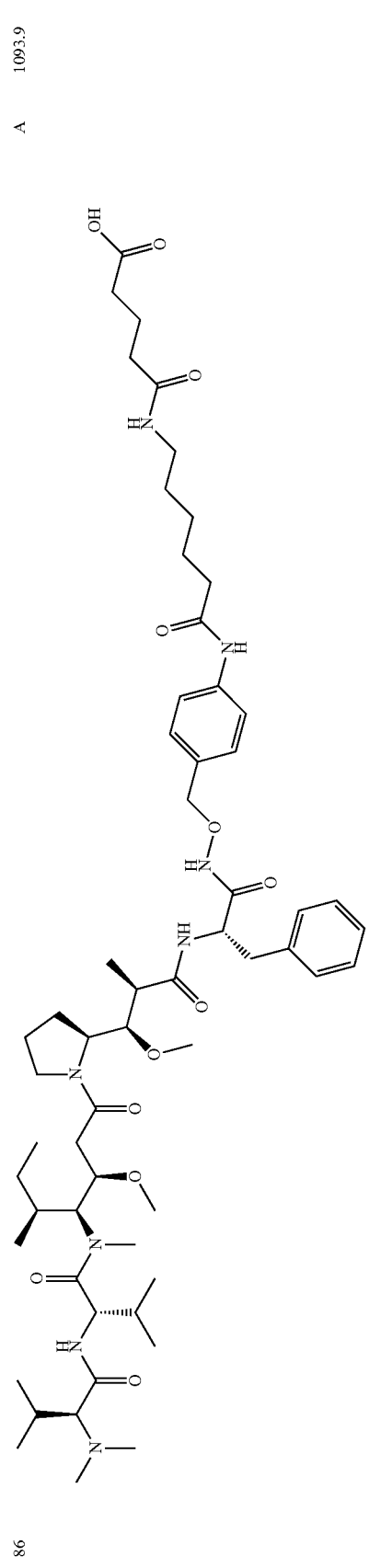 | A | 1093.9 |

-continued

| ID | Structure of -L¹-(L²-D) | Conj. Method | MS found [M + H]⁺ |
|---|---|---|---|
| 88 | | A | 1091.9 |
| 89 | | A | 1118.0 |

-continued
| ID | Structure of -L¹-(L²-D) | Conj. Method | MS found [M + H]⁺ |
|---|---|---|---|
| 90 | 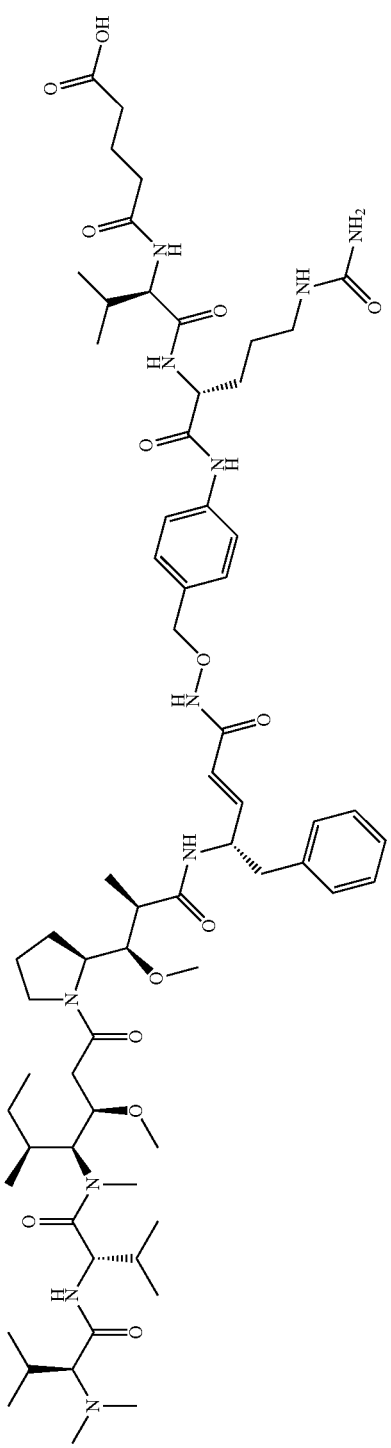 | A | 1263.1 |
| 91 | 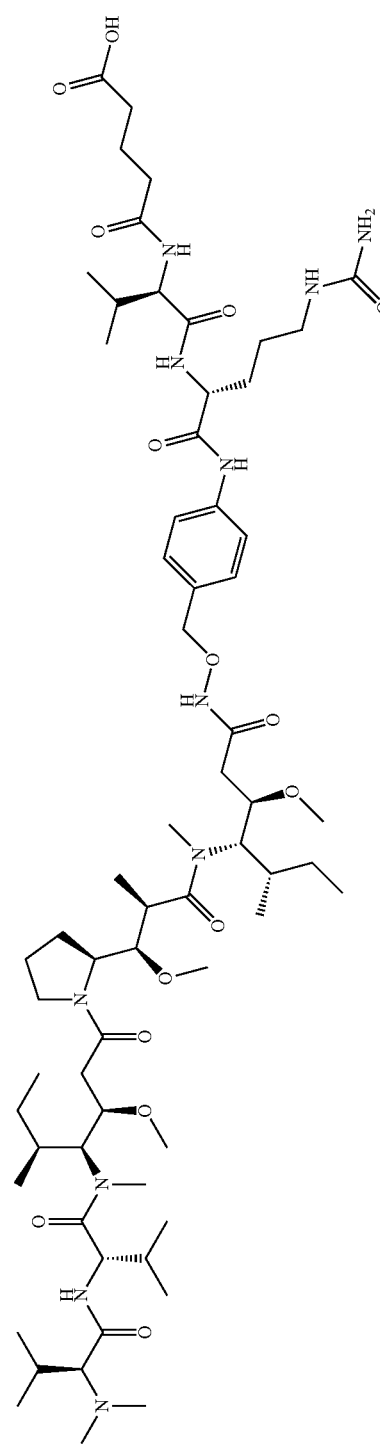 | A | 1274.8 |

-continued

| ID | Structure of -L¹-(L²-D) | Conj. Method | MS found [M + H]⁺ |
|---|---|---|---|
| 93 | | A | 1278.9 |
| 92 | | A | 1218.9 |

-continued
| ID | Structure of -L¹-(L²-D) | Conj. Method | MS found [M + H]⁺ |
|---|---|---|---|
| 94 | 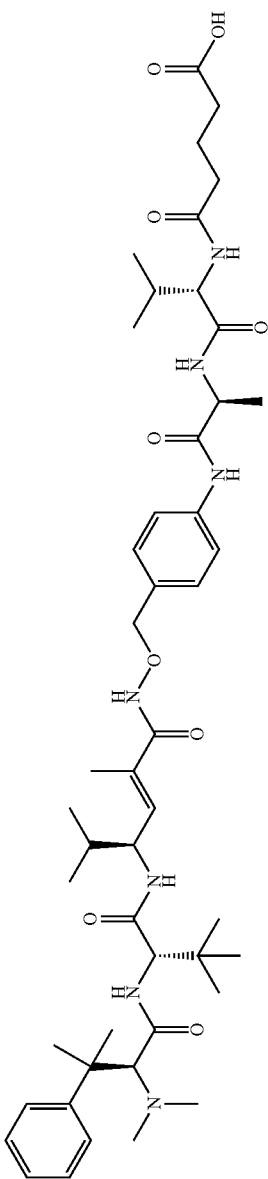 | A | 878.4 |

Scheme 11.
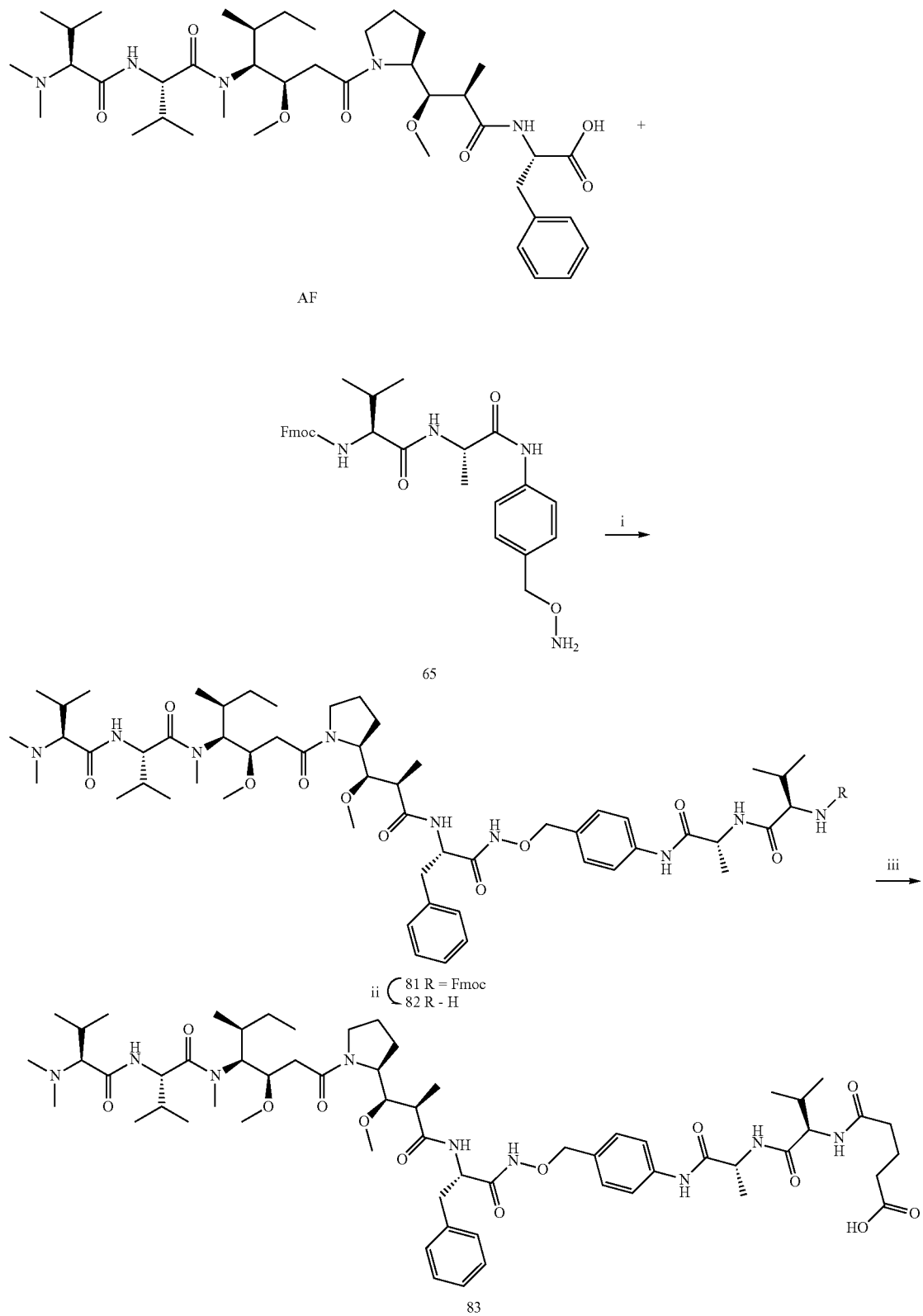
Reagents and conditions:
i. DIC, HOAt, DMF, r.t.;
ii. Piperidine, DMF;
iii. Glutaric anhydride, DIEA, DMF, rt.

Example VIII-1

Synthesis of Compound 83

Compound 83 was synthesized using the general procedures described above as following: DIC/HOAt mediated amide bond formation (General procedure B) between Auristatin F and compound 65, followed by removal of Fmoc (General procedure D), and reaction with glutaric anhydride (General procedure H). The final compound was purified by reverse phase HPLC to give compound 83 as a white powder after lyophilization. MS m/z Calcd for $C_{60}H_{95}N_9O_{13}$ 1149.7, Found 1150.9 ([M+H]$^+$).

84

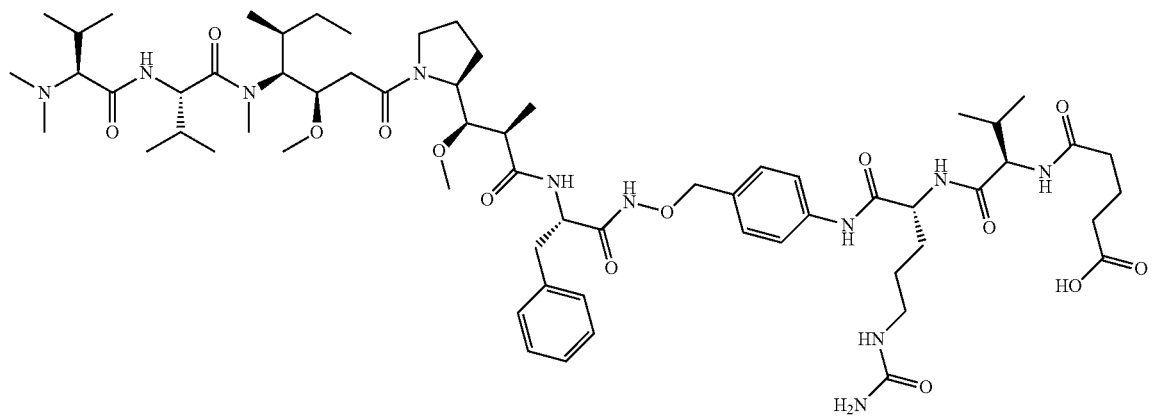

85

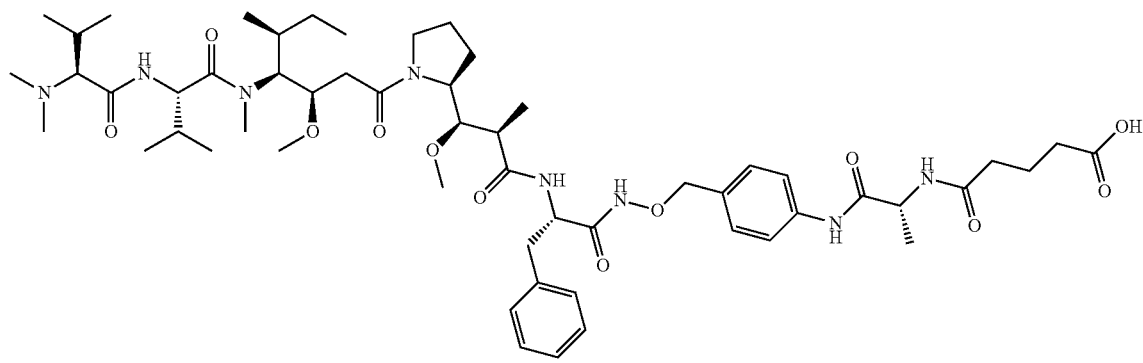 [SMILES: CC[C@H](C)[C@@H]([C@@H](CC(=O)N1CCC[C@H]1[C@H](OC)[C@@H](C)C(=O)N[C@@H](Cc1ccccc1)C(=O)NOCc1ccc(NC(=O)[C@@H](C)NC(=O)CCCC(=O)O)cc1)OC)N(C)C(=O)[C@@H](NC(=O)[C@H](C(C)C)N(C)C)C(C)C]

86

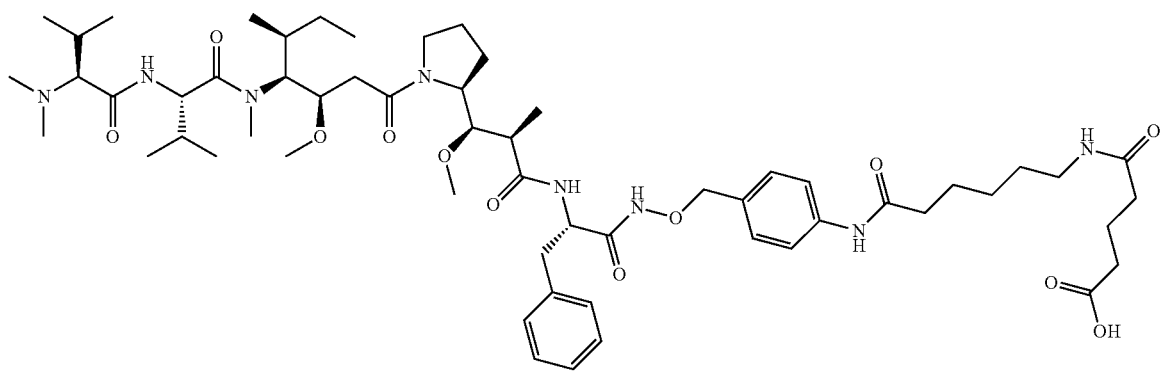

Example VIII-2

Synthesis of Compound 84

Compound 84 was synthesized using the general procedures described above as following: DIC/HOAt mediated amide bond formation (General procedure B) between Auristatin F and compound 66, followed by removal of Fmoc (General procedure D), and reaction with glutaric anhydride (General procedure H). The final compound was purified by reverse phase HPLC to give compound 84 as a white powder after lyophilization. MS m/z Calcd for $C_{63}H_{101}N_{11}O_{14}$ 1235.8, Found 1237.1 ([M+H]$^+$).

Example VIII-3

Synthesis of Compound 85

Compound 85 was synthesized using the general procedures described above as following: DIC/HOAt mediated amide bond formation (General procedure B) between Auristatin F and compound 67, followed by removal of Fmoc (General procedure D), and reaction with glutaric anhydride (General procedure H). The final compound was purified by reverse phase HPLC to give compound 85 as a white powder after lyophilization. MS m/z Calcd for $C_{55}H_{86}N_8O_{12}$ 1050.6, Found 1051.9 ([M+H]$^+$).

Example VIII-4

Synthesis of Compound 86

Compound 86 was synthesized using the general procedures described above as following: DIC/HOAt mediated amide bond formation (General procedure B) between Auristatin F and compound 68, followed by removal of Fmoc (General procedure D), and reaction with glutaric anhydride (General procedure H). The final compound was purified by reverse phase HPLC to give compound 86 as a white powder after lyophilization. MS m/z Calcd for $C_{58}H_{92}N_8O_{12}$ 1092.7, Found 1093.9 ([M+H]$^+$).

Example VIII-5

Synthesis of Compound 88

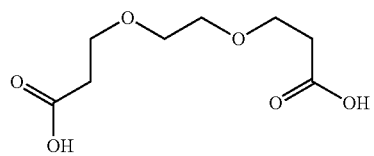

87

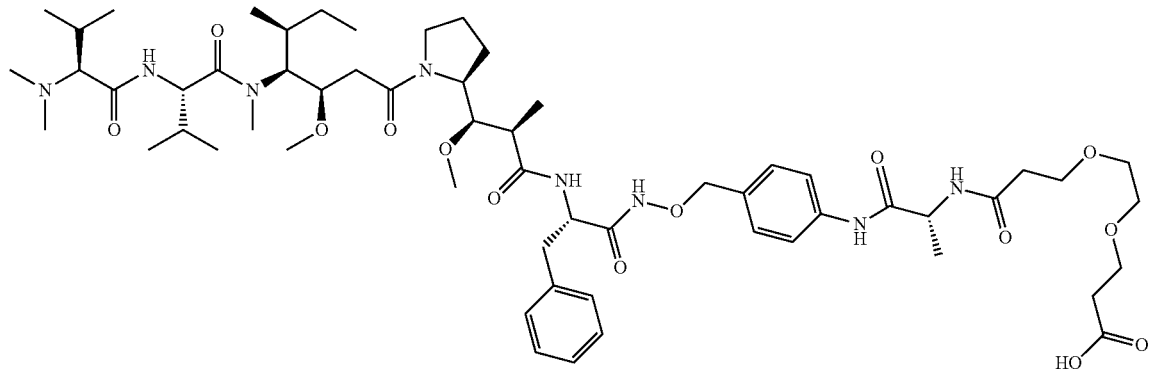

88

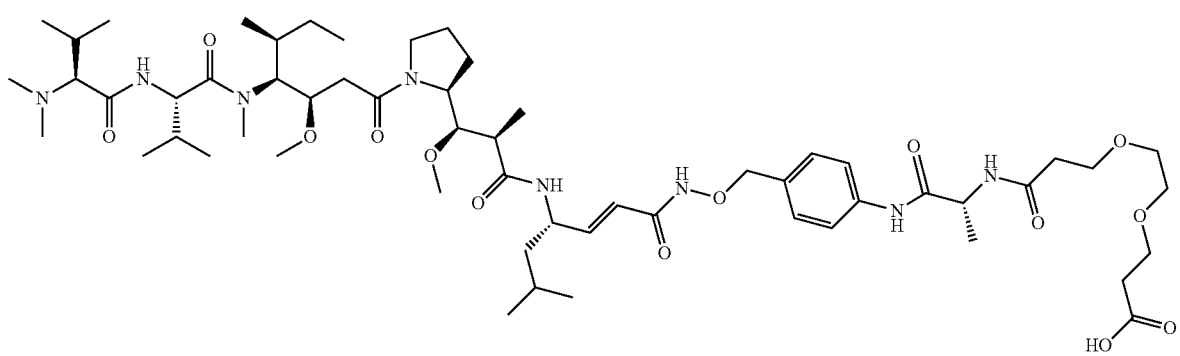

89

Compound 88 was synthesized using the general procedures described above as following: DIC/HOAt mediated amide bond formation (General procedure B) between compound 49 and compound 67, followed by removal of Fmoc (General procedure D), and amide formation with acid 87 using HATU (General procedure A, 3 eq of acid 87 and 1 eq of HATU were used). The final compound was purified by reverse phase HPLC to give compound 88 as a white powder after lyophilization. MS m/z Calcd for $C_{55}H_{94}N_8O_{14}$ 1090.7, Found 1091.9 ($[M+H]^+$).

Example VIII-6

Synthesis of Compound 89

Compound 89 was synthesized using the general procedures described above as following: DIC/HOAt mediated amide bond formation (General procedure B) between compound 50 and compound 67, followed by removal of Fmoc (General procedure D), and amide formation with acid 87 using HATU (General procedure A, 3 eq of acid 87 and 1 eq of HATU were used). The final compound was purified by reverse phase HPLC to give compound 89 as a white powder after lyophilization. MS m/z Calcd for C59H96N8O14 1116.7, Found 1118.0 ($[M+H]^+$).

Example VIII-7

Synthesis of Compound 90

Compound 90 was synthesized using the general procedures described above as following: DIC/HOAt mediated amide bond formation (General procedure B) between compound 54 and compound 66, followed by removal of Fmoc (General procedure D), and reaction with glutaric anhydride (General procedure H). The final compound was purified by reverse phase HPLC to give compound 90 as a white powder after lyophilization. MS m/z Calcd for $C_{65}H_{103}N_{11}O_{14}$ 1261.8, Found 1263.1 ($[M+H]^+$).

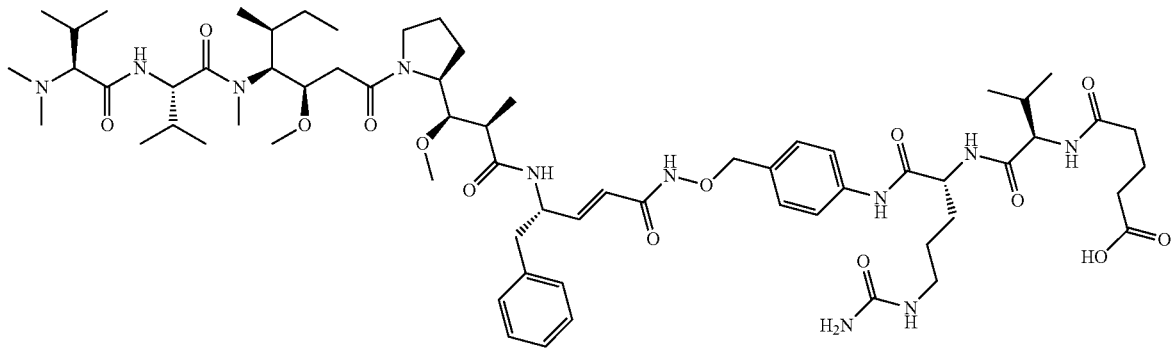

90

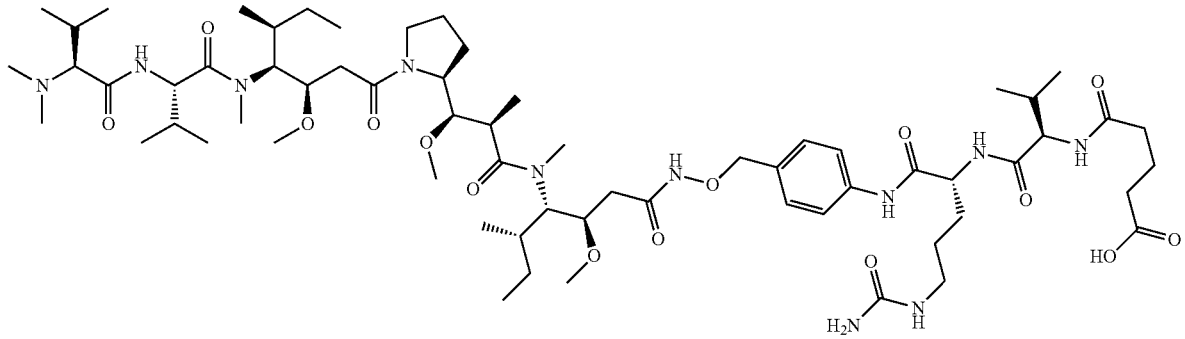

91

92

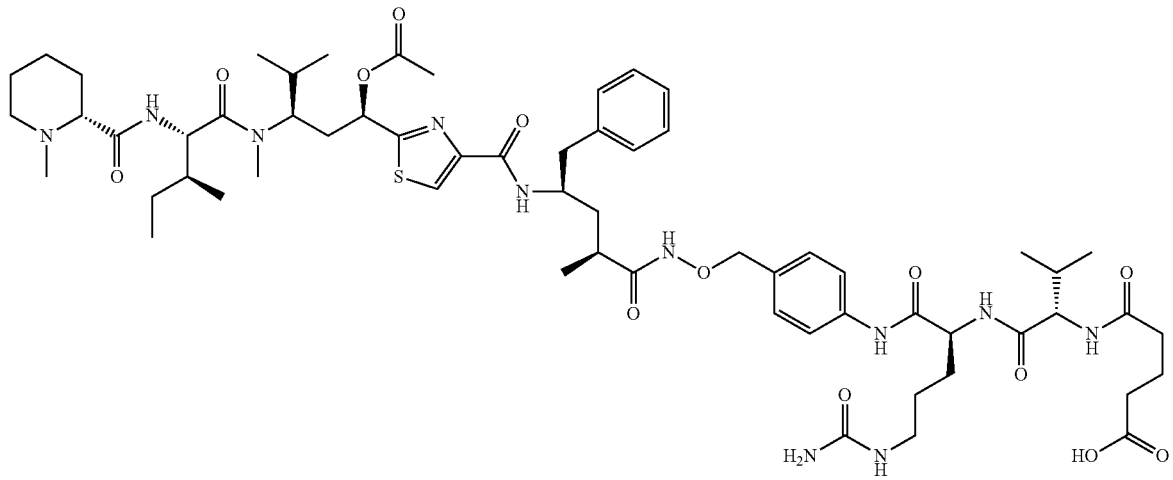

Example VIII-8

Synthesis of Compound 91

Compound 91 was synthesized using the general procedures described above as following: DIC/HOAt mediated amide bond formation (General procedure B) between compound 52 and compound 66, followed by removal of Fmoc (General procedure D), and reaction with glutaric anhydride (General procedure H). The final compound was purified by reverse phase HPLC to give compound 91 as a white powder after lyophilization. MS m/z Calcd for $C_{64}H_{111}N_{11}O_{15}$ 1273.8, Found 1274.8 ([M+H]$^+$).

Example VIII-9

Synthesis of Compound 92

Compound 92 was synthesized using the general procedures described above as following: DIC/HOAt mediated amide bond formation (General procedure B) between Tubulysin M and compound 66, followed by removal of Fmoc (General procedure D), and reaction with glutaric anhydride (General procedure H). The final compound was purified by reverse phase HPLC to give compound 92 as a white powder after lyophilization. MS m/z Calcd for $C_{61}H_{91}N_{11}O_{13}S$ 1217.7, Found 1218.9 ([M+H]$^+$).

Example VIII-10

Synthesis of Compound 93

Compound 93 was synthesized using the general procedures described above as following: DIC/HOAt mediated amide bond formation (General procedure B) between compound 53 and compound 66, followed by removal of Fmoc (General procedure D), and reaction with glutaric anhydride (General procedure H). The final compound was purified by reverse phase HPLC to give compound 93 as a white powder after lyophilization. MS m/z Calcd for $C_{66}H_{107}N_{11}O_{14}$ 1277.8, Found 1278.9 ([M+H]$^+$).

93

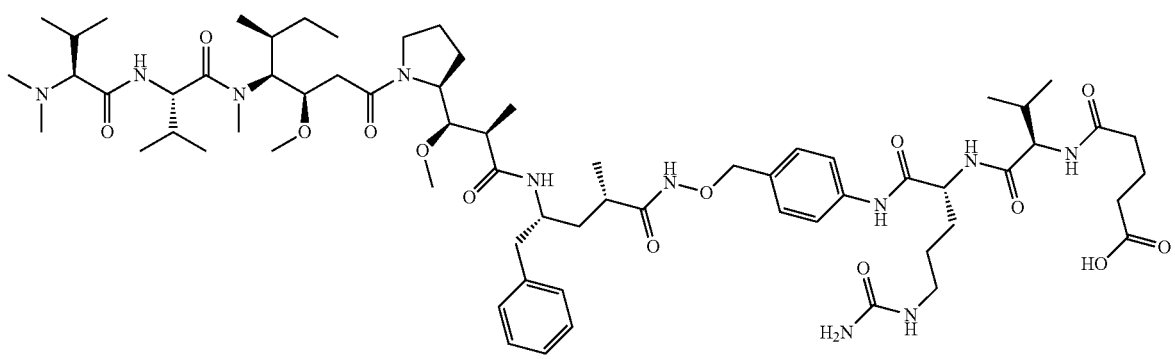

-continued

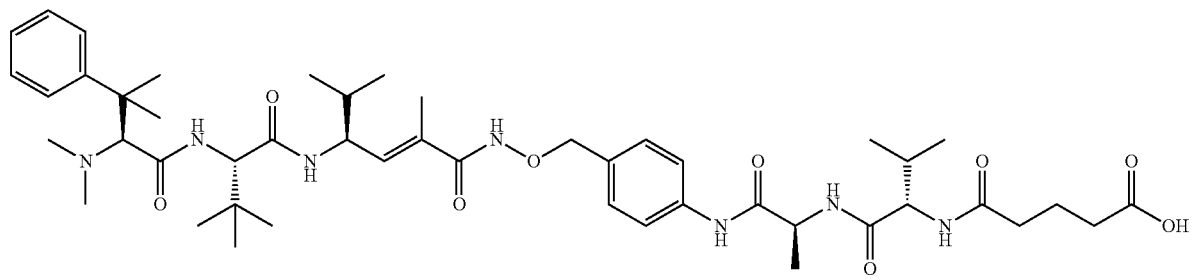 [SMILES: C/C(=C\[C@@H](NC(=O)[C@@H](NC(=O)[C@@H](N(C)C)C(C)(C)c1ccccc1)C(C)(C)C)C(C)C)C(=O)NOCc1ccc(NC(=O)[C@H](C)NC(=O)[C@@H](NC(=O)CCCC(=O)O)C(C)C)cc1]

94

Example VIII-11

Synthesis of Compound 94

Compound 94 was synthesized using the general procedures described above as following: DIC/HOAt mediated amide bond formation (General procedure B) between compound HTI-286 and compound 66, followed by removal of Fmoc (General procedure D), and reaction with glutaric anhydride (General procedure H). The final compound was purified by reverse phase HPLC to give compound 94 as a white powder after lyophilization. MS m/z Calcd for $C_{47}H_{71}N_7O_9$ 877.5, Found 878.4 ([M+H]$^+$).

Example IX

Synthesis of L1-(L2-D)-

| ID | Structure of -L1-(L2-D) | Conj. Method | MS found [M+H]+ |
|---|---|---|---|
| 97 | 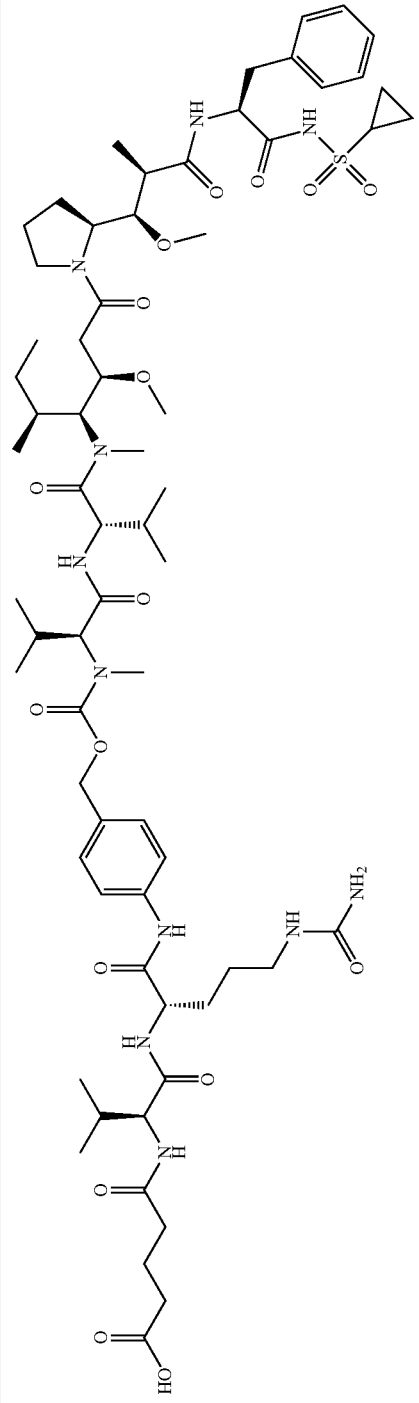 | A | 1354.9 |
| 98 | 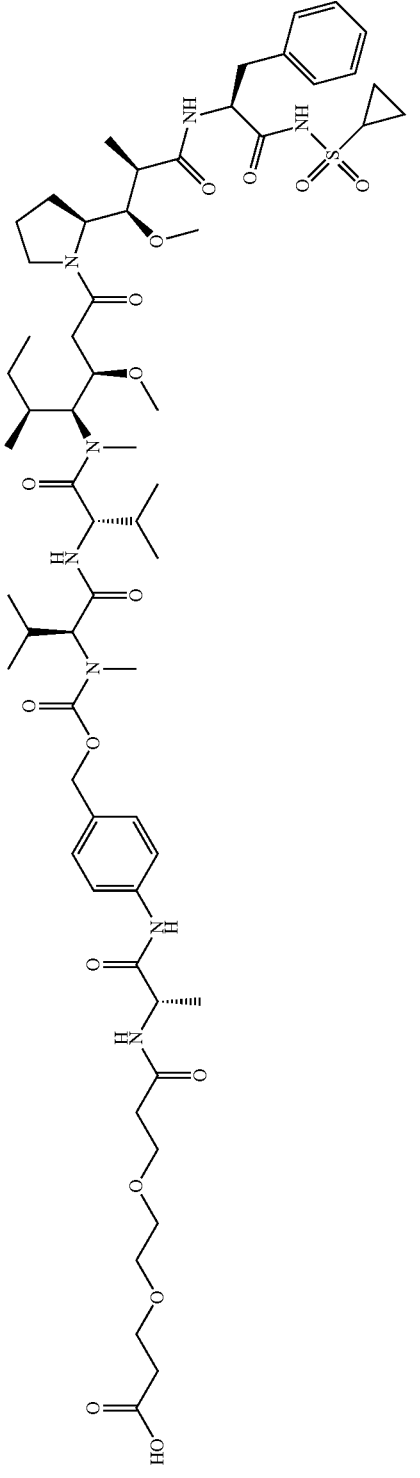 | A | 1243.8 |

| ID | Structure of -L1-(L2-D) | Conj. Method | MS found [M+H]+ |
|---|---|---|---|
| 99 | 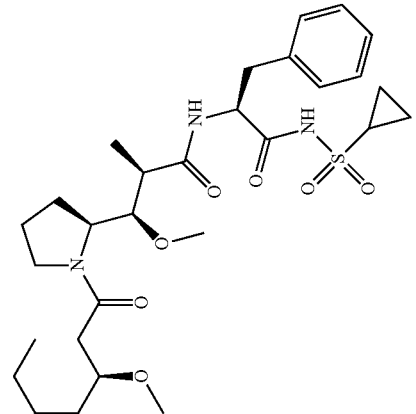 | A | 995.8 |
| 102 | 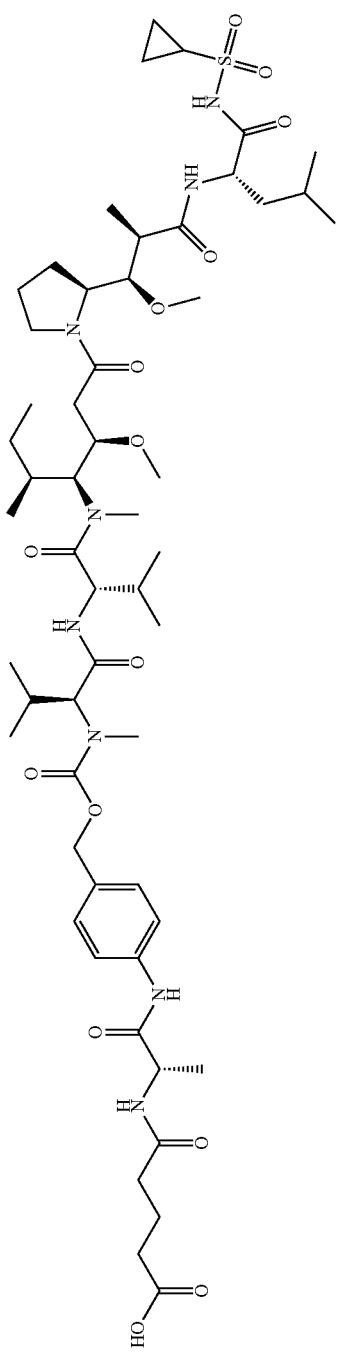 | A | 1135.6 |

| ID | Structure of -L1-(L2-D) | Conj. Method | MS found [M+H]+ |
|---|---|---|---|
| 103 | 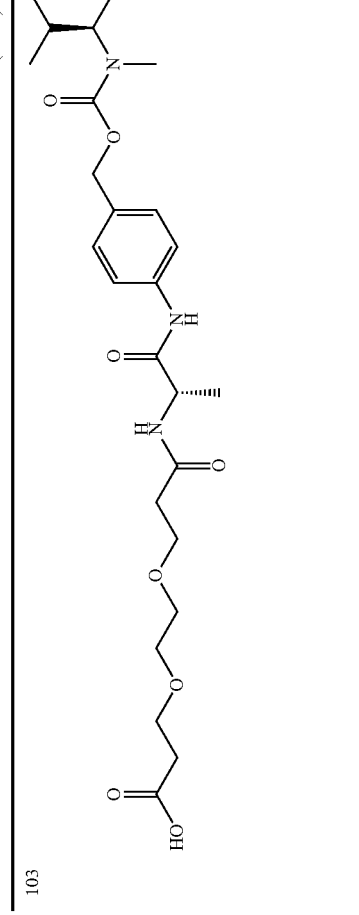 | A | 1209.8 |
| 104 | 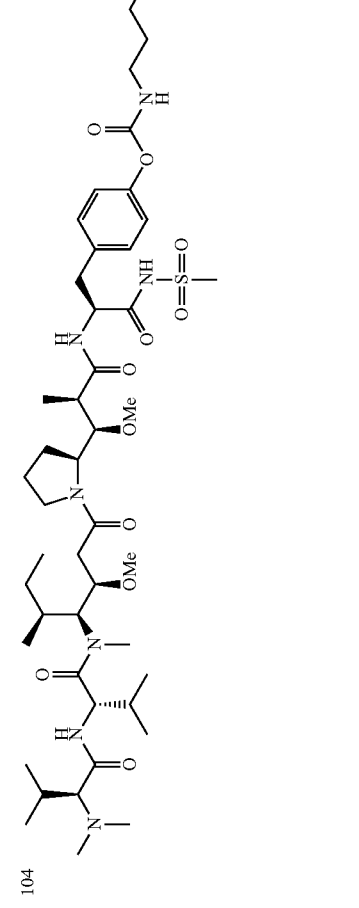 | A | 1486.9 |

| ID | Structure of -L1-(L2-D) | Conj. Method | MS found [M + H]+ |
|---|---|---|---|
| 105 | | A | 1512.9 |
| 131 | | A | 1444.0 |

| ID | Structure of -L1-(L2-D) | Conj. Method | MS found [M+H]+ |
|---|---|---|---|
| 110 | 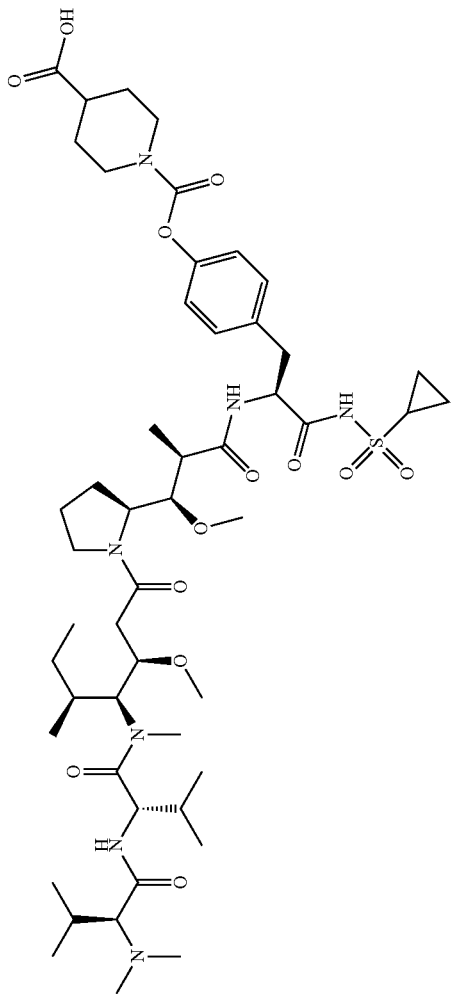 | A | 1020.8 |
| 113 | 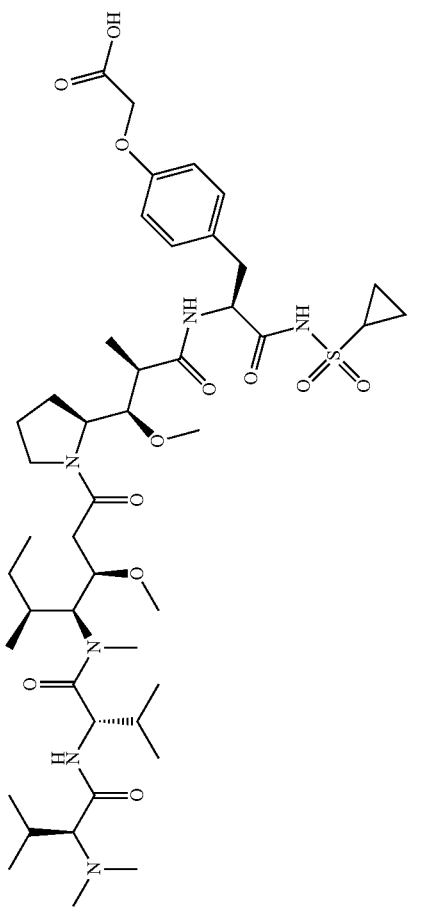 | A | 923.7 |

-continued
| ID | Structure of -L1-(L2-D) | Conj. Method | MS found [M + H]+ |
|---|---|---|---|
| 114 | 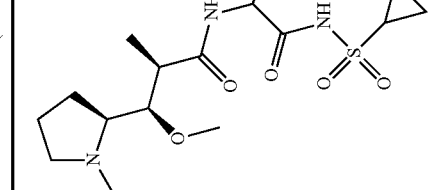 | A | 1034.7 |
| 115 | 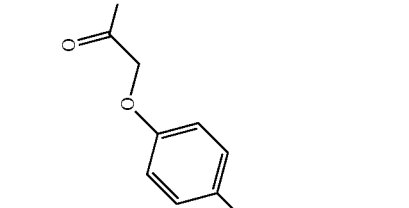 | A | 1325.9 |

-continued

| ID | Structure of -L1-(L2-D) | Conj. Method | MS found [M + H]+ |
|---|---|---|---|
| 132 | (structure) | A | 976.3 |

Example IX-1
Synthesis of Compound 97
Scheme IX.
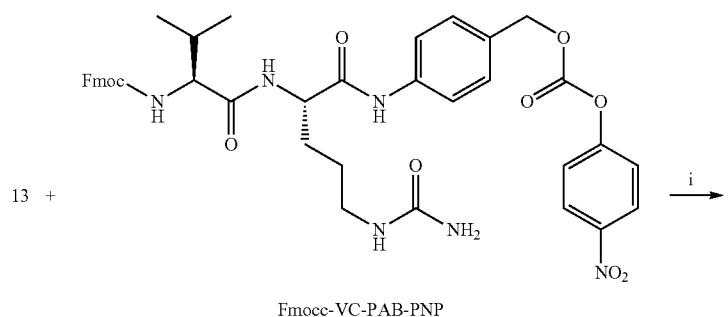
Fmocc-VC-PAB-PNP
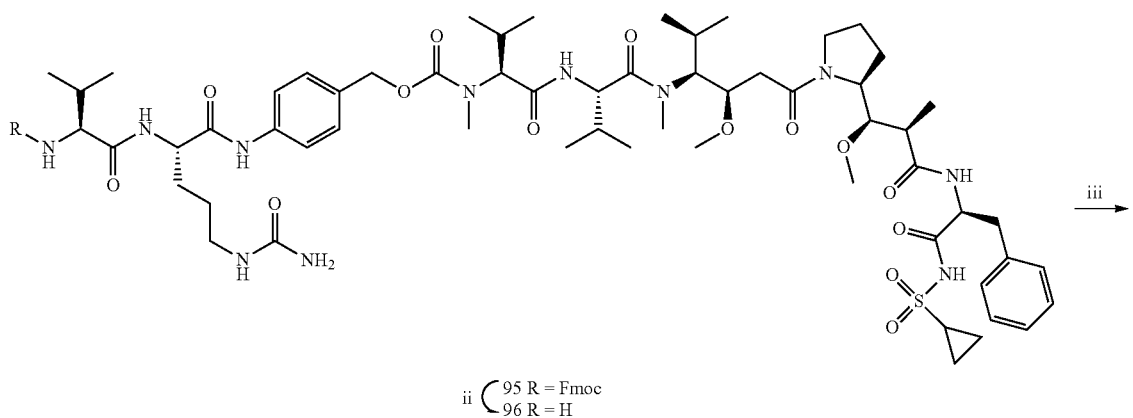
ii ⎰ 95 R = Fmoc
   ⎱ 96 R = H
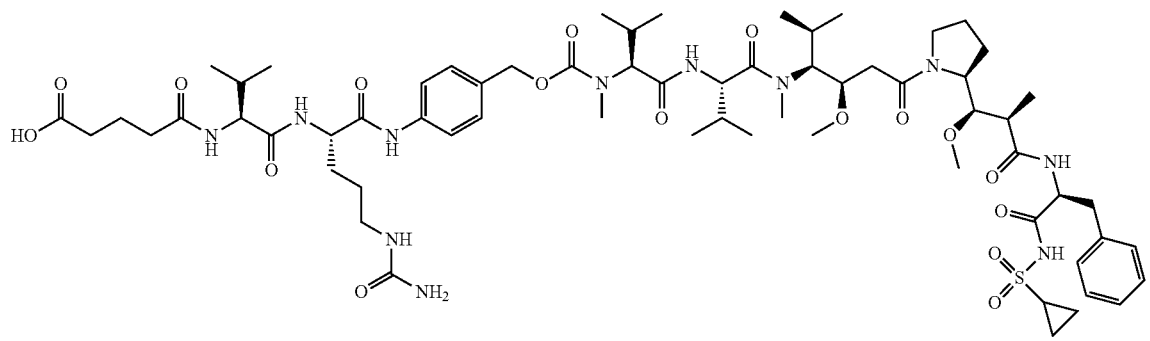 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCC(=O)O)C(C)C)cc1)C(C)C]
97
Reagents and conditions:
i. DIEA, HOBt, (5%), DMF, rt, 48 h;
ii. Piperidine, DMF;
iii. glutaric anhydride, DIEA, DMF Compound 97 was synthesized using the general procedures described above as following: Carbamate formation (General procedure I) between compound 13 and Fmoc-VC-PAB-PNP, followed by removal of Fmoc (General procedure D), and reaction with glutaric anhydride (General procedure H). The final compound was purified by reverse phase HPLC to give compound 97 as a white powder after lyophilization. MS m/z Calcd for $C_{66}H_{103}N_{11}O_{17}S$ 1353.7, Found 1354.9 ([M+H]$^+$).

Example IX-2

Synthesis of Compound 98

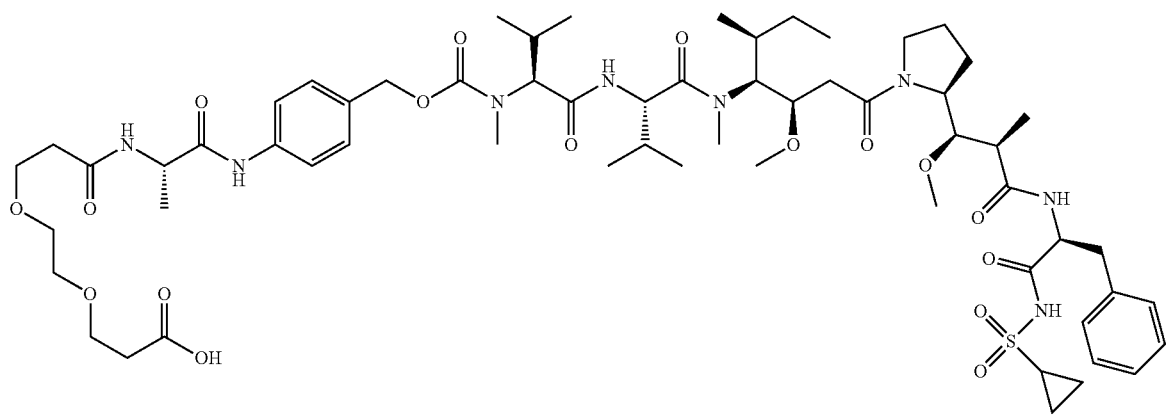

98

Compound 98 was synthesized using the general procedures described above as following: Carbamate formation (General procedure I) between compound 4 and Fmoc-A-PAB-PNP, followed by removal of Fmoc (General procedure D), and amide formation with acid 87 using HATU (General procedure A, 3 eq of acid 87 and 1 eq of HATU were used). The final compound was purified by reverse phase HPLC to give compound 98 as a white powder after lyophilization. MS m/z Calcd for $C_{61}H_{94}N_8O_{17}S$ 1242.7, Found 1243.8 ([M+H]$^+$).

Example IX-3

Synthesis of Compound 99

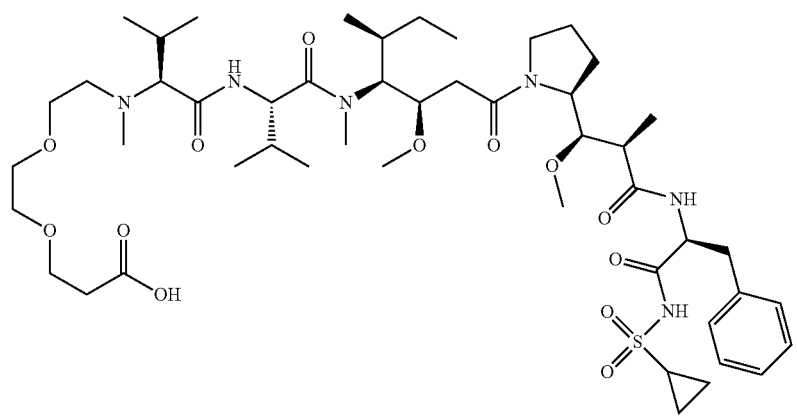

99

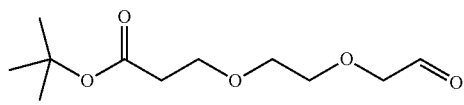

100

Compound 99 was synthesized using the general procedures described above as following: reaction of compound 13 and aldehyde 100 under reductive alkylation conditions (General procedure E) and Fmoc-A-PAB-PNP, followed by removal of t-Bu ester (General procedure C). The final compound was purified by reverse phase HPLC to give compound 99 as a white powder after lyophilization. MS m/z Calcd for $C_{49}H_{82}N_6O_{13}S$ 994.6, Found 995.8 ([M+H]$^+$).

Example IX-4

Synthesis of Compound 102

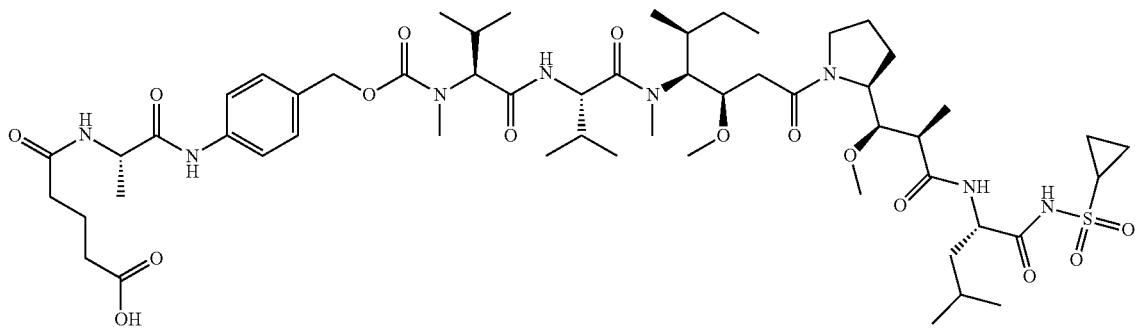

102

Compound 102 was synthesized using the general procedures described above as following: Carbamate formation (General procedure I) between compound 16 and Fmoc-A-PAB-PNP, followed by removal of Fmoc (General procedure D), and reaction with glutaric anhydride (General procedure H). The final compound was purified by reverse phase HPLC to give compound 102 as a white powder after lyophilization. MS m/z Calcd for $C_{55}H_{90}N_8O_{15}S$ 1134.6, Found 1135.6 ([M+H]$^+$).

Example IX-5

Synthesis of Compound 103

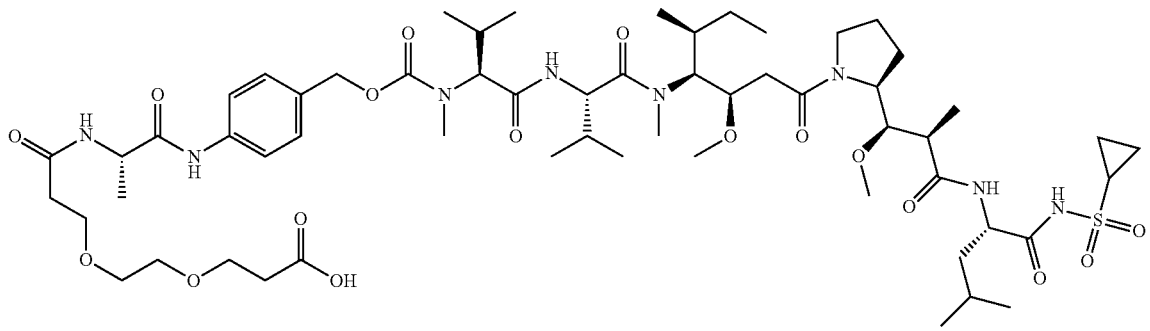

103

Compound 103 was synthesized using the general procedures described above as following: Carbamate formation (General procedure I) between compound 16 and Fmoc-A-PAB-PNP, followed by removal of Fmoc (General procedure D), and amide formation with acid 87 using HATU (General procedure A, 3 eq of acid 87 and 1 eq of HATU were used). The final compound was purified by reverse phase HPLC to give compound 103 as a white powder after lyophilization. MS m/z Calcd for $C_{58}H_{96}N_8O_{17}S$ 1208.7, Found 1209.8 ($[M+H]^+$).

Example IX-6

Synthesis of Compound 104

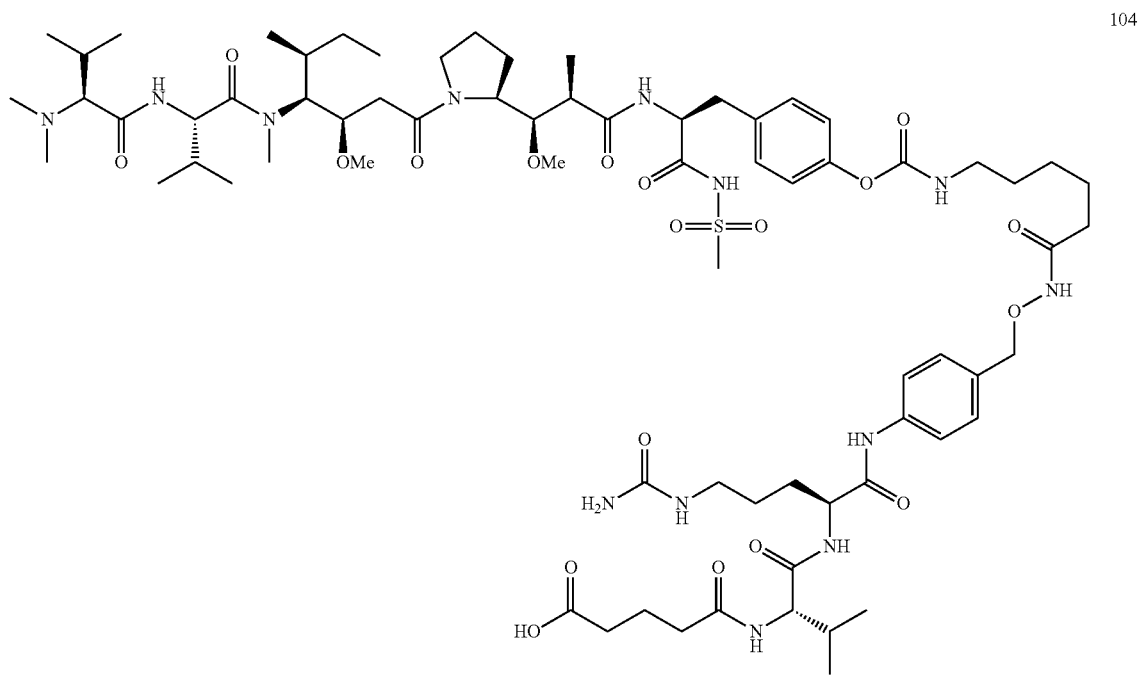 [SMILES: CC[C@H](C)[C@@H]([C@@H](CC(=O)N1CCC[C@H]1[C@H](OC)[C@@H](C)C(=O)N[C@@H](Cc1ccc(OC(=O)NCCCCCC(=O)NOCc2ccc(NC(=O)[C@H](CCCNC(N)=O)NC(=O)[C@@H](NC(=O)CCCC(=O)O)C(C)C)cc2)cc1)C(=O)NS(C)(=O)=O)OC)N(C)C(=O)[C@@H](NC(=O)[C@H](C(C)C)N(C)C)C(C)C]

104

Compound 104 was synthesized using the general procedures described above as following: DIC/HOAt mediated amide bond formation (General procedure B) between compound 42 and compound 66, followed by removal of Fmoc (General procedure D), and reaction with glutaric anhydride (General procedure H). The final compound was purified by reverse phase HPLC to give compound 104 as a white powder after lyophilization. MS m/z Calcd for $C_{71}H_{115}N_{13}O_{19}S$ 1485.8, Found 1486.9 ($[M+H]^+$).

Example IX-7
Synthesis of Compound 105
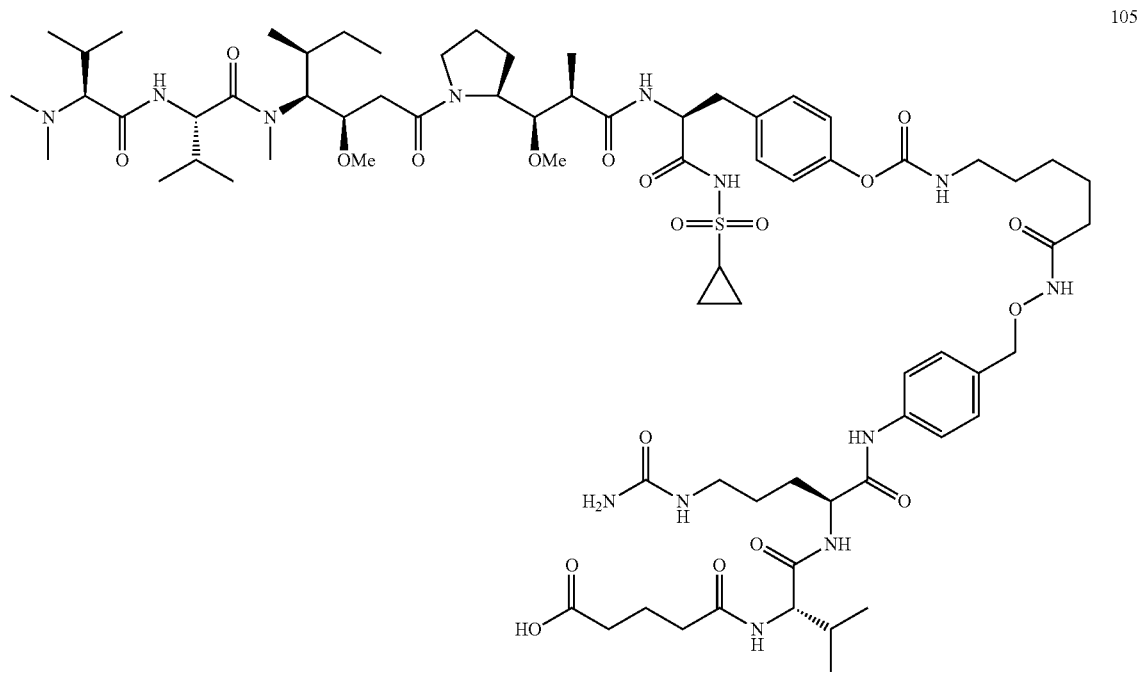 [SMILES: CC[C@H](C)[C@@H]([C@@H](CC(=O)N1CCC[C@H]1[C@H](OC)[C@@H](C)C(=O)N[C@@H](Cc1ccc(OC(=O)NCCCCCC(=O)NOCc2ccc(NC(=O)[C@H](CCCNC(N)=O)NC(=O)[C@@H](NC(=O)CCCC(=O)O)C(C)C)cc2)cc1)C(=O)NS(=O)(=O)C1CC1)OC)N(C)C(=O)[C@@H](NC(=O)[C@H](C(C)C)N(C)C)C(C)C]
Compound 105 was synthesized in the same manner as described for the synthesis of compound 104. The final compound was purified by reverse phase HPLC to give compound 105 as a white powder after lyophilization. MS m/z Calcd for $C_{73}H_{117}N_{13}O_{19}S$ 1511.8, Found 1512.9 ([M+H]$^+$).
Example IX-8
Synthesis of Compound 110
Scheme IX-8.
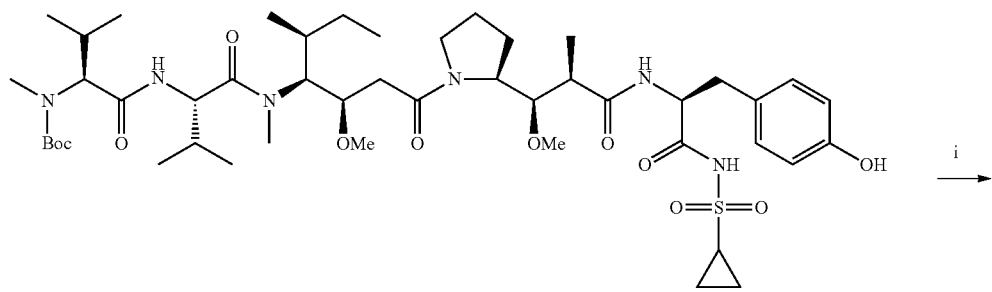

-continued

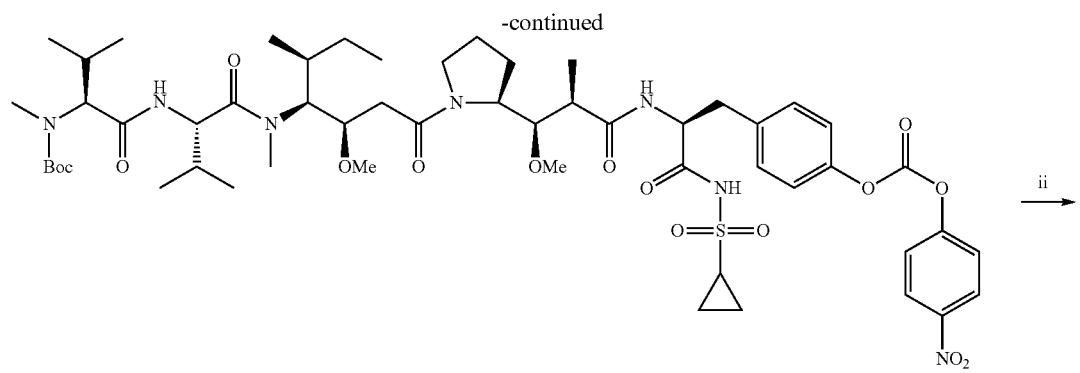

107

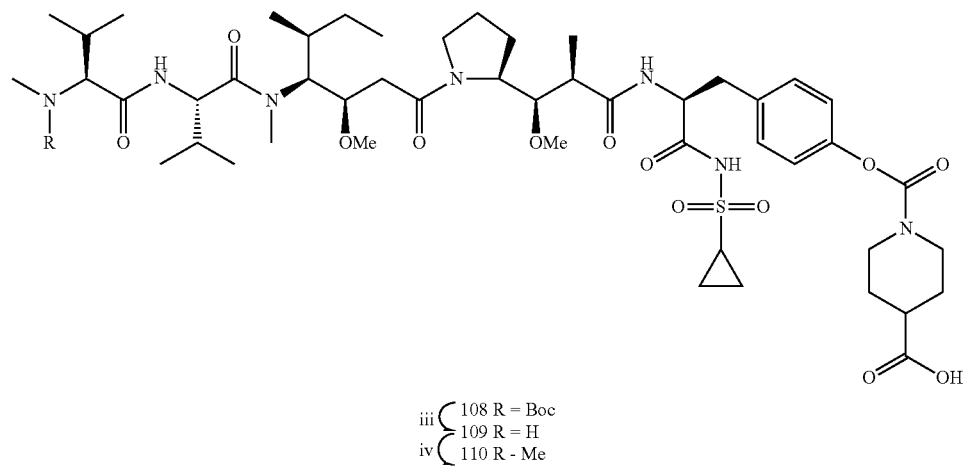

iii { 108 R = Boc
   { 109 R = H
iv { 110 R - Me

Reagents and conditions:
i. bis(nitrophenyl) carbonate, DIEA, THF/DMF, r.t.;
ii. Piperdine 4-carboxylic acid, NaHCO₃ (aq.);
iii. HCl/Dixoane (4N);
iv. HCHO, NaCNBH₃, DMF, HOAc.

The phenol 106 (1 mmol) was treated with 3 eq of bis(p-nitrophenyl)carbonate to form the activated carbonate 107 (general procedure G). The crude product was used directly without further purification. Piperidine 4-carboxylic acid (5 eq) was dissolved in sat. aq. NaHCO₃ (5 mL) and the solution was added. The reaction mixture was stirred at room temperature for 8 h. Citric acid (aq. 10%) was added to acidify the reaction (pH=4-5) and then diluted with EtOAc (150 mL). Organic layer was dried (over Na₂SO₄) and concentrated to give the crude product 108 which underwent the following procedures: removal of Boc (General procedure C), and reductive alkylation using HCHO (General procedure E). The final compound was purified by reverse phase HPLC to give compound 110 as a white powder after lyophilization. MS m/z Calcd for $C_{50}H_{81}N_7O_{13}S$ 1019.6, Found 1020.8 ([M+H]⁺).

Example IX-9

Synthesis of Compound 113

Scheme X.

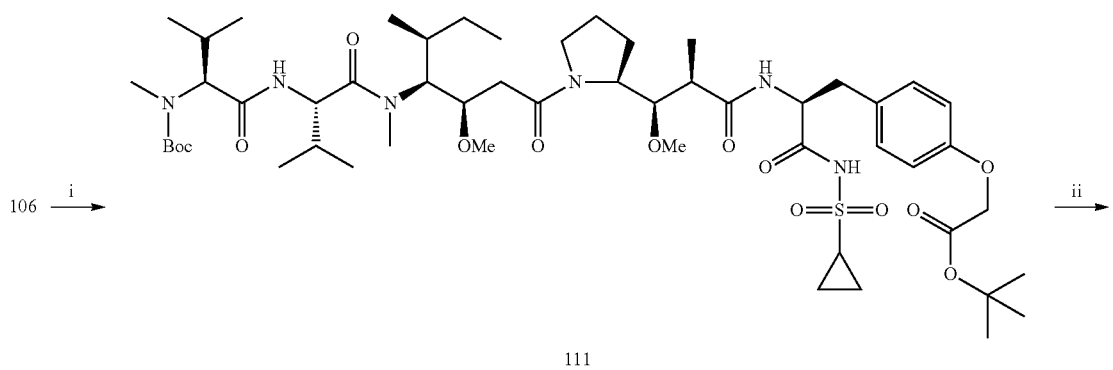

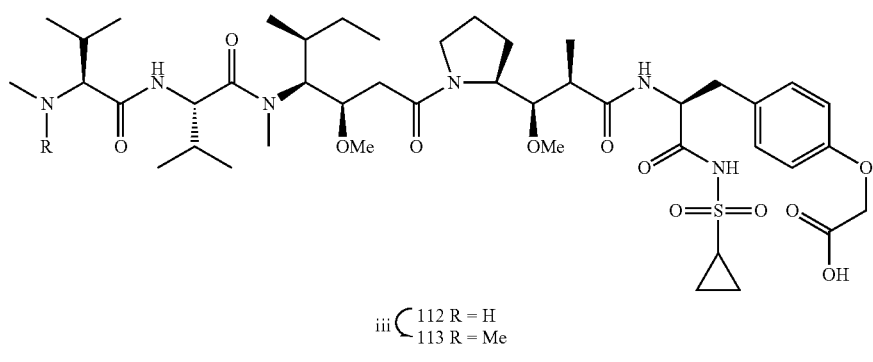

Reagents and conditions:
i. t-Butylbromoacetate, K$_2$CO$_3$, DMF, rt, 2 h;
ii. HCl/dioxane (4N);
iii. HCHO, NaCNBH$_3$, HOAc, DMF To a stirred solution of compound 106 (0.2 mmol, 190 mg) in anhydrous DMF (5 mL) was added t-butyl bromoacetate (0.3 mmol), followed by solid potassium carbonate (55 mg, 0.4 mmol). The reaction mixture was stirred at room temperature for 2 h. LC/MS confirmed that the completion of the reaction. The mixture was diluted with EtOAc (100 mL) and washed with 10% aq. Citric acid and brine. The organic layer was dried and concentrated to dryness to give the crude compound 111, which underwent the following procedures: removal of Boc and t-Bu (General procedure C), and reductive alkylation using HCHO (General procedure E). The final compound was purified by reverse phase HPLC to give compound 113 as a white powder after lyophilization. MS m/z Calcd for $C_{45}H_{74}N_6O_{12}S$, 922.5 Found 923.7 ([M+H]$^+$).

Example IX-10

Synthesis of Compound 114

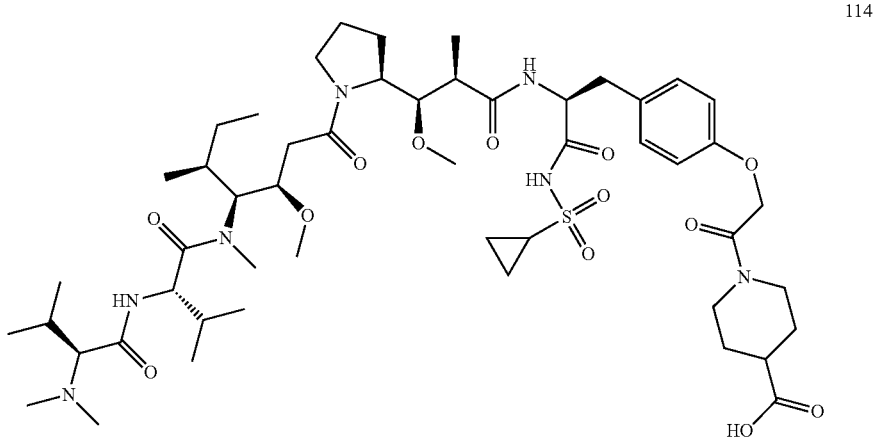 [SMILES: CC[C@H](C)[C@@H]([C@@H](CC(=O)N1CCC[C@H]1[C@H](OC)[C@@H](C)C(=O)N[C@@H](Cc1ccc(OCC(=O)N2CCC(C(=O)O)CC2)cc1)C(=O)NS(=O)(=O)C1CC1)OC)N(C)C(=O)[C@@H](NC(=O)[C@H](C(C)C)N(C)C)C(C)C]

114

Compound 114 was synthesized using the general procedures described above as following: HATU mediated amide bond formation (General procedure A) between compound 113 and methyl isonipecotate, followed by saponification to remove methyl group from ester (General procedure F). The final compound was purified by reverse phase HPLC to give compound 114 as a white powder after lyophilization. MS m/z Calcd for $C_{51}H_{83}N_7O_{13}S$ 1033.6, Found 1034.7 ([M+H]$^+$).

Example IX-11

Synthesis of Compound 115

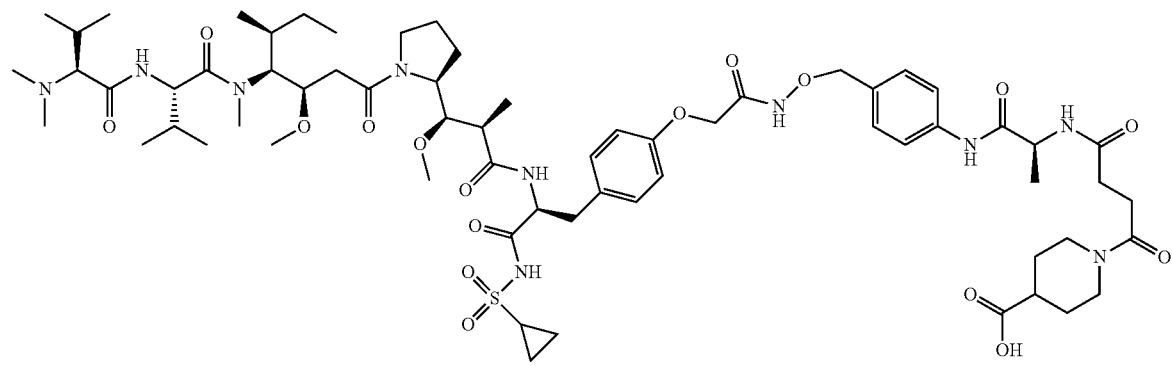

115

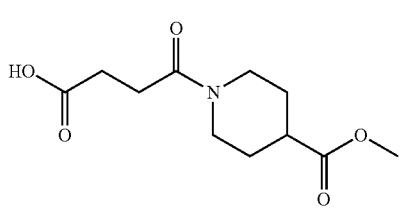

116

Compound 115 was synthesized using the general procedures described above as following: DIC/HOAt mediated amide bond formation (General procedure B) between compound 113 and compound 67, followed by removal of Fmoc (General procedure D), HATU mediated amidation reaction with acid 116 (General procedure A), and saponification to remove methyl group from ester (General procedure F). The final compound was purified by reverse phase HPLC to give compound 115 as a white powder after lyophilization. MS m/z Calcd for $C_{65}H_{100}N_{10}O_{17}5$ 1324.7, Found 1325.9 ([M+H]$^+$).

Example X

Introduction of the Final Function Group Prior to Conjugation

| ID | Structure | Conjugation Method | MS found [M + H]+ |
|---|---|---|---|
| 101 | 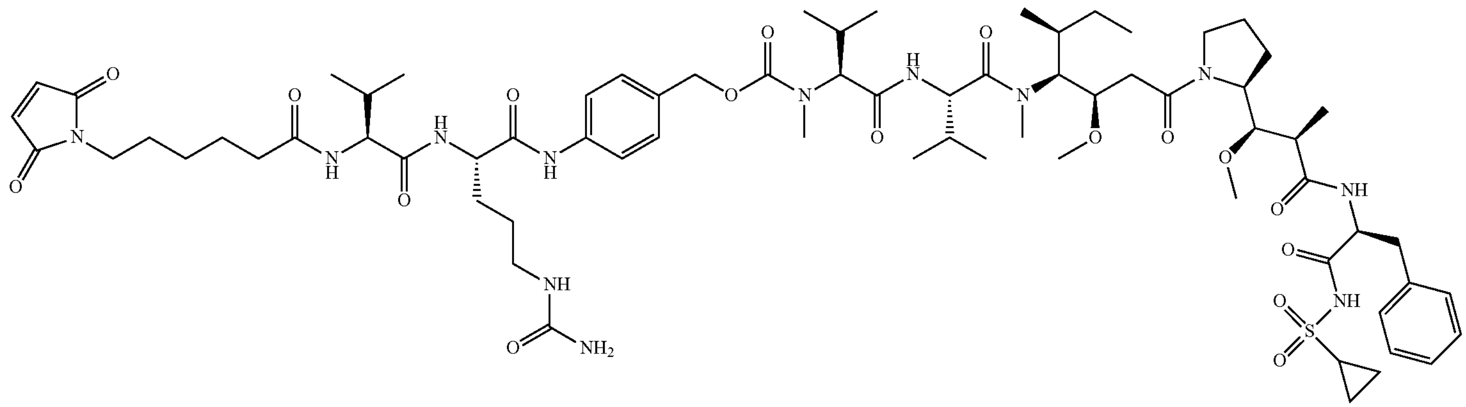 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C] | C | 1433.9 |
| 118 | 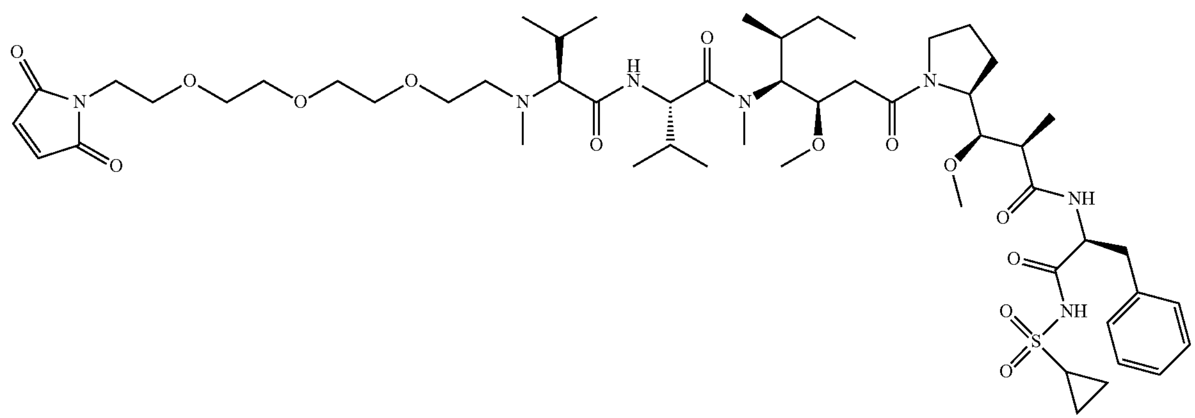 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)C1CC1)OC)N(C)C(=O)[C@@H](NC(=O)[C@H](C(C)C)N(C)CCOCCOCCOCCN1C(=O)C=CC1=O)C(C)C] | C | 1091.2 |

| ID | Structure | Conjugation Method | MS found [M + H]+ |
|---|---|---|---|
| 120 | 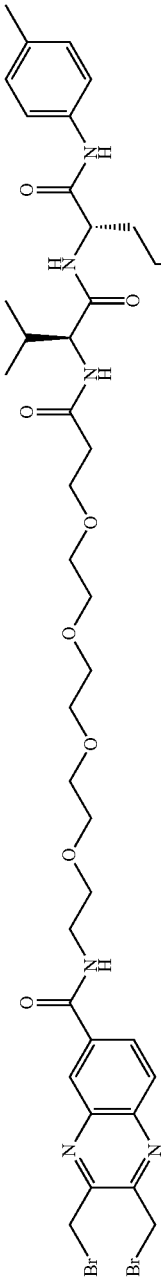 | D | 1829.5 |

-continued
| ID | Structure | Conjugation Method | MS found [M + H]+ |
|---|---|---|---|
| 133 | 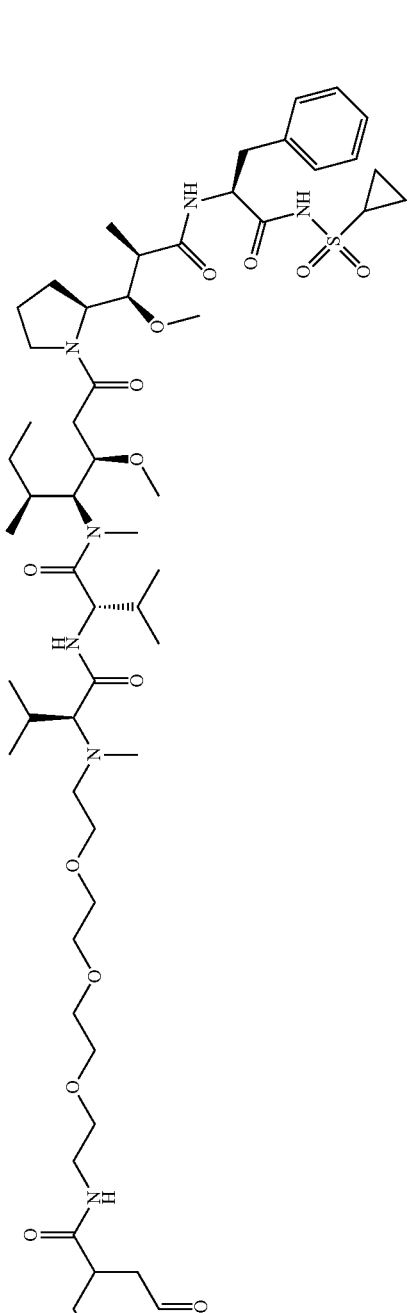 | B | 1136.6 |
| 136 | 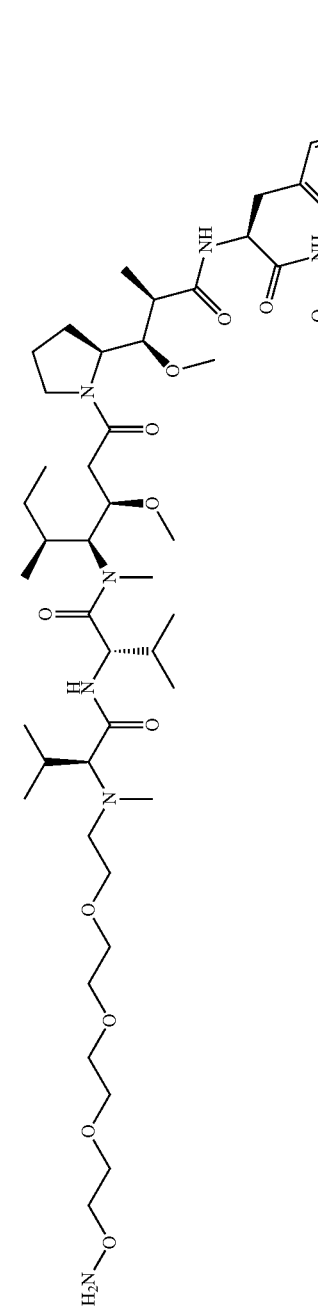 | E | 1026.6 |

| ID | Structure | Conjugation Method | MS found [M+H]+ |
|---|---|---|---|
| 139 | 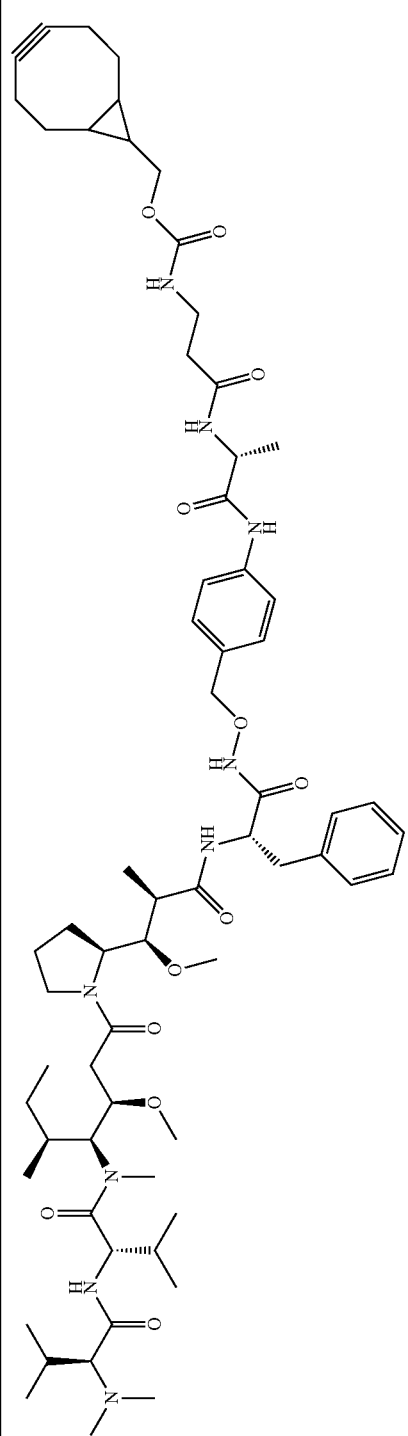 | F | 1184.8 |

Example X-1

Synthesis of Compound 101

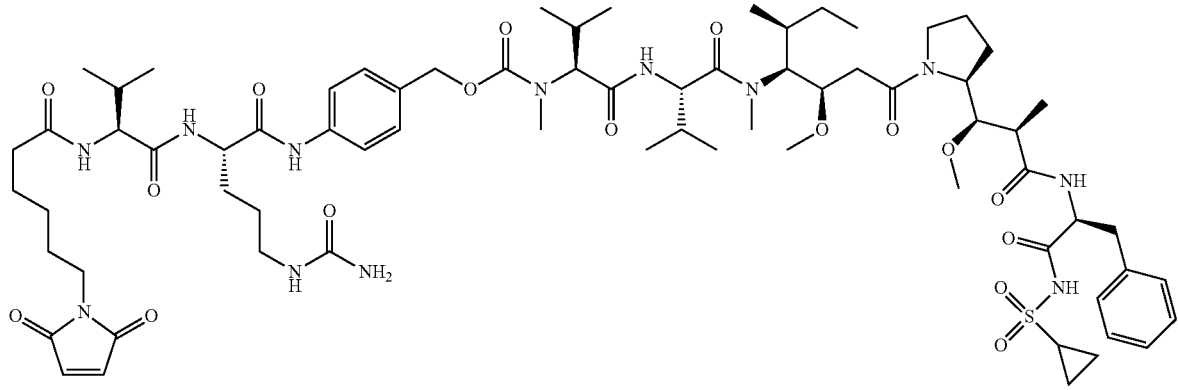

Compound 101 was synthesized using the general procedures described above as following: Carbamate formation (General procedure I) between compound 13 and FmocVC-PAB-PNP, followed by removal of Fmoc (General procedure D), and amidation reaction with 6-maleimidohexanoic acid (General procedure A). The final compound was purified by reverse phase HPLC to give compound 101 as a white powder after lyophilization. MS m/z Calcd for $C_{71}H_{108}N_{12}O_{17}S$ 1432.8, Found 1433.9 ($[M+H]^+$).

Example X-2

Converting an Existing Amino Group to Maleimide Directly Using N-Methoxy-Carbonylmaleimide

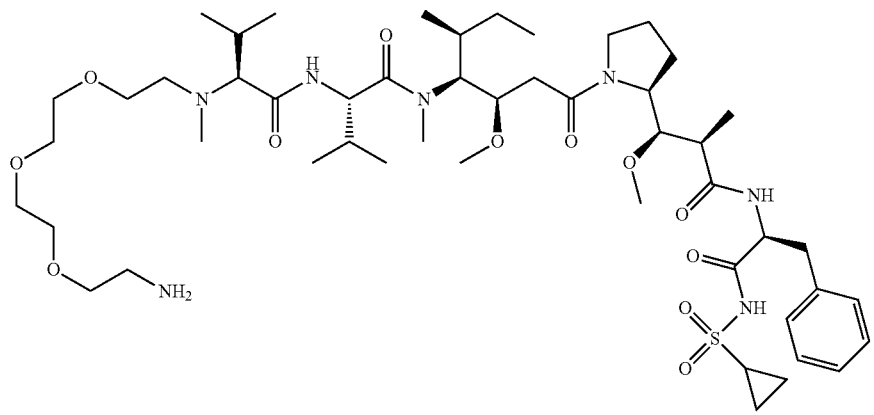

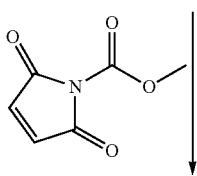

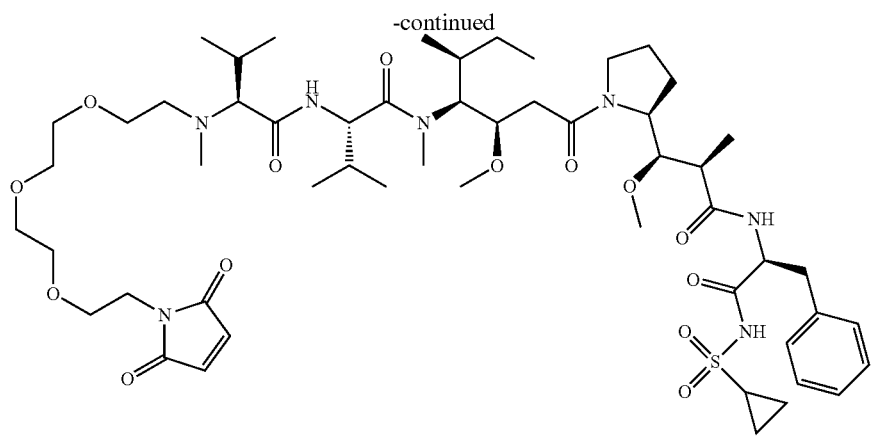

118

The amine (117, 0.1 mmol) was dissolved in acetonitrile/water (6/4, v/v, 3 mL). The mixture was cooled in an ice-water bath and treated with sat. aq. NaHCO$_3$ (0.5 mL), followed by N-methoxycarbonylmaleimide (0.12 mmol). The mixture was stirred at room temperature for 1 h. The pH was adjusted to 6-7 with citric acid and the solution was concentrated. The residue was purified by RP-HPLC to yield the desired maleimide 118 as a white powder after lyophilization (58%). MS found: 1091.2 (M+H)$^+$.

Example X-3

Formation of Dibromomethyl Quinoxaline

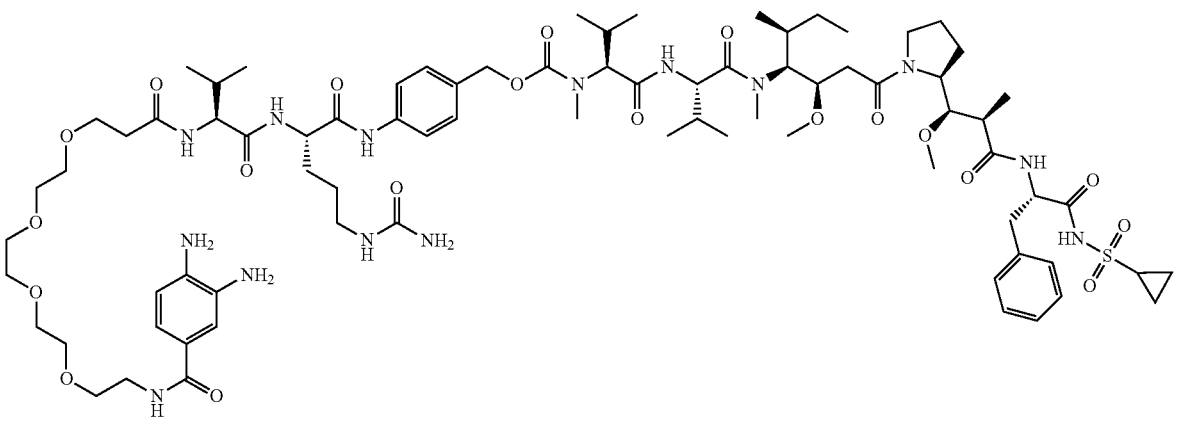

119

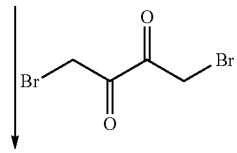

249 250

-continued

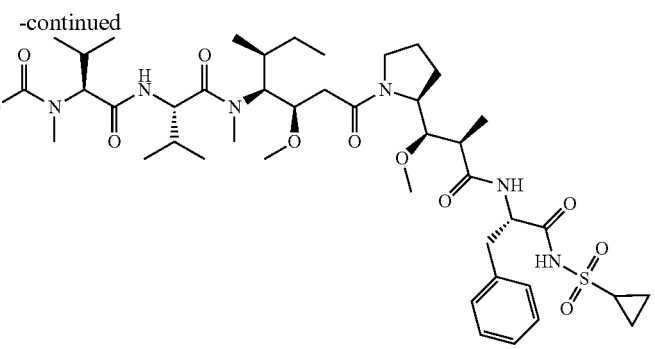

120

The o-phenylenediamino compound 119 (12 mg) was dissolved in acetonitrile/water (6/4, v/v, 1 mL). NaOAc buffer (100 mM, pH=4.0, 0.3 mL) was added, followed by addition of dibromomethyl diketone (10 mg). The mixture was stirred at room temperature for 10 min and purified directly by RP-HPLC to give the desired quinoxaline 120 as a white powder (12 mg) after lyophilization. MS found 1829.5 (M+H)$^+$.

Example X-4

Synthesis of Compound 136

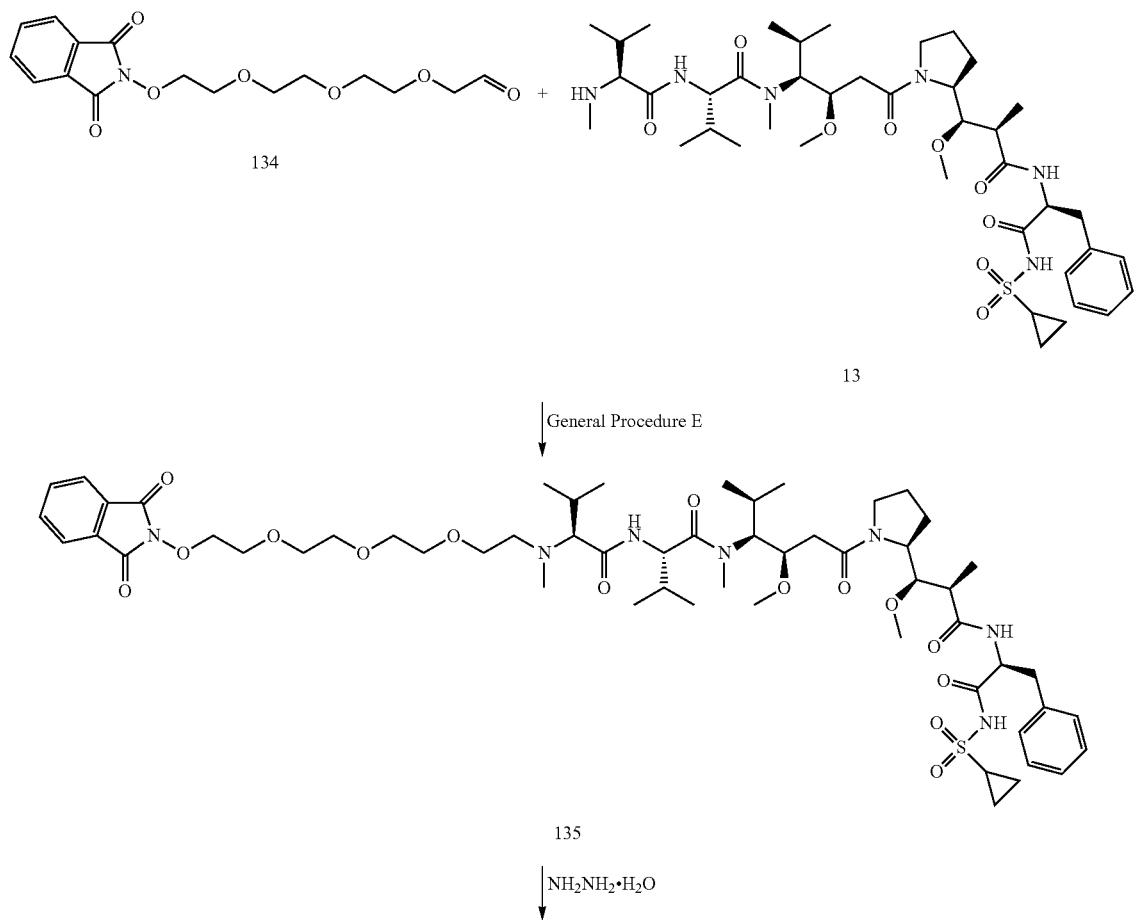

-continued
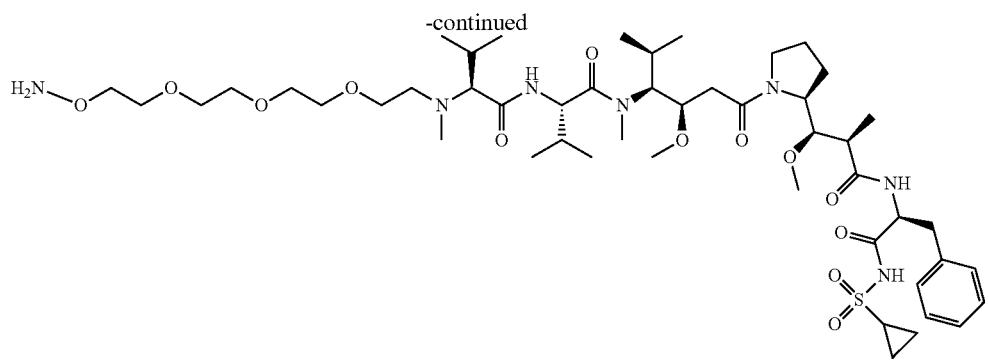
136
Compound 13 (50 mg) was treated with aldehyde under reductive alkylation conditions (General procedure E). Without any purification, hydrazine hydrate (20 μL) was added to the reaction mixture. After 10 min, the crude mixture was purified by RP-HPLC to give compound 136 as a white powder (46 mg). MS found 1026.6 (M+H)$^+$.
Example X-5
Synthesis of Compound 139
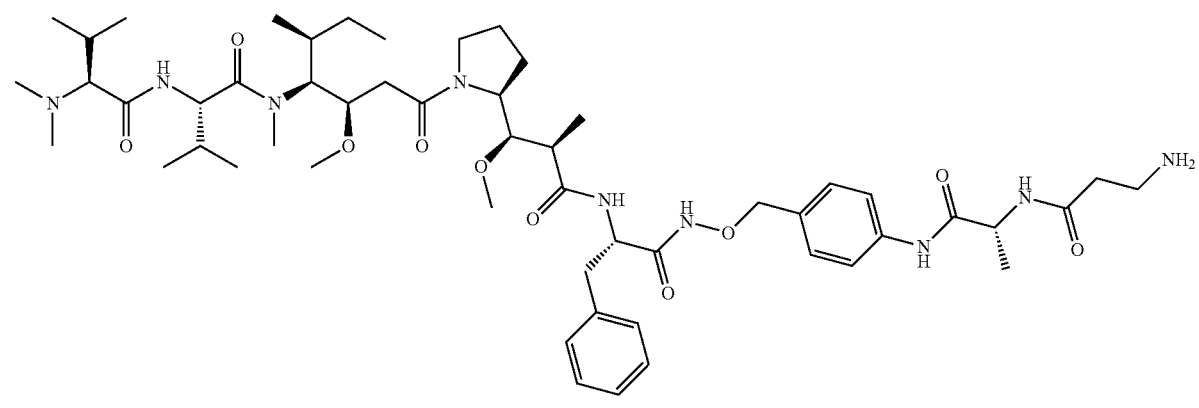
137
138
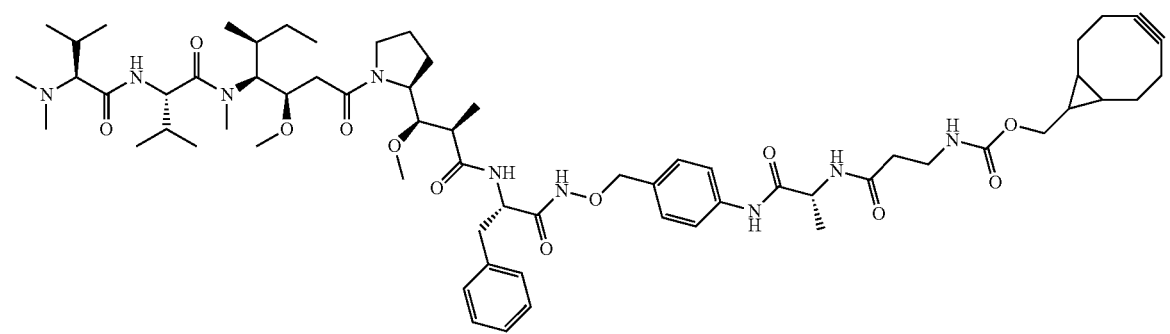 [SMILES: CC[C@H](C)[C@@H]([C@@H](CC(=O)N1CCC[C@H]1[C@H](OC)[C@@H](C)C(=O)N[C@@H](Cc1ccccc1)C(=O)NOCc1ccc(NC(=O)[C@@H](C)NC(=O)CCNC(=O)OCC2C3CCC#CCCC32)cc1)OC)N(C)C(=O)[C@@H](NC(=O)[C@H](C(C)C)N(C)C)C(C)C]
139

Compound 139 was synthesized from compound 137 and carbonate 138 according to General procedure I. MS found: 1184.8 (M+H)⁺.

The Antibody Drug Conjugates depicted in the Figures were prepared according to Example XI.

Example XI

Preparation of Antibody Drug Conjugate

To a solution of 0.5-50 mgs/mL of Trastuzumab in buffet at pH 6.0-9.0 with 0-30% organic solvent, was added 0.1-10 eq of carboxylic acid activated derivatives of compounds 84, 92, 93, or 98 in a portion wise or continuous flow manner. The reaction was performed at 0-40° C. for 0.5-50 hours with gentle stirring or shaking, monitored by HIC-HPLC (Hydrophobic Interaction Chromatography-HPLC). The resultant crude ADC product underwent necessary downstream steps of desalt, buffet changes/formulation, and optionally, purification, using the state-of-art procedures. The final ADC product was characterized by HIC-HPLC, SEC, RP-HPLC, and optionally LC-MS. The average DAR (drug antibody ratio) was calculated by UV absorption and/or MS spectroscopy.

Example XI

In vitro cytotoxicity experiment

Figure 2:
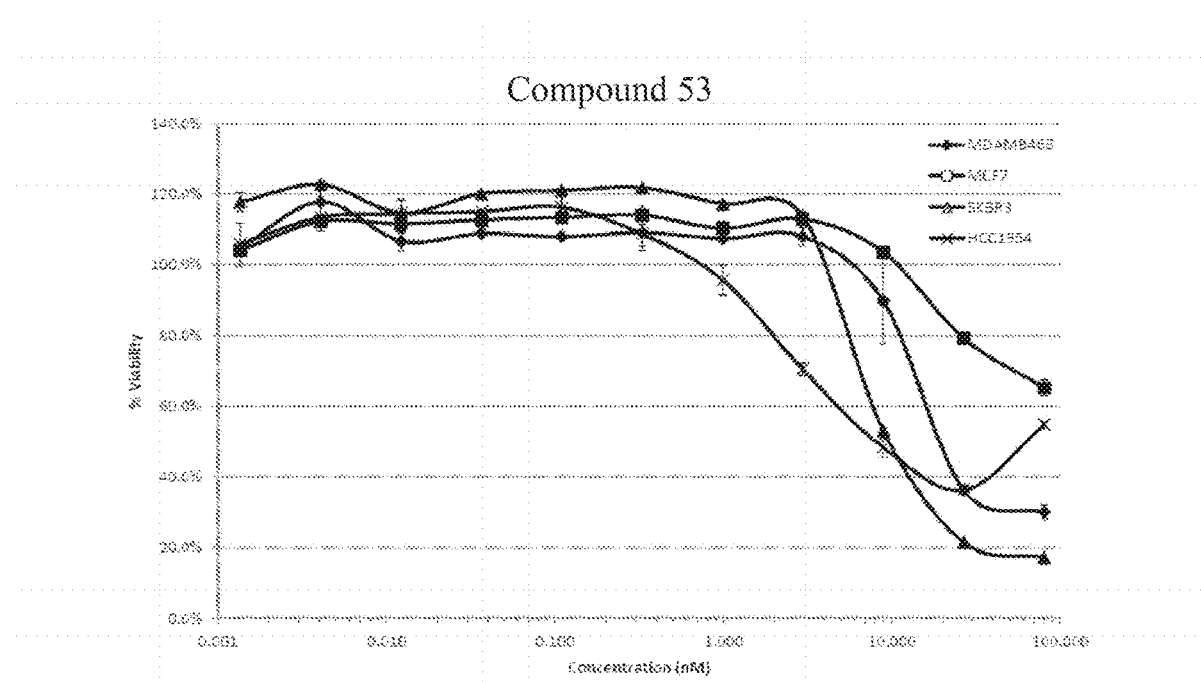
Figure 3:
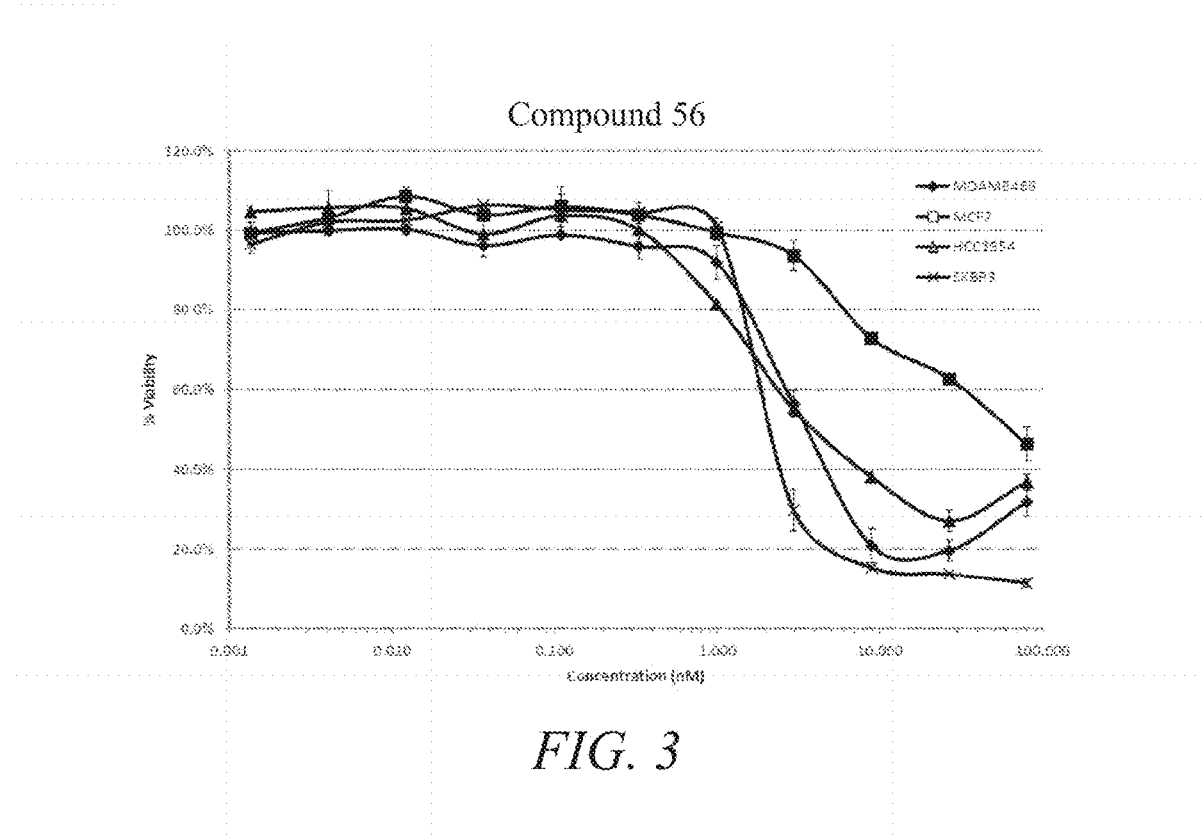
Figure 4:
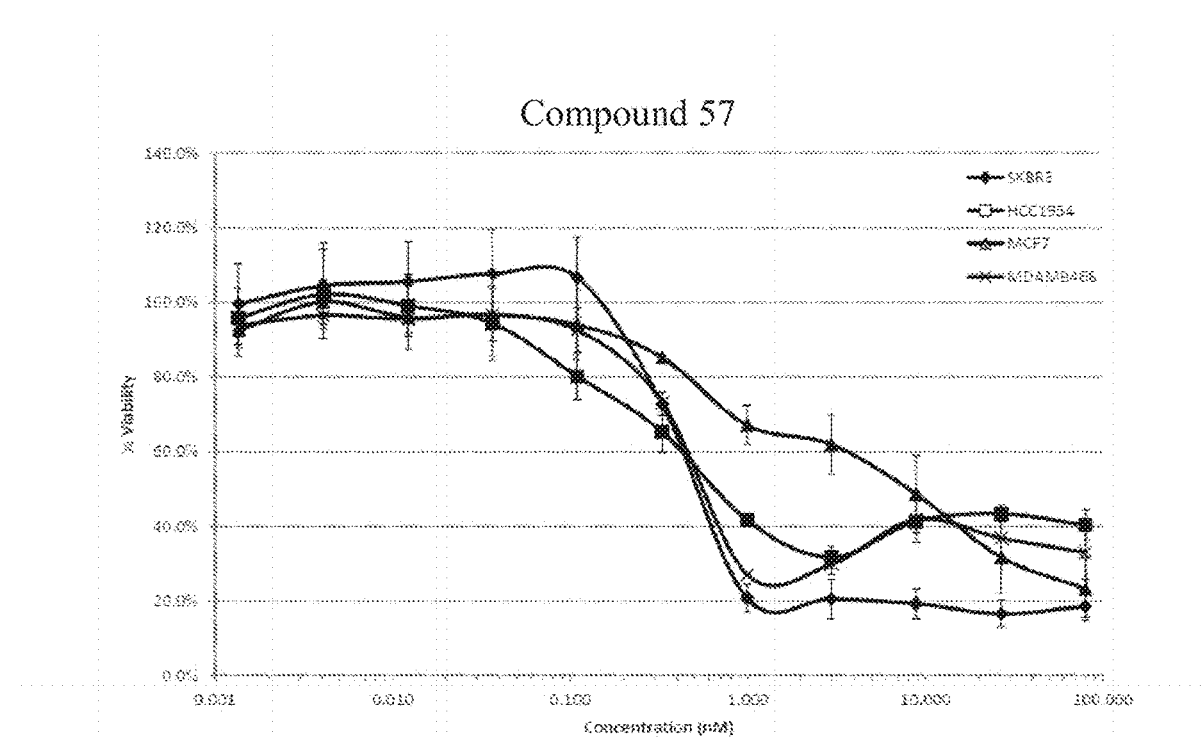
Figure 5:
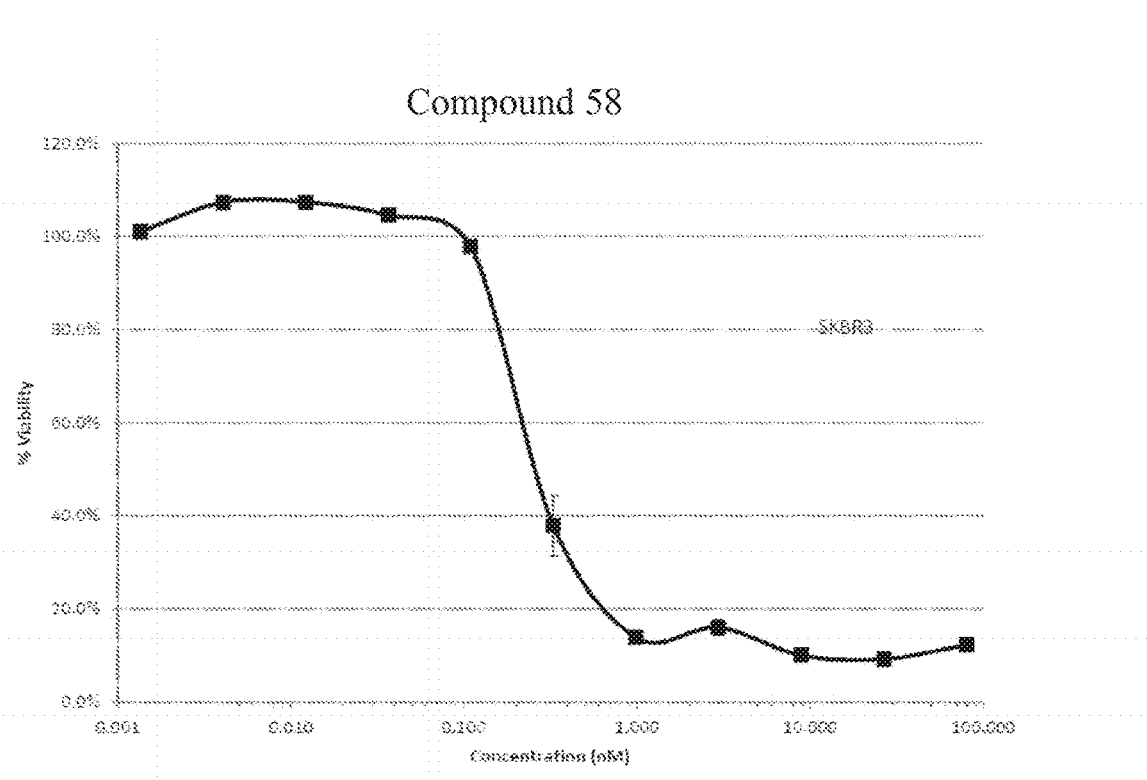
Figure 6:
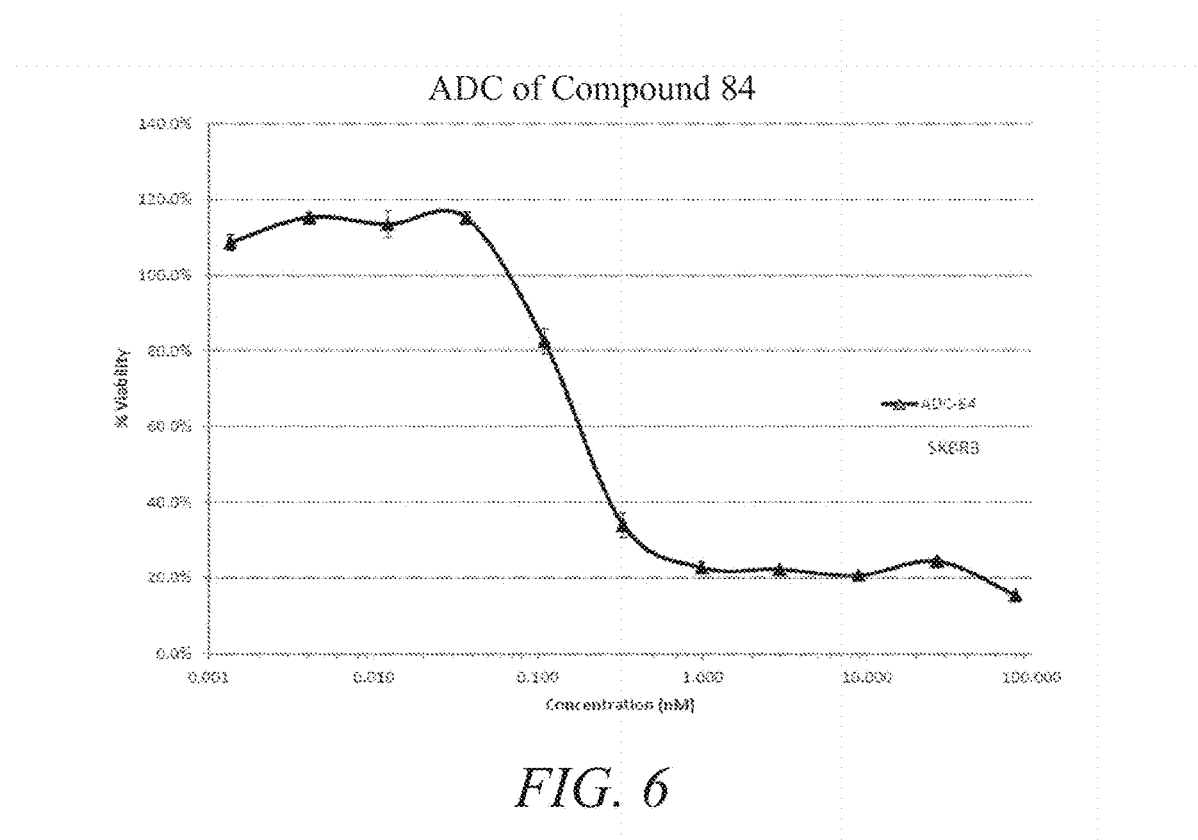
Figure 7:
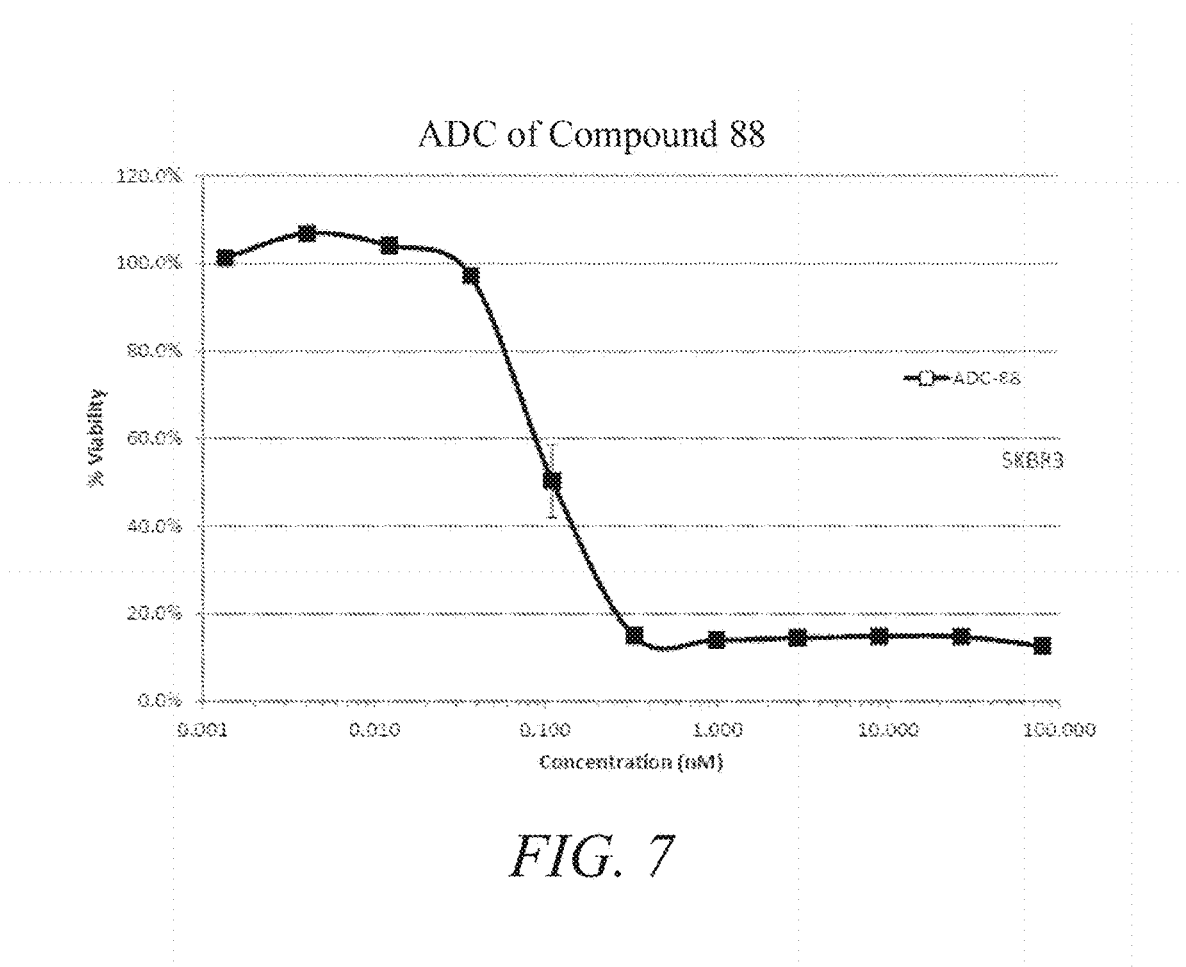
Figure 8:
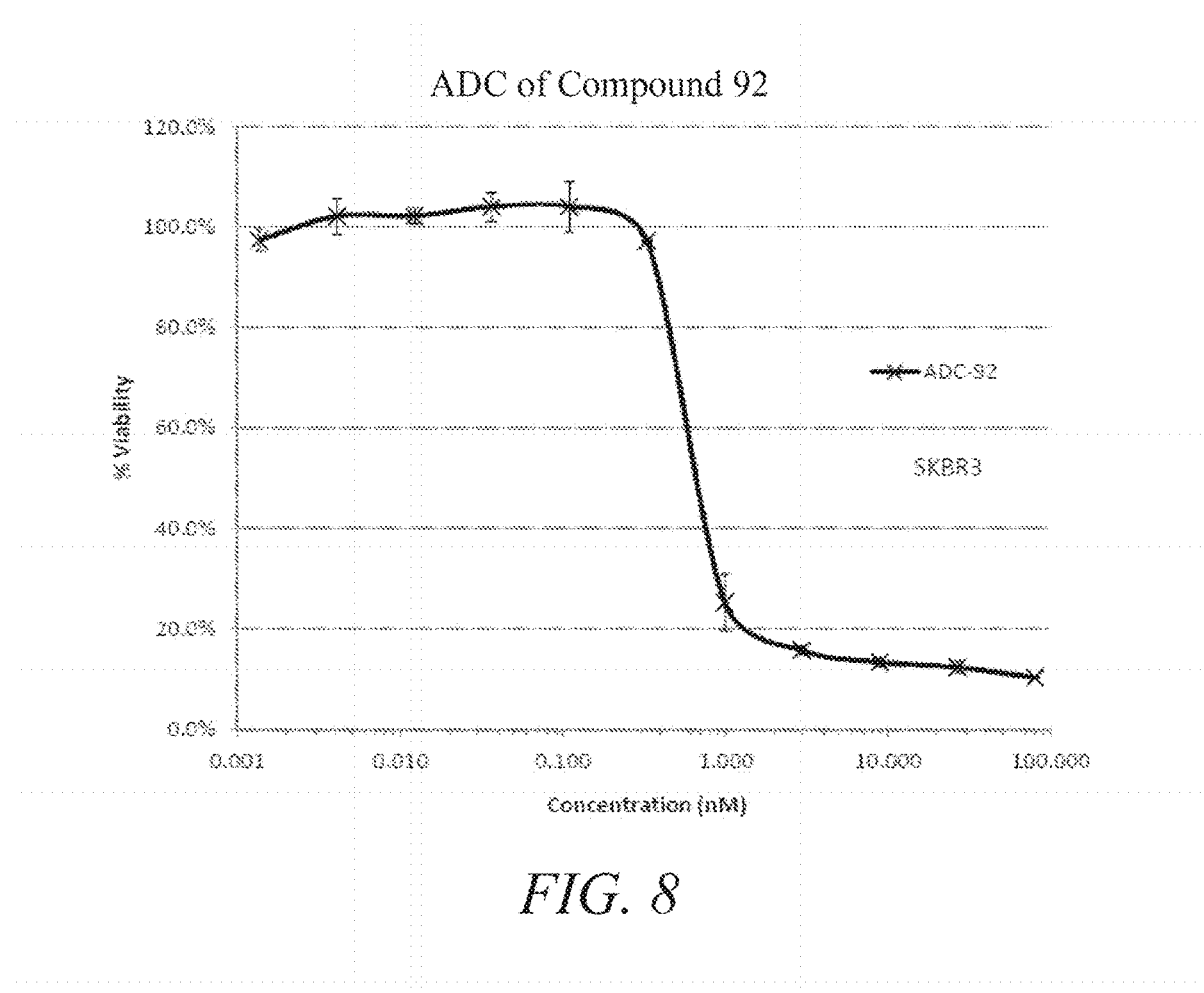
Figure 9:
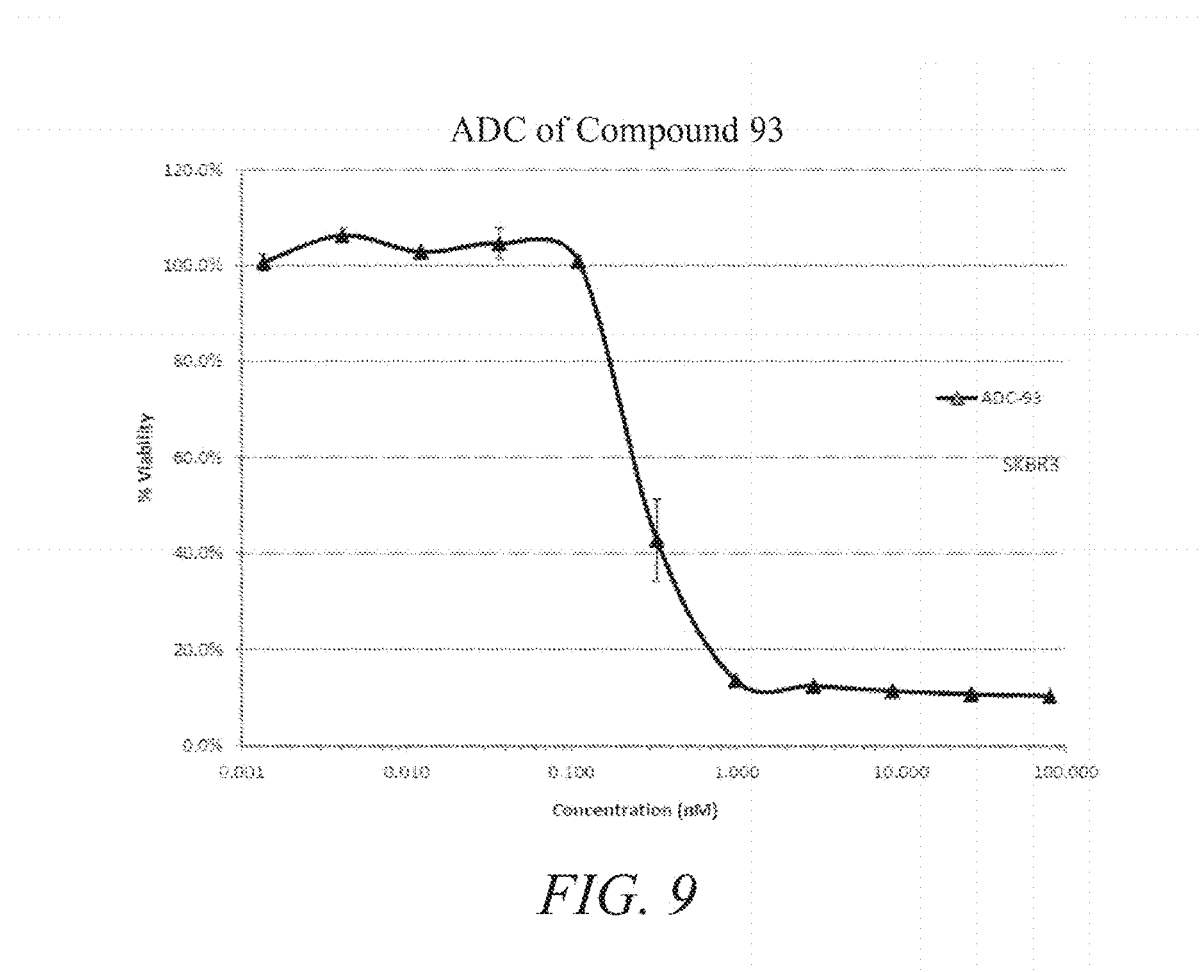
Figure 10:
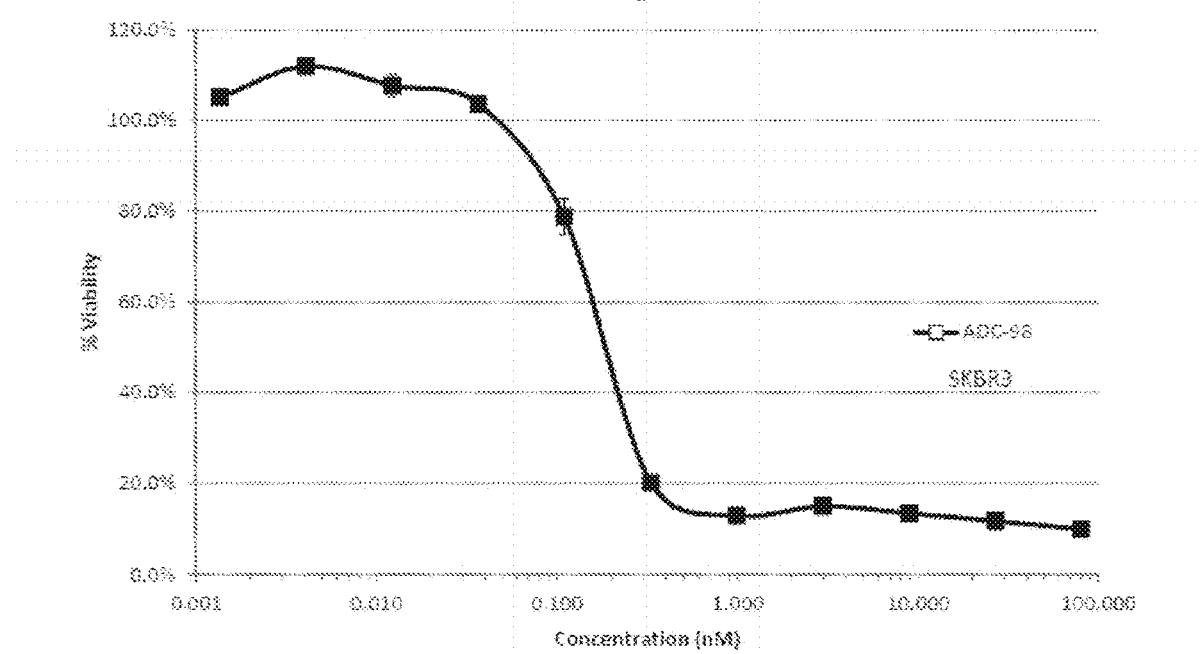

The cell lines used were SK-BR-3 human breast adenocarcinoma (HER2 triple positive), HCC1954 human Ductal Carcinoma (HER2 triple positive), MCF7 human breast adenocarcinoma (HER2 normal), and MDA-MB-468 human breast adenocarcinoma (HER2 negative). These cells were available from ATCC. SK-BR-3 cells were grown in McCoy's 5A medium (Caisson Labs, North Logan, UT) supplemented with 10% fetal bovine serum. HCC1954 cells were grown in RPMI-1640 medium (Caisson Labs, North Logan, UT) supplemented with 10% fetal bovine serum. MCF7 and MDA-MB-468 cells were grown in DMEM/F12 medium (Caisson Labs, North Logan, UT) supplemented with 10% fetal bovine serum. SK-BR-3, MCF7, and MDA-MB-468 cells were plated in 96-well plates at approximately 7,500 cells/well, and HCC1954 cells were plated in 96-well plates at approximately 20,000 cells/well. Compounds or the antibody-drug conjugates were added in duplicates in the same day. After 72 hour incubation at 37° C., CellTiter -Glo (Promega, Madison, WI) were added and cell viability was determined as describe by the manufacture's protocol. Results are shown in FIGS. 1-10. The percent viability was determined as following:

% Viability =Average Luminescence Value of the duplicates (treated wells)/Average Luminescence Value of the untreated wells.

What is claimed is:
1. A compound having the structure of Formula II:

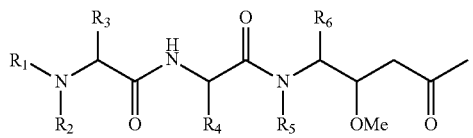

(II)

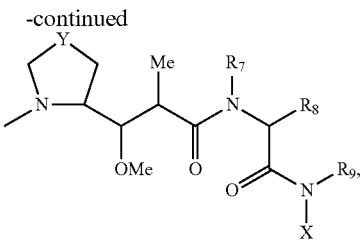

or a pharmaceutically acceptable salt thereof, wherein:
Y is $CH_2$;
$R^9$ is selected from the group consisting of H (hydrogen), optionally substituted $C_1$-$C_8$ alkyl, optionally substituted $C_3$-$C_8$ cycloalkyl, optionally substituted aryl, and optionally substituted heteroaryl;
optionally $R^1$ and $R^2$, $R^1$ and $R^3$, $R^7$ and $R^8$, $R^8$ and $R^9$, or $R^7$ and $R^9$ together with the atoms to which they are attached form an optionally substituted cyclic 5- to 7-membered ring;
X is selected from the group consisting of —$OR^{10}$ and —$SO_2$—$R^{10}$;
$R^{10}$ is $R^C$;
$R^1$ is H (hydrogen), optionally substituted $C_1$-$C_6$ alkyl, $R^{1A}$, or $R^{1B}$;
$R^{1A}$ is a monoclonal antibody or an antibody fragment;
$R^{1B}$ is -$L^1(CH_2)_nR^C$, -$L^1O(CH_2)_nR^C$ or —$(CH_2)_nR^C$;
$R^2$-$R^7$ are each independently selected from the group consisting of H (hydrogen), optionally substituted $C_1$-$C_8$ alkyl, optionally substituted $C_3$-$C_8$ cycloalkyl, optionally substituted aryl, and optionally substituted heteroaryl;
$R^8$ is selected from the group consisting of H (hydrogen), —$(CH_2)_nR^C$, optionally substituted $C_1$-$C_8$ alkyl, optionally substituted $C_3$-$C_8$ cycloalkyl, optionally, substituted aryl, and optionally substituted heterocyclyl;
$R^C$ is $C_1$-$C_8$ alkyl, $C_3$-$C_8$ cycloalkyl, aryl, heteroaryl, and heterocyclyl, each optionally substituted with one or more $R^D$, or $R^C$ is a monoclonal antibody or an antibody fragment;
each $R^D$ is independently selected from the group consisting of —OH, —$N_3$, halo, cyano, nitro, —$(CH_2)_n$ $NR^ER^F$, —$(CH_2)_nC(=O)NR^ER^F$, —$O(CH_2)_nNR^ER^F$, —$O(CH_2)_nC(=O)NR^ER^F$, —$O(CH_2)_mOC(=O)$ $NR^ER^F$, —$NR^GC(=O)R^H$, —$NR^GS(O)_zR^H$, —$O(CH_2)_mO(CH_2)_mR^J$, —$O(CH_2)_nC(=O)R^J$, —$O(CH_2)_nR^J$, optionally substituted $C_1$-$C_8$ alkyl, optionally substituted $C_3$-$C_8$ cycloalkyl, optionally substituted aryl, optionally substituted heteroaryl, optionally substituted heterocyclyl, and optionally substituted —O—($C_1$-$C_8$ alkyl);
$R^E$ and $R^F$ are each independently selected from hydrogen, -[($L^1$)$_s$($C(R^{2A})_2$)$_r$($NR^{2A}$)$_s$($C(R^{2A})_2$)$_r$]-[$L^1$(C $(R^{2A})_2$)$_r$($NR^{2A}$)$_s$($C(R^{2A})_2$)$_r$]$_s$- ($L^1$)$_s$-$R^J$, -[($L^1$)$_s$(C $(R^{2A})_2$)$_r$($NR^{2A}$)$_s$($C(R^{2A})_2$)$_r$]-($L^1$)$_s$[($C(R^{2A})_2$)$_r$O(C $(R^{2A})_2$)$_r$($L^2$)$_s$]$_s$-($L^1$)$_s$-$R^J$, optionally substituted $C_{1-8}$ alkyl, optionally substituted $C_{3-8}$ cycloalkyl, optionally substituted aryl, optionally substituted heteroaryl, and optionally substituted heterocyclyl;
each $R^G$ is independently hydrogen, optionally substituted $C_1$-$C_8$ alkyl, optionally substituted $C_3$-$C_8$ cycloalkyl, optionally substituted aryl, optionally substituted heteroaryl, or optionally substituted heterocyclyl;
each $R^H$ is independently hydrogen, optionally substituted $C_1$-$C_8$ alkyl, optionally substituted $C_3$-$C_8$ cycloalkyl, optionally substituted aryl, optionally substituted heteroaryl, optionally substituted heterocyclyl, or —$NR^E R^F$;

each $R^J$ is independently selected from the group consisting of hydrogen, optionally substituted $C_1$-$C_8$ alkyl, optionally substituted —O—($C_1$-$C_8$ alkyl), optionally substituted $C_3$-$C_8$ cycloalkyl, optionally substituted aryl, optionally substituted heteroaryl, optionally substituted heterocyclyl, —$(CH_2)_n OR^{2B}$, —$O(CH_2)_n OR^{2B}$, —$(CH_2)_n NR^{2B} R^{2B}$, —$C(R^{2A})_2 NR^{2B} R^{2B}$, —$(CH_2)_n C(=O)OR^{2B}$, and —$C(=O)NHR^{2B}$;

each $R^{2A}$ is independently selected, wherein $R^{2A}$ is selected from the group consisting of hydrogen, halo, —OH, optionally substituted $C_1$-$C_8$ alkyl, optionally substituted —O—($C_1$-$C_8$ alkyl), optionally substituted $C_3$-$C_8$ cycloalkyl, optionally substituted aryl, optionally substituted heteroaryl, optionally substituted heterocyclyl, —$(CH_2)_n OR^{2B}$, —$(CH_2)_n NR^{2C} R^{2C}$, —$C(=O)OR^{2B}$, and —$C(=O)NR^{2C} R^{2C}$, or optionally two geminal $R^{2A}$ and the carbon to which they are attached form an optionally substituted three- to six-membered carbocyclic ring;

each $R^{2B}$ is independently selected from the group consisting of hydrogen, —OH, —$(CH_2)_n C(=O)OH$, —$C(=O)(C(R^{2D})_2)_n L^3 R^{2E}$, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl;

each $R^{2C}$ is independently selected from the group consisting of hydrogen, —OH, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl, or optionally both $R^{2C}$ together with the nitrogen to which they are attached form a optionally substituted heterocyclyl;

each $R^{2D}$ is independently selected from the group consisting of hydrogen, optionally substituted $C_1$-$C_8$ alkyl, optionally substituted $C_3$-$C_8$ cycloalkyl, optionally substituted —O—($C_1$-$C_8$ alkyl), optionally substituted aryl, optionally substituted heteroaryl, and optionally substituted heterocyclyl;

each $R^{2E}$ is independently selected from the group consisting of optionally substituted $C_1$-$C_8$ alkyl, optionally substituted $C_3$-$C_8$ cycloalkyl, optionally substituted aryl, optionally substituted heteroaryl, and optionally substituted heterocyclyl, and —$(CH_2)_n C(=O)OR^{2F}$;

each $R^{2F}$ is independently selected from the group consisting hydrogen, optionally substituted $C_1$-$C_8$ alkyl, optionally substituted $C_3$-$C_8$ cycloalkyl, optionally substituted aryl, optionally substituted heteroaryl, and optionally substituted heterocyclyl;

each $L^1$ is independently selected from the group consisting of —C(=O)—, —S(=O)—, —C(=S)—, —S(=O)$_2$—, —C(=O)O—, —C(=O)NR$^{2A}$—, —S(=O)NR$^{2A}$—, —S(=O)$_2$NR$^{2A}$—, —C(=O) NR$^{2A}$C(=O)—, and —C(CF$_3$)$_2$NR$^{2A}$—;

each $L^2$ is independently selected from the group consisting of optionally substituted aryl, optionally substituted heteroaryl, and optionally substituted heterocyclyl;

each $L^3$ is independently selected from the group consisting of —C(=O)—, —S(=O)—, —C(=S)—, —S(=O)$_2$—, —C(=O)O—, —C(=O)NR$^{2A}$—, —S(=O)NR$^{2A}$—, —S(=O)$_2$NR$^{2A}$—, —C(=O) NR$^{2A}$C(=O)—, and —C(CF$_3$)$_2$NR$^{2A}$—;

each m independently is 1 or 2;
each n independently is 0, 1, 2, 3, 4, 5, or 6;
each r independently is 0, 1, 2, 3, 4, 5, or 6;
each s independently is 0 or 1; and
each z independently is 1 or 2.

2. The compound of claim 1, wherein $R^9$ is selected from the group consisting of H (hydrogen), $C_1$-$C_8$ alkyl, $C_3$-$C_8$ cycloalkyl, substituted $C_1$-$C_8$ alkyl, aryl, and heteroaryl;

$R^1$ is H (hydrogen), or unsubstituted $C_1$-$C_6$ alkyl, $R^{1A}$, or $R^{1B}$;

$R^2$-$R^7$ are each independently selected from the group consisting of H (hydrogen), $C_1$-$C_8$ alkyl, $C_3$-$C_8$ cycloalkyl, aryl, and heteroaryl, or $R^1$ and $R^2$ together with the nitrogen to which they are attached form a cyclic 5- to 7-membered ring;

$R^8$ is selected from is selected from the group consisting of H (hydrogen), —$(CH_2)_n R^C$, $C_1$-$C_8$ alkyl, $C_3$-$C_8$ cycloalkyl, aryl, and heterocyclyl;

$R^C$ is $C_1$-$C_8$ alkyl, $C_3$-$C_8$ cycloalkyl, aryl, heteroaryl, and heterocyclyl, each optionally substituted with one or more $R^D$, or $R^C$ is a monoclonal antibody or an antibody fragment;

each $R^D$ is independently selected from the group consisting of —OH, —$N_3$, halo, cyano, nitro, —$(CH_2)_n NR^E R^F$, —$(CH_2)_n C(=O)NR^E R^F$, —$O(CH_2)_n NR^E R^F$, —$O(CH_2)_n C(=O)NR^E R^F$, —$O(CH_2)_m OC(=O) NR^E R^F$, —$NR^G C(=O)R^H$, —$NR^G S(O)_z R^H$, —$O(CH_2)_m O(CH_2)_m R^J$, —$O(CH_2)_n C(=O)R^J$, —$O(CH_2)_n R^J$, $C_1$-$C_8$ alkyl, $C_3$-$C_8$ cycloalkyl, aryl, heteroaryl, heterocyclyl, and —O—($C_1$-$C_8$ alkyl);

$R^E$ and $R^F$ are each independently selected from hydrogen, -[(L$^1$)$_s$(C(R$^{2A}$)$_2$)$_r$(NR$^{2A}$)$_s$(C(R$^{2A}$)$_2$)$_r$]-[L$^1$(C(R$^{2A}$)$_2$)$_r$(NR$^{2A}$)$_s$(C(R$^{2A}$)$_2$)$_r$]$_s$- (L$^1$)$_s$-R$^J$, -[(L$^1$)$_s$(C(R$^{2A}$)$_2$)$_r$(NR$^{2A}$)$_s$(C(R$^{2A}$)$_2$)$_r$]-(L$^1$)$_s$[(C(R$^{2A}$)$_2$)$_r$O(C(R$^{2A}$)$_2$)$_r$](L$^2$)$_s$]$_s$-(L$^1$)$_s$-R$^J$, $C_{1-8}$ alkyl, $C_{3-8}$ cycloalkyl, aryl, heteroaryl, and heterocyclyl;

each $R^G$ is independently hydrogen, $C_1$-$C_8$ alkyl, $C_3$-$C_8$ cycloalkyl, aryl, heteroaryl, or heterocyclyl;

each $R^H$ is independently hydrogen, $C_1$-$C_8$ alkyl, $C_3$-$C_8$ cycloalkyl, aryl, heteroaryl, heterocyclyl, or —$NR^E R^F$;

each $R^J$ is independently selected from the group consisting of hydrogen, $C_1$-$C_8$ alkyl, —O—($C_1$-$C_8$ alkyl), $C_3$-$C_8$ cycloalkyl, aryl, heteroaryl, heterocyclyl, —$(CH_2)_n OR^{2B}$, —$O(CH_2)_n OR^{2B}$, —$(CH_2)_n NR^{2B} R^{2B}$, —$C(R^{2A})_2 NR^{2B} R^{2B}$, —$(CH_2)_n C(=O)OR^{2B}$, and —$C(=O)NHR^{2B}$;

each $R^{2A}$ is independently selected, wherein $R^{2A}$ is selected from the group consisting of hydrogen, halo, —OH, $C_1$-$C_8$ alkyl, —O—($C_1$-$C_8$ alkyl), $C_3$-$C_8$ cycloalkyl, aryl, heteroaryl, heterocyclyl, —$(CH_2)_n OR^{2B}$, —$(CH_2)_n NR^{2C} R^{2C}$, —$C(=O)OR^{2B}$, and —$C(=O)NR^{2C} R^{2C}$, or optionally two geminal $R^{2A}$ and the carbon to which they are attached form a three- to six-membered carbocyclic ring;

each $R^{2B}$ is independently selected from the group consisting of hydrogen, —OH, —$(CH_2)_n C(=O)OH$, —$C(=O)(C(R^{2D})_2)_n L^3 R^{2E}$, $C_1$-$C_8$ alkyl, $C_3$-$C_8$ cycloalkyl, —O—($C_1$-$C_8$ alkyl), aryl, heteroaryl, and unsubstituted heterocyclyl;

each $R^{2C}$ is independently selected from the group consisting of hydrogen, —OH, $C_1$-$C_8$ alkyl, $C_3$-$C_8$ cycloalkyl, —O—($C_1$-$C_8$ alkyl), aryl, heteroaryl, and heterocyclyl, or optionally both $R^{2C}$ together with the nitrogen to which they are attached form a heterocyclyl;

each $R^{2D}$ is independently selected from the group consisting of hydrogen, $C_1$-$C_8$ alkyl, $C_3$-$C_8$ cycloalkyl, —O—($C_1$-$C_8$ alkyl), aryl, heteroaryl, and heterocyclyl;

each $R^{2E}$ is independently selected from the group consisting of $C_1$-$C_8$ alkyl, $C_3$-$C_8$ cycloalkyl, aryl, heteroaryl, and heterocyclyl, and —(CH$_2$)$_n$C(=O)OR$^{2F}$;

each $R^{2F}$ is independently selected from the group consisting hydrogen, $C_1$-$C_8$ alkyl, $C_3$-$C_8$ cycloalkyl, aryl, heteroaryl, and heterocyclyl; and each $L^2$ is independently selected from the group consisting of aryl, heteroaryl, and heterocyclyl.

3. The compound of claim 1, wherein
$R^{1B}$ is —C(=O)(CH$_2$)$_n$R$^C$ or R$^C$;
$R^C$ is $C_1$-$C_8$ alkyl substituted with one or more R$^D$;
$R^D$ is —O(CH$_2$)$_m$O(=O)NR$^E$R$^F$, —O(CH$_2$)$_m$O(CH$_2$)$_m$R$^J$, or optionally substituted heterocyclyl;
$R^J$ is —C(=O)OR$^{2B}$; and
$R^{2B}$ is —OH.

4. The compound of claim 1, wherein $R^{1B}$ is —C(=O)O(CH$_2$)$_n$R$^C$.

5. The compound of claim 4, wherein
$R^C$ is aryl substituted with one or more R$^D$;
$R^D$ is —(CH$_2$)$_n$NR$^E$R$^F$;
$R^E$ is hydrogen; and
$R^F$ is -[(L$^1$)$_s$(C(R$^{2A}$)$_2$)$_r$(NR$^{2A}$)$_s$(C(R$^{2A}$)$_2$)$_r$]-[L$^1$(C(R$^{2A}$)$_2$)$_r$(NR$^{2A}$)$_s$(C(R$^{2A}$)$_2$)$_r$]$_s$-(L$^1$)$_s$-R$^J$.

6. The compound of claim 5, wherein
$R^F$ is —[C(=O)(C(R$^{2A}$)$_2$)(NR$^{2A}$)]-[L$^1$(C(R$^{2A}$)$_2$)$_r$]-R$^J$ or —[C(=O)(C(R$^{2A}$)$_2$)(NR$^{2A}$)]-L$^1$[(C(R$^{2A}$)$_2$)$_r$O(C(R$^{2A}$)$_2$)$_r$]-R$^J$;
$R^J$ is —(CH$_2$)$_n$OR$^{2B}$ or —C(=O)OR$^{2B}$; and
$R^{2B}$ is hydrogen or —(CH$_2$)$_n$C(=O)OH.

7. The compound of claim 1, wherein R$^C$ is aryl substituted with one or more R$^D$.

8. The compound of claim 7, wherein
$R^D$ is —(CH$_2$)$_n$NR$^E$R$^F$;
$R^E$ is hydrogen; and
$R^F$ is -[(L$^1$)$_s$(C(R$^{2A}$)$_2$)$_r$(NR$^{2A}$)$_s$(C(R$^{2A}$)$_2$)$_r$]-[L$^1$(C(R$^{2A}$)$_2$)$_r$(NR$^{2A}$)$_s$(C(R$^{2A}$)$_2$)$_r$]$_s$-(L$^1$)$_s$-R$^J$.

9. The compound of claim 8, wherein R$^F$ is —[C(=O)(C(R$^{2A}$)$_2$)(NR$^{2A}$)]—[C(=O)(C(R$^{2A}$)$_2$)$_r$(NR$^{2A}$)]—C(=O)—R$^J$.

10. The compound of claim 7, wherein
$R^D$ is —(CH$_2$)$_n$NR$^E$R$^F$;
$R^E$ is hydrogen; and
$R^F$ is -[(L$^1$)$_s$(C(R$^{2A}$)$_2$)$_r$(NR$^{2A}$)$_s$(C(R$^{2A}$)$_2$)$_r$]-(L$^1$)$_s$-R$^J$.

11. The compound of claim 10, wherein R$^F$ is —[C(=O)(C(R$^{2A}$)$_2$)$_r$(NR$^{2A}$)]—C(=O)—R$^J$.

12. The compound of claim 11, wherein R$^J$ is —(CH$_2$)$_n$C(=O)OR$^{2B}$; and R$^{2B}$ is hydrogen.

13. The compound of claim 8, wherein
$R^F$ is —[C(=O)(C(R$^{2A}$)$_2$)(NR$^{2A}$)]—C(=O)[(C(R$^{2A}$)$_2$)$_r$O(C(R$^{2A}$)$_2$)$_r$]—R$^J$;
$R^J$ is —O(CH$_2$)$_n$C(=O)OR$^{2B}$; and
$R^{2B}$ is hydrogen.

14. The compound of claim 1, wherein R$^8$ is —(CH$_2$)$_n$R$^C$.

15. The compound of claim 14, wherein
$R^C$ is aryl substituted with one or more R$^D$;
$R^D$ is —O(CH$_2$)$_n$R$^J$ or —O(CH$_2$)$_n$C(=O)NR$^E$R$^F$;
$R^J$ is —(CH$_2$)$_n$C(=O)OR$^{2B}$; and
$R^{2B}$ is hydrogen.

16. The compound of claim 15, wherein
$R^D$ is —O(CH$_2$)$_n$C(=O)NR$^E$R$^F$;
$R^E$ is hydrogen; and
$R^F$ is -[(L$^1$)$_s$(C(R$^{2A}$)$_2$)$_r$(NR$^{2A}$)$_s$(C(R$^{2A}$)$_2$)$_r$]-(L$^1$)$_s$[(C(R$^{2A}$)$_2$)$_r$O(C(R$^{2A}$)$_2$)$_r$(L$^2$)$_s$]$_s$-(L$^1$)$_s$R$^J$.

17. A pharmaceutical composition comprising the compound of claim 1, or a pharmaceutically acceptable salt thereof; and a pharmaceutically acceptable carrier.

18. A pharmaceutical composition comprising the compound of claim 2, or a pharmaceutically acceptable salt thereof; and a pharmaceutically acceptable carrier.

* * * * *